US012668593B2

(12) United States Patent
Tian et al.

(10) Patent No.: US 12,668,593 B2
(45) Date of Patent: Jun. 30, 2026

(54) PYRAZOLE COMPOUND AND PREPARATION METHOD THEREFOR AND USE THEREOF

(71) Applicant: Sichuan Kelun-Biotech Biopharmaceutical Co., Ltd., Chengdu (CN)

(72) Inventors: Qiang Tian, Chengdu (CN); Yitao Zhang, Chengdu (CN); Xiaoling Jiang, Chengdu (CN); Chunchi Liu, Chengdu (CN); Bingqiang Kang, Chengdu (CN); Ruihong Liu, Chengdu (CN); Hongmei Song, Chengdu (CN); Tongtong Xue, Chengdu (CN); Jingyi Wang, Chengdu (CN)

(73) Assignee: Sichuan Kelun-Biotech Biopharmaceutical Co., Ltd., Chengdu (CN)

( * ) Notice: Subject to any disclaimer, the term of this patent is extended or adjusted under 35 U.S.C. 154(b) by 453 days.

(21) Appl. No.: 18/018,440

(22) PCT Filed: Sep. 17, 2021

(86) PCT No.: PCT/CN2021/119002
§ 371 (c)(1),
(2) Date: Jan. 27, 2023

(87) PCT Pub. No.: WO2022/063050
PCT Pub. Date: Mar. 31, 2022

(65) Prior Publication Data

US 2023/0303562 A1 Sep. 28, 2023

(30) Foreign Application Priority Data

Sep. 28, 2020 (CN) ......................... 202011043288.2

(51) Int. Cl.

| | |
|---|---|
| ***C07D 471/04*** | (2006.01) |
| ***C07D 401/14*** | (2006.01) |
| ***C07D 417/14*** | (2006.01) |
| ***C07D 487/04*** | (2006.01) |
| ***C07D 519/00*** | (2006.01) |

(52) U.S. Cl.
CPC ......... *C07D 471/04* (2013.01); *C07D 401/14* (2013.01); *C07D 417/14* (2013.01); *C07D 487/04* (2013.01); *C07D 519/00* (2013.01)

(58) Field of Classification Search
None
See application file for complete search history.

(56) References Cited

U.S. PATENT DOCUMENTS

2019/0194198 A1 6/2019 Lee
2021/0300916 A1 9/2021 Xu

FOREIGN PATENT DOCUMENTS

| | | | | |
|---|---|---|---|---|
| CN | 101062916 | | 10/2007 | |
| CN | 101528752 | A | 9/2009 | |
| CN | 109020890 | A | 12/2018 | |
| CN | 109415346 | A | 3/2019 | |
| EP | 2074128 | B1 | 8/2013 | |
| WO | 199958523 | A1 | 11/1999 | |
| WO | 02094833 | A1 | 11/2002 | |
| WO | WO-2006044528 | A1 * | 4/2006 | .............. A61P 43/00 |
| WO | 2008047198 | A1 | 4/2008 | |
| WO | 2009150547 | A2 | 12/2009 | |
| WO | 2014089364 | A1 | 6/2014 | |
| WO | 2017035118 | A1 | 3/2017 | |
| WO | 2018019106 | A1 | 2/2018 | |
| WO | 2018222601 | A1 | 12/2018 | |
| WO | 2019195159 | A1 | 10/2019 | |
| WO | 2020013803 | A1 | 1/2020 | |
| WO | 2020046813 | A1 | 3/2020 | |
| WO | WO-2023142985 | A1 * | 8/2023 | ........... C07D 487/04 |

OTHER PUBLICATIONS

Fuertes, Progress in Solid State Chemistry, 2018, 51, 63-70. (Year: 2018).*
Pasche. Journal of Cellular Physiology, 2001, 186, 153-168 (Year: 2001).*
Schabath. Cancer Progress and Priorities, 2019, 28 (10), pp. 1563-1579 (Year: 2019).*
Goodman and Gilman. The Pharmacological Basis of Therapeutics, 1990, 13-20 (Year: 1990).*

(Continued)

*Primary Examiner* — Noble E Jarrell
(74) *Attorney, Agent, or Firm* — MORRISON & FOERSTER LLP

(57) ABSTRACT

The present invention relates to a pyrazole compound and a preparation method therefor and a use thereof. In particular, the present invention relates to a compound shown in Formula I, a pharmaceutical composition containing same or a pharmaceutically acceptable form thereof, a pharmaceutical composition thereof, a preparation method therefor, and a use thereof. The compound can be used as a drug for treating cancer or fibrosis disease,

I

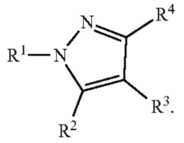

30 Claims, No Drawings

(56) References Cited

OTHER PUBLICATIONS

Derynck, R. et al. (Oct. 9, 2003). "Smad-Dependent and Smad-Independent Pathways in TGF-β Family Signalling," Nature 425:577-584.
He, Y. et al. (Jul. 2014). "ALK5-Dependent TGF-β Signaling is a Major Determinant of Late Stage Adult Neurogenesis," Nat. Neurosci. 17(7):943-952, 28 pages.
International Preliminary Report on Patentability, issued Mar. 28, 2023, for PCT Application No. PCT/CN2021/119002, filed Sep. 17, 2021, 7 pages with English Translation.
International Search Report and Written Opinion, mailed Dec. 27, 2021, for PCT Application No. PCT/CN2021/119002, filed Sep. 17, 2021, 21 pages, with English Translations.
Masood, M.A. et al. (2012). "Lead Diversification 2: Application to P38, gMTP and Lead Compounds," Bioorganic & Medicinal Chemistry Letters 22:1255-1262.
Monsivais, D. et al. (May 7, 2019). "ALK5-Mediated Tumor Suppressor Signaling Through SMAD2 and SMAD3 in the Uterus," Proc. Natl. Acad. Sci. USA 116(19):9166-9167.
Zhang, Y. et al. (Oct. 17, 2018). "Discovery of 4-Azaindole Inhibitors of TGFβRI as Immuno-Oncology Agents," ACS Med. Chem. Lett. 9:1117-1122.
Chinese Office Action, (No Date), for Chinese Patent Application, 202180059416.9, 6 pages. English Translation.
Extended European Search Report, dated Sep. 9, 2024, for European Patent Application No. 21871420.2, 15 pages.
Genin, M.J. et al. (Jan. 1, 2000). "Novel 1,5-Diphenylpyrazole Nonnucleoside HIV-1 Reverse Transcriptase Inhibitors with Enhanced Activity Versus the Delavirdine-Resistant P236L Mutant: Lead Identification and SAR of 3- and 4-Substituted Derivatives," Journal of Medicinal Chemistry 43:1034-1040.
Rosati, O. et al. (Apr. 7, 2007, e-pub. Mar. 6, 2007). "Synthesis, Docking Studies and Anti-Inflammatory Activity of 4,5,6,7-Tetrahydro-2H-Indazole Derivatives," Bioorganic & Medicinal Chemistry 15(10):3463-3473.

* cited by examiner

PYRAZOLE COMPOUND AND PREPARATION METHOD THEREFOR AND USE THEREOF

CROSS REFERENCE TO RELATED APPLICATIONS

This application is a national stage application under 35 U.S.C. § 371 of International Application No. PCT/CN2021/119002, filed internationally on Sep. 17, 2021, which claims the benefit of priority of Chinese application No. 202011043288.2, filed on Sep. 28, 2020, the contents of each are hereby incorporated by reference in their entirety and for all purposes.

TECHNICAL FIELD

The present application belongs to the field of medicinal chemistry, and relates to a pyrazole compound with TGF-β1 inhibitory activity, as well as its preparation method, pharmaceutical composition and medicinal use.

BACKGROUND ART

Transforming growth factor-β (TGF-β) is a multifunctional cytokine that regulates various cellular responses such as cell proliferation, differentiation, migration and apoptosis. The TGF-β superfamily includes TGF-β1, TGF-β2, TGF-β3, activin, inhibin, bone morphogenetic protein, and the like. The signal transduction of TGF-β is performed through two highly conserved single-transmembrane serine/threonine kinases, TGFβR1 and TGFβR2 (ACS Med. Chem. Lett., 2018, 9, 1117).

Smads are important TGF-β signal transduction and regulation molecules in cells, which can directly transduce TGF-β signals from the cell membrane to the nucleus. The TGF-β/Smads signaling pathway plays an important role in the occurrence and development of tumors. In TGF-β/Smads signal transduction, activated TGF-β first binds to TGFβR2 on the cell membrane surface to form a heterodimeric complex, which is recognized and bound by TGFβR1. Activated TGFβR1 phosphorylates Smad2/Smad3 protein, and the phosphorylated Smad2/Smad3 protein further binds to Smad4 to form a heterotrimeric complex, the complex enters the nucleus and cooperates with co-activator/repressor to regulate the transcription of target genes (Nature, 2003, 425, 577). As long as any part of the TGF-β/Smads signaling pathway is altered, it will lead to abnormalities in the signal transduction pathway (PNAS, 2019, 116, 9166).

Activation of the TGF-β signaling pathway triggers obvious pathological effects in the tumor stroma, including immunosuppression, angiogenesis, and connective tissue hyperplasia. In addition, the TGF-β signaling pathway can enhance tumor cell invasiveness, promote epithelial-to-mesenchymal transition, and improve tolerance to tumor epithelial cell therapy (Nat. Neurosci., 2014, 17, 943).

At present, the development of inhibitors targeting TGFβR1, a key target in the TGF-β signaling pathway, has gradually attracted attention in the pharmaceutical industry, and published patent applications include WO 02/094833 A1, WO 2009/150547 A1, WO 2017/035118 A1, WO 2018/019106 A1, etc. However, there is still an urgent need in the art for new TGFβR1 inhibitors, especially TGFβR1 inhibitors with high activity and selectivity.

CONTENTS OF THE INVENTION

Through extensive research, the present application provides a pyrazole compound and its preparation method. The compound can significantly inhibit the activity of TGFβR1, and can be used as a TGFβR1 inhibitor for the treatment of a disease mediated at least in part by TGF-β signaling pathway including proliferative disease and a disease or disorder of dysregulated apoptosis, especially a disease mediated at least in part by TGFβR1, such as a cancer or fibrotic disease.

In a first aspect, the present invention provides a compound having the structure of Formula I or a pharmaceutically acceptable form thereof,

I

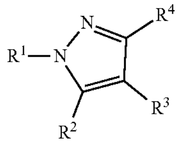

wherein, $R^1$ is selected from the group consisting of $C_{6-10}$ aryl and 5- to 10-membered heteroaryl, the $C_{6-10}$ aryl or 5- to 10-membered heteroaryl is optionally substituted with one or more $R^5$;

$R^2$ is selected from the group consisting of $C_{6-10}$ aryl and 5- to 10-membered heteroaryl, the $C_{6-10}$ aryl or 5- to 10-membered heteroaryl is optionally substituted with one or more $R^6$;

$R^3$ is selected from the group consisting of hydrogen, halogen, $C_{1-6}$ alkyl, $C_{1-6}$ haloalkyl, $C_{3-8}$ cycloalkyl, $C_{1-6}$ alkoxyl and $C_{1-6}$ alkylamino;

$R^4$ is selected from the group consisting of hydrogen, $C_{1-6}$ alkyl, $C_{1-6}$ haloalkyl, $C_{3-8}$ cycloalkyl, $C_{3-8}$ cycloalkyl-$C_{1-6}$ alkylamino, 3- to 8-membered heterocyclylamino, hydroxyalkyl, aminoalkyl, $C_{1-6}$ alkyloxy, $C_{1-6}$ alkylthio, cyano, hydroxyl, amino, $C_{1-6}$ alkylamino, $C_{1-6}$ haloalkylamino, $C_{3-8}$ cycloalkylamino, phenylamino, benzylamino, 5- to 10-membered heteroarylamino and 5- to 10-membered heteroarylalkylamino, the $C_{1-6}$ alkyl, $C_{1-6}$ haloalkyl, $C_{3-8}$ cycloalkyl, $C_{3-8}$ cycloalkyl-$C_{1-6}$ alkylamino, 3- to 8-membered heterocyclylamino, hydroxyalkyl, aminoalkyl, $C_{1-6}$ alkyloxy, $C_{1-6}$ alkylthio, $C_{1-6}$ alkylamino, $C_{1-6}$ haloalkylamino, $C_{3-8}$ cycloalkylamino, phenylamino, benzylamino, 5- to 10-membered heteroarylamino and 5- to 10-membered heteroarylalkylamino are each optionally substituted with one or more groups independently selected from the group consisting of the followings: $C_{1-6}$ alkyl, halogen, cyano, amido, carbamoyl, mono- or di-$C_{1-6}$ alkyl-substituted carbamoyl, sulfonyl, phenyl, halophenyl and 4- to 6-membered heterocyclyl;

or, $R^3$ and $R^4$ together with the attached carbon atoms form a 5- to 7-membered saturated carbocyclic ring or a 5- to 7-membered saturated heterocyclic ring, and the 5- to 7-membered saturated heterocyclic ring is not a lactam structure, and the 5- to 7-membered carbocyclic ring and the 5- to 7-membered saturated heterocyclic ring are optionally substituted with one or more $R^8$;

$R^5$ at each occurrence is independently selected from the group consisting of hydrogen, deuterium, halogen, cyano, $C_{1-6}$ alkyl, $C_{1-6}$ haloalkyl and $C_{3-8}$ cycloalkyl;

$R^6$ at each occurrence is independently selected from the group consisting of hydrogen, deuterium, cyano, halogen, $C_{1-6}$ alkyl, $C_{1-6}$ haloalkyl, $C_{1-6}$ alkoxyalkyl, $C_{3-8}$ cycloalkyl, 3- to 8-membered heterocyclylalkyl, 3- to 8-membered heterocyclyl, $C_{6-10}$ aryl, 5- to 10-membered heteroaryl, —$NR^aR^b$, —$NR^aC(=O)R^b$, —$OR^c$, —$OC(=O)R^c$, —$C(=O)R^c$, —$C(=O)OR^c$, —$C(=O)NR^aR^b$, —$(CR^aR^b)_mC(=O)NR^aR^b$, —$(CR^c=CR^c)_mC(=O)NR^aR^b$ and —$(C≡C)_mC(=O)NR^aR^b$, the $C_{1-6}$ alkyl, $C_{1-6}$ haloalkyl, $C_{1-6}$ alkoxyalkyl, $C_{3-8}$ cycloalkyl, 3- to 8-membered heterocyclylalkyl, 3- to 8-membered heterocyclyl, $C_{6-10}$ aryl, 5- to 10-membered heteroaryl, —$NR^aR^b$, —$OC(=O)R^c$ and —$NR^aC(=O)R^b$ are optionally substituted with one or more $R^7$;

$R^7$ at each occurrence is independently selected from the group consisting of hydrogen, deuterium, halogen, $C_{1-6}$ alkyl, $C_{1-6}$ haloalkyl, hydroxy-$C_{1-6}$ alkyl, $C_{1-6}$ alkoxyalkyl, substituted or unsubstituted carbamoyl, 3- to 8-membered heterocyclylalkyl, 3- to 8-membered heterocyclyl optionally substituted with $C_{1-6}$ alkyl, —$(CR^aR^b)_mS(=O)$—$R^c$, —$OR^c$, —$NR^aR^b$, —$C(=O)R^c$, —$C(=O)OR^c$ and —$C(=O)NR^aR^b$;

$R^8$ at each occurrence is independently selected from the group consisting of $C_{1-6}$ alkyl, $C_{1-6}$ haloalkyl and $C_{3-6}$ cycloalkyl;

$R^a$ and $R^b$ at each occurrence are each independently selected from the group consisting of hydrogen, $C_{1-6}$ alkyl, hydroxy-$C_{1-6}$ alkyl, $C_{1-6}$ alkoxyalkyl, $C_{1-6}$ alkylaminoalkyl, $C_{3-8}$ cycloalkyl, 3- to 8-membered heterocyclyl and 3- to 8-membered heterocyclylalkyl, or $R^a$ and $R^b$ together with the atoms to which they are attached form a 4- to 7-membered ring;

$R^c$ at each occurrence is independently selected from the group consisting of hydrogen, $C_{1-6}$ alkyl, $C_{3-8}$ cycloalkyl, 3- to 8-membered heterocyclylalkyl, 3- to 8-membered heterocyclyl and substituted or unsubstituted carbamoyl;

m is 0, 1 or 2;

n is 1 or 2;

provided that, (1) when $R^4$ is selected from the group consisting of cyano, amino, hydroxyl, $C_{1-6}$ alkyl, $C_{1-6}$ alkoxy and $C_{1-6}$ alkylthio, $R^3$ is not hydrogen;

(2) when $R^3$ and $R^4$ are both hydrogen or $C_{1-6}$ alkyl, or $R^3$ is $C_{1-6}$ alkyl, $R^4$ is hydrogen, or $R^3$ and $R^4$ together with the attached carbon atoms form a 5- to 7-membered saturated carbocyclic ring, and $R^1$ is substituted or unsubstituted pyridyl, $R^2$ is not substituted or unsubstituted thienopyridine nor substituted or unsubstituted quinazolinone;

the pharmaceutically acceptable form is selected from the group consisting of pharmaceutically acceptable salts, esters, stereoisomers, tautomers, polymorphs, solvates, oxynitrides, isotopically labeled compounds, metabolites and prodrugs.

In a second aspect, the present invention provides a pharmaceutical composition comprising the compound according to the first aspect of the present invention or a pharmaceutically acceptable form thereof, and one or more pharmaceutically acceptable carriers.

In a third aspect, the present invention provides a kit comprising:

a) at least one compound of the first aspect of the present invention or a pharmaceutically acceptable form thereof as a first therapeutic agent, or the pharmaceutical composition of the second aspect as a first pharmaceutical composition;

b) optionally, at least one other therapeutic agent as a second therapeutic agent, or a pharmaceutical composition comprising the other therapeutic agent as a second pharmaceutical composition; and c) optionally, packaging and/or instruction.

In a fourth aspect, the present invention provides a method for preparing the compound described in the first aspect, comprising one or more of the following methods:

(1) when the compound is I-1, the method is selected from Method I to Method III:

Method I:

Step 1-1: reacting Compound SM1 with N,O-dimethylhydroxylamine hydrochloride to obtain Weinreb amide IM1;

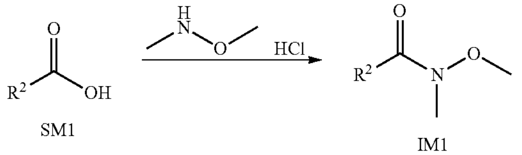

SM1 IM1

Step 1-2: reacting Weinreb amide IM1 with methyl magnesium bromide to obtain Compound IM2;

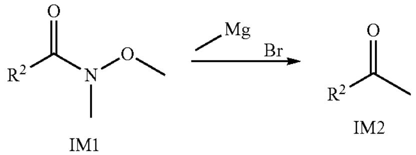

IM1 IM2

Step 1-3: subjecting Compound IM2 and N,N-dimethylformamide dimethyl acetal to a condensation reaction to obtain Compound IM3;

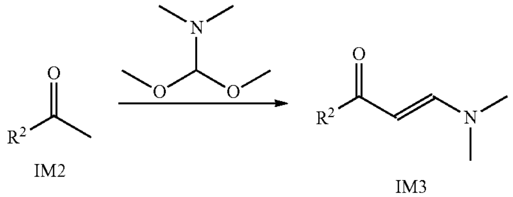

IM2 IM3

Step 1-4: subjecting Compounds IM3 and SM2 to a cyclization reaction to obtain a compound of Formula I-1;

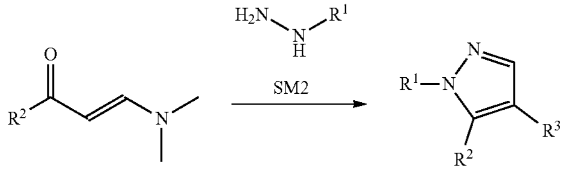

IM3 I-1 wherein, $R^1$ and $R^2$ are as defined in any item of the first aspect of the present invention, and $R^3$ is hydrogen;

Method II:

Step 2-1: subjecting Compound SM3 and methyl magnesium bromide to an addition reaction to obtain Compound IM4;

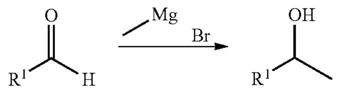

SM3 IM4

Step 2-2: subjecting Compound IM4 to an oxidation reaction to obtain Compound IM2;

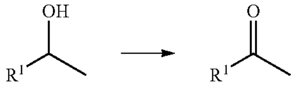

IM4 IM2

Step 2-3: subjecting Compound IM2 and N,N-dimethylformamide dimethyl acetal to a condensation reaction to obtain Compound IM3;

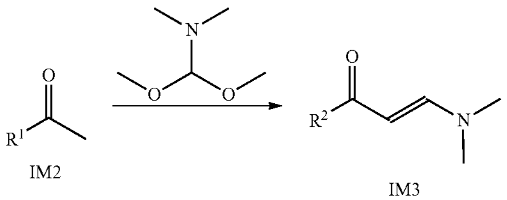

IM2 IM3

Step 2-4: subjecting Compounds IM3 and SM2 to a cyclization reaction to obtain a compound of Formula I-1;

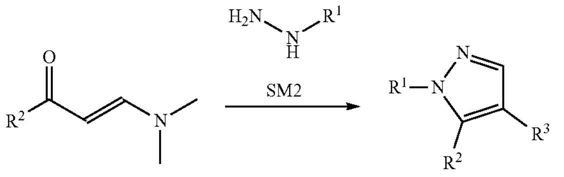

IM3 I-1 wherein, $R^1$ and $R^2$ are as defined in any item of the first aspect of the present invention, and $R^3$ is hydrogen;

Method III:

Step 3-1: subjecting Compound SM4 and N,N-dimethylformamide dimethyl acetal to a condensation reaction to obtain Compound IM5;

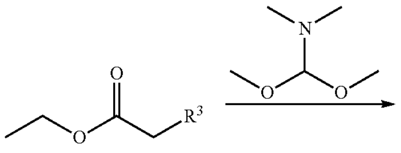

SM4

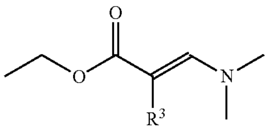

IM5

Step 3-2: subjecting Compounds IM5 and SM2 to a cyclization reaction to obtain Compound IM6;

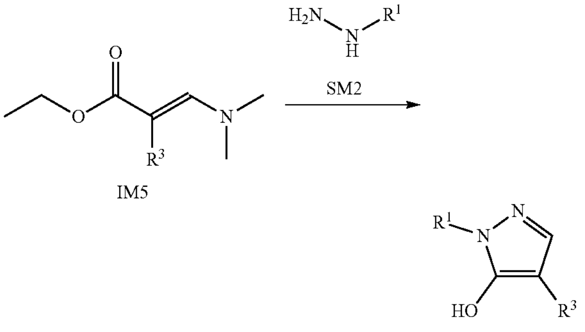

IM5

IM6

Step 3-3: subjecting Compound IM6 to a sulfonylation reaction or halogenation reaction to obtain Compound IM7;

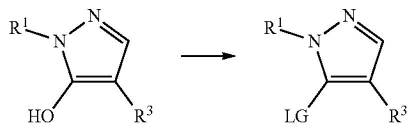

IM6 IM7

Step 3-4: subjecting Compound IM7 and Compound SM5 to a coupling reaction to obtain a compound of Formula I-2;

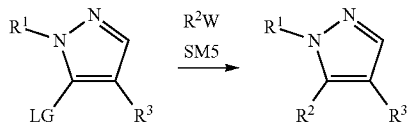

IM7 I-1 wherein, LG is a leaving group, which is selected from the group consisting of methanesulfonyl, trifluoromethanesulfonyloxy and halogen, preferably trifluoromethanesulfonyloxy or chloro; W is selected from the group consisting of boronic acid group, 4,4,5,5-tetramethyl-1,3,2-dioxaborolan-2-yl, tri-$^n$butylstannyl and sodium sulfinate group; wherein $R^1$, $R^2$ and $R^3$ are as defined in any item of the first aspect.

(2) when the compound is of Formula I-2, the method comprises the following steps:

Step 4-1: subjecting Compounds SM6 and SM2 to a condensation reaction to obtain Compound IM8;

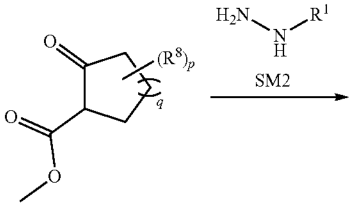

SM6

-continued

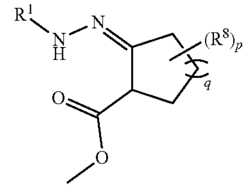

IM8

Step 4-2: subjecting Compound IM8 to a cyclization reaction with sodium methoxide to obtain Compound IM9;

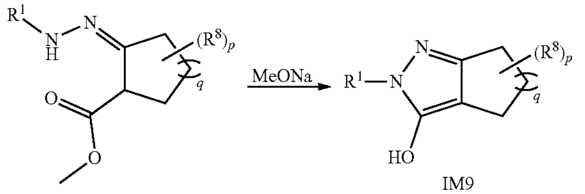

IM8 IM9

Step 4-3: subjecting Compound IM9 to a sulfonylation reaction or halogenation reaction to obtain Compound IM10;

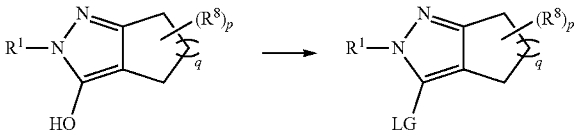

IM9 IM10

Step 4-4: subjecting Compounds IM10 and SM5 to a coupling reaction to obtain a compound of Formula I-2;

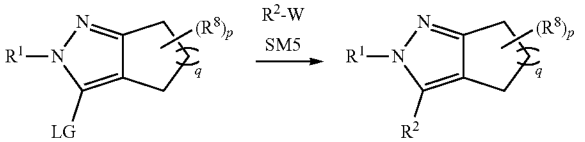

IM10 I-2 wherein, LG is a leaving group, which is selected from the group consisting of methanesulfonyl, trifluoromethanesulfonyloxy and halogen, preferably trifluoromethanesulfonyloxy or chloro; W is selected from the group consisting of boronic acid group, 4,4,5,5-tetramethyl-1,3,2-dioxolaboran-2-yl, tri-$^n$butylstannyl and sodium sulfinate group; wherein, $R^1$, $R^2$, $R^8$, p and q are as defined in any items of the first aspect;

(3) when the compound is of Formula I-3, the method comprises the following steps:

Step 5-1: subjecting Compound SM2 to a cyclization reaction with diethyl oxaloacetate sodium salt to obtain Compound IM11;

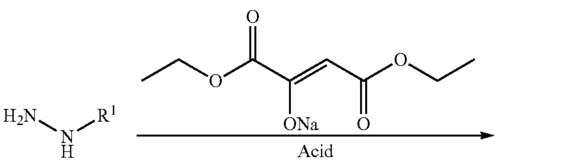

SM2

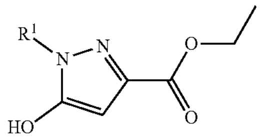

IM11

Step 5-2: subjecting Compound IM11 to Vilsmeier-Haack reaction to obtain Compound IM12;

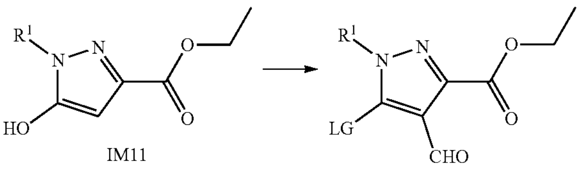

IM11 IM12

Step 5-3: subjecting Compound IM12 to a coupling reaction with Compound SM5 to obtain Compound IM13;

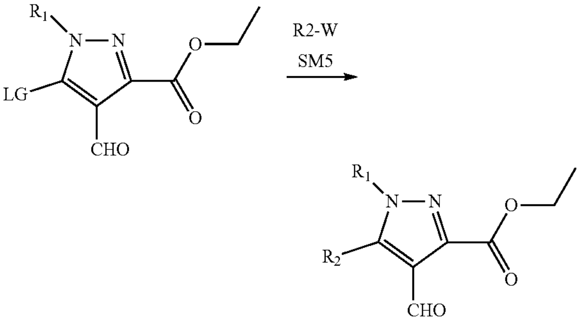

Step 5-4: subjecting Compound IM13 to Wittig reaction with a compound of methoxymethylphosphorus ylide to obtain Compound IM14;

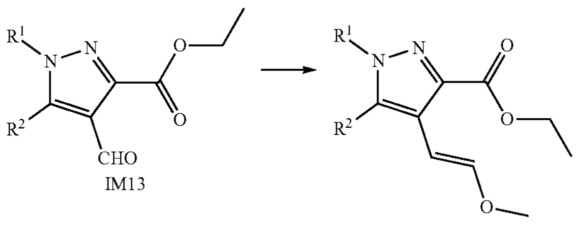

IM13 IM14

Step 5-5: subjecting Compound IM14 to a demethylation reaction to obtain Compound IM15;

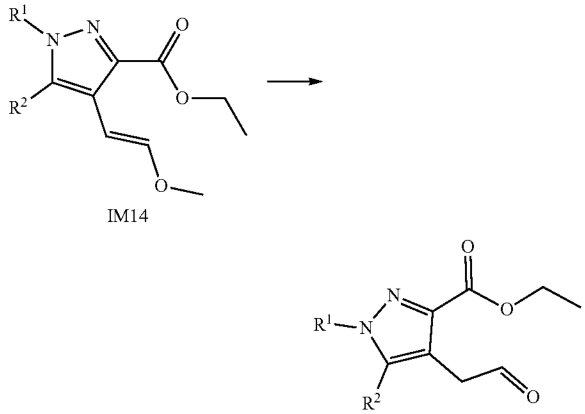

IM14

IM15

Step 5-6: subjecting Compound IM15 to a reduction reaction to obtain Compound IM16;

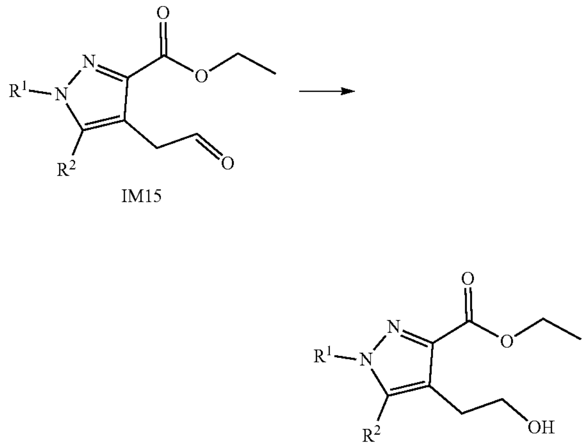

IM15

IM16

Step 5-7: subjecting Compound IM16 to a substitution reaction to obtain Compound IM17;

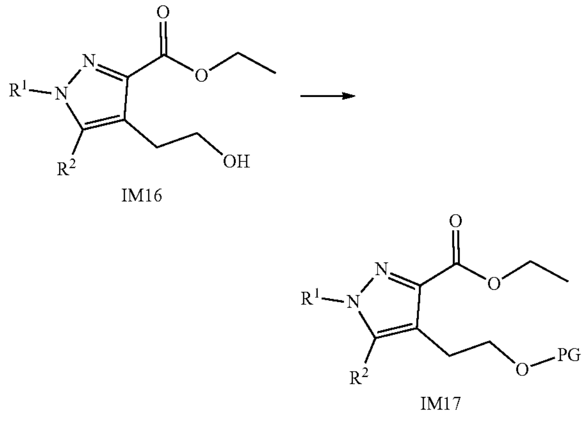

IM16

IM17

Step 5-8: subjecting Compound IM17 to a hydrolysis reaction to obtain Compound IM18;

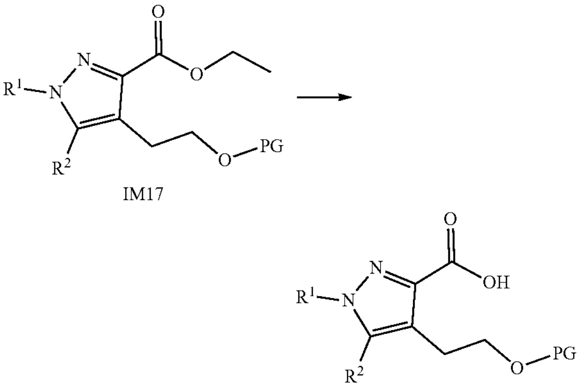

IM17

IM18

Step 5-9: subjecting Compound IM18 to Curtius rearrangement reaction to obtain Compound IM19;

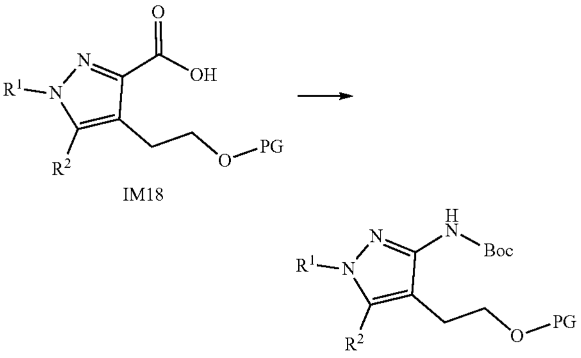

IM18

IM19

Step 5-10: deprotecting Compound IM19 to obtain Compound IM20;

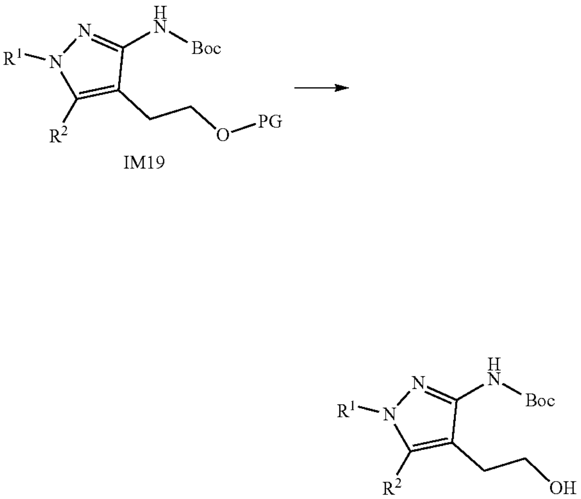

IM19

IM20

Step 5-11: subjecting Compound IM20 to a sulfonylation reaction or halogenation reaction to obtain Compound IM21;

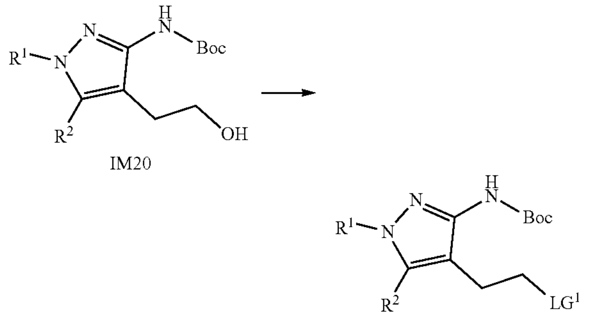

IM20

IM21

Step 5-12: deprotecting Compound IM21 to obtain Compound IM22;

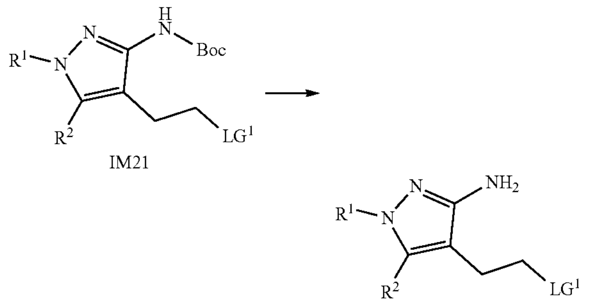

IM21

IM22

Step 5-13: subjecting Compound IM22 to a substitution reaction to obtain a compound of Formula I-3;

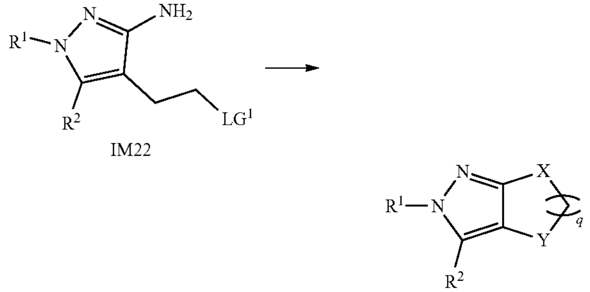

IM22

I-3 wherein, LG is halogen, which is selected from the group consisting of chloro, bromo, preferably chloro; PG is a protecting group, which is selected from the group consisting of trimethylsilyl, triethylsilyl, triisopropylsilyl, tert-butyl-dimethyl-silyl, tert-butyl-diphenyl-silyl, preferably tert-butyl-dimethylsilyl; $LG^1$ is a leaving group, which is selected from the group consisting of methanesulfonyl, trifluoromethanesulfonyloxy and halogen, preferably trifluoromethanesulfonyloxy or chloro; W is selected from the group consisting of boronic acid group, 4,4,5,5-tetramethyl-1,3,2-dioxaborolan-2-yl, tri-$^n$butylstannyl and sodium sulfinate; wherein, X is —NH—, Y is —$CH_2$—, $R^1$, $R^2$ and q are as defined in any item of the first aspect;

(4) when the compound is of Formula I-4, the method optionally comprises the following Method I to Method III:

Method I:

Step 6-1: subjecting Compounds SM2 and SM7 to a cyclization reaction to obtain Compound IM23;

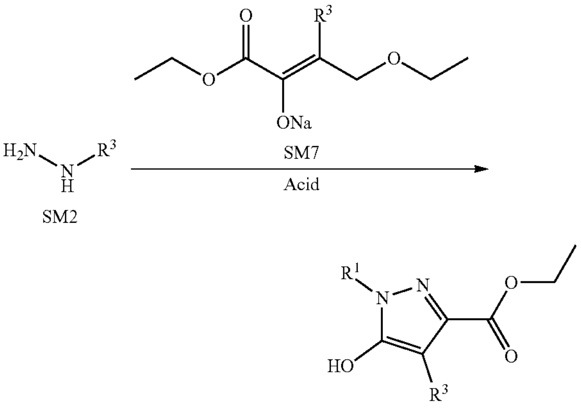

SM2

IM23

Step 6-2: subjecting Compound IM23 to a sulfonylation reaction or halogenation reaction to obtain Compound IM24;

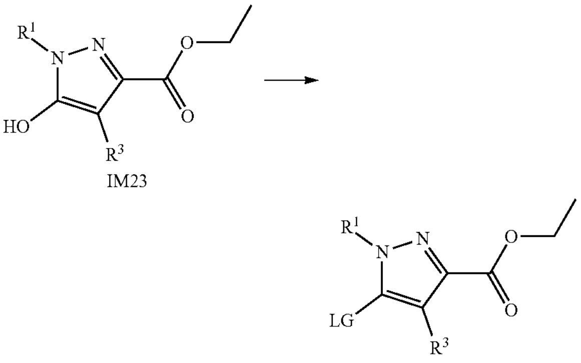

IM23

IM24

Step 6-3: subjecting Compound IM24 and Compound SM5 to a coupling reaction to obtain Compound IM25;

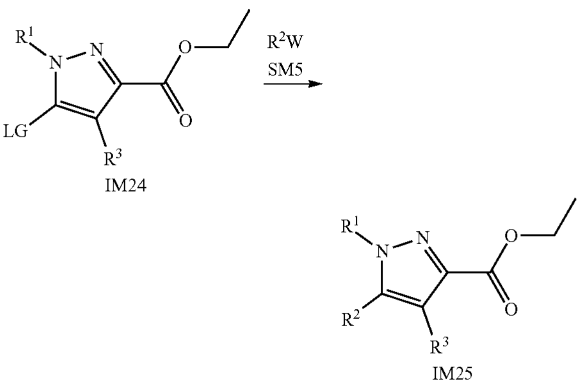

IM24

IM25

Step 6-4: subjecting Compound IM25 to a hydrolysis reaction to obtain Compound IM26;

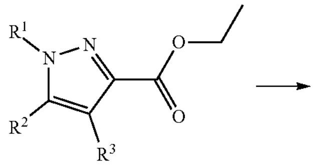

IM25

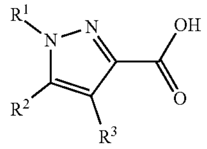

IM26

Step 6-5: subjecting Compound IM26 to Curtius rearrangement reaction to obtain Compound IM27;

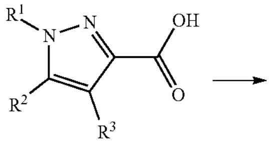

IM26

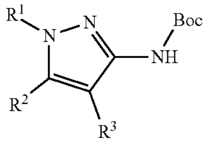

IM27

Step 6-6: subjecting Compound IM27 and Compound SM8 to a substitution reaction to obtain Compound IM28;

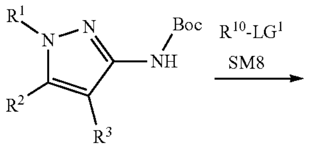

IM27

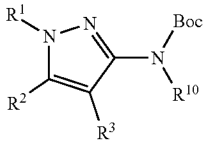

IM28

Step 6-7: deprotecting Compound IM28 to obtain a compound of Formula I-4;

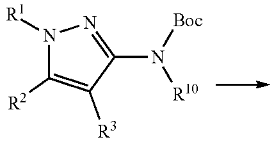

IM28

-continued

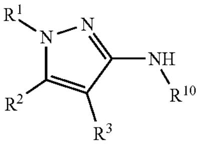

I-4 wherein, LG is a leaving group, which is selected from the group consisting of methanesulfonyloxy, trifluoromethanesulfonyloxy and halogen, preferably trifluoromethanesulfonyloxy or chloro; $LG^1$ is a leaving group, which is selected from the group consisting of methanesulfonyloxy, trifluoromethanesulfonyloxy and halogen, preferably trifluoromethanesulfonyloxy or iodine; W is selected from boronic acid group, 4,4,5,5-tetramethyl-1,3,2-dioxaborolan-2-yl, tri-"butylstannyl and sodium sulfinate group; $R^1$, $R^2$, $R^3$ and $R^{10}$ are as defined in any item of the first aspect;

Method Two:

Step 7-1: deprotecting Compound IM27 to obtain Compound IM28;

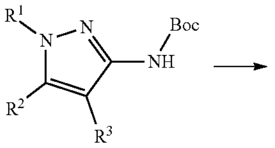

IM27

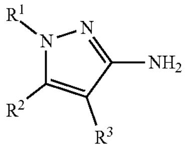

IM28

Step 7-2: subjecting Compound IM28 and Compound SM9 to a reductive amination reaction to obtain a compound of Formula I-4;

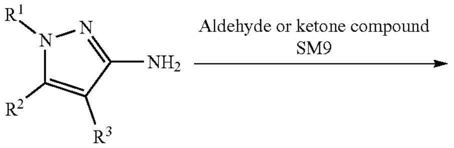

IM28

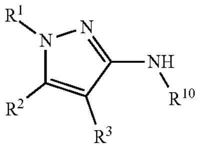

I-4 wherein $R^1$, $R^2$, $R^3$ and $R^{10}$ are as defined in any item of the first aspect;

Method 3: Synthesis of IM27

Step 8-1: hydrolyzing Compound IM23 to obtain Compound IM29;

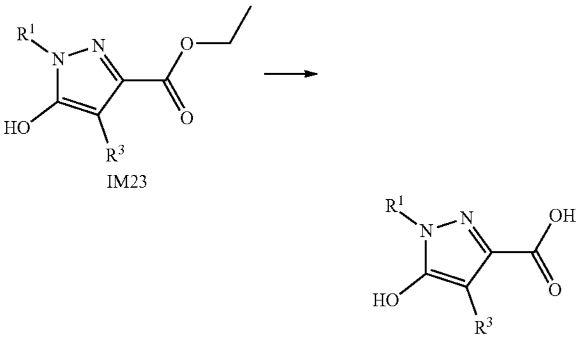

IM23

I29

Step 8-2: subjecting Compound IM29 to Curtius rearrangement reaction to obtain Compound IM30;

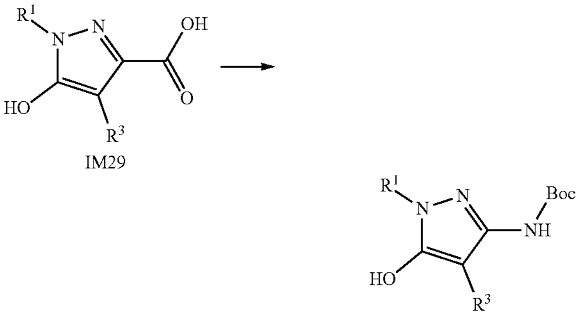

IM29

IM30

Step 8-3: subjecting Compound IM30 to a sulfonylation reaction or halogenation reaction to obtain Compound IM31;

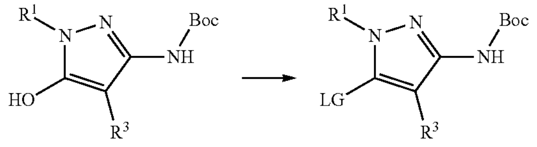

IM30 IM31

Step 8-4: subjecting Compound IM31 and Compound SM5 to a coupling reaction to obtain Compound IM27;

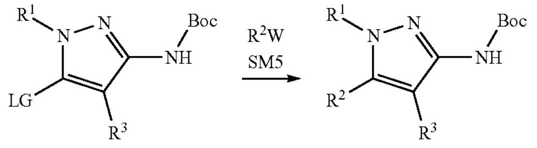

IM31 IM27 wherein, LG is a leaving group, which is selected from the group consisting of methanesulfonyloxy, trifluoromethanesulfonyloxy and halogen, preferably trifluoromethanesulfonyloxy or chloro; W is selected from the group consisting of boronic acid group, 4,4,5,5-tetramethyl-1,3,2-dioxaborolan-2-yl, tri-$^n$butylstannyl and sodium sulfinate group; $R^1$, $R^2$ and $R^3$ are as defined in any item of the first aspect.

In a fifth aspect, the present invention provides a method for preventing and/or treating a disease or disorder mediated at least in part by TGFβR1, comprising a step of administering to a subject in need thereof an effective amount of the compound of the first aspect or its pharmaceutically acceptable form or the pharmaceutical composition of the second aspect.

In a sixth aspect, the present invention provides the compound of the first aspect or a pharmaceutically acceptable form thereof or the pharmaceutical composition of the second aspect, for use in the prevention and/or treatment of a disease or disorder mediated at least in part by TGFβR1.

In a seventh aspect, the present invention provides use of the compound of the first aspect or a pharmaceutically acceptable form thereof or the pharmaceutical composition of the second aspect in the manufacture of a TGFβR1 inhibitor.

In an eighth aspect, the present invention provides a method for inhibiting the activity of TGFβR1, comprising a step of administering to a subject or cell in need thereof an effective amount of the compound of the first aspect or a pharmaceutically acceptable form thereof or the pharmaceutical composition of the second aspect.

In a ninth aspect, the present invention provides the compound of the first aspect or a pharmaceutically acceptable form thereof or the pharmaceutical composition of the second aspect, for use in inhibiting the activity of TGFβR1.

In a tenth aspect, the present invention provides a pharmaceutical combination, which comprises the compound of the first aspect or a pharmaceutically acceptable form thereof or the pharmaceutical composition of the second aspect, and at least one additional TGFβR1 inhibitor.

DETAILED DESCRIPTION OF THE INVENTION

In the present invention, unless otherwise specified, the scientific and technical terms used herein have the meanings commonly understood by those skilled in the art. In addition, the cell culture, molecular genetics, nucleic acid chemistry, and immunology laboratory operation steps used herein are all routine steps widely used in the corresponding fields. Meanwhile, for a better understanding of the present invention, definitions and explanations of related terms are provided below.

The terms "comprising", "including", "having" or "containing" or any other variations thereof are intended to encompass open-ended or non-exclusive content. For example, a composition, method or device comprising a series of elements is not necessarily limited to those explicitly listed, but may also include other elements not explicitly listed or elements inherent to the above-described composition, method or device.

The term "pharmaceutically acceptable salt" refers to a salt of the compound of the present invention that is substantially non-toxic to an organism. The pharmaceutically acceptable salt generally includes (but is not limited to) a salt formed by a reaction of the compound of the present invention with a pharmaceutically acceptable inorganic/organic acid or inorganic/organic base, and such salt is also known as an acid addition salt or base addition salt.

The term "pharmaceutically acceptable ester" refer to an ester that is substantially non-toxic to an organism and that can be hydrolyzed in an organism to form the compound of the present invention or a salt thereof. The pharmaceutically acceptable ester generally includes, but is not limited to, an ester of the compound of the present invention that is formed with a pharmaceutically acceptable carboxylic acid or sulfonic acid, and such ester is also known as a carboxylate or sulfonate.

The term “isomer” refers to a compound that have the same molecular weight due to the same number and type of atoms, but differ in the spatial arrangement or configuration of the atoms.

The term “stereoisomer” (or “optical isomer”) refers to a stable isomer having a vertical asymmetric plane resulted by at least one chiral factor (including chiral center, chiral axis, chiral plane, etc.) and thereby being capable of rotating plane-polarized light. Since the compounds of the present invention have asymmetric centers and other chemical structures that may lead to stereoisomerism, the present invention also includes these stereoisomers and mixtures thereof. Since the compounds of the present invention (or pharmaceutically acceptable salts thereof) comprise asymmetric carbon atoms, they may exist in the form of a single stereoisomer, a racemate, a mixture of enantiomers and diastereomers. Generally, these compounds can be prepared in the form of racemates. However, if desired, such compounds can be prepared or isolated as a pure stereoisomer, i.e. single enantiomer or diastereomer, or a mixture enriched with a single stereoisomer (purity ≥98%, ≥95%, ≥93%, ≥90%, ≥88%, ≥85% or ≥80%). As described hereinafter, a single stereoisomer of the compound is prepared synthetically from optically active starting materials containing the desired chiral center, or obtained by separation or resolution after the mixture of enantiomeric products is prepared, for example, after a mixture of diastereomers is obtained by conversion, it is subjected to separation or recrystallization, chromatography treatment, use of chiral resolving agent, or direct separation of enantiomers on chiral chromatography column. The starting compound with specific stereochemistry is either commercially available or can be prepared according to the methods described below and resolved by methods well known in the art.

The term “enantiomers” refers to a pair of stereoisomers with mirror images that are not superimposable between each other.

The term “diastereoisomers” or “diastereomers” refers to optical isomers that do not form mirror images between each other.

The term “racemic mixture” or “racemate” refers to a mixture containing equal parts of single enantiomers (i.e., an equimolar mixture of the two R and S enantiomers).

The term “non-racemic mixture” refers to a mixture containing unequal parts of single enantiomers. Unless otherwise indicated, all stereoisomeric forms of the compounds of the present invention are within the scope of the present invention.

The term “tautomers” (or “tautomeric forms”) refers to structural isomers with different energies that can be interconverted through a low energy barrier. A chemical equilibrium of tautomers can be achieved if tautomerism is possible (e.g., in solution). For example, proton tautomers (or proton transfer tautomers) include, but are not limited to, interconversion by proton transfer, such as keto-enol isomerization, imine-enamine isomerization, amide-imino alcohol isomerization, etc. Unless otherwise indicated, all tautomeric forms of the compounds of the present invention are within the scope of the present invention.

The term “polymorph” (or “polymorphic form”) refers to a solid crystalline form of a compound or complex. Polymorphs of molecule can be obtained by a lot of methods known by those skill in the art. These methods include, but are not limited to, melt recrystallization, melt cooling, solvent recrystallization, desolvation, rapid evaporation, rapid cooling, slow cooling, vapor phase diffusion, and sublimation. Additionally, polymorphs may be detected, classified and identified using well known techniques including, but not limited to, Differential Scanning calorimetry (DSC), Thermogravimetric analysis (TGA), X-ray Powder Diffraction (XRPD), Single Crystal X-ray Diffraction (SCXRD), solid-state Nuclear Magnetic Resonance (NMR), infrared Spectroscopy (IR), Raman Spectroscopy and Scanning Electron Microscopy (SEM), etc.

The term “solvate” refers to a substance formed by association of the compound of the present invention with at least one solvent molecule through a non-covalent intermolecular force. Common solvates include, but are not limited to, hydrates (including hemihydrates, monohydrates, dihydrates, trihydrates, and the like), ethanolates, acetonates, and the like.

The term “nitrogen oxide” refers to a compound formed by oxidation of a nitrogen atom in the structure of tertiary amine or nitrogen-containing (aromatic) heterocyclic compound. For example, a nitrogen atom at position 1 in the parent nucleus of a compound of Formula I can form a corresponding nitrogen oxide.

The term “isotopically labeled compound” refers to a derivative compound formed by substituting a particular atom in a compound of the present invention for its isotopic atom. Unless otherwise indicated, the compounds of the present invention include various isotopes of H, C, N, O, F, P, S, Cl, such as $^{2}H(D)$, $^{3}H(T)$, $^{13}C$, $^{14}C$, $^{15}N$, $^{17}O$, $^{18}O$, $^{18}F$, $^{31}P$, $^{32}P$, $^{35}S$, $^{36}S$ and $^{37}Cl$.

The term “metabolite” refers to a derivative compound formed by metabolism of a compound of the present invention. Further information on metabolism can be found in Goodman and Gilman’s. The Pharmacological Basis of Therapeutics ($9^{th}$ ed.) [M], McGraw-Hill international Editions, 1996.

The term “prodrug” refers to a derivative compound capable of providing, directly or indirectly, a compound of the present invention upon administration to an individual. Particularly preferred, the derivative compound or prodrug is a compound capable of increasing the bioavailability (e.g., being more readily absorbed into the blood) of the compound of the present invention upon administration to an individual, or capable of facilitating the delivery of the parent compound to the action site (e.g., lymphatic system). Unless otherwise indicated, all prodrug forms of the compounds of the present invention are within the scope of the present invention, and various prodrug forms are well known in the art.

The term “each independently” means that at least two groups (or ring systems) with same or similar value ranges in the structure may have the same or different meanings under certain circumstances. For example, substituent X and substituent Y are each independently hydrogen, halogen, hydroxyl, cyano, alkyl or aryl, then when substituent X is hydrogen, substituent Y can be either hydrogen or halogen, hydroxyl, cyano, alkyl or aryl; similarly, when the substituent Y is hydrogen, the substituent X can be either hydrogen or halogen, hydroxyl, cyano, alkyl or aryl.

The term “halogen” refers to fluorine (F), chlorine (Cl), bromine (Br) and iodine (I).

The term “alkyl” refers to a straight or branched chain-like saturated aliphatic hydrocarbonyl. For example, the term “$C_{1-6}$ alkyl” as used in the present invention refers to an alkyl group having 1 to 6 carbon atoms. Common alkyl groups include, but are not limited to, methyl, ethyl, n-propyl, isopropyl, n-butyl, sec-butyl, isobutyl, tert-butyl, n-pentyl, n-hexyl, and the like. The alkyl groups of the present invention are optionally substituted with one or more substituents (e.g., halogen) described herein.

The term "haloalkyl" refers to an alkyl group substituted with one or more, such as 1 to 3, same or different halogen atoms. For example, the term "$C_{1-6}$ haloalkyl" as used in the present invention refers to a haloalkyl having 1 to 6 carbon atoms. Common haloalkyl groups include, but are not limited to, $—CH_2F$, $—CHF_2$, $—CF_3$, $—CH_2CF_3$, $—CF_2CF_3$, $—CH_2CH_2CF_3$, $—CH_2Cl$, and the like. The haloalkyl groups of the present invention are optionally substituted with one or more of the substituents described herein.

The term "alkoxy" refers to a group having the structure "alkyl-O—". For example, $C_{1-6}$ alkoxy, $C_{1-4}$ alkoxy, $C_{1-3}$ alkoxy or $C_{1-2}$ alkoxy and the like. Common alkoxy groups include, but are not limited to, methoxy, ethoxy, n-propoxy, isopropoxy, n-butoxy, isobutoxy, tert-butoxy, pentyloxy, hexyloxy and the like. The alkoxy groups in the present invention are optionally substituted with one or more of the substituents described in the present invention.

The term "alkylamino" refers to a mono- or di-alkyl substituted amino. For example, $C_{1-6}$ alkylamino, $C_{1-4}$ alkylamino, $C_{1-3}$ alkylamino or $C_{1-2}$ alkylamino, etc. Common alkylamino groups include, but are not limited to, methylamino, dimethylamino, ethylamino, diethylamino, methylisopropylamino, and the like. The alkylamino groups of the present invention are optionally substituted with one or more of the substituents described herein.

The term "alkylthio" refers to a group having the structure "alkyl-S—". For example, $C_{1-6}$ alkylthio, $C_{1-4}$ alkylthio, $C_{1-3}$ alkylthio or $C_{1-2}$ alkylthio, etc. Common alkylthio groups include, but are not limited to, methylthio, ethylthio, n-propylthio, isopropylthio, n-butylthio, isobutylthio, tert-butylthio, pentylthio, hexylthio and the like. The alkylthio groups of the present invention are optionally substituted with one or more of the substituents described herein.

The term "cycloalkyl" refers to a saturated, monocyclic or polycyclic (e.g., bicyclic) non-aromatic cyclic hydrocarbonyl. For example, the term "$C_{3-8}$ cycloalkyl" as used in the present invention refers to a cycloalkyl group having 3 to 8 carbon atoms. Common cycloalkyl groups include, but are not limited to, monocyclic cycloalkyl groups such as cyclopropyl, cyclobutyl, cyclopentyl, cyclohexyl, cycloheptyl, cyclooctyl, cyclononyl, etc.; or bicyclic cycloalkyl groups, including fused rings, bridged rings or spiro rings, such as bicyclo[1.1.1]pentyl, bicyclo[2.2.1]heptyl, bicyclo[3.2.1]otyl, bicyclo[5.2.0]nonyl, decahydronaphthyl, etc. The cycloalkyl groups of the present invention are optionally substituted with one or more of the substituents (e.g., methyl) described herein.

The term "heterocyclyl" refers to a saturated or partially saturated, monocyclic or polycyclic (e.g., bicyclic) non-aromatic cyclic group which ring atoms consist of carbon atoms and at least one heteroatoms selected from the group consisting of nitrogen, oxygen and sulfur. If the valence requirements are met, the heterocyclyl can be attached to the rest moiety of the molecule through any one of the ring atoms. For example, the term "3- to 8-membered heterocyclyl" used in the present invention refers to a heterocyclyl having 3 to 8 ring atoms. Common heterocyclyl groups include, but are not limited to, oxiranyl, aziridinyl, azetidinyl, oxetanyl, tetrahydrofuryl, pyrrolidinyl, pyrrolidinonyl, imidazolidinyl, pyrazolidinyl, tetrahydropyranyl, piperidinyl, piperazinyl, morpholinyl, thiomorpholinyl, dithianyl or trithianyl. The heterocyclyl groups of the present invention are optionally substituted with one or more of the substituents described herein.

The term "heterocyclylalkyl" refers to a group with the structure of "heterocyclyl-alkyl-". For example, "3- to 8-membered heterocyclylalkyl" refers to a 3- to 8-membered heterocyclyl-alkyl-; "4- to 8-membered heterocyclylalkyl" refers to a 4- to 8-membered heterocyclyl-alkyl-.

The term "aryl" refers to a monocyclic or fused polycyclic aromatic hydrocarbonyl having a conjugated $\pi$ electron system. For example, the term "$C_{6-10}$ aryl" used in the present invention refers to an aryl having 6 to 10 carbon atoms. Common aryl groups include, but are not limited to, phenyl, naphthyl, anthracyl, phenanthryl, acenaphthenyl, azulenyl, fluorenyl, indenyl, pyrenyl, and the like. The aryl groups in the present invention are optionally substituted with one or more of the substituents (e.g., halogen, hydroxy, cyano, nitro, $C_{1-6}$ alkyl, etc.) described herein.

The term "heteroaryl" refers to a monocyclic or fused polycyclic (especially benzo-fused polycyclic) aromatic group having a conjugated $\pi$ electron system, the ring atoms of which are composed of carbon atoms and at least one heteroatom selected from nitrogen, oxygen and sulfur. If the valence requirements are met, the heteroaryl can be attached to the rest moiety of the molecule through any one of the ring atoms. For example, the term "5- to 10-membered heteroaryl" as used in the present invention refers to a heteroaryl group having 5 to 10 ring atoms. Common heteroaryl groups include, but are not limited to, thienyl, furyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl and benzo derivatives thereof, etc. The heteroaryl groups in the present invention are optionally substituted with one or more of the substituents (e.g., halogen, $C_{1-6}$ alkyl, etc.) described herein.

The term "alkenyl" refers to a straight or branched chain-like aliphatic hydrocarbonyl having at least one C═C double bond. For example, the term "$C_{2-6}$ alkenyl" as used in the present invention refers to an alkenyl group having 2 to 6 carbon atoms. Common alkenyl groups include, but are not limited to, vinyl, propenyl, n-butenyl, 3-methylbut-2-enyl, n-pentenyl, n-octenyl, n-decenyl, and the like. The alkenyl groups of the present invention are optionally substituted with one or more of the substituents described herein.

The term "alkynyl" refers to a straight or branched chain-like aliphatic hydrocarbonyl having at least one CC triple bond. For example, the term "$C_{2-6}$ alkynyl" as used in the present invention refers to an alkynyl group having 2 to 6 carbon atoms. Common alkynyl groups include, but are not limited to, ethynyl, 2-propynyl, 2-butynyl, 1,3-butadiynyl, and the like. The alkynyl groups in the present invention are optionally substituted with one or more of the substituents described in the present invention.

The term "carbocyclic ring" refers to a cyclic structure in which the ring atoms are all carbon atoms, including saturated or unsaturated, aromatic or aliphatic carbocyclic ring, for example, 3- to 8-membered carbocyclic ring, 5- to 7-membered carbocyclic ring, etc., specifically for example 3-membered carbocyclic ring, 4-membered carbocyclic ring, 5-membered carbocyclic ring, 6-membered carbocyclic ring, 7-membered carbocyclic ring or 8-membered carbocyclic ring, etc., and more specifically for example, cyclopentyl ring (i.e., a saturated 5-membered carbocyclic ring) or cyclohexyl ring (i.e., a saturated 6-membered carbocyclic ring), etc.

The term "heterocyclic ring" refers to a cyclic structure in which, in addition to carbon atoms, the ring-forming atoms further comprise a heteroatom selected from the group consisting of N, O, and S, including saturated or unsaturated, aromatic or aliphatic heterocyclic ring, as compared to the aforementioned "carbocyclic ring". For example, 3- to 8-membered heterocyclic ring, 5- to 7-membered heterocyclic ring, etc., specifically for example, 3-membered heterocyclic ring, 4-membered heterocyclic ring, 5-membered heterocyclic ring, 6-membered heterocyclic ring, 7-membered heterocyclic ring or 8-membered heterocyclic ring, etc.

The term "alkylamino" refers to an amino group substituted with one or more of the alkyl groups as described herein.

The term "heterocyclylamino" refers to an amino group substituted with one or more of the heterocyclyl groups described herein.

The term "haloalkylamino" refers to an amino group substituted with one or more of the haloalkyl groups described herein.

The term "cycloalkylamino" refers to an amino group substituted with one or more of the cycloalkyl groups described herein.

The term "heteroarylamino" refers to an amino group substituted with one or more of the heteroaryl groups described herein.

The term "heteroarylalkylamino" refers to an amino group substituted with one or more of the alkyl groups described herein, which are further substituted with the heteroaryl group described herein.

The term "substituted" means that one or more (e.g., 1, 2, 3, or 4) atoms (e.g., hydrogen atoms) or atomic groups (e.g., triflate groups) of the specified group are substituted with other atoms or atomic groups, provided that the specified group satisfies the valence requirements in the present case and forms a stable compound after substitution. A combination of substituents and/or variables is permissible only if such combination is capable of forming a stable compound. If a substituent is described as "optionally substituted", the substituent can be unsubstituted or substituted. If the first substituent is described as being optionally substituted with one or more of the list of second substituents, one or more hydrogen atoms of the first substituent may be individually or independently substituted with one or more of the list of second substituents, or is not substituted.

The term "one or more" refers to 1 or more than 1 under reasonable conditions, such as 2, 3, 4, 5, 6, 7, 8, 9 or 10.

Compound

The present invention provides a compound having the structure of Formula I or a pharmaceutically acceptable form thereof, wherein the pharmaceutically acceptable form is selected from the group consisting of pharmaceutically acceptable salts, esters, stereoisomers, tautomers, polymorphs, solvates, oxynitrides, isotopically labeled compounds, metabolites and prodrugs;

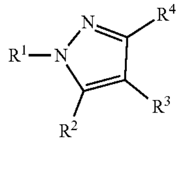

I wherein, $R^1$ is selected from the group consisting of $C_{6-10}$ aryl and 5- to 10-membered heteroaryl, the $C_{6-10}$ aryl or 5- to 10-membered heteroaryl is optionally substituted with one or more $R^5$;

$R^2$ is selected from the group consisting of $C_{6-10}$ aryl and 5- to 10-membered heteroaryl, the $C_{6-10}$ aryl or 5- to 10-membered heteroaryl is optionally substituted with one or more $R^6$;

$R^3$ is selected from the group consisting of hydrogen, halogen, $C_{1-6}$ alkyl, $C_{1-6}$ haloalkyl, $C_{3-8}$ cycloalkyl, $C_{1-6}$ alkoxyl and $C_{1-6}$ alkylamino;

$R^4$ is selected from the group consisting of hydrogen, $C_{1-6}$ alkyl, $C_{1-6}$ haloalkyl, $C_{3-8}$ cycloalkyl, $C_{3-8}$ cycloalkyl-$C_{1-6}$ alkylamino, 3- to 8-membered heterocyclylamino, hydroxyalkyl, aminoalkyl, $C_{1-6}$ alkyloxy, $C_{1-6}$ alkylthio, cyano, hydroxyl, amino, $C_{1-6}$ alkylamino, $C_{1-6}$ haloalkylamino, $C_{3-8}$ cycloalkylamino, phenylamino, benzylamino, 5- to 10-membered heteroarylamino and 5- to 10-membered heteroarylalkylamino, the $C_{1-6}$ alkyl, $C_{1-6}$ haloalkyl, $C_{3-8}$ cycloalkyl, $C_{3-8}$ cycloalkyl-$C_{1-6}$ alkylamino, 3- to 8-membered heterocyclylamino, hydroxyalkyl, aminoalkyl, $C_{1-6}$ alkyloxy, $C_{1-6}$ alkylthio, $C_{1-6}$ alkylamino, $C_{1-6}$ haloalkylamino, $C_{3-8}$ cycloalkylamino, phenylamino, benzylamino, 5- to 10-membered heteroarylamino and 5- to 10-membered heteroarylalkylamino are each optionally substituted with one or more groups independently selected from the group consisting of the followings: $C_{1-6}$ alkyl, halogen, cyano, amido, carbamoyl, mono- or di-$C_{1-6}$ alkyl-substituted carbamoyl, sulfonyl, phenyl, halophenyl and 4- to 6-membered heterocyclyl;

or, $R^3$ and $R^4$ together with the attached carbon atoms form a 5- to 7-membered saturated carbocyclic ring or a 5- to 7-membered saturated heterocyclic ring, and the 5- to 7-membered saturated heterocyclic ring is not a lactam structure, and the 5- to 7-membered carbocyclic ring and the 5- to 7-membered saturated heterocyclic ring are optionally substituted with one or more $R^8$;

$R^5$ at each occurrence is independently selected from the group consisting of hydrogen, deuterium, halogen, cyano, $C_{1-6}$ alkyl, $C_{1-6}$ haloalkyl and $C_{3-8}$ cycloalkyl;

$R^6$ at each occurrence is independently selected from the group consisting of hydrogen, deuterium, cyano, halogen, $C_{1-6}$ alkyl, $C_{1-6}$ haloalkyl, $C_{1-6}$ alkoxyalkyl, $C_{3-8}$ cycloalkyl, 3- to 8-membered heterocyclylalkyl, 3- to 8-membered heterocyclyl, $C_{6-10}$ aryl, 5- to 10-membered heteroaryl, $-NR^aR^b$, $-NR^aC(=O)R^b$, $-OR^c$, $-OC(=O)R^c$, $-C(=O)R^c$, $-C(=O)OR^c$, $-C(=O)NR^aR^b$, $-(CR^aR^b)_mC(=O)NR^aR^b$, $-(CR^c=CR^c)_mC(=O)NR^aR^b$ and $-(C\equiv C)_mC(=O)NR^aR^b$, the $C_{1-6}$ alkyl, $C_{1-6}$ haloalkyl, $C_{1-6}$ alkoxyalkyl, $C_{3-8}$ cycloalkyl, 3- to 8-membered heterocyclylalkyl, 3- to 8-membered heterocyclyl, $C_{6-10}$ aryl, 5- to 10-membered heteroaryl, $-NR^aR^b$, $-OC(=O)R^c$ and $-NR^aC(=O)R^b$ are optionally substituted with one or more $R^7$;

$R^7$ at each occurrence is independently selected from the group consisting of hydrogen, deuterium, halogen, $C_{1-6}$ alkyl, $C_{1-6}$ haloalkyl, hydroxy-$C_{1-6}$ alkyl, $C_{1-6}$ alkoxyalkyl, substituted or unsubstituted carbamoyl, 3- to 8-membered heterocyclylalkyl, 3- to 8-membered heterocyclyl optionally substituted with $C_{1-6}$ alkyl, $-(CR^aR^b)_mS(=O)-R^c$, $-OR^c$, $-NR^aR^b$, $-C(=O)R^c$, $-C(=O)OR^c$ and $-C(=O)NR^aR^b$;

$R^8$ at each occurrence is independently selected from the group consisting of $C_{1-6}$ alkyl, $C_{1-6}$ haloalkyl and $C_{3-6}$ cycloalkyl;

$R^a$ and $R^b$ at each occurrence are each independently selected from the group consisting of hydrogen, $C_{1-6}$ alkyl, hydroxy-$C_{1-6}$ alkyl, $C_{1-6}$ alkoxyalkyl, $C_{1-6}$ alkylaminoalkyl, $C_{3-8}$ cycloalkyl, 3- to 8-membered heterocyclyl and 3- to 8-membered heterocyclylalkyl, or $R^a$ and $R^b$ together with the atom to which they are attached form a 4- to 7-membered ring;

$R^c$ at each occurrence is independently selected from the group consisting of hydrogen, $C_{1-6}$ alkyl, $C_{3-8}$ cycloalkyl, 3- to 8-membered heterocyclylalkyl, 3- to 8-membered heterocyclyl and substituted or unsubstituted carbamoyl;

m is 0, 1 or 2;

n is 1 or 2;

provided that, (1) when $R^4$ is selected from the group consisting of cyano, amino, hydroxyl, $C_{1-6}$ alkyl, $C_{1-6}$ alkoxy and $C_{1-6}$ alkylthio, $R^3$ is not hydrogen;

(2) when $R^3$ and $R^4$ are both hydrogen or $C_{1-6}$ alkyl, or $R^3$ is $C_{1-6}$ alkyl, $R^4$ is hydrogen, or $R^3$ and $R^4$ together with the attached carbon atoms form a 5- to 7-membered saturated carbocyclic ring, and $R^1$ is substituted or unsubstituted pyridyl, $R^2$ is not substituted or unsubstituted thienopyridine nor substituted or unsubstituted quinazolinone.

In some embodiments, $R^2$ is not substituted or unsubstituted thienopyridine nor substituted or unsubstituted quinazolinone.

In some embodiments, $R^1$ is selected from the group consisting of phenyl and 5- to 6-membered heteroaryl, and the phenyl or 5- to 6-membered heteroaryl is optionally substituted with one or more $R^5$;

$R^2$ is selected from the group consisting of phenyl and 5- to 10-membered heteroaryl, and the phenyl or 5- to 10-membered heteroaryl is optionally substituted with one or more $R^6$;

$R^3$ is selected from the group consisting of hydrogen, $C_{1-6}$ alkyl, $C_{1-6}$ haloalkyl, $C_{3-6}$ cycloalkyl, $C_{1-6}$ alkoxy and $C_{1-6}$ alkylamino;

$R^4$ is selected from the group consisting of hydrogen, $C_{1-6}$ alkyl, $C_{3-8}$ cycloalkyl-$C_{1-6}$ alkylamino, 3- to 8-membered heterocyclylamino, hydroxyl-$C_{1-6}$ alkyl, amino-$C_{1-6}$ alkyl, $C_{1-6}$ alkoxy, $C_{1-6}$ alkylthio, hydroxyl, amino, $C_{1-6}$ alkylamino, $C_{1-6}$ haloalkylamino, $C_{3-8}$ cycloalkylamino, phenylamino, benzylamino, 5- to 6-membered heteroarylamino and 5- to 6-membered heteroarylalkylamino, the $C_{1-6}$ alkyl, $C_{3-8}$ cycloalkyl-$C_{1-6}$ alkylamino, 3- to 8-membered heterocyclylamino, hydroxyl-$C_{1-6}$ alkyl, amino-$C_{1-6}$ alkyl, $C_{1-6}$ alkoxy, $C_{1-6}$ alkylthio, $C_{1-6}$ alkylamino, $C_{1-6}$ haloalkylamino, $C_{3-8}$ cycloalkylamino, phenylamino, benzylamino, 5- to 6-membered heteroarylamino, and 5- to 6-membered heteroarylalkylamino are each optionally substituted with one or more groups independently selected from the group consisting of the followings: $C_{1-6}$ alkyl, halogen, cyano, amido, carbamoyl, mono- or di-$C_{1-6}$ alkyl-substituted carbamoyl, sulfonyl, phenyl, halophenyl, $C_{3-6}$ cycloalkyl and 4- to 6-membered heterocyclyl;

or, $R^3$ and $R^4$ together with the attached carbon atoms form a 5- to 7-membered saturated carbocyclic ring or a 5- to 7-membered saturated heterocyclic ring, and the 5- to 7-membered saturated heterocyclic ring is not a lactam structure, and the 5- to 7-membered saturated carbocyclic ring and 5- to 7-membered saturated heterocyclic ring are optionally substituted with one or more $R^8$;

$R^5$ at each occurrence is independently selected from the group consisting of hydrogen, deuterium, halogen, $C_{1-6}$ alkyl, $C_{1-6}$ haloalkyl and $C_{3-8}$ cycloalkyl;

$R^6$ at each occurrence is independently selected from the group consisting of hydrogen, deuterium, cyano, halogen, $C_{1-6}$ alkyl, $C_{1-6}$ haloalkyl, $C_{1-6}$ alkoxyalkyl, $C_{3-8}$ cycloalkyl, 4- to 8-membered heterocyclylalkyl, 4- to 8-membered heterocyclyl, phenyl, 5- to 10-membered heteroaryl, $-NR^aR^b$, $-NR^aC(=O)R^c$, $-OR^c$, $-OC(=O)R^c$, $-C(=O)R^c$, $-C(=O)OR^c$, $-C(=O)NR^aR^b$, $-(CR^aR^b)_mC(=O)NR^aR^b$, $-(CR^c=CR^c)_mC(=O)NR^aR^b$, $-(C\equiv C)_mC(=O)NR^aR^b$, the $C_{1-6}$ alkyl, $C_{1-6}$ haloalkyl, $C_{1-6}$ alkoxyalkyl, $C_{3-8}$ cycloalkyl, 4- to 8-membered heterocyclylalkyl, 4- to 8-membered heterocyclyl, phenyl, 5- to 10-membered heteroaryl, $-NR^aR^b$, $-OC(=O)R^c$ and $-NR^aC(=O)R^b-$ are optionally substituted with one or more $R^7$;

$R^7$ at each occurrence is independently selected from the group consisting of hydrogen, deuterium, halogen, $C_{1-6}$ alkyl, $C_{1-6}$ haloalkyl, hydroxyl-$C_{1-6}$ alkyl, $C_{1-6}$ alkoxyalkyl, substituted or unsubstituted carbamoyl, 4- to 8-membered heterocyclylalkyl, 3- to 8-membered heterocyclyl optionally substituted with $C_{1-6}$ alkyl, $-(CR^aR^b)_mS(=O)_n-R^c$, $-OR^c$, $-NR^aR^b$, $-C(=O)R^c$, $-C(=O)OR^c$ and $-C(=O)NR^aR^b$;

$R^8$ at each occurrence is independently selected from the group consisting of $C_{1-6}$ alkyl, $C_{1-6}$ haloalkyl and $C_{3-6}$ cycloalkyl;

$R^a$ and $R^b$ at each occurrence are each independently selected from the group consisting of hydrogen, $C_{1-6}$ alkyl, hydroxyl-$C_{1-6}$ alkyl, $C_{1-6}$ alkoxyalkyl, $C_{1-6}$ alkylaminoalkyl, $C_{3-8}$ cycloalkyl, 4- to 8-membered heterocyclyl and 4- to 8-membered heterocyclylalkyl, or $R^a$ and $R^b$ together with the atom to which they are attached form a 4- to 7-membered ring;

$R^c$ at each occurrence is independently selected from the group consisting of hydrogen, $C_{1-6}$ alkyl, $C_{3-8}$ cycloalkyl, 4- to 8-membered heterocyclylalkyl, 4- to 8-membered heterocyclyl, and substituted or unsubstituted carbamoyl;

m is 0, 1 or 2;

n is 1 or 2;

provided that, (1) when $R^4$ is selected from the group consisting of cyano, amino, hydroxyl, $C_{1-6}$ alkyl, $C_{1-6}$ alkoxy and $C_{1-6}$ alkylthio, $R^3$ is not hydrogen;

(2) when $R^3$ and $R^4$ are both hydrogen or $C_{1-6}$ alkyl, or $R^3$ is $C_{1-6}$ alkyl, $R^4$ is hydrogen, or $R^3$ and $R^4$ together with the attached carbon atoms form a 5- to 7-membered saturated carbocyclic ring, and $R^1$ is a substituted or unsubstituted pyridyl, $R^2$ is not substituted or unsubstituted thienopyridine nor substituted or unsubstituted quinazolinone.

In some embodiments, the compound has the structure of Formula I-1,

I-1

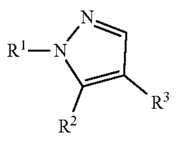

wherein $R^1$, $R^2$ and $R^3$ are as defined herein. In some preferred embodiments, $R^3$ is hydrogen or $C_{1-6}$ alkyl.

In some embodiments, the compound has the structure of Formula I-2,

I-2

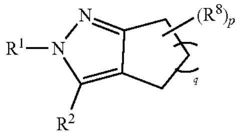

wherein $R^1$, $R^2$ and $R^8$ are as defined in any of the items herein;

q is 1, 2 or 3; preferably, q is 1 or 2;

p is 0, 1, 2 or 3; preferably, p is 0.

In some embodiments, the compound has the structure of Formula I-3,

I-3

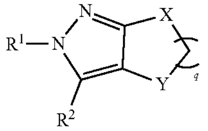

wherein $R^1$ and $R^2$ are as defined in any of the items herein;

X is selected from the group consisting of —$NR^9$—, —O— and —S—;

Y is selected from the group consisting of —$CR^{11}R^{12}$—, —O—, —S— and —$NR^9$—;

$R^9$, $R^{11}$ and $R^{12}$ at each occurrence is independently selected from the group consisting of hydrogen, $C_{1-6}$ alkyl, $C_{1-6}$ haloalkyl, $C_{3-8}$ cycloalkyl, or $R^{11}$ and $R^{12}$ together with the carbon atom to which they attached form a 3- to 7-membered ring;

q is 1, 2 or 3.

In some embodiments, $R^1$ and $R^2$ in the Formula I-3 are as defined in any of the items herein;

X is selected from the group consisting of —NH—, —O— and —S—; preferably, X is —NH—;

Y is selected from the group consisting of —$CH_2$—, —O—, —S— and —NH—; preferably, Y is selected from the group consisting of —$CH_2$—;

q is 1, 2 or 3; preferably, q is 1 or 2.

In some embodiments, the compound has the structure of Formula I-4,

I-4

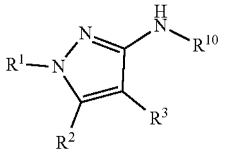

wherein $R^1$, $R^2$ and $R^3$ are as defined in any of the items herein;

$R^{10}$ is selected from the group consisting of $C_{1-6}$ alkyl, $C_{1-6}$ haloalkyl, $C_{3-8}$ cycloalkyl, $C_{3-8}$ cycloalkyl-$C_{1-6}$ alkyl, 3- to 8-membered heterocyclyl, benzyl, 5- to 6-membered heteroarylalkyl, phenyl and 5- to 6-membered heteroaryl, the $C_{1-6}$ alkyl, $C_{1-6}$ haloalkyl, $C_{3-8}$ cycloalkyl, $C_{3-8}$ cycloalkyl-$C_{1-6}$ alkyl, 3- to 8-membered heterocyclyl, benzyl, 5- to 6-membered heteroarylalkyl, phenyl and 5- to 6-membered heteroaryl are each optionally substituted with one or more groups independently selected from the group consisting of the followings: $C_{1-6}$ alkyl, halogen, cyano, amido, carbamoyl, mono- or di-$C_{1-6}$ alkyl-substituted carbamoyl, sulfonyl, phenyl, halophenyl and 4- to 6-membered heterocyclyl.

In some preferred embodiments, $R^{10}$ is selected from the group consisting of $C_{1-6}$ alkyl, $C_{3-6}$ cycloalkyl, $C_{3-6}$ cycloalkyl-$C_{1-4}$ alkyl, 3- to 6-membered heterocyclyl, benzyl, 5- to 6-membered heteroarylalkyl, phenyl and 5- to 6-membered heteroaryl, the $C_{1-6}$ alkyl, $C_{3-6}$ cycloalkyl, $C_{3-6}$ cycloalkyl-$C_{1-4}$ alkyl, 3- to 6-membered heterocyclyl, benzyl, 5- to 6-membered heteroarylalkyl, phenyl and 5- to 6-membered heteroaryl are each optionally substituted with one or more groups independently selected from the group consisting of the followings: $C_{1-6}$ alkyl, halogen, cyano, amido, carbamoyl, mono- or di-$C_{1-4}$ alkyl-substituted carbamoyl and sulfonyl.

In some preferred embodiments, $R^{10}$ is selected from the group consisting of $C_{1-6}$ alkyl, $C_{3-6}$ cycloalkyl, benzyl, pyridyl and pyrazolyl, the $C_{1-6}$ alkyl, $C_{3-6}$ cycloalkyl, benzyl, pyridyl and pyrazolyl are each optionally substituted with one or more groups independently selected from the group consisting of the followings: methyl, fluoro, chloro, bromo, and cyano.

In some preferred embodiments, $R^{10}$ is selected from the group consisting of $C_{1-6}$ alkyl, $C_{3-6}$ cycloalkyl, benzyl, pyridylmethyl and pyrazolylmethyl, the $C_{1-6}$ alkyl, $C_{3-6}$ cycloalkyl, benzyl, pyridylmethyl and pyrazolylmethyl are each optionally substituted with one or more groups independently selected from the group consisting of the followings: methyl, fluoro, chloro, bromo, and cyano.

The compound of any items of the first aspect herein, wherein, $R^1$ is selected from the group consisting of 5- to 10-membered heteroaryl, the 5- to 10-membered heteroaryl is optionally substituted with one or more $R^5$;

$R^5$ at each occurrence is independently selected from the group consisting of $C_{1-6}$ alkyl.

In some embodiments, $R^1$ is selected from the group consisting of the following moieties:

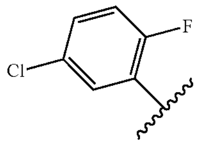
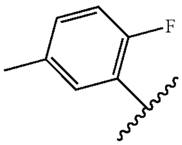
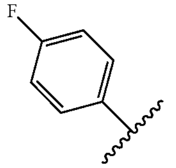
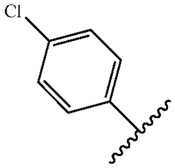
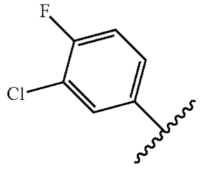
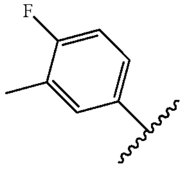

-continued

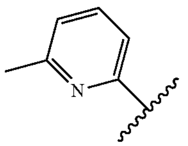

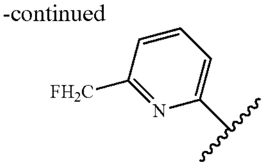

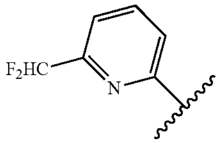

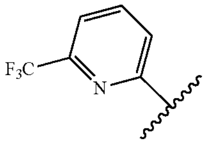

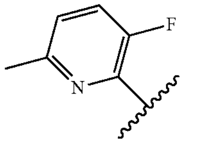

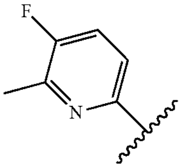

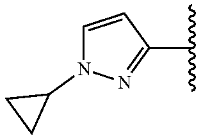

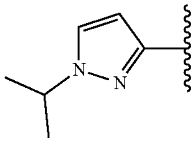

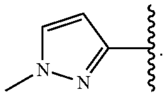.

In some preferred embodiments, $R^1$ is

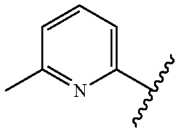.

The compound according to any items of the first aspect herein, wherein $R^2$ is selected from the group consisting of phenyl and 5- to 10-membered heteroaryl, the phenyl or 5- to 10-membered heteroaryl is optionally substituted with one or more $R^6$;

$R^6$ at each occurrence is independently selected from the group consisting of hydrogen, deuterium and —C(═O)$NR^aR^b$;

$R^a$ and $R^b$ at each occurrence are each independently selected from the group consisting of hydrogen, $C_{1-6}$ alkyl and hydroxy-$C_{1-6}$ alkyl.

In some preferred embodiments, $R^2$ is selected from

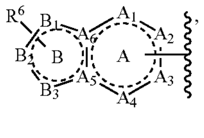, wherein, ring A is a benzene ring or a 6-membered heteroaromatic ring;

ring B is a 5-membered heteroaromatic ring;

$A_1$-$A_6$ and $B_1$-$B_3$ is selected from the group consisting of C, CH, N, NH, O and S; preferably, $A_1$-$A_6$ and $B_1$-$B_3$ are selected from the group consisting of C, CH, N, O and S;

$R^6$ is selected from the group consisting of hydrogen, deuterium, cyano, halogen, $C_{1-6}$ alkyl, $C_{1-6}$ haloalkyl, $C_{1-6}$ alkoxyalkyl, $C_{3-8}$ cycloalkyl, 3- to 8-membered heterocyclylalkyl, 3- to 8-membered heterocyclyl, $C_{6-10}$ aryl, 5- to 10-membered heteroaryl, —$NR^aR^b$, —$NR^aC$(═O)$R^b$, —$OR^c$, —OC(═O)$R^c$, —C(═O)$R^c$, —C(═O)$OR^c$, —C(═O)$NR^aR^b$, —$(CR^aR^b)_m$C(═O)$NR^aR^b$, —$(CR^c$═$CR^c)_m$C(═O)$NR^aR^b$ and —$(C≡C)_m$C(═O)$NR^aR^b$, the $C_{1-6}$ alkyl, $C_{1-6}$ haloalkyl, $C_{1-6}$ alkoxyalkyl, $C_{3-8}$ cycloalkyl, 3- to 8-membered heterocyclylalkyl, 3- to 8-membered heterocyclyl, $C_{6-10}$ aryl, 5- to 10-membered heteroaryl, —$NR^aR^b$, —OC(═O)$R^c$ and —$NR^aC$(═O)$R^b$ is optionally substituted with one or more $R^7$;

$R^7$ at each occurrence is independently selected from the group consisting of hydrogen, deuterium, halogen, $C_{1-6}$ alkyl, $C_{1-6}$ haloalkyl, hydroxy-$C_{1-6}$ alkyl, $C_{1-6}$ alkoxyalkyl, substituted or unsubstituted carbamoyl, 3- to 8-membered heterocyclylalkyl, 3- to 8-membered heterocyclyl optionally substituted with $C_{1-6}$ alkyl, —$(CR^aR^b)_m$S(═O)$_n$—$R^c$, —$OR^c$, —$NR^aR^b$, —C(═O)$R^c$, —C(═O)$OR^c$ and —C(═O)$NR^aR^b$;

$R^a$ and $R^b$ at each occurrence is independently selected from the group consisting of hydrogen, $C_{1-6}$ alkyl, hydroxy-$C_{1-6}$ alkyl, $C_{1-6}$ alkoxyalkyl, $C_{1-6}$ alkylaminoalkyl, $C_{3-8}$ cycloalkyl, 3- to 8-membered heterocyclyl and 3- to 8-membered heterocyclylalkyl, or $R^a$ and $R^b$ together with the atom to which they are attached form a 4- to 7-membered ring;

$R^c$ at each occurrence is independently selected from the group consisting of hydrogen, $C_{1-6}$ alkyl, $C_{3-8}$ cycloalkyl, 3- to 8-membered heterocyclylalkyl, 3- to 8-membered heterocyclyl and substituted or unsubstituted carbamoyl;

m is 0, 1 or 2;

n is 1 or 2.

In some preferred embodiments, $R^2$ is selected from

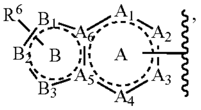, wherein, ring A is a benzene ring or a 6-membered heteroaromatic ring;

ring B is a 5-membered heteroaromatic ring;

$A_1$-$A_6$ and $B_1$-$B_3$ is selected from the group consisting of C, CH, N, NH, O and S; preferably, $A_1$-$A_6$ and $B_1$-$B_3$ is selected from the group consisting of C, CH, N, O and S;

$R^6$ at each occurrence is independently selected from the group consisting of hydrogen, deuterium and —C(═O)$NR^aR^b$;

$R^a$ and $R^b$ at each occurrence is independently selected from the group consisting of hydrogen, $C_{1-6}$ alkyl and hydroxy-$C_{1-6}$ alkyl.

In some preferred embodiments, $R^2$ is selected from the group consisting of the following moieties:

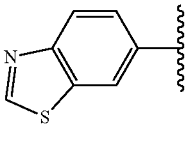

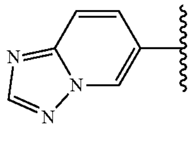

-continued
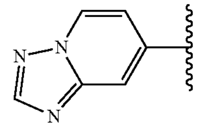
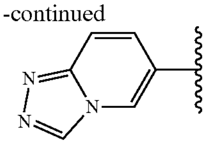
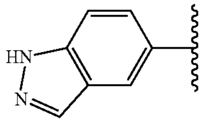
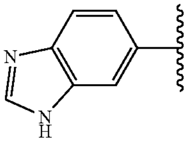
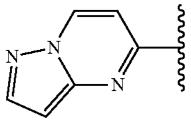
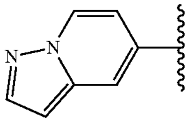
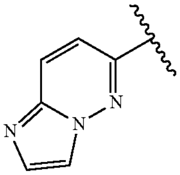
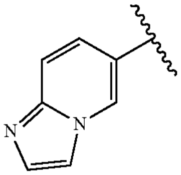
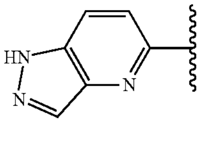
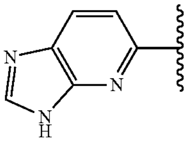
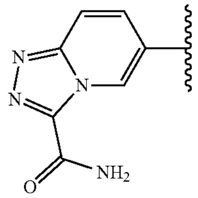
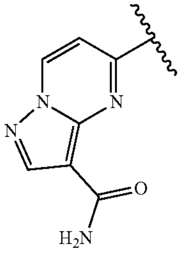
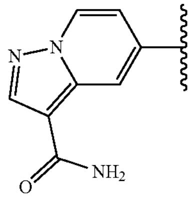
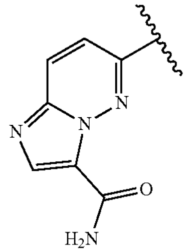
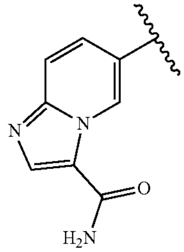
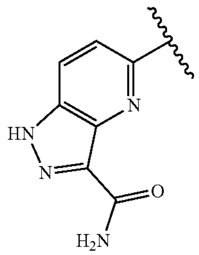
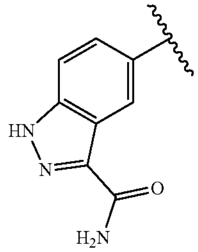
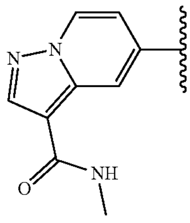
-continued
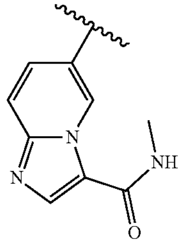
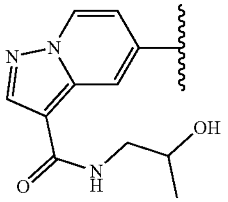
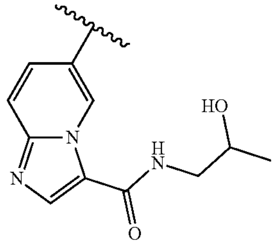
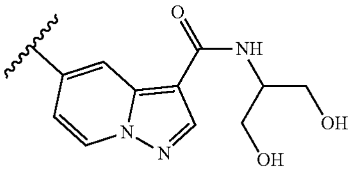
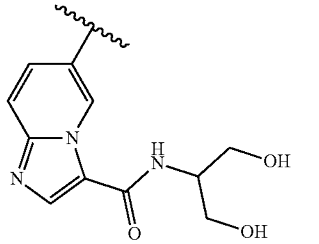
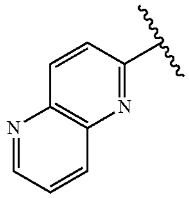
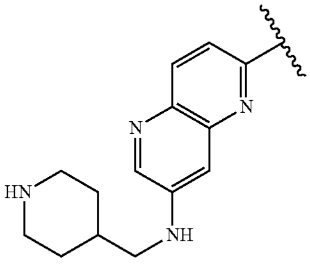
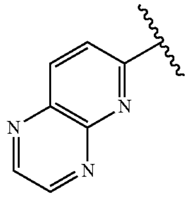
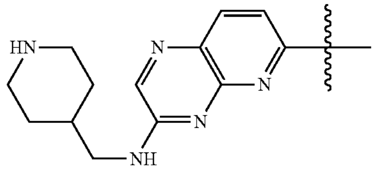
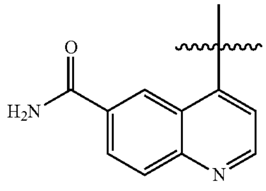

-continued
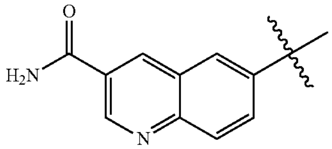
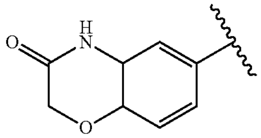
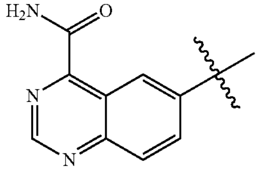
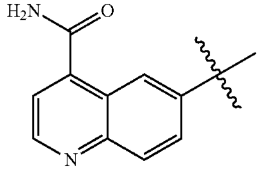
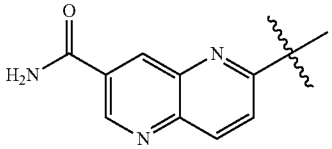
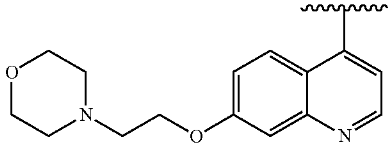
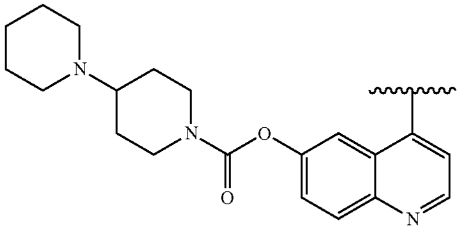
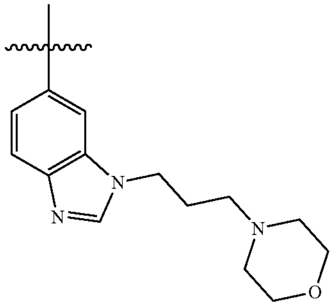
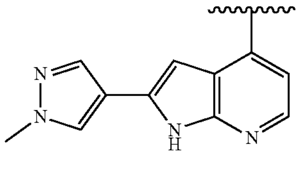
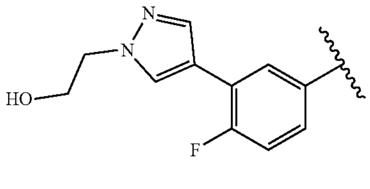
-continued
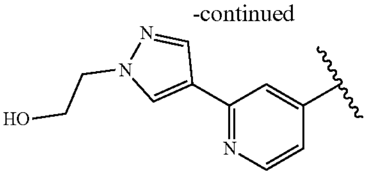
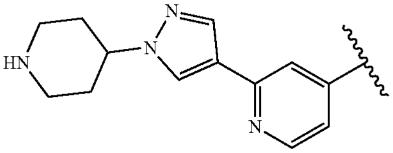
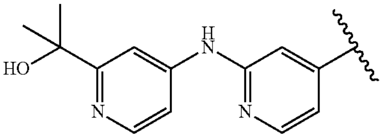
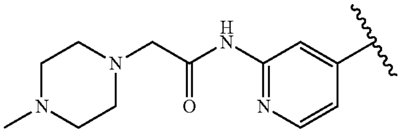
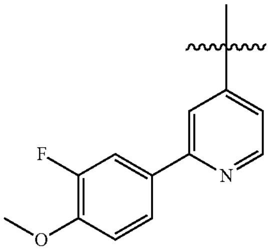
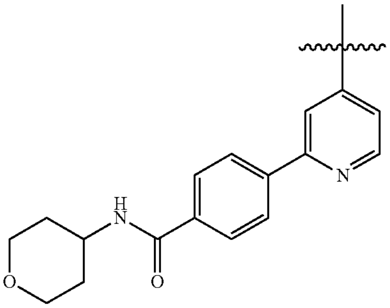
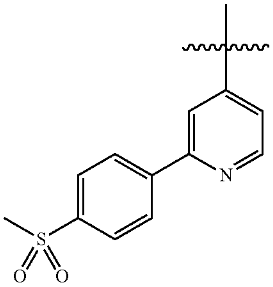
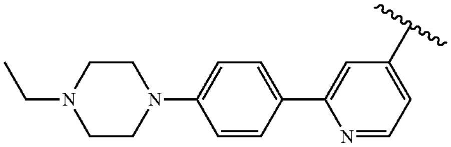
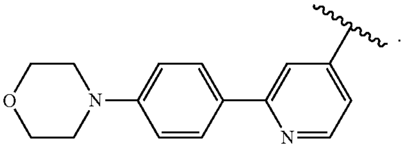

In some preferred embodiments, $R^2$ is selected from the group consisting of:

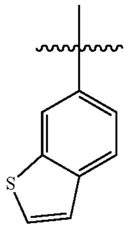
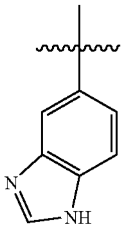
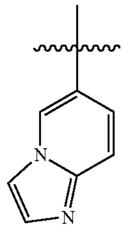
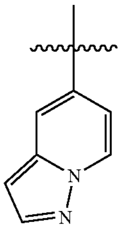
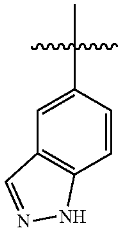
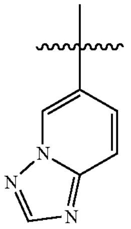
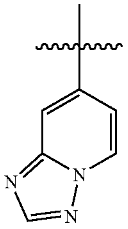
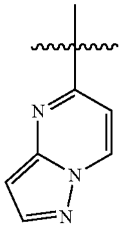
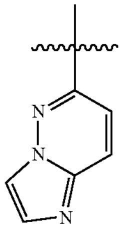
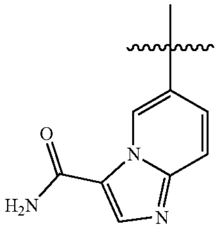
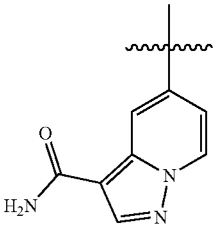
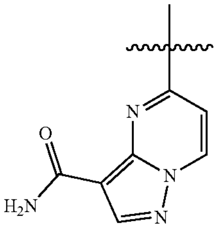
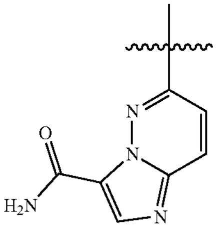
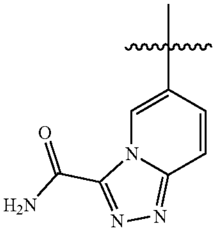
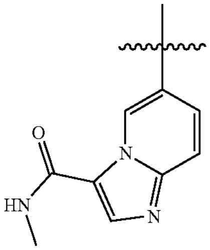
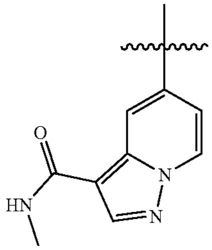
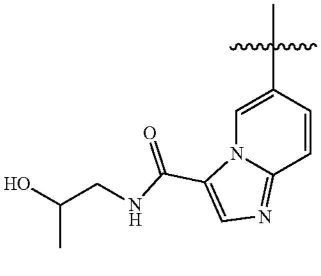

-continued

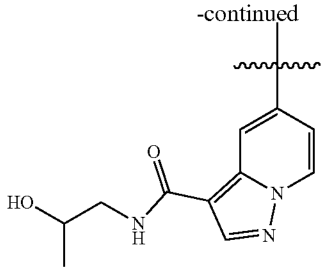
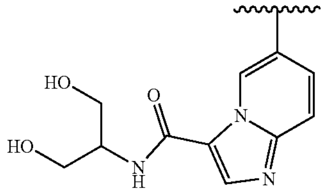
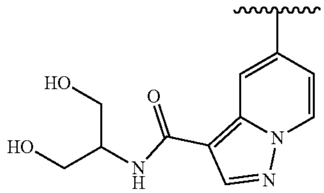
.

In some preferred embodiments, $R^2$ is selected from the group consisting of

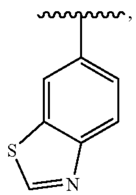
,
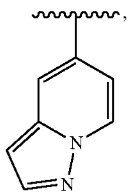
,
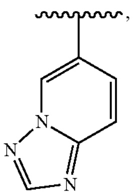
,
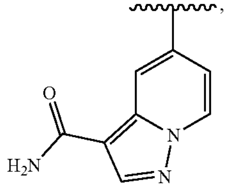
,
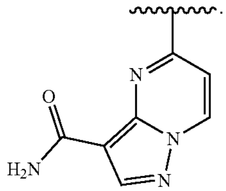
.

The compound of any item of the first aspect herein, wherein, $R^3$ is selected from the group consisting of hydrogen and $C_{1-6}$ alkyl.

In some preferred embodiments, $R^3$ is selected from the group consisting of hydrogen, methyl, ethyl, propyl and isopropyl.

In some preferred embodiments, $R^3$ is selected from the group consisting of hydrogen and isopropyl.

In some preferred embodiments, $R^3$ is hydrogen.

In some preferred embodiments, $R^3$ is isopropyl.

The compound of any item of the first aspect herein, wherein, $R^4$ is selected from the group consisting of hydrogen, $C_{1-6}$ alkylamino, $C_{3-8}$ cycloalkylamino, benzylamino and 5- to 10-membered heteroarylalkylamino, the $C_{1-6}$ alkylamino, $C_{3-8}$ cycloalkylamino, benzylamino and 5- to 10-membered heteroarylalkylamino are each optionally substituted with one or more groups independently selected from the group consisting of the followings: $C_{1-6}$ alkyl, halogen and cyano.

In some embodiments, $R^4$ is selected from the group consisting of hydrogen, $C_{1-6}$ alkylamino, $C_{3-6}$ cycloalkylamino, benzylamino and 5- to 6-membered heteroaryl-$C_{1-4}$ alkylamino, and the $C_{1-6}$ alkylamino, $C_{3-6}$ cycloalkylamino, benzylamino and 5- to 6-membered heteroaryl-$C_{1-4}$ alkylamino are each optionally substituted with one or more groups selected from the group consisting of the followings: $C_{1-6}$ alkyl, halogen and cyano.

In some embodiments, $R^4$ is selected from the group consisting of hydrogen and —$NHR^{10}$, wherein, $R^{10}$ is selected from the group consisting of $C_{1-6}$ alkyl, $C_{3-6}$ cycloalkyl, benzyl and 5- to 6-membered heteroaryl-$C_{1-4}$ alkyl, and the $C_{1-6}$ alkyl, $C_{3-6}$ cycloalkyl, benzyl and 5- to 6-membered heteroaryl-$C_{1-4}$ alkyl are each optionally substituted with one or more groups independently selected from the group consisting of the followings: $C_{1-6}$ alkyl, fluoro, chloro, bromo, and cyano; preferably, $R^{10}$ is selected from the group consisting of $C_{1-6}$ alkyl, $C_{3-6}$ cycloalkyl, benzyl, —$C_{1-3}$ alkyl-pyridyl and —$C_{1-3}$ alkyl-pyrazolyl, and the $C_{1-6}$ alkyl, $C_{3-6}$ cycloalkyl, benzyl, —$C_{1-3}$ alkyl-pyridyl and —$C_{1-3}$ alkyl-pyrazolyl are each optionally substituted with one or more groups independently selected from the group consisting of the followings: methyl, fluoro, chloro, bromo, and cyano.

In some embodiments, $R^4$ is selected from the group consisting of hydrogen and —$NHR^{10}$, wherein, $R^{10}$ is selected from the group consisting of $C_{1-6}$ alkyl, benzyl and pyridylmethyl, and the benzyl and pyridylmethyl are each optionally substituted with one or more groups independently selected from the group consisting of the followings: $C_{1-6}$ alkyl, fluoro, chloro, bromo, and cyano; preferably, $R^{10}$ is selected from the group consisting of $C_{1-6}$ alkyl, benzyl and pyridylmethyl, and the benzyl and pyridylmethyl are each optionally substituted with one or more groups independently selected from the group consisting of the followings: methyl and fluoro.

In some embodiments, $R^4$ is selected from the group consisting of hydrogen and —$NHR^{10}$; $R^{10}$ is selected from the group consisting of benzyl, pyridylmethyl and pyrazolylmethyl, and the benzyl, pyridylmethyl and pyrazolylmethyl are each optionally substituted with one or more groups independently selected from the group consisting of the followings: $C_{1-2}$ alkyl, fluoro, chloro, bromo, and cyano; $R^{10}$ is selected from the group consisting of benzyl and pyridylmethyl, the benzyl and pyridylmethyl are each optionally substituted with one or more groups independently selected from the group consisting of the followings: methyl and fluoro;

preferably, $R^{10}$ is selected from the group consisting of:

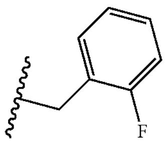
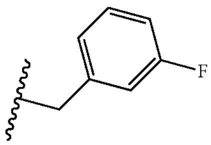
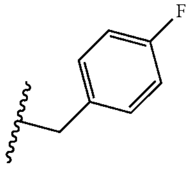
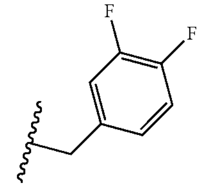
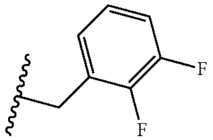
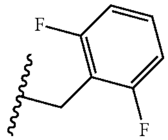

-continued

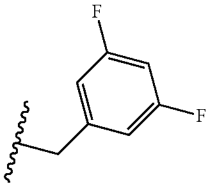
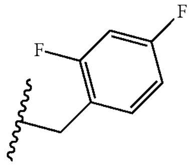
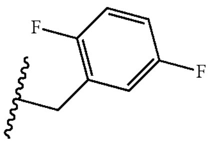
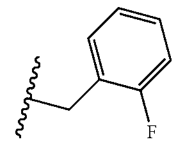
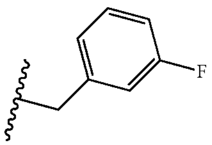
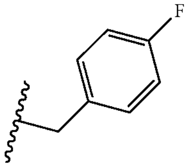
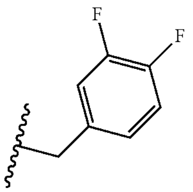
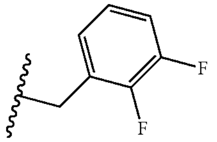
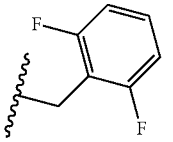
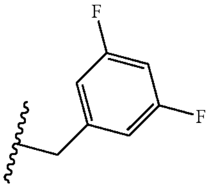
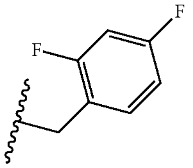
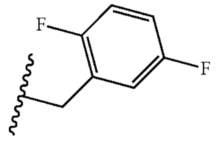
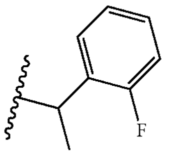
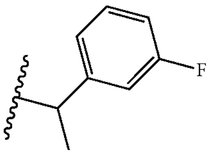
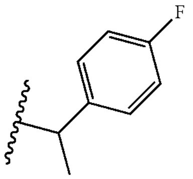
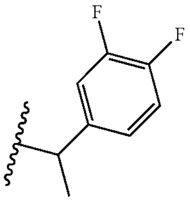
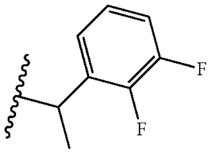
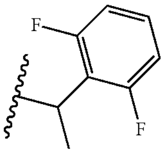

-continued
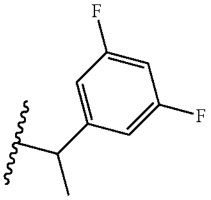
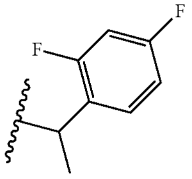
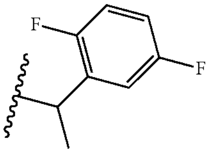
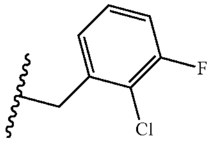
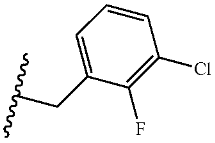
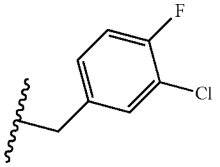
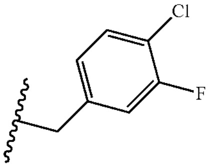
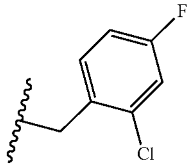
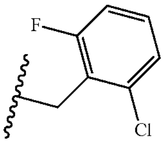
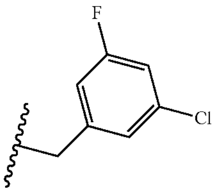
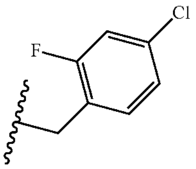
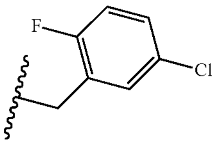
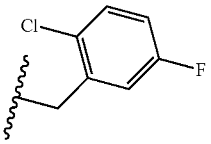
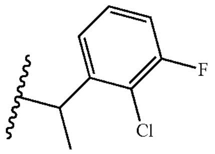
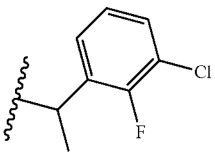
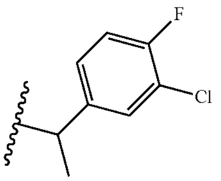
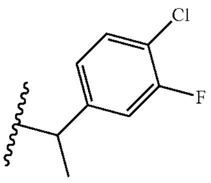
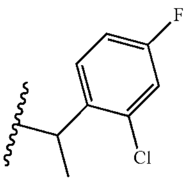
-continued
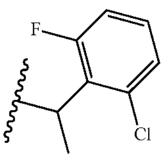
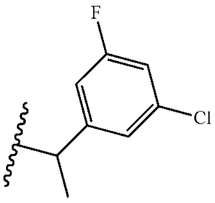
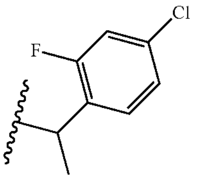
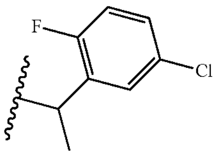
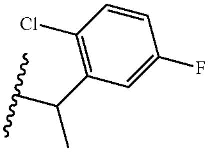
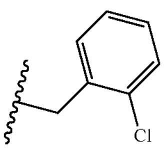
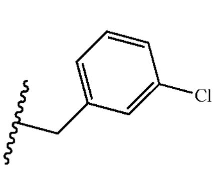
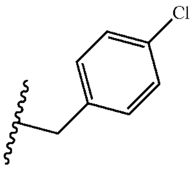
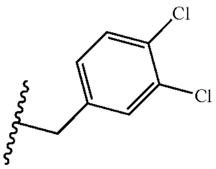
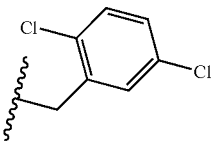
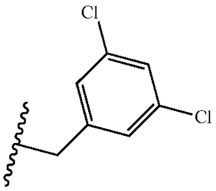
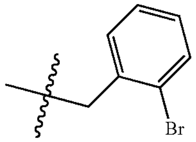
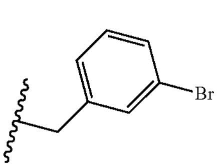
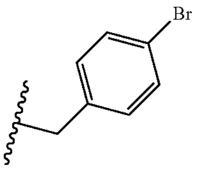
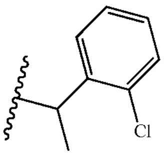
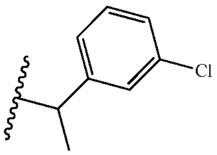
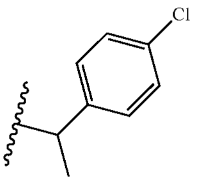
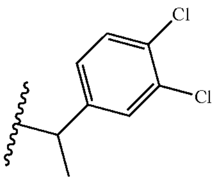

-continued

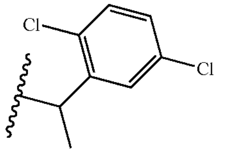
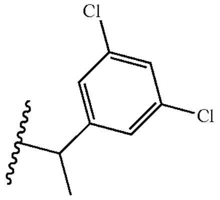
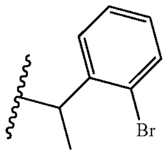
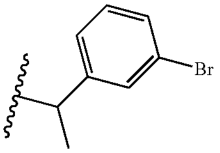
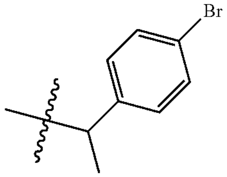
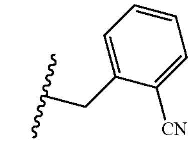
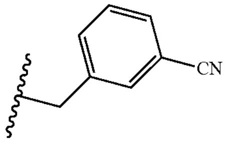
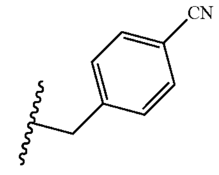
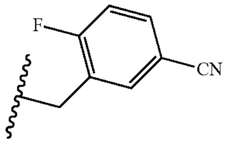
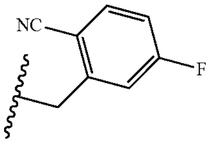
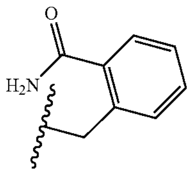
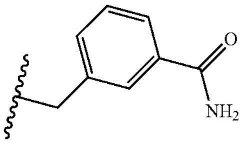
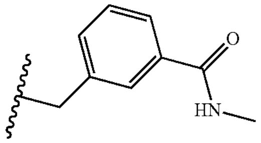
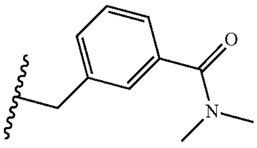
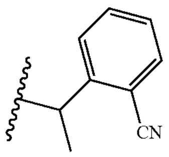
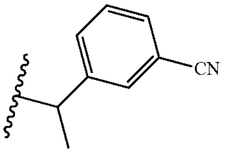
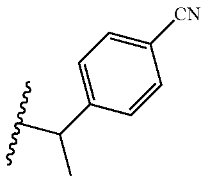
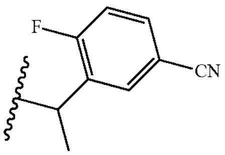
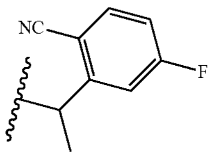
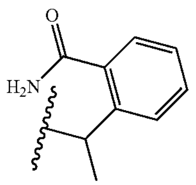

-continued

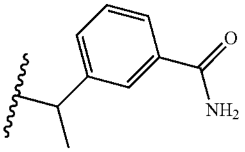
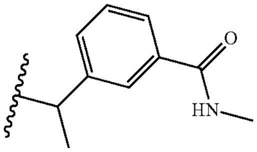
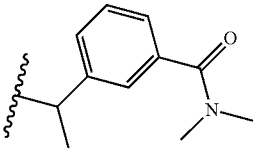
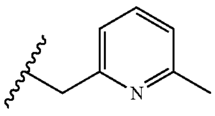
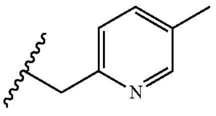
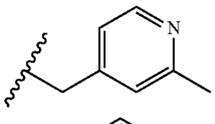
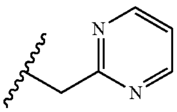
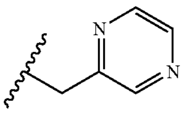
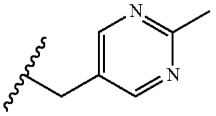
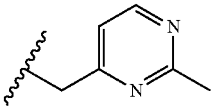
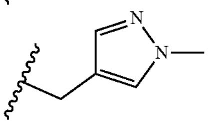
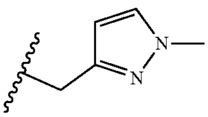
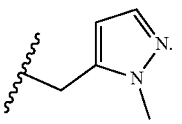

In some embodiments, $R^4$ is selected from the group consisting of hydrogen and —$NHR^{10}$;

$R^{10}$ is selected from the group consisting of:

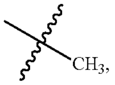
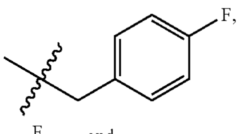
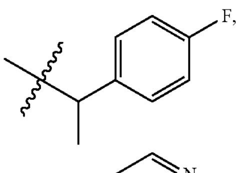
and
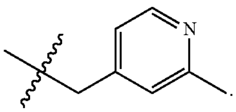

In some embodiments, $R^3$ and $R^4$ together with the attached carbon atoms form a 5- to 6-membered saturated carbocyclic ring or 5- to 6-membered saturated heterocyclic ring, and the 5- to 6-membered saturated heterocyclic ring is not a lactam structure.

In some preferred embodiments, $R^3$ and $R^4$ together with the attached carbon atoms form a cyclopentyl ring, cyclohexyl ring, pyrrolidine ring or piperidine ring.

The compound of any item of the first aspect herein, wherein, $R^1$ is selected from the group consisting of 5- to 10-membered heteroaryl, the 5- to 10-membered heteroaryl is optionally substituted with one or more $R^5$;

$R^2$ is selected from the group consisting of 5- to 10-membered heteroaryl, the 5- to 10-membered heteroaryl is optionally substituted with one or more $R^6$;

$R^3$ is selected from the group consisting of hydrogen and $C_{1-6}$ alkyl;

$R^4$ is selected from the group consisting of hydrogen, $C_{1-6}$ alkylamino, $C_{3-8}$ cycloalkylamino, benzylamino and 5- to 10-membered heteroarylalkylamino, and the $C_{1-6}$ alkylamino, $C_{3-8}$ cycloalkylamino, benzylamino and 5- to 10-membered heteroarylalkylamino are each optionally substituted with one or more groups independently selected from the group consisting of the followings: $C_{1-6}$ alkyl, halogen and cyano;

or, $R^3$ and $R^4$ together with the attached carbon atoms form a 5- to 7-membered saturated carbocyclic ring or a 5- to 7-membered saturated heterocyclic ring, and the 5- to 7-membered saturated heterocyclic ring is not a lactam structure, the 5- to 7-membered carbocyclic ring and the 5- to 7-membered saturated heterocyclic ring are optionally substituted with one or more $R^8$;

$R^5$ at each occurrence is independently selected from the group consisting of $C_{1-6}$ alkyl;

$R^6$ at each occurrence is independently selected from the group consisting of hydrogen, deuterium and —C(═O)$NR^aR^b$;

$R^a$ and $R^b$ at each occurrence is independently selected from the group consisting of hydrogen, $C_{1-6}$ alkyl and hydroxy-$C_{1-6}$ alkyl;

$R^8$ at each occurrence is independently selected from the group consisting of $C_{1-6}$ alkyl, $C_{1-6}$ haloalkyl and $C_{3-6}$ cycloalkyl;

provided that, when $R^3$ and $R^4$ are both hydrogen, or $R^3$ is $C_{1-6}$ alkyl, $R^4$ is hydrogen, or $R^3$ and $R^4$ together with the attached carbon atoms form a 5- to 7-membered saturated carbocyclic ring, and $R^1$ is a substituted or unsubstituted pyridyl, $R^2$ is not substituted or unsubstituted thienopyridine nor substituted or unsubstituted quinazolinone.

The compound of any item of the first aspect herein, wherein, $R^1$ is

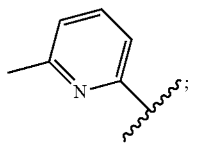 [SMILES: *c1cccc(C)n1]

$R^2$ is selected from

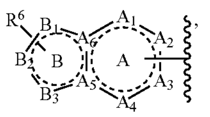

wherein, ring A is benzene ring or 6-membered heteroaromatic ring, ring B is 5-membered heteroaromatic ring, $A_1$-$A_6$ and $B_1$-$B_3$ is selected from the group consisting of C, CH, N, NH, O and S;

$R^3$ is selected from the group consisting of hydrogen and $C_{1-6}$ alkyl;

$R^4$ is selected from the group consisting of hydrogen, $C_{1-6}$ alkylamino, $C_{3-6}$ cycloalkylamino, benzylamino and 5- to 6-membered heteroaryl-$C_{1-4}$ alkylamino, and the $C_{1-6}$ alkylamino, $C_{3-8}$ cycloalkylamino, benzylamino and 5- to 6-membered heteroarylalkylamino are each optionally substituted with one or more groups independently selected from the group consisting of the followings: $C_{1-6}$ alkyl, halogen and cyano;

or, $R^3$ and $R^4$ together with the attached carbon atoms form a 5- to 6-membered saturated carbocyclic ring or a 5- to 6-membered saturated heterocyclic ring, and the 5- to 6-membered saturated heterocyclic ring is not a lactam structure;

$R^6$ at each occurrence is independently selected from the group consisting of hydrogen, deuterium and —C(═O)$NR^aR^b$;

$R^a$ and $R^b$ at each occurrence is independently selected from the group consisting of hydrogen, $C_{1-6}$ alkyl and hydroxy-$C_{1-6}$ alkyl;

provided that, when $R^3$ and $R^4$ are both hydrogen, or $R^3$ is $C_{1-6}$ alkyl, $R^4$ is hydrogen, or $R^3$ and $R^4$ together with the attached carbon atoms form a 5- to 6-membered saturated carbocyclic ring, and $R^1$ is a substituted or unsubstituted pyridyl, $R^2$ is not substituted or unsubstituted thienopyridine nor substituted or unsubstituted quinazolinone.

The compound of any item of the first aspect herein, wherein, $R^1$ is

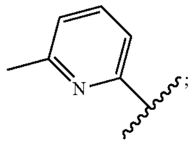 [SMILES: *c1cccc(C)n1]

$R^2$ is selected from the group consisting of

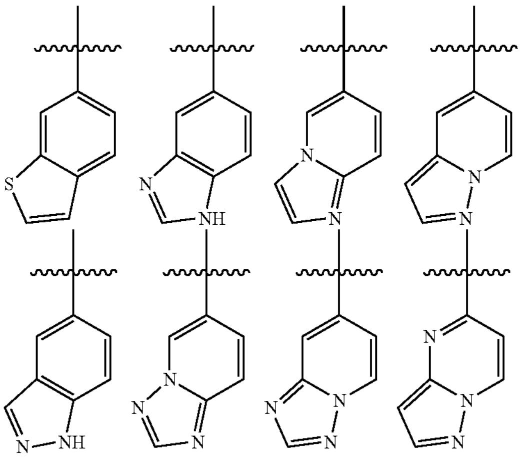

-continued

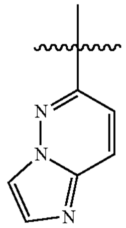
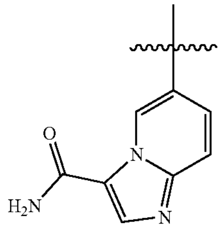
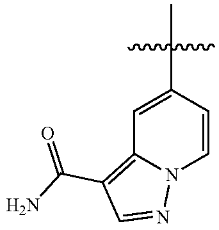
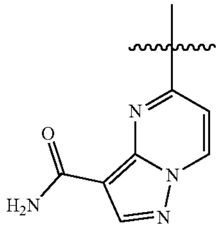
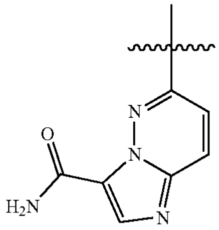
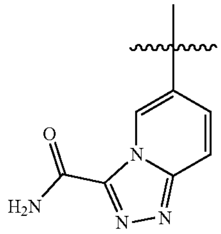
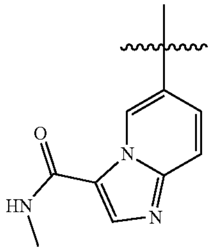
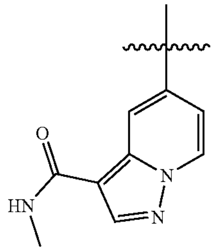
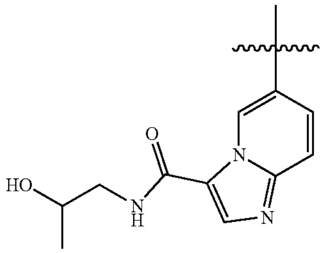
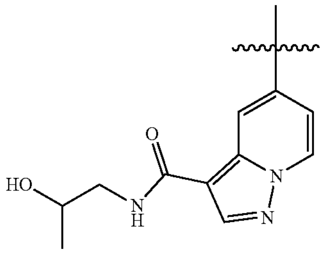
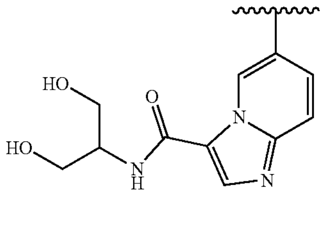

-continued

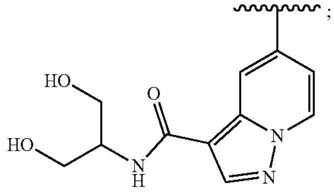
;

$R^3$ is selected from the group consisting of hydrogen and $C_{1-6}$ alkyl;

$R^4$ is selected from the group consisting of hydrogen and —$NHR^{10}$, wherein, $R^{10}$ is selected from the group consisting of $C_{1-6}$ alkyl, $C_{3-6}$ cycloalkyl, benzyl and 5- to 6-membered heteroaryl-$C_{1-4}$ alkyl, and the $C_{1-6}$ alkyl, $C_{3-6}$ cycloalkyl, benzyl and 5- to 6-membered heteroaryl-$C_{1-4}$ alkyl are each optionally substituted with one or more groups independently selected from the group consisting of the followings: $C_{1-6}$ alkyl, fluoro, chloro, bromo, and cyano; preferably, $R^{10}$ is selected from the group consisting of $C_{1-6}$ alkyl, $C_{3-6}$ cycloalkyl, benzyl, —$C_{1-3}$ alkyl-pyridyl and —$C_{1-3}$ alkyl-pyrazolyl, and the $C_{1-6}$ alkyl, $C_{3-6}$ cycloalkyl, benzyl, —$C_{1-3}$ alkyl-pyridyl and —$C_{1-3}$ alkyl-pyrazolyl are each optionally substituted with one or more groups independently selected from the group consisting of the followings: methyl, fluoro, chloro, bromo, and cyano;

or, $R^3$ and $R^4$ together with the attached carbon atoms form a cyclopentyl ring, cyclohexyl ring, pyrrolidine ring or piperidine ring.

The compound of any item of the first aspect herein, wherein, $R^1$ is

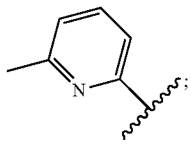 [SMILES: *c1cccc(C)n1]
;

$R^2$ is selected from the group consisting of

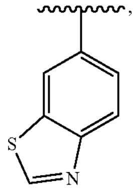
,
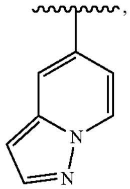
,
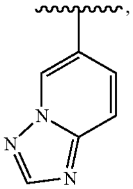
,
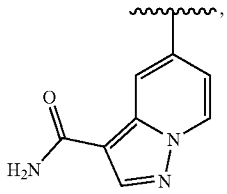
,
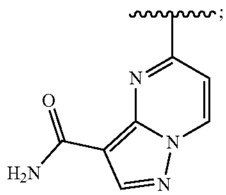
;

$R^3$ is hydrogen;

$R^4$ is selected from the group consisting of hydrogen and —$NHR^{10}$, wherein, $R^{10}$ is selected from the group consisting of $C_{1-6}$ alkyl, benzyl and pyridylmethyl, the benzyl and pyridylmethyl are each optionally substituted with one or more groups independently selected from the group consisting of the followings: $C_{1-6}$ alkyl, fluoro, chloro, bromo, and cyano; preferably, $R^{10}$ is selected from the group consisting of $C_{1-6}$ alkyl, benzyl and pyridylmethyl, the benzyl and pyridylmethyl are each optionally substituted with one or more groups independently selected from the group consisting of the followings: methyl and fluoro;

or, $R^3$ and $R^4$ together with the attached carbon atoms form a cyclopentyl ring.

The compound of any item of the first aspect herein, wherein, $R^1$ is selected from the group consisting of the following moieties:

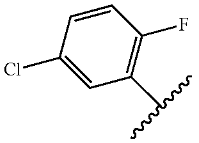
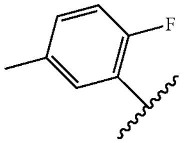
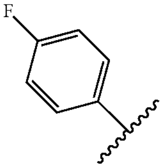
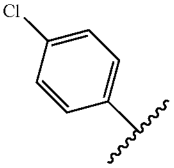
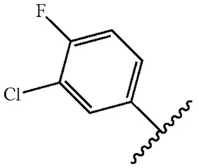
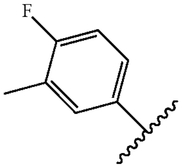
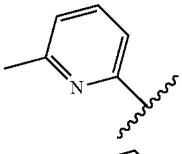
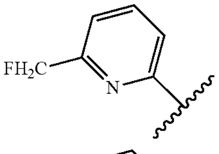
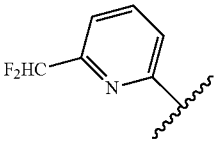
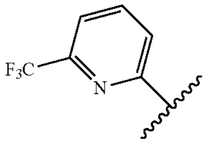
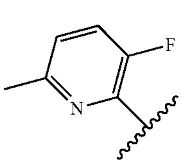
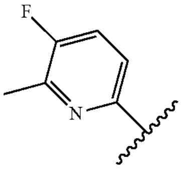
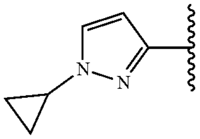
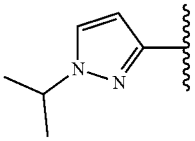
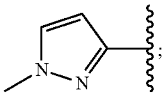;

$R^2$ is selected from the group consisting of following structures:

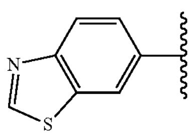
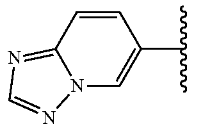
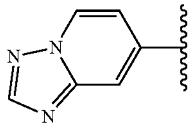
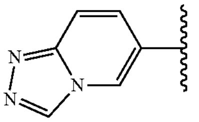
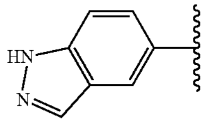
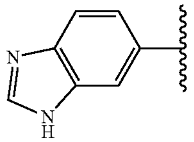
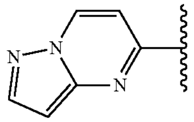
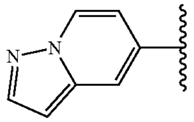
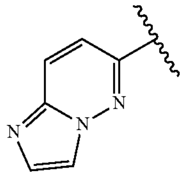
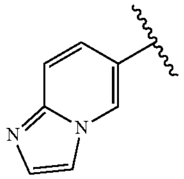
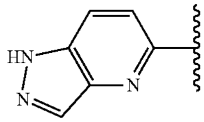
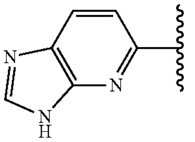
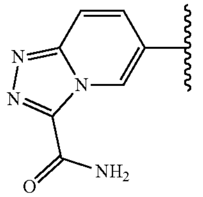
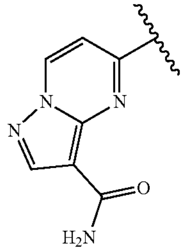
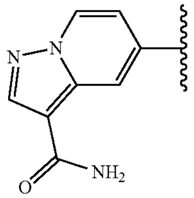
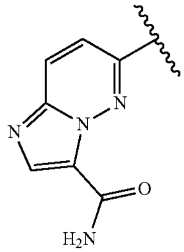
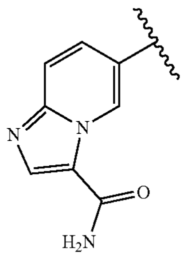
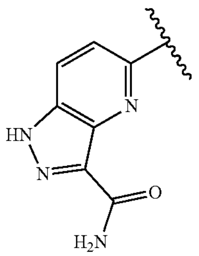

-continued
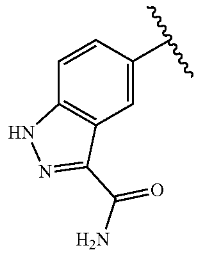
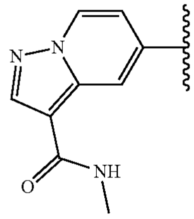
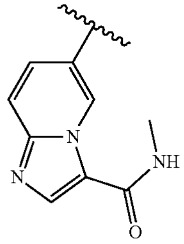
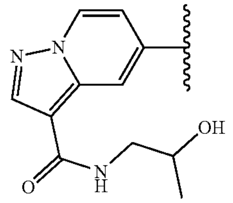
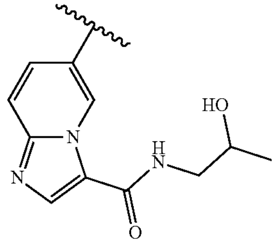
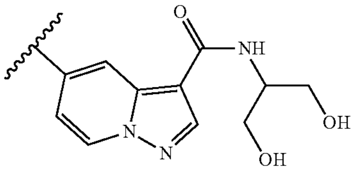
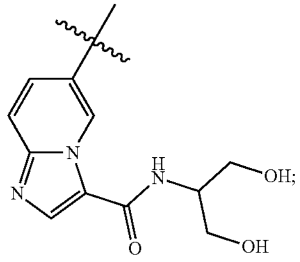
$R^3$ is selected from the group consisting of hydrogen, methyl, ethyl, isopropyl, cyclopropyl, difluoroethyl, alkoxy and alkylamino;
$R^4$ is selected from the group consisting of hydrogen, amino and —$NHR^{10}$; preferably, $R^4$ is selected from the group consisting of hydrogen and —$NHR^{10}$;
$R^{10}$ is selected from the group consisting of:
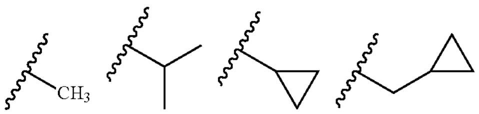
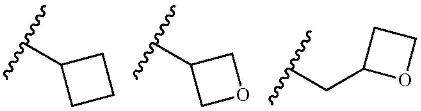
-continued
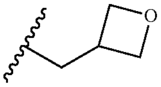
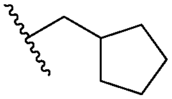
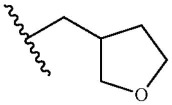
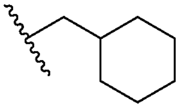
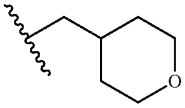
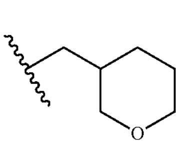
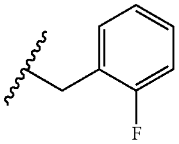
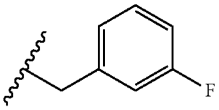
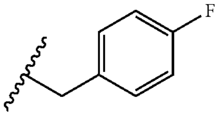
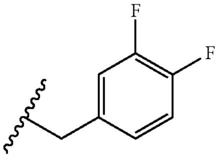
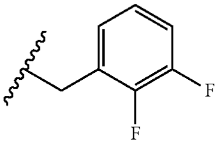
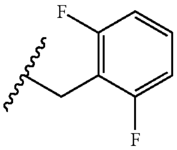
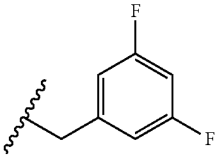
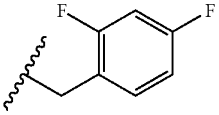
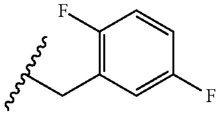
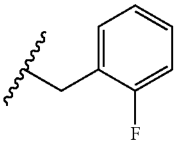
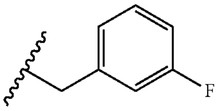
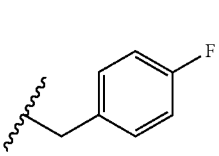
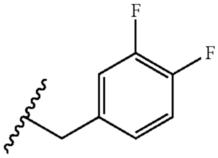
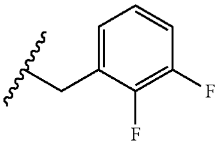
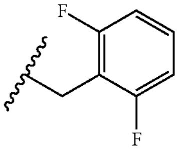
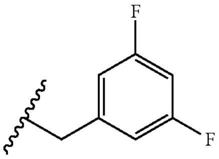
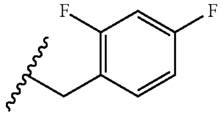
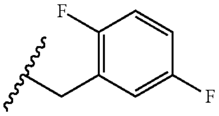
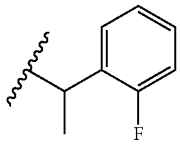

-continued
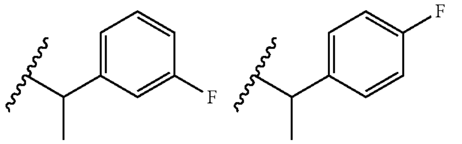
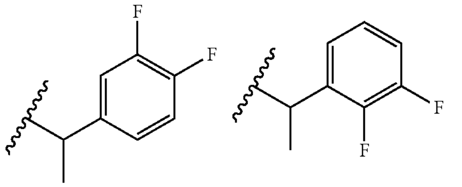
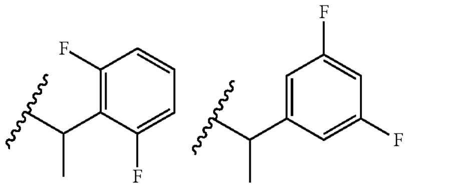
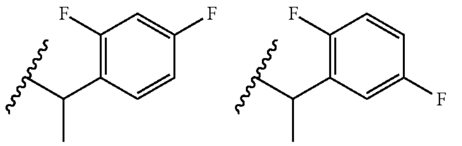
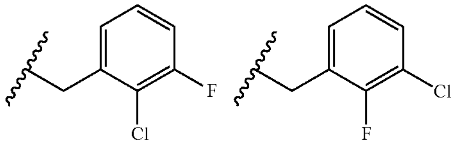
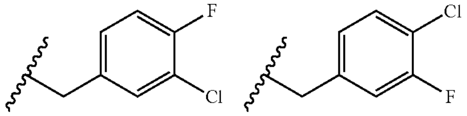
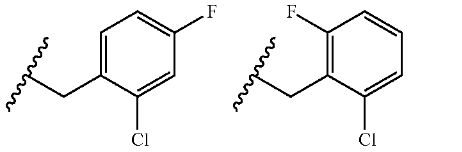
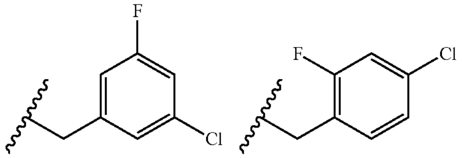
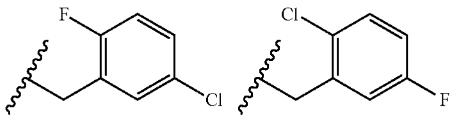
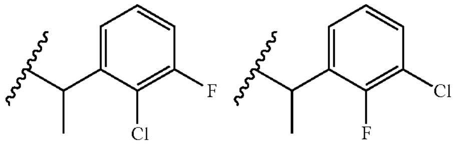
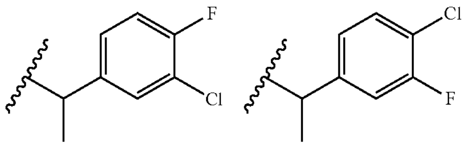
-continued
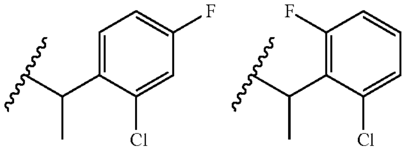
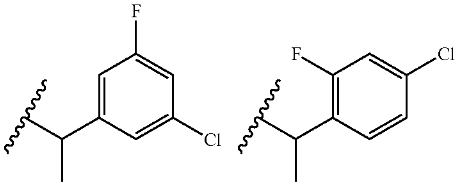
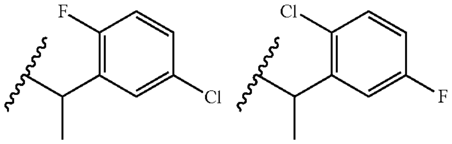
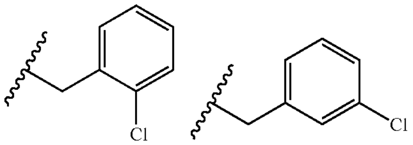
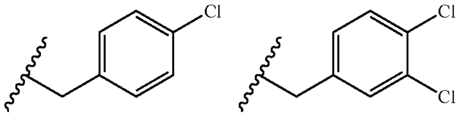
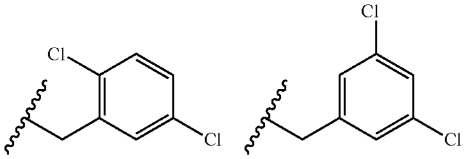
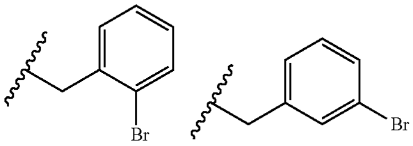
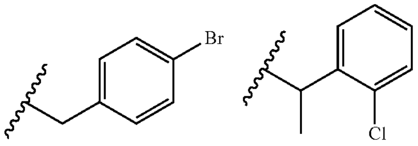
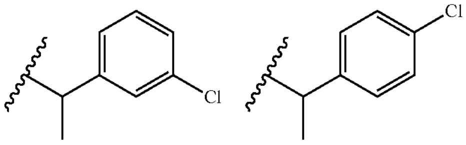
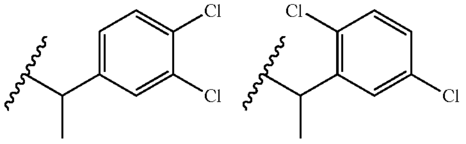
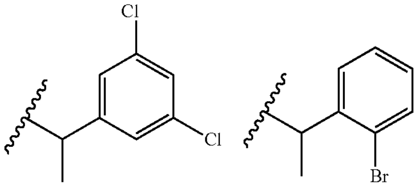

-continued
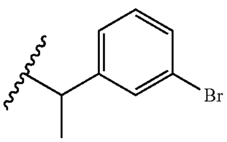 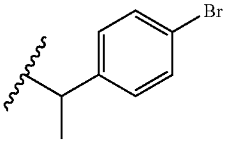
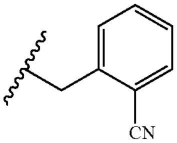 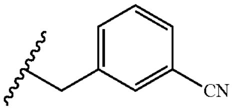
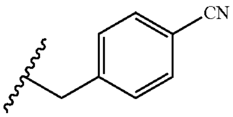 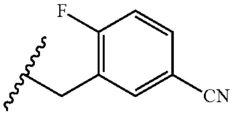
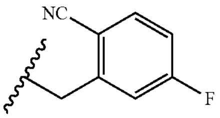 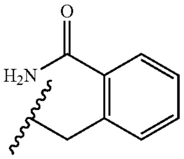
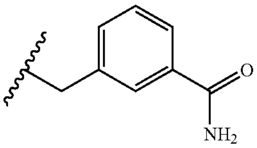 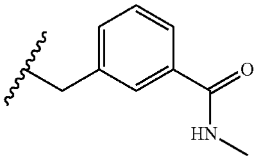
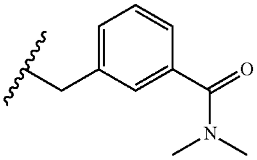 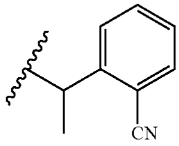
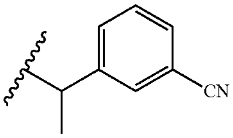 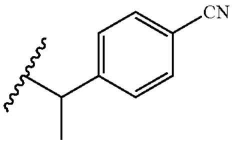
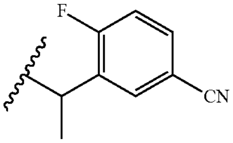 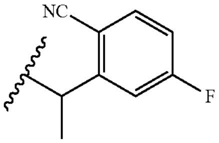
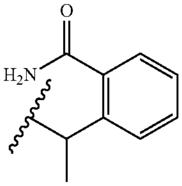 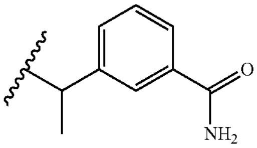
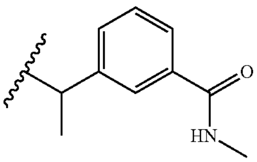 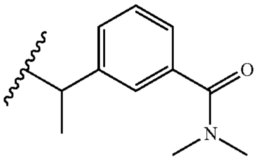
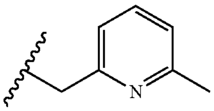 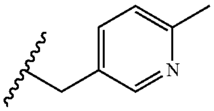
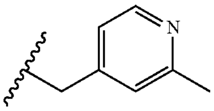 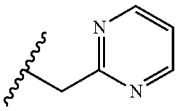
-continued
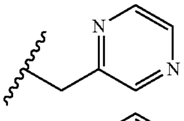 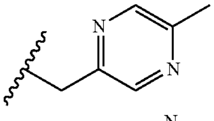
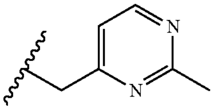 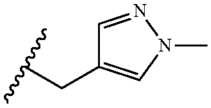
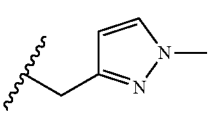 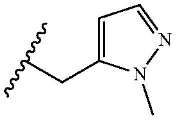
or, $R^3$ and $R^4$ together with the attached carbon atoms form a cyclopentyl ring, cyclohexyl ring, pyrrolidine ring or piperidine ring.
The compound of any item of the first aspect herein, wherein,
$R^1$ is
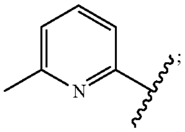 [SMILES: *c1cccc(C)n1];
$R^2$ is selected from the group consisting of
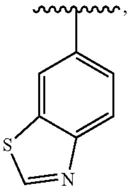, 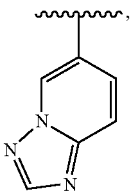, 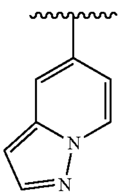
is
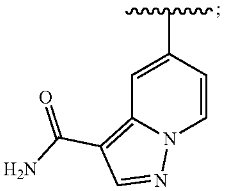 [SMILES: *c1ccn2ncc(C(N)=O)c2c1];
$R^3$ is H;
$R^4$ is H or —$NHR^{10}$; $R^{10}$ is selected from the group consisting of
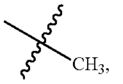
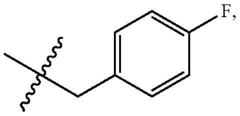

-continued
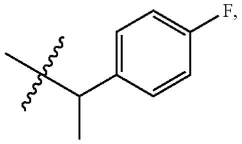
and
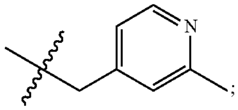
or, $R^3$ and $R^4$ together with the attached carbon atoms form a cyclopentyl ring.
In some embodiments, the present invention provides the following compounds, or a pharmaceutically acceptable salt, ester, stereoisomer, tautomer, polymorph, solvate, oxynitrides, isotopically labeled compound, metabolite or prodrug thereof:
1
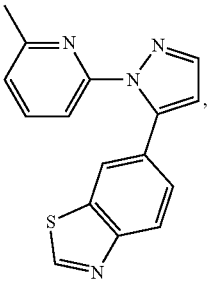
2
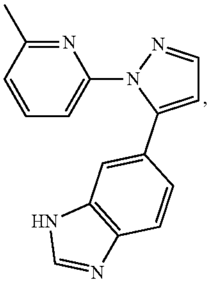
3
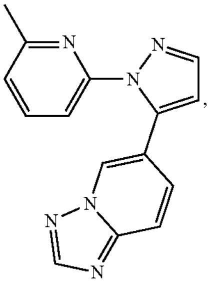
-continued
4
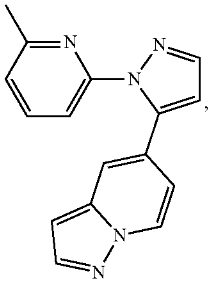
5
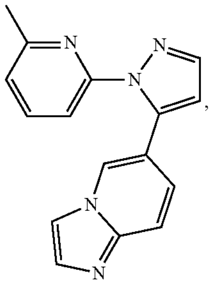
6
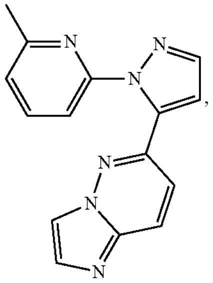
7
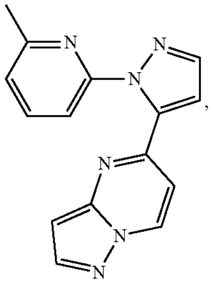
8
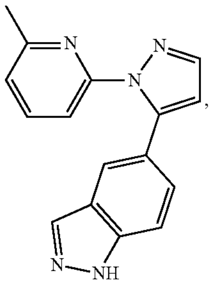

-continued
9
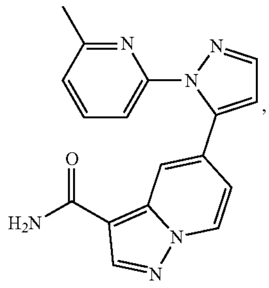
10
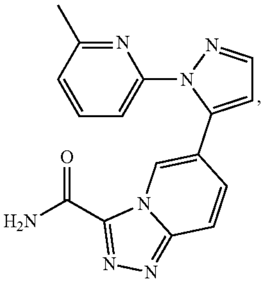
11
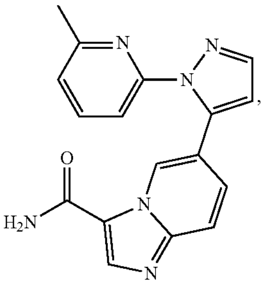
12
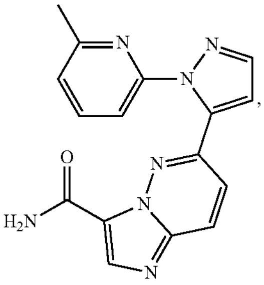
13
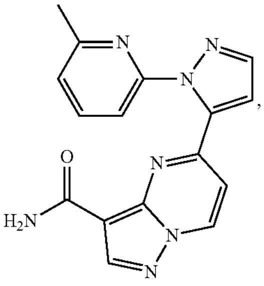
-continued
14
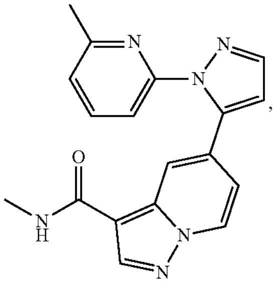
15
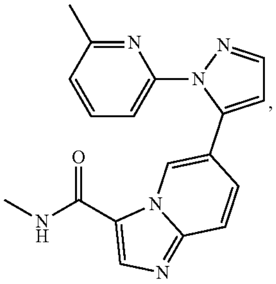
16
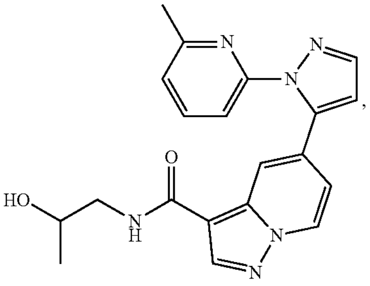
18
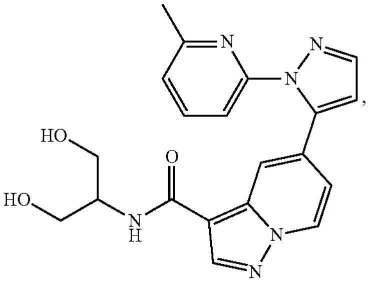
19
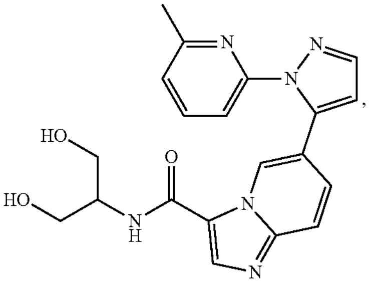

-continued
20
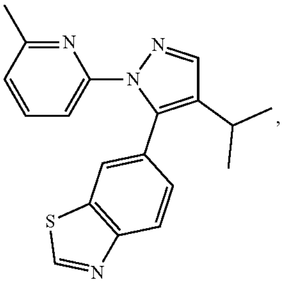
21
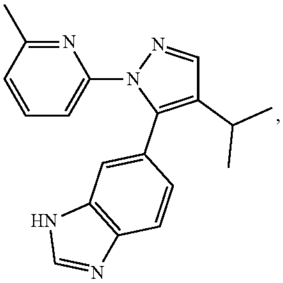
22
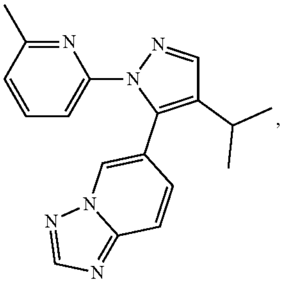
23
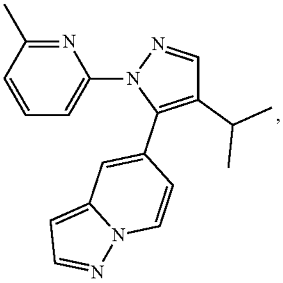
24
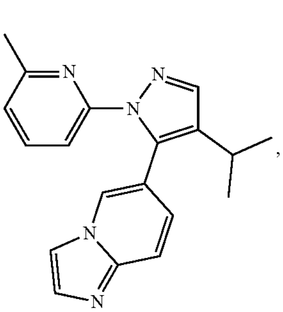
-continued
25
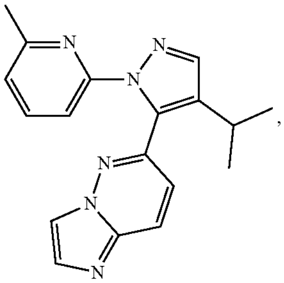
26
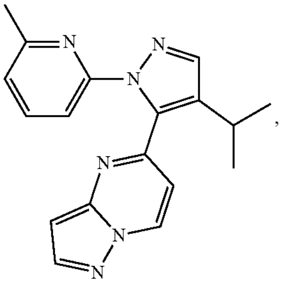
27
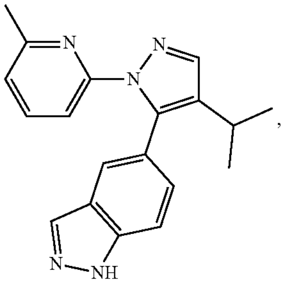
28
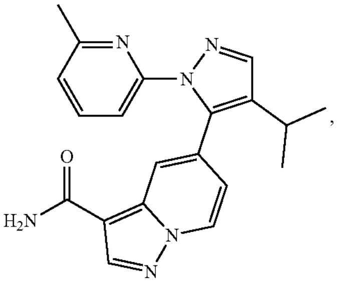
29
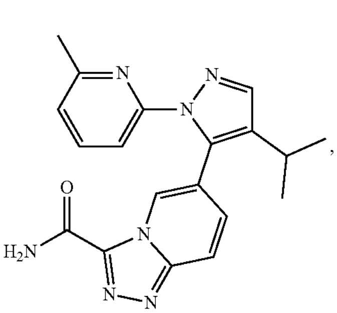

-continued
30
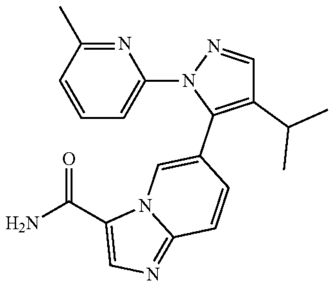
,
31
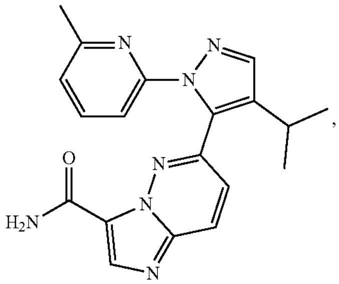
,
32
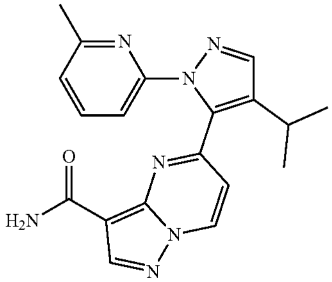
,
33
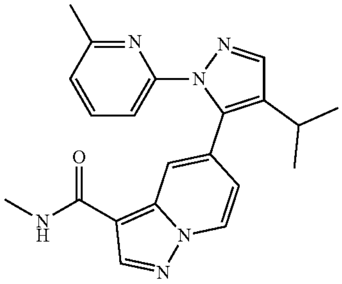
,
34
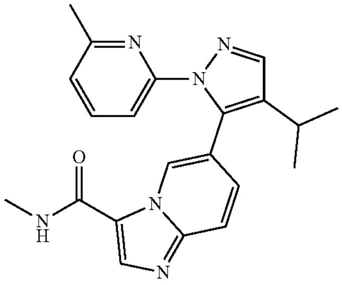
,
-continued
35
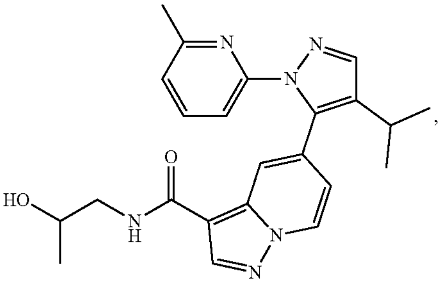
,
36
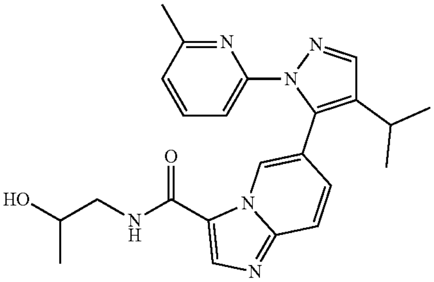
,
37
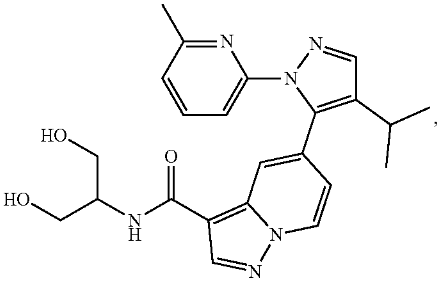
,
38
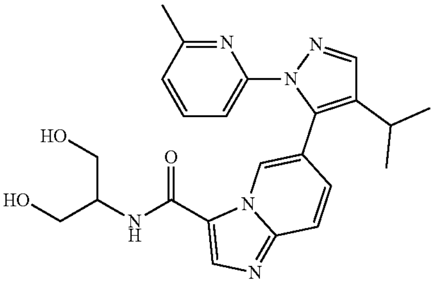
,
39
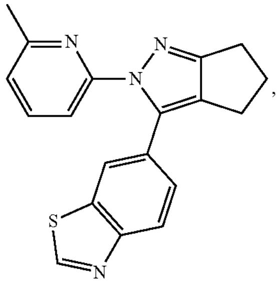
, -continued
40
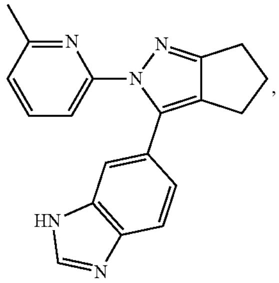,
41
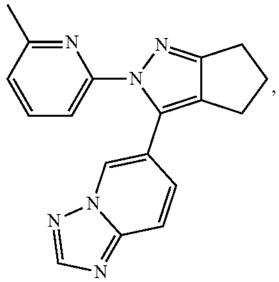,
42
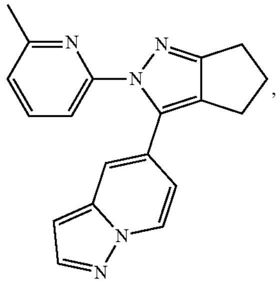,
43
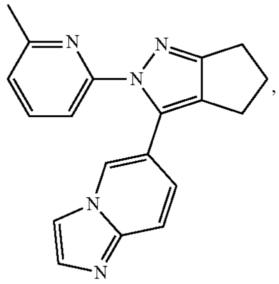,
44
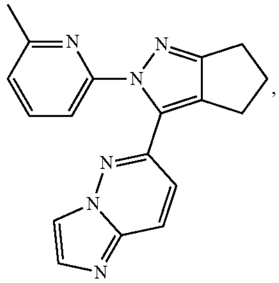,
-continued
45
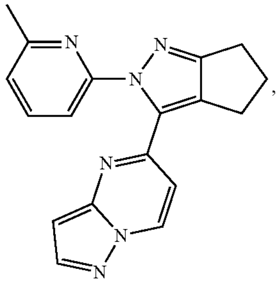,
46
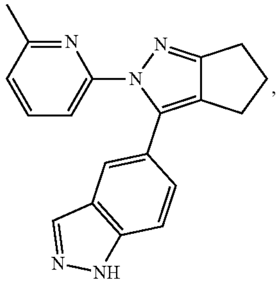,
47
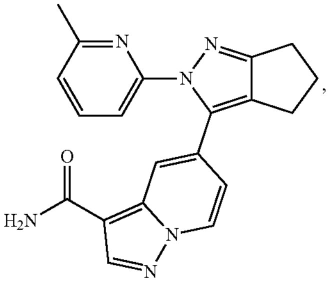,
48
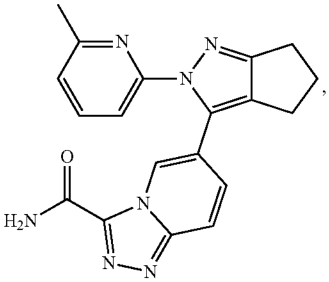,
49
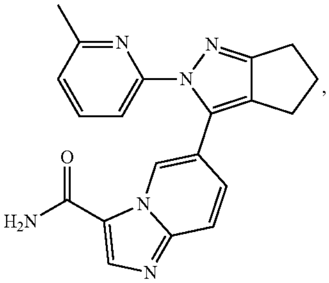, -continued
50
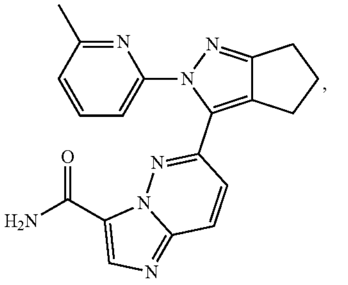
51
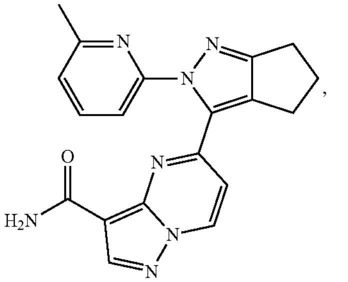
52
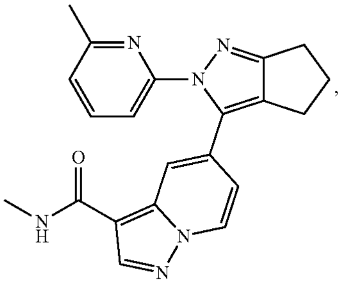
53
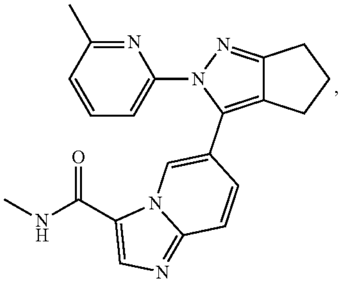
54
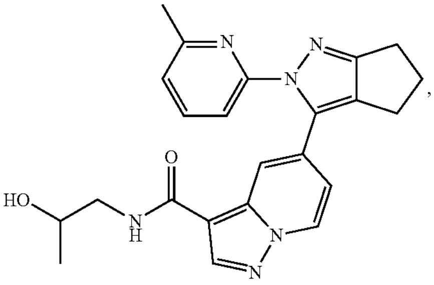
-continued
55
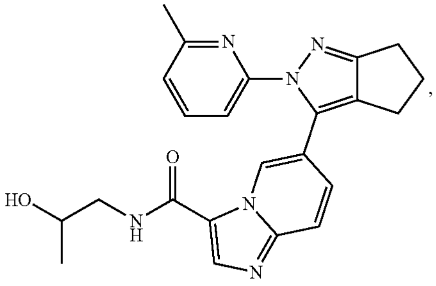
56
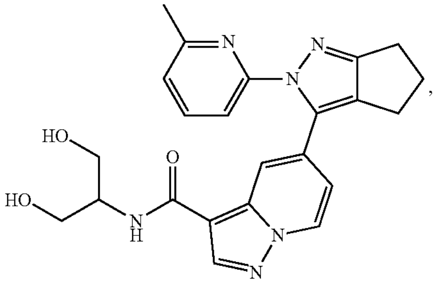
57
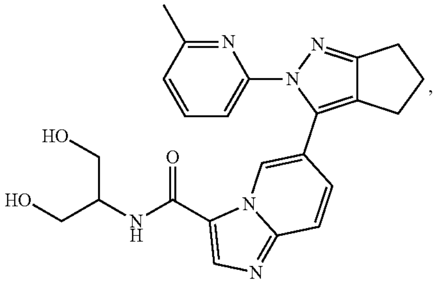
58
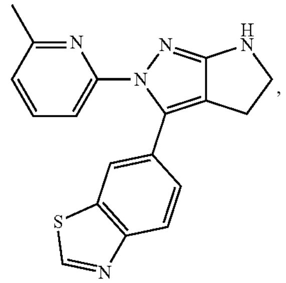
59
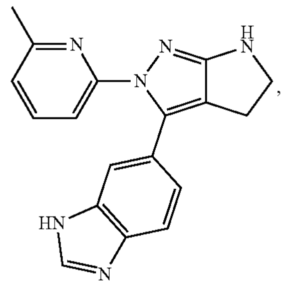

-continued
60
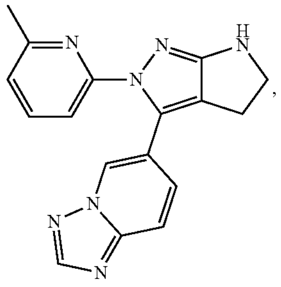
61
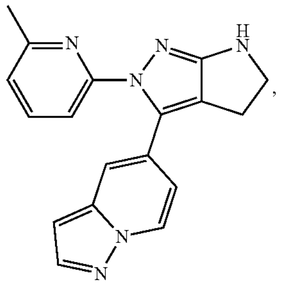
62
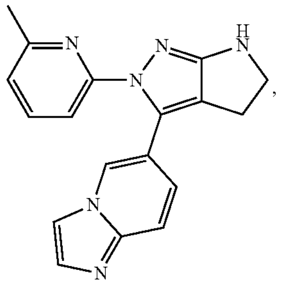
63
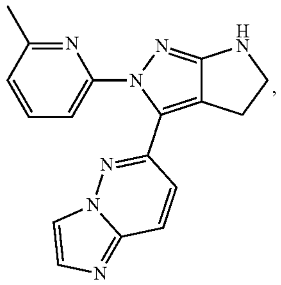
64
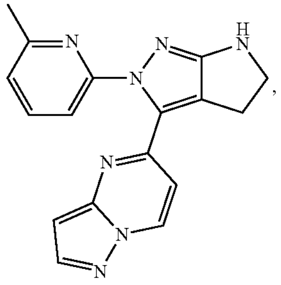
-continued
65
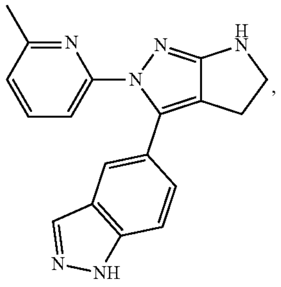
66
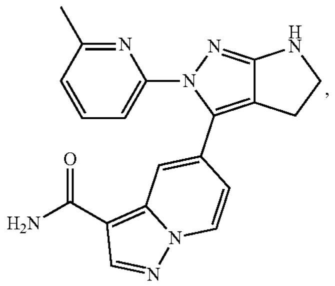
67
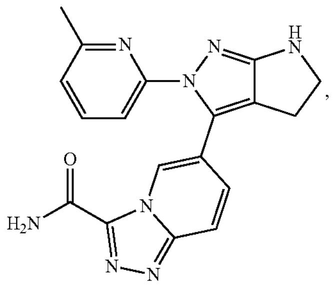
68
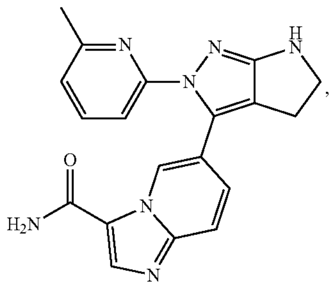
69
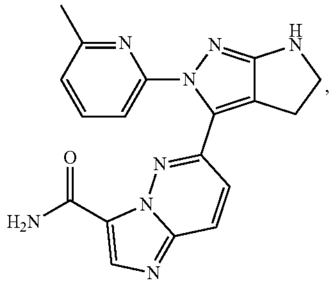

-continued
70
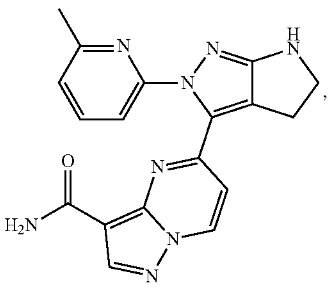
71
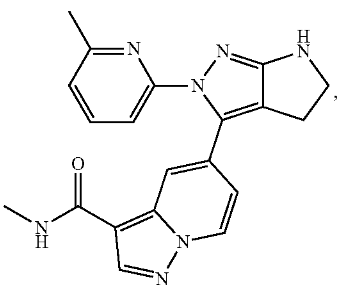
72
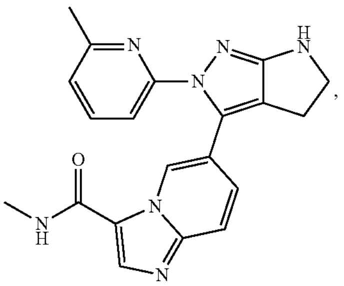
73
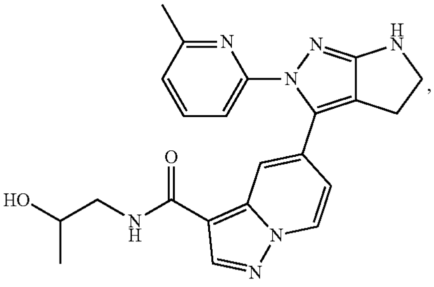
74
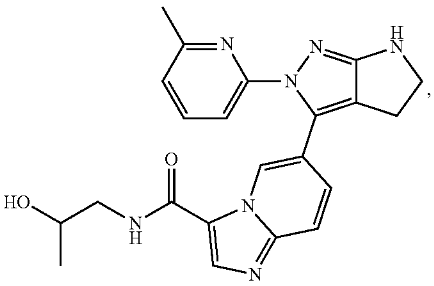
-continued
75
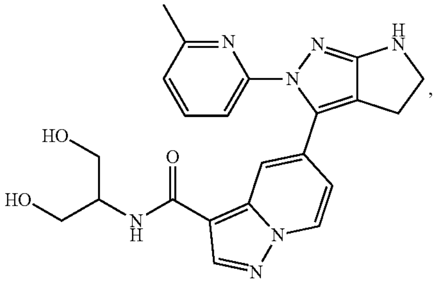
76
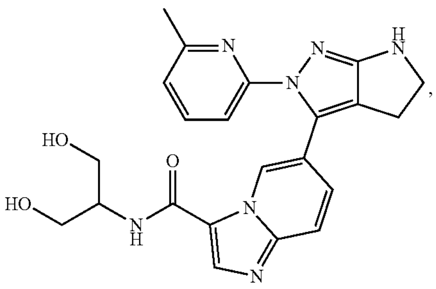
77
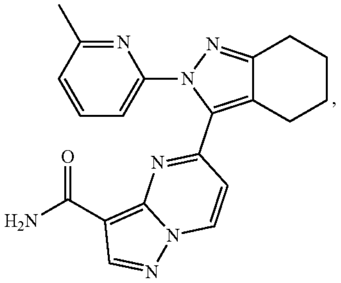
78
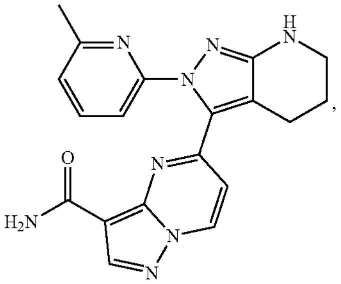
79
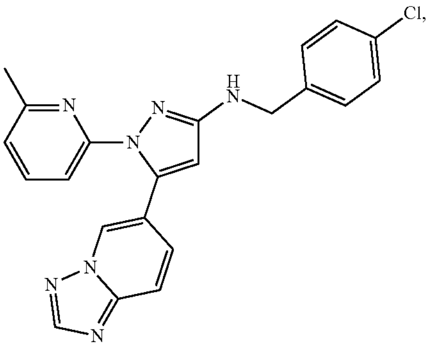

-continued
80
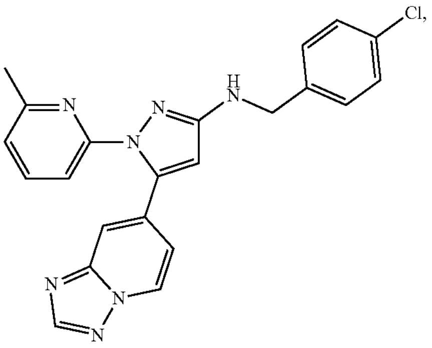
81
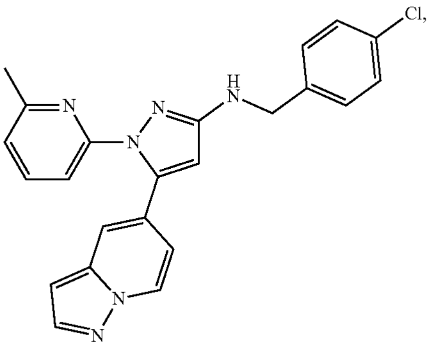
82
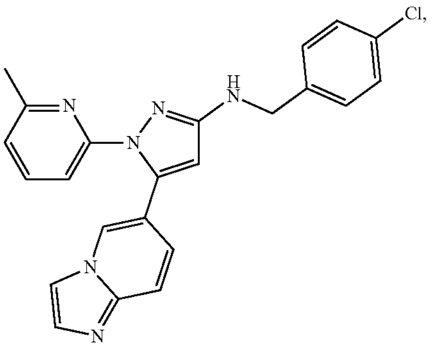
83
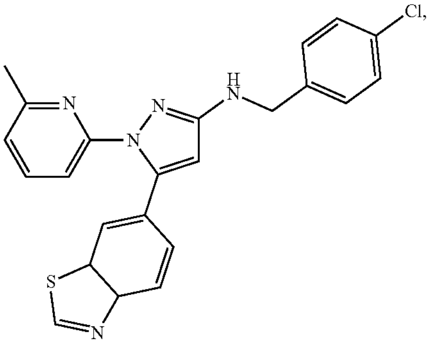
-continued
84
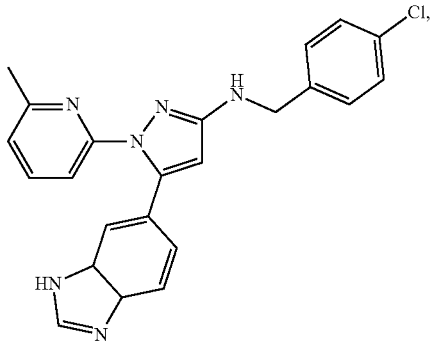
85
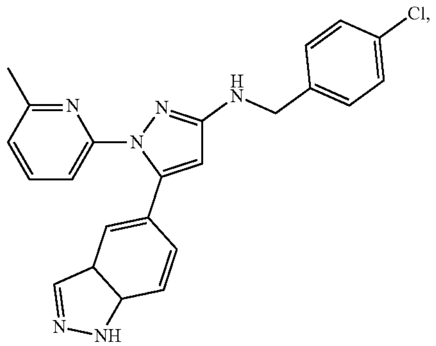
86
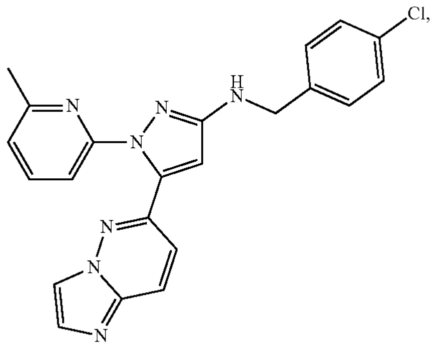
87
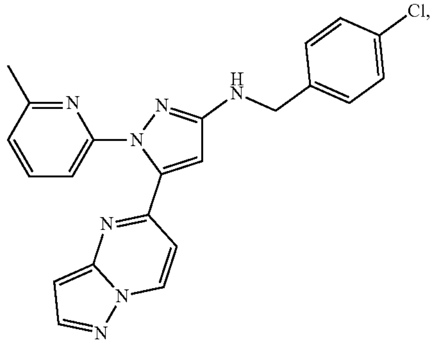

-continued
88
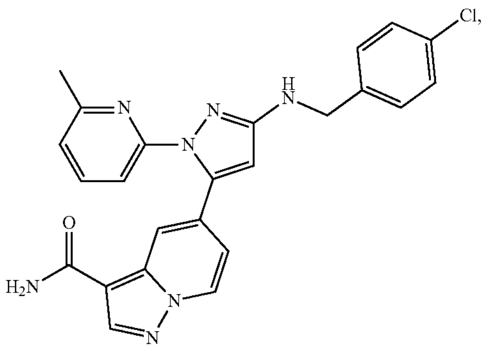
89
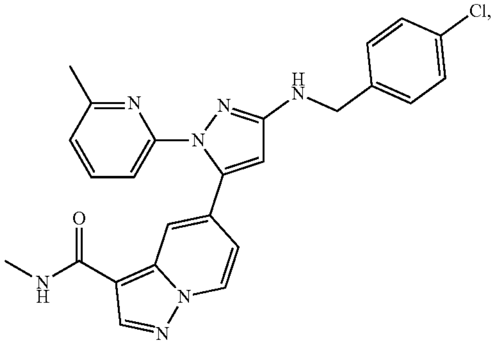
90
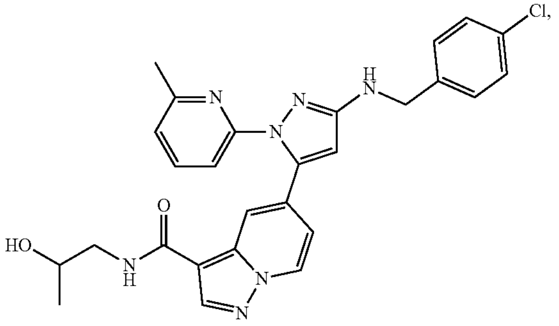
91
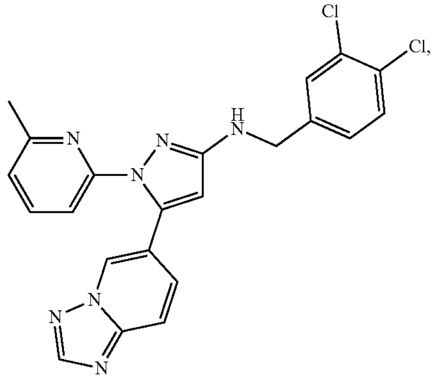
-continued
92
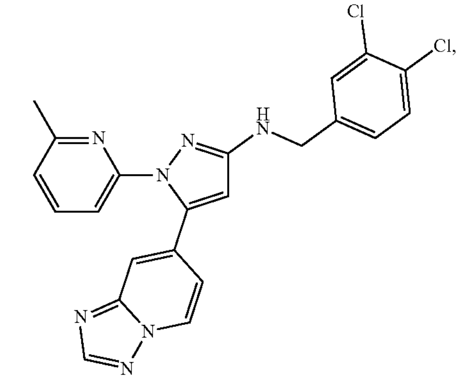
93
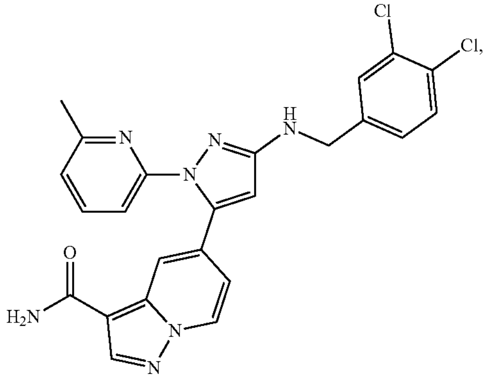
94
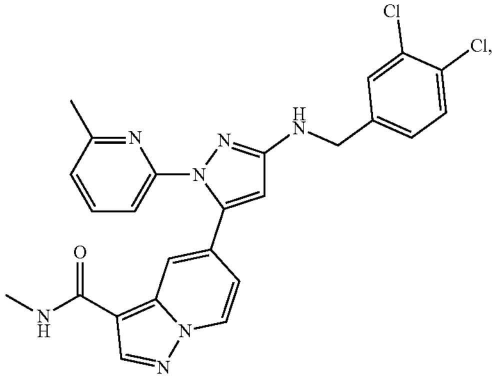
95
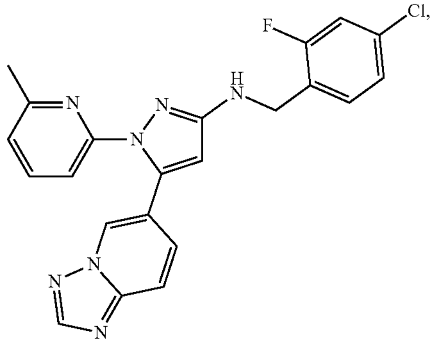

-continued
96
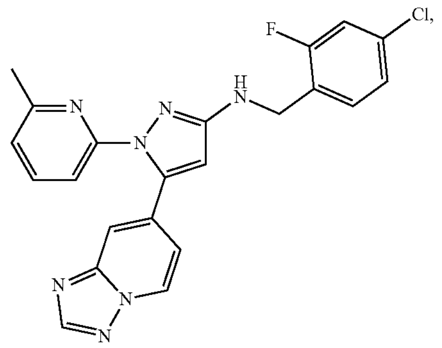
97
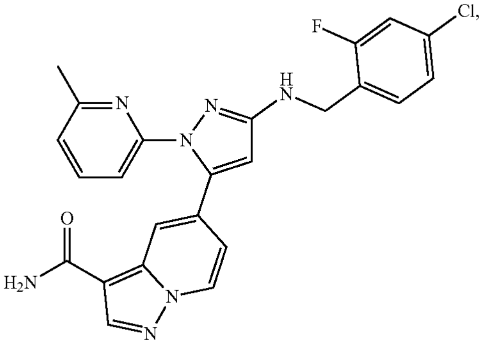
98
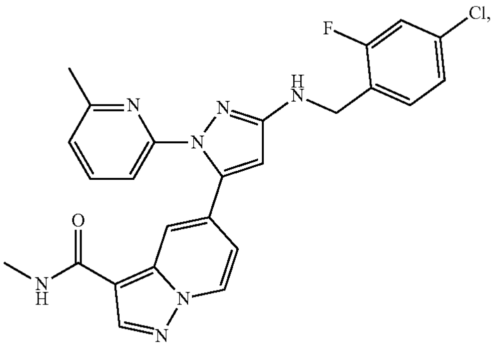
99
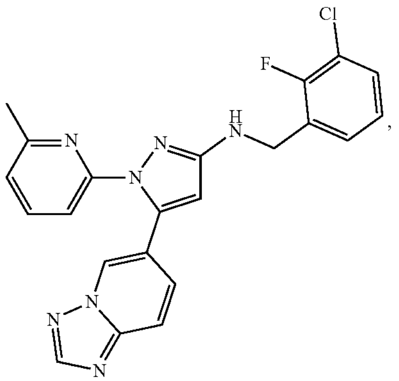
-continued
100
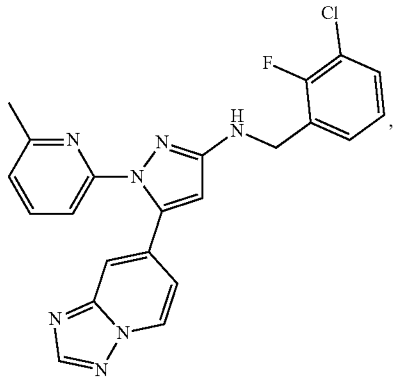
101
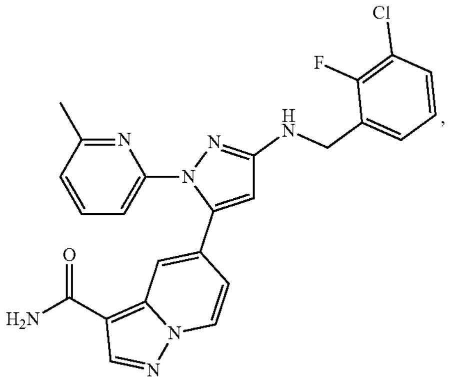
102
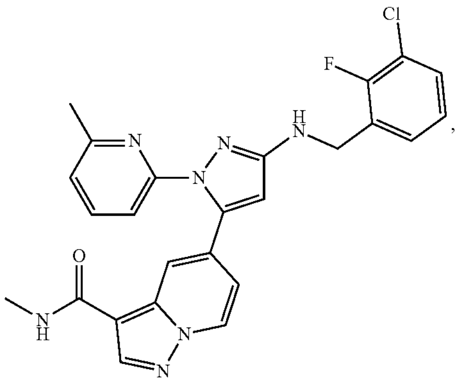
103
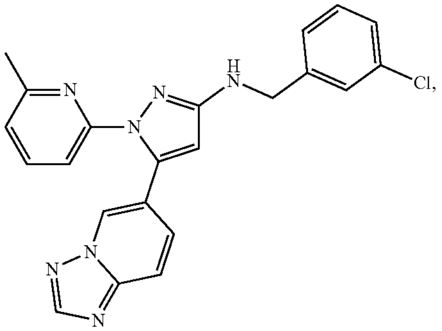

-continued
104
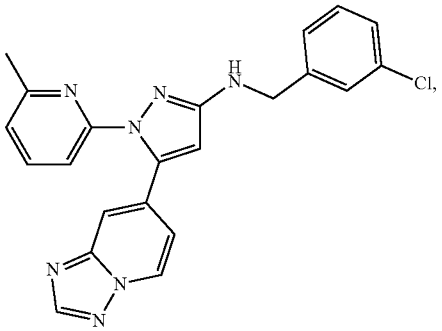
105
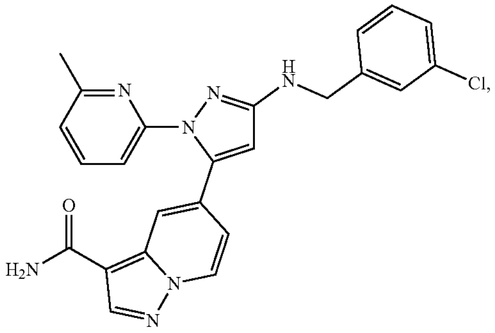
106
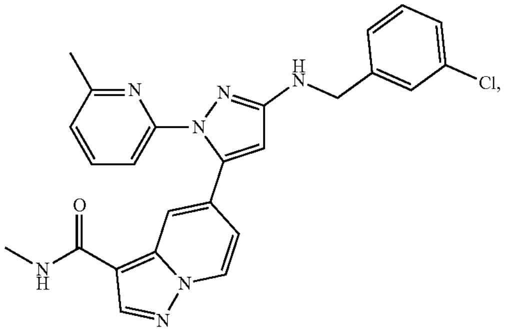
107
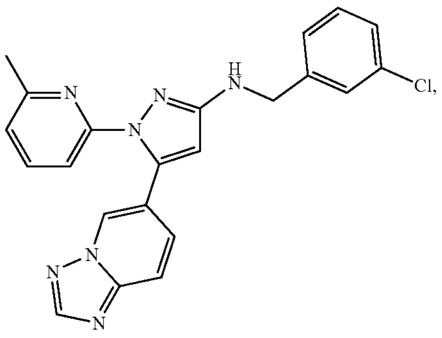
-continued
108
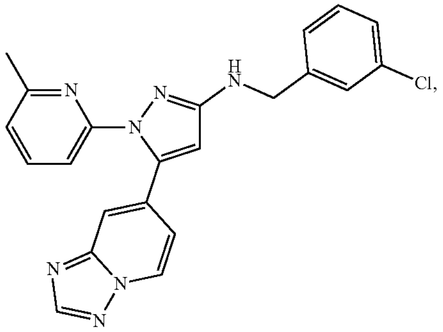
109
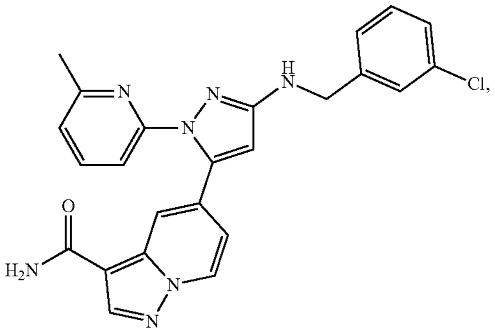
110
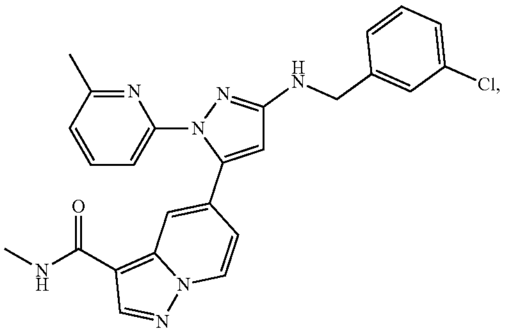
111
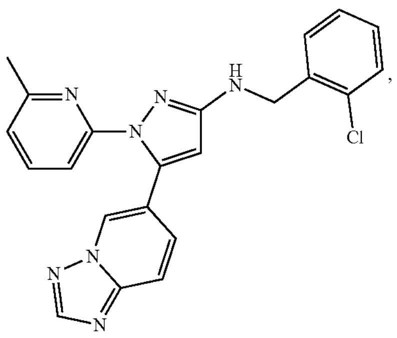

-continued
112
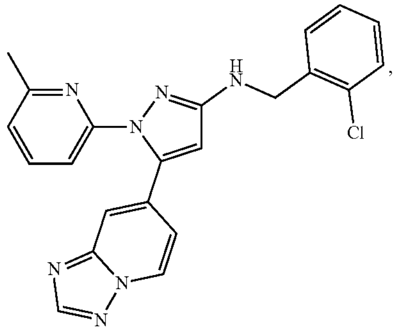
113
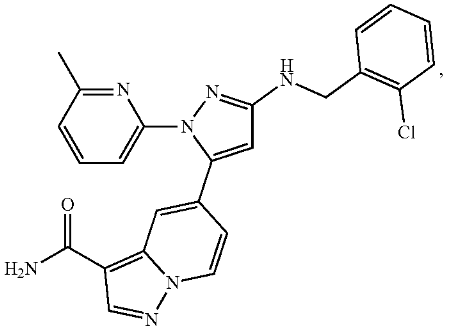
114
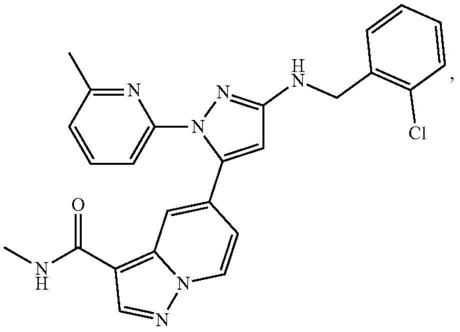
115
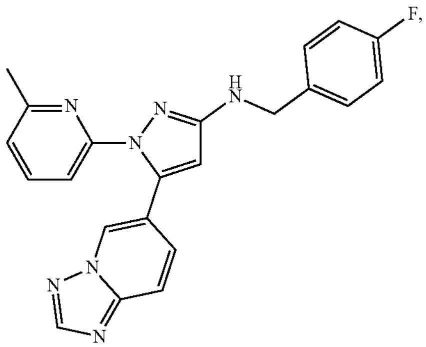
-continued
116
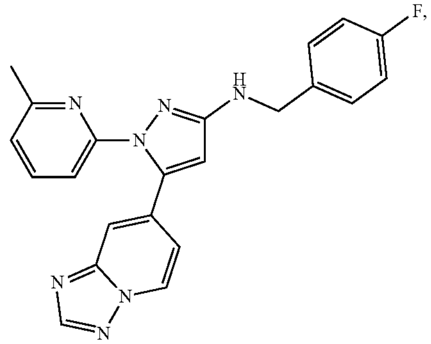
117
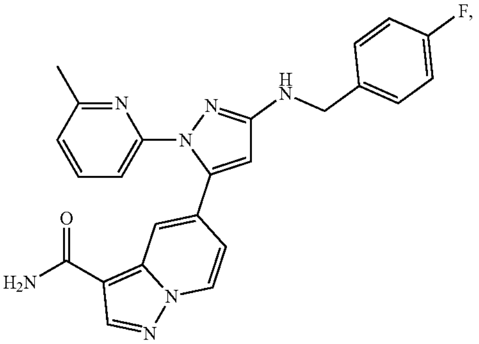
118
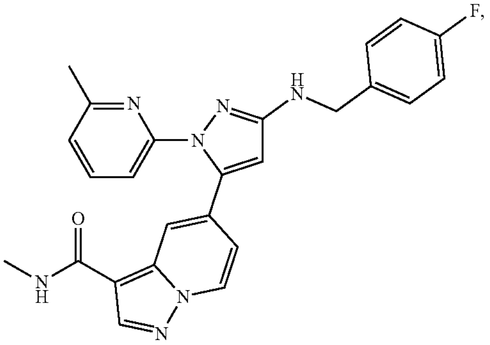
119
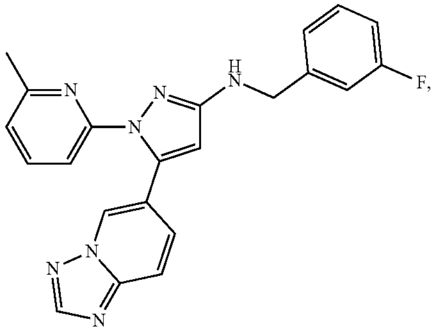

-continued
120
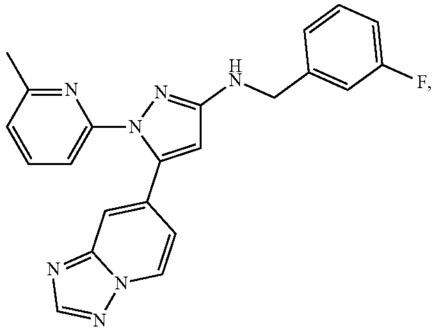
,
121
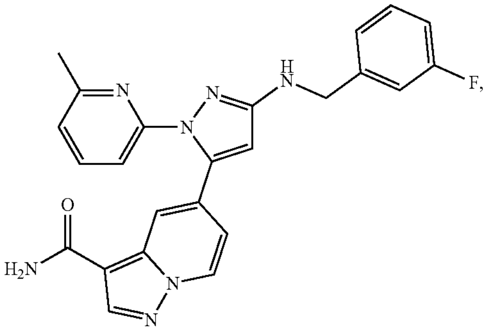
,
122
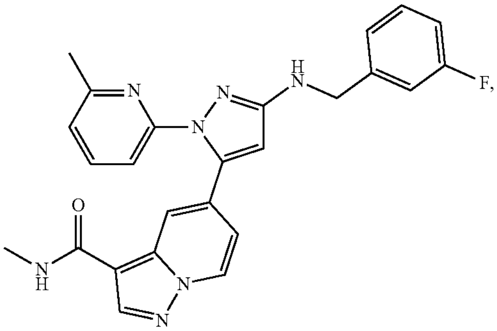
,
123
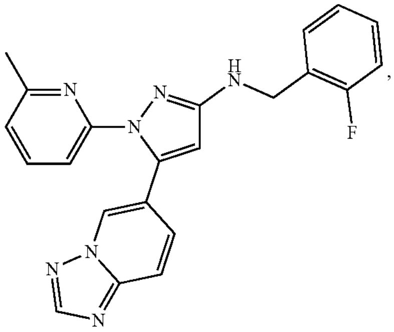
,
124
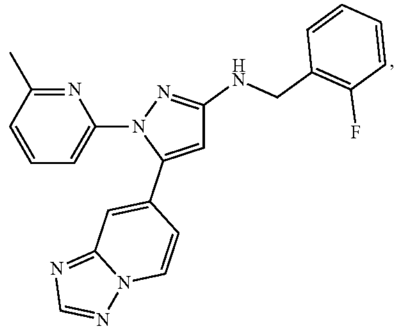
,
125
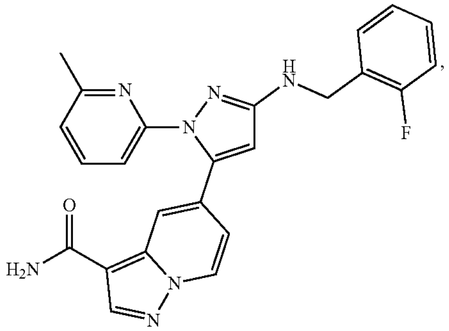
,
126
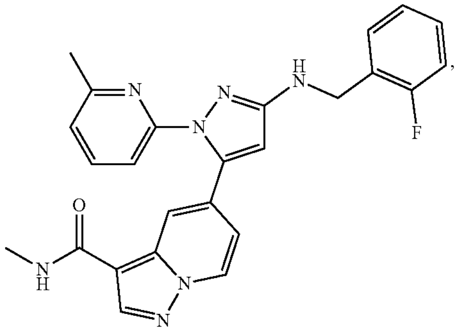
,
127
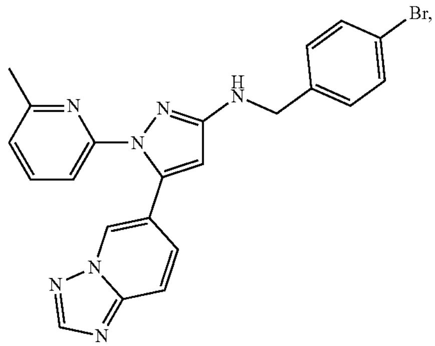
, -continued
128
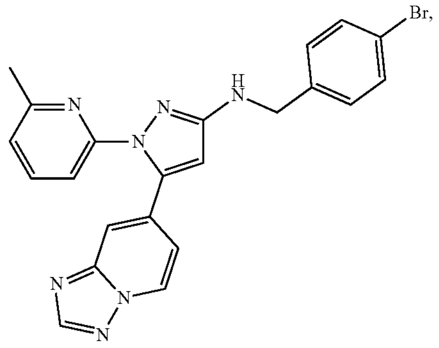
129
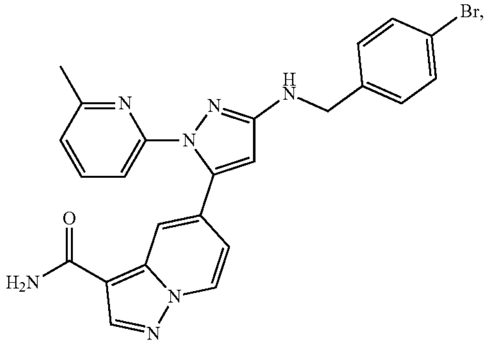
130
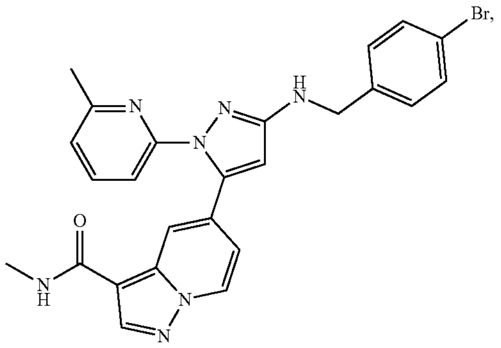
131
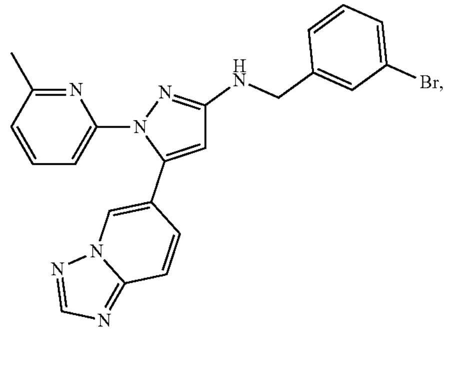
-continued
132
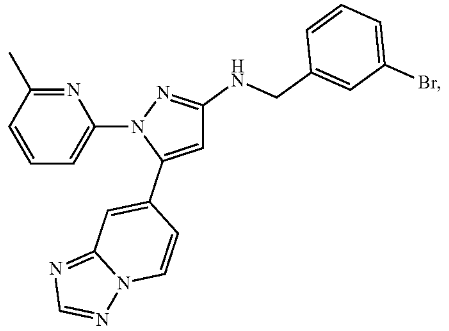
133
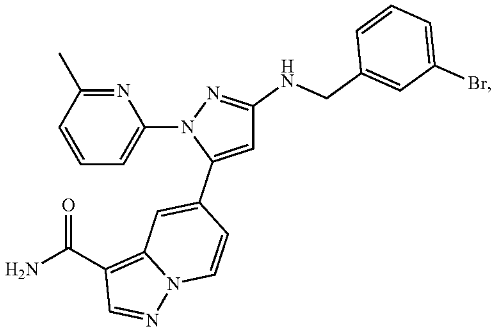
134
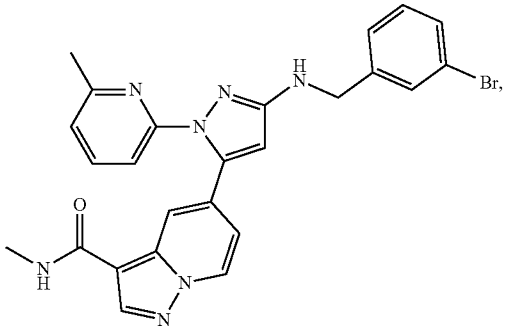
135
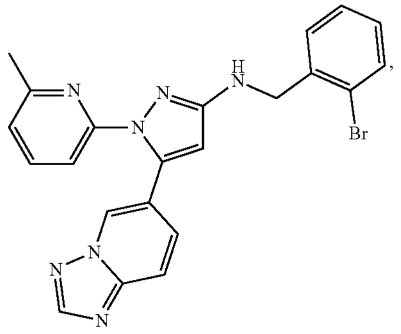

-continued
136
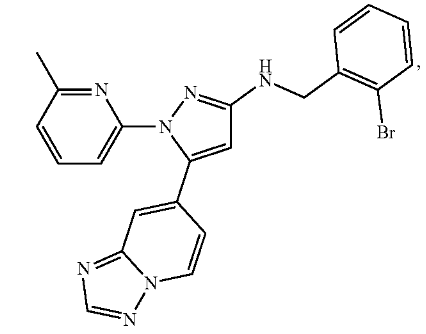
,
137
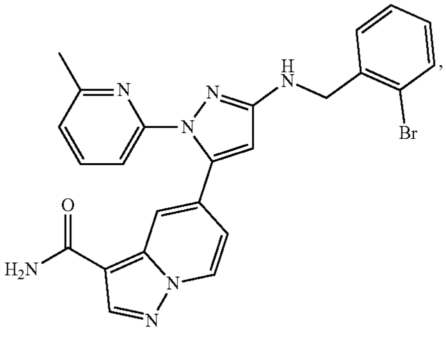
,
138
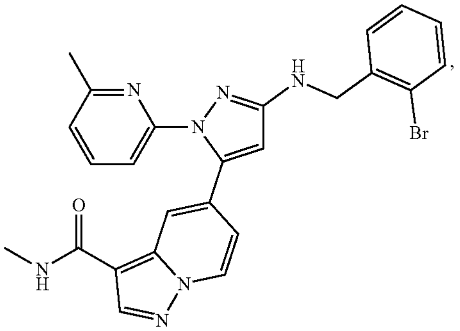
,
139
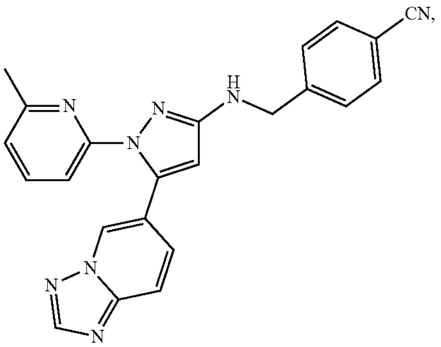
,
-continued
140
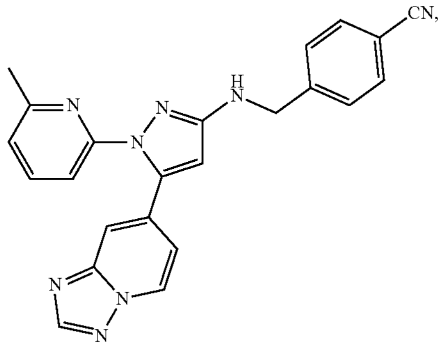
,
141
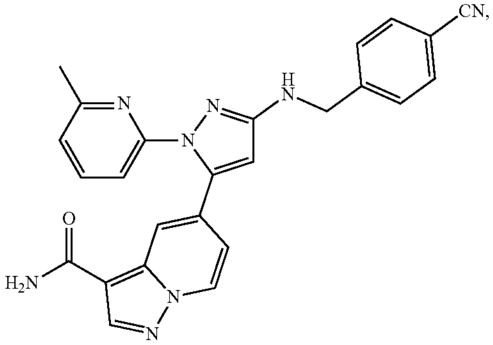
,
142
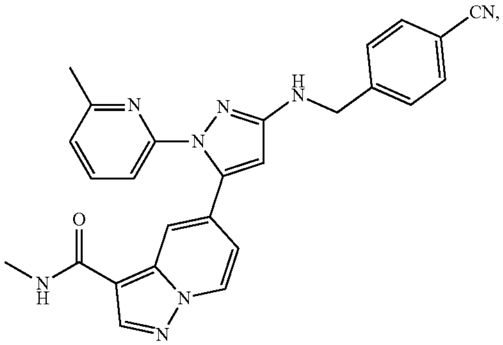
,
143
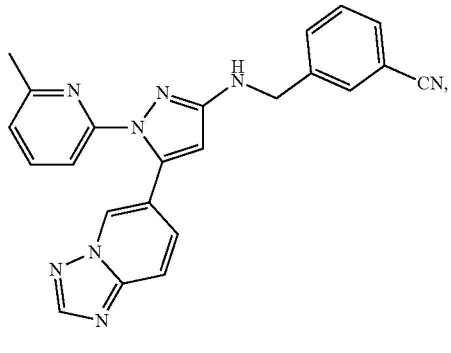
, 144
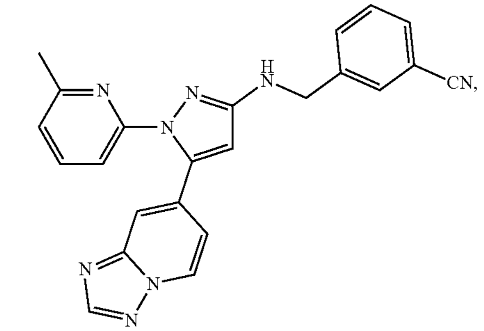
145
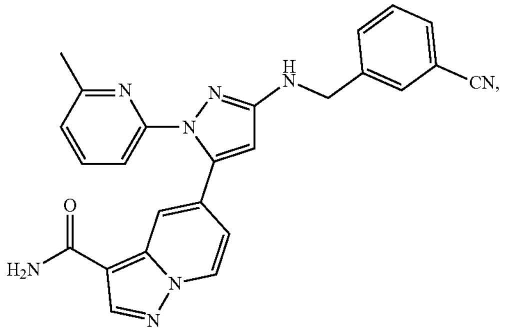
146
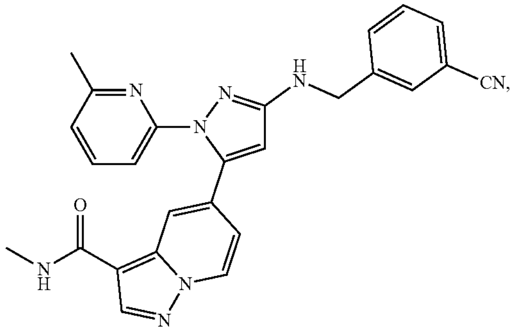
147
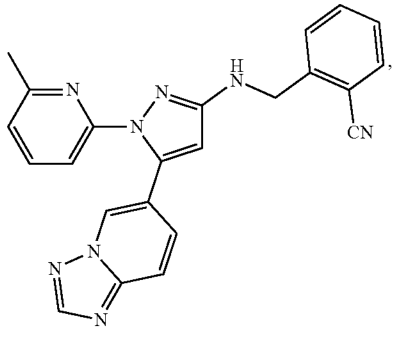
148
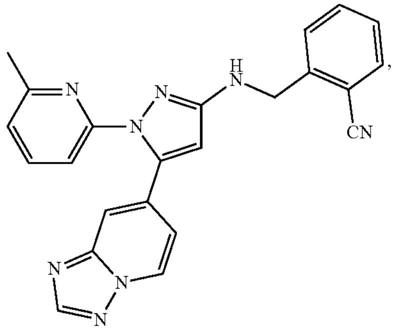
149
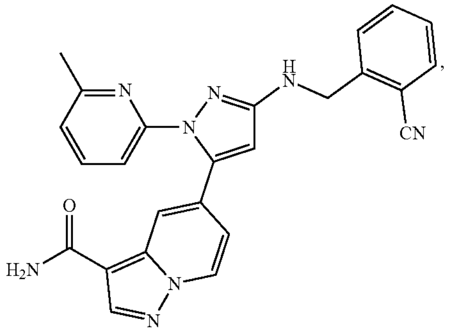
150
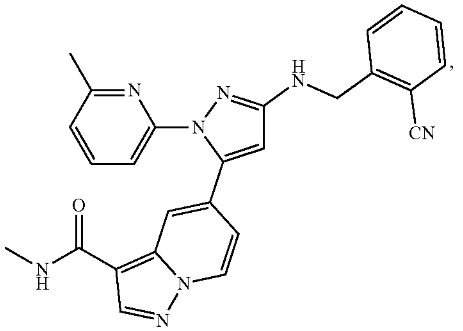
151
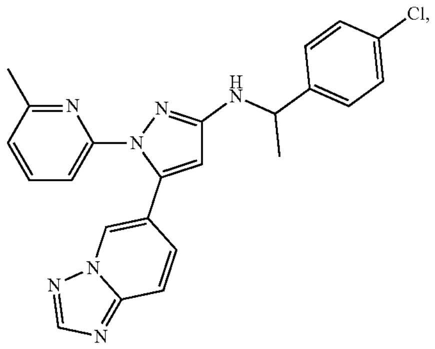

-continued
152
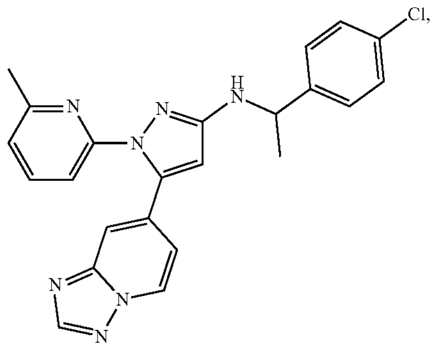
153
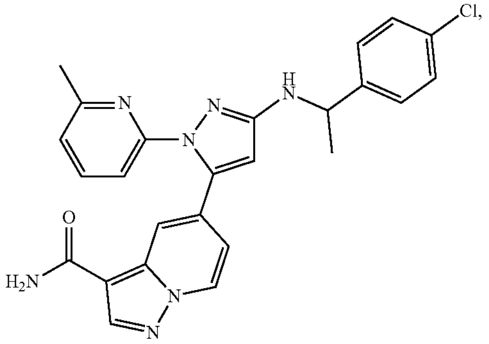
154
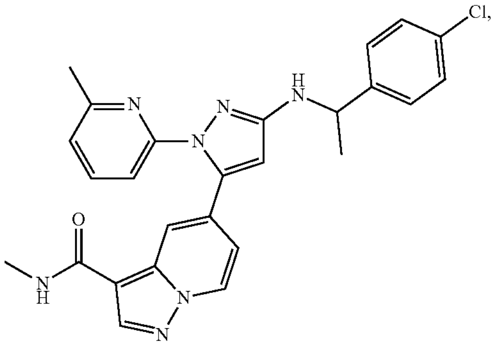
155
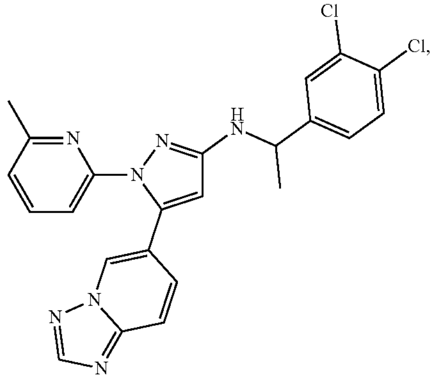
-continued
156
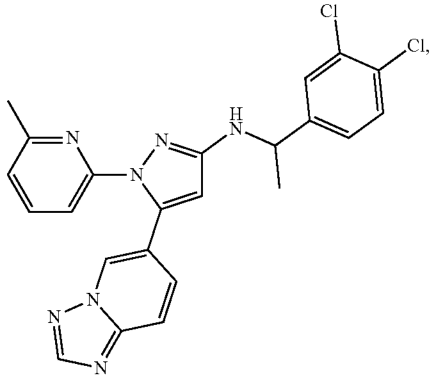
157
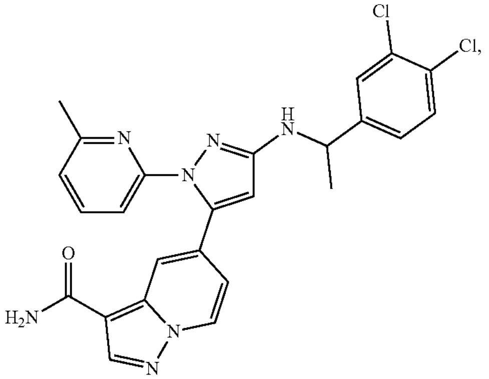
158
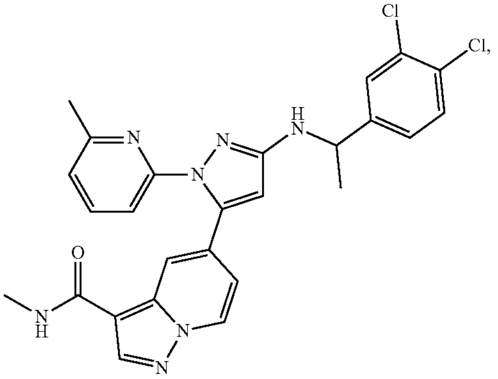
159
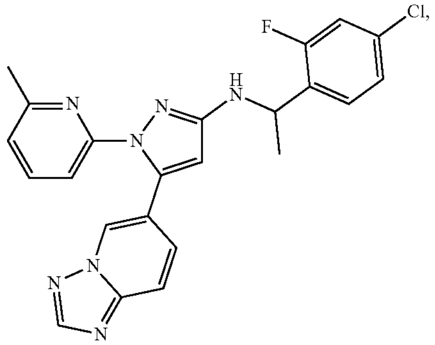

-continued
160
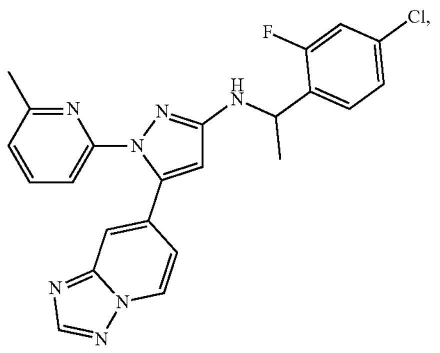
161
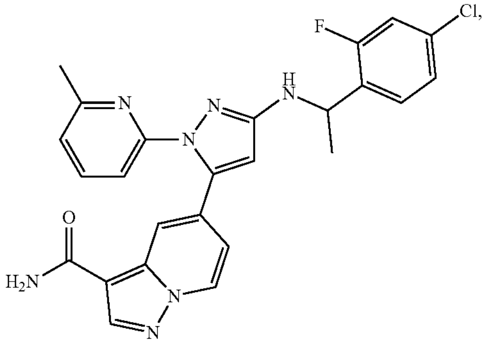
162
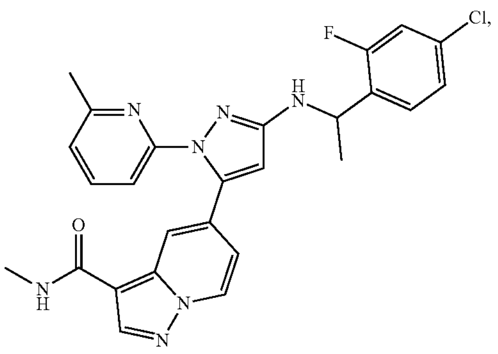
163
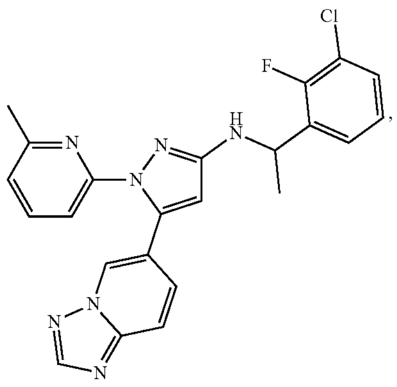
-continued
164
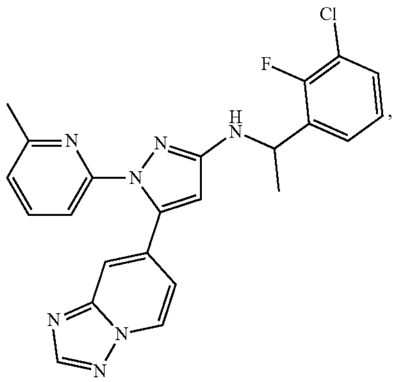
165
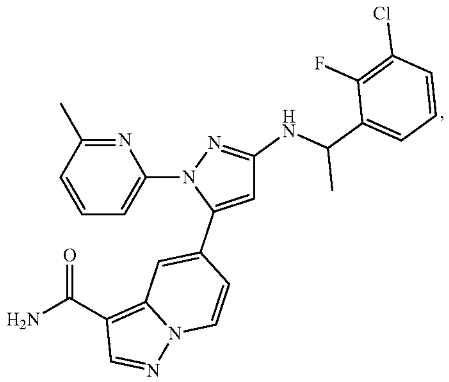
166
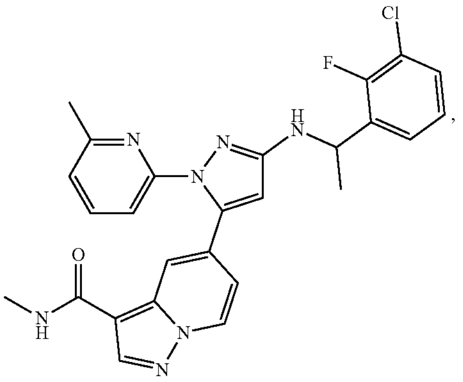
167
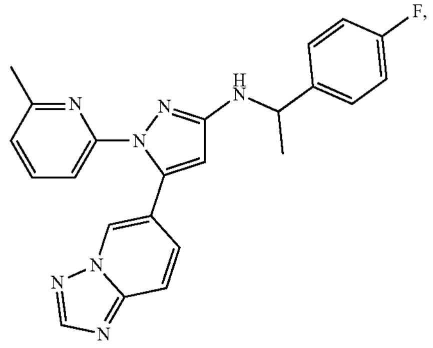

-continued
168
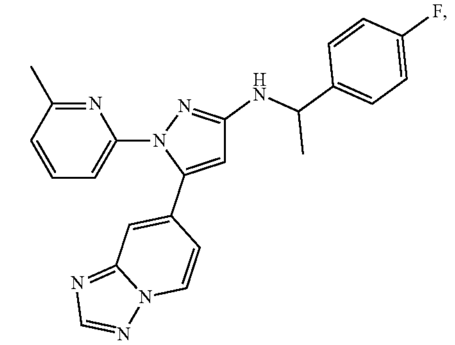
169
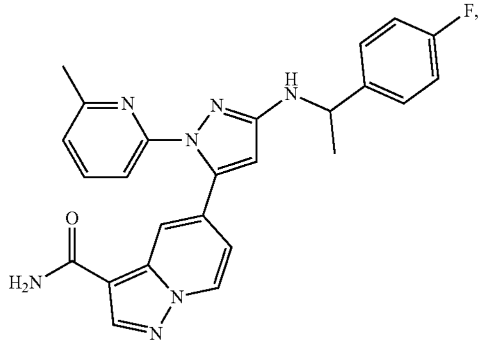
170
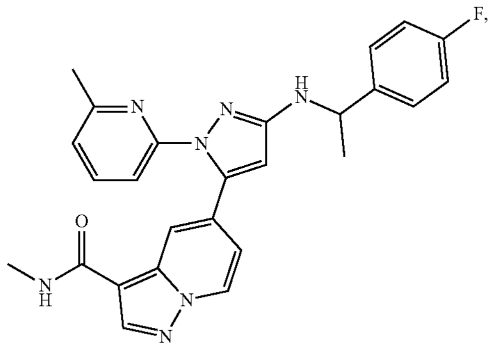
171
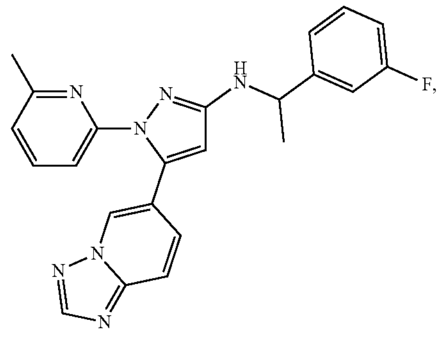
-continued
172
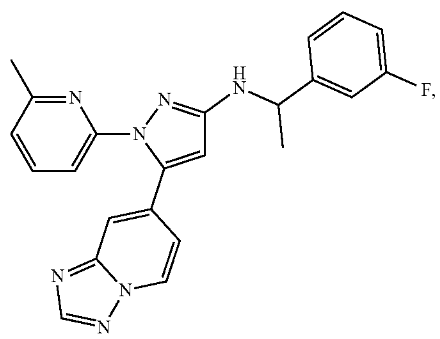
173
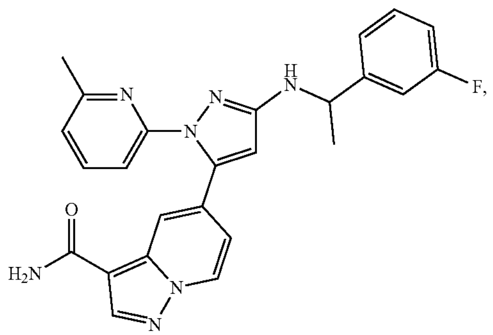
174
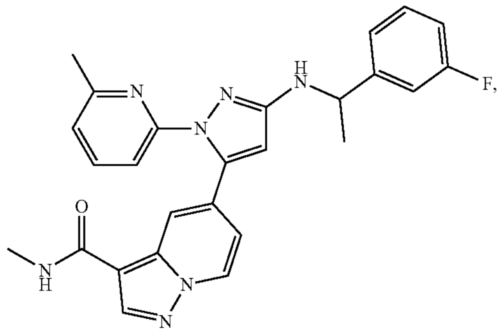
175
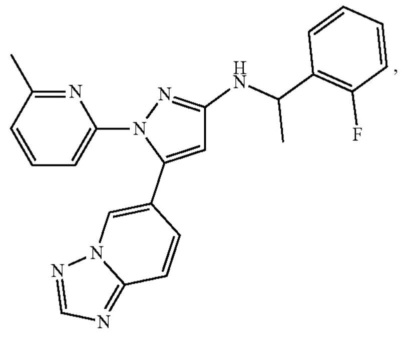

-continued
176
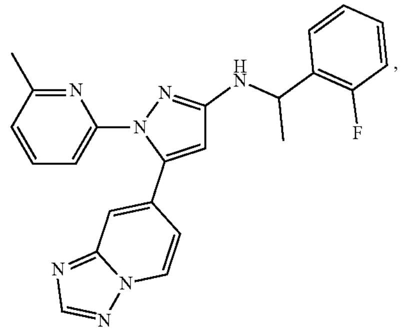
,
177
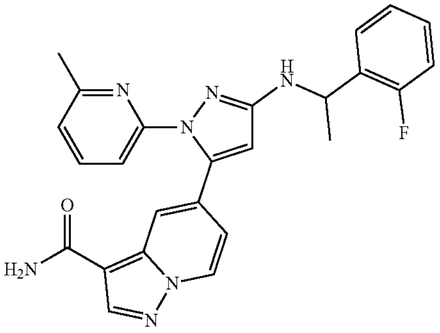
,
178
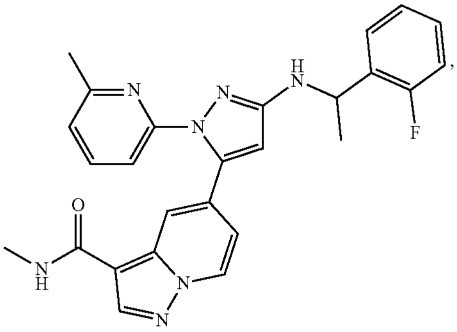
,
179
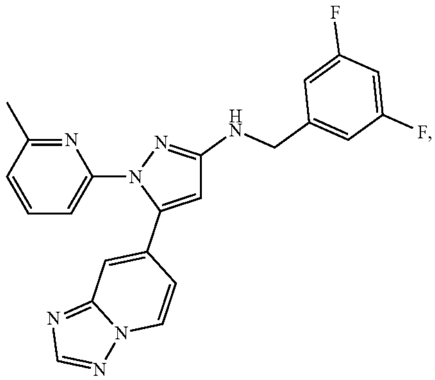
,
-continued
180
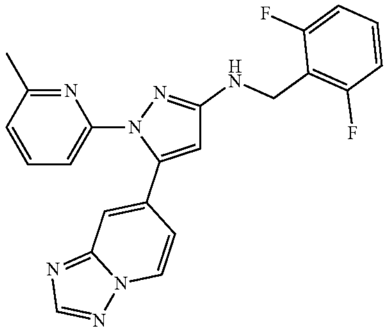
,
181
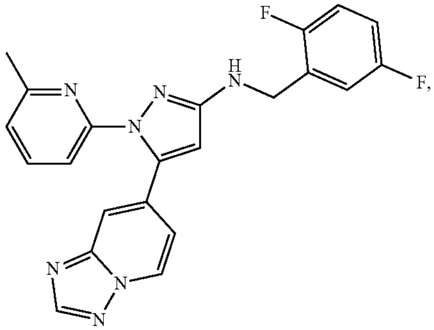
,
182
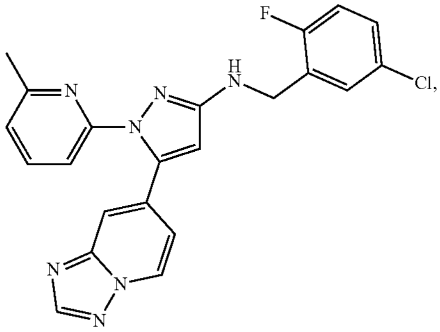
,
183
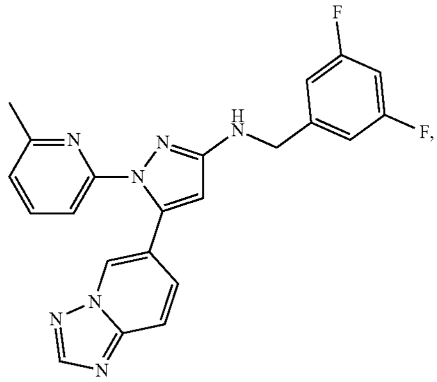
, -continued
184
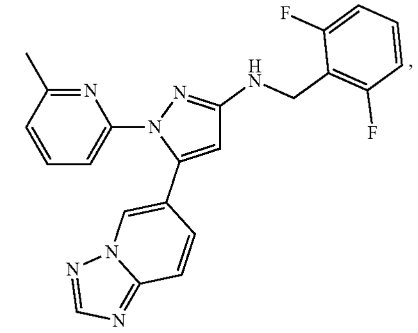
185
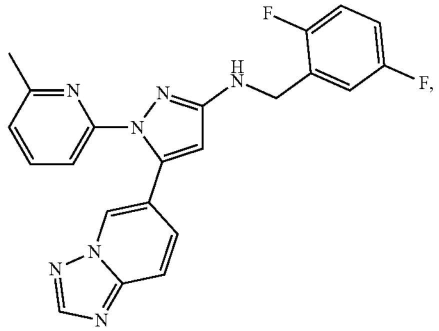
186
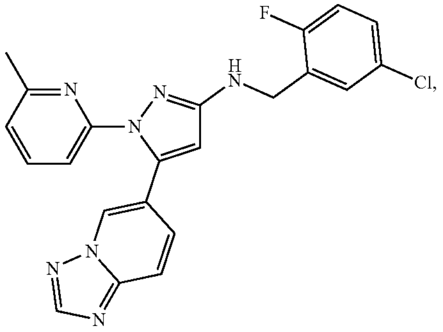
187
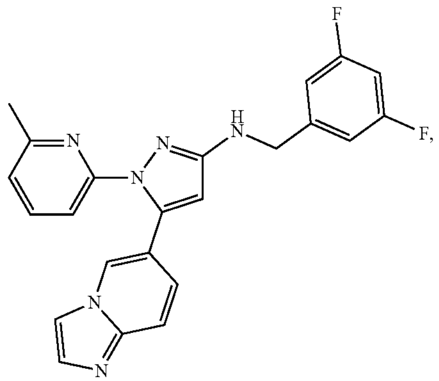
-continued
188
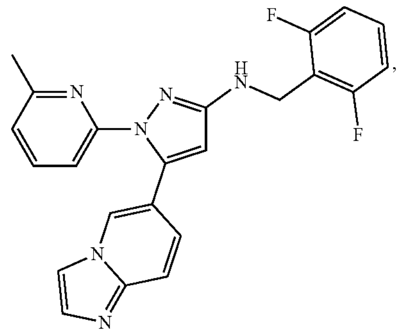
189
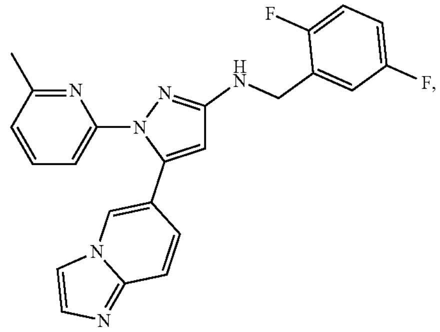
190
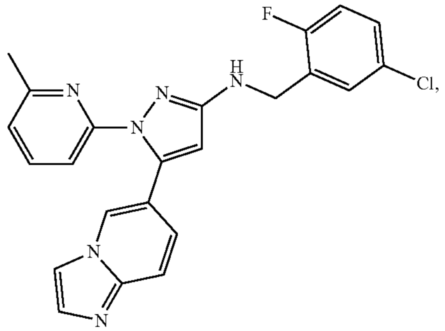
191
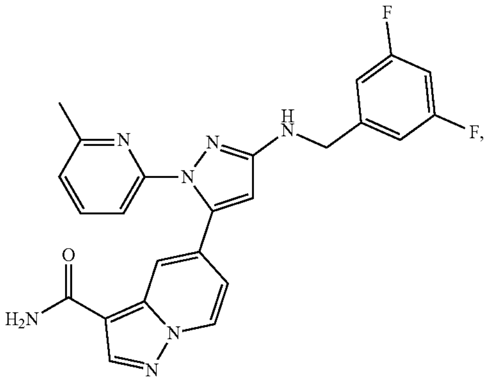

-continued
192
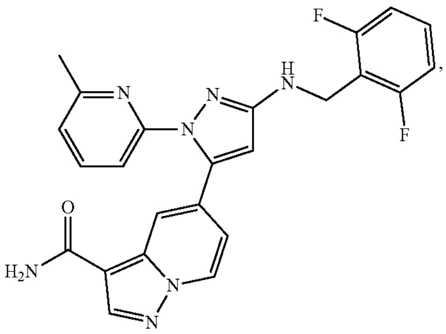
193
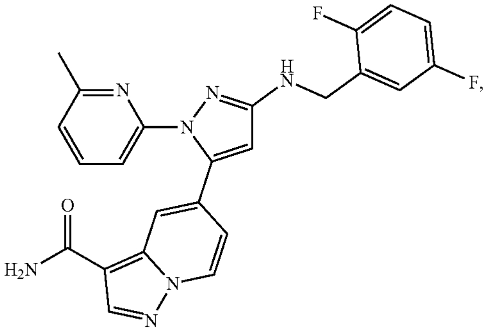
194
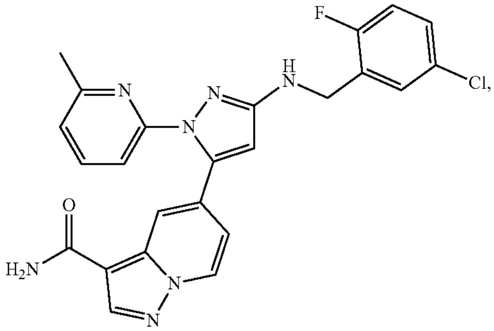
195
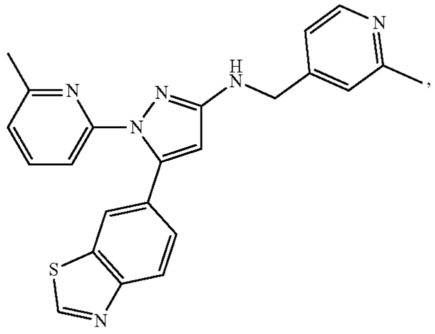
-continued
196
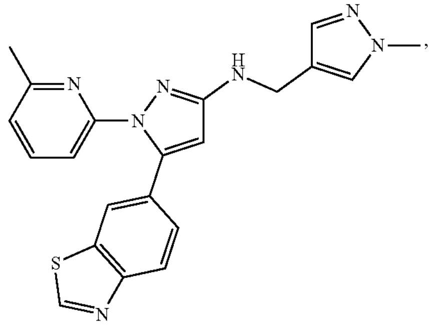
197
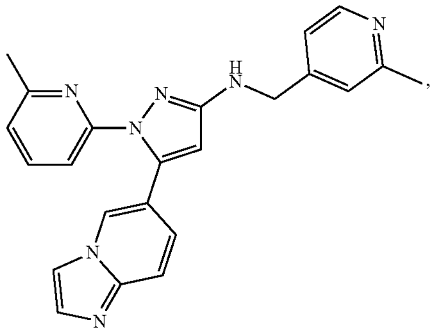
198
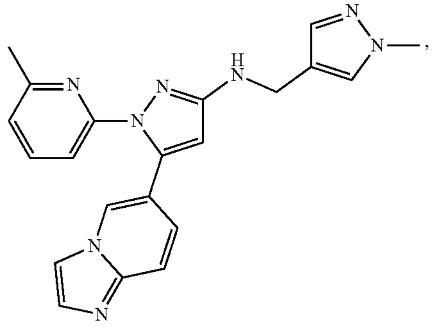
199
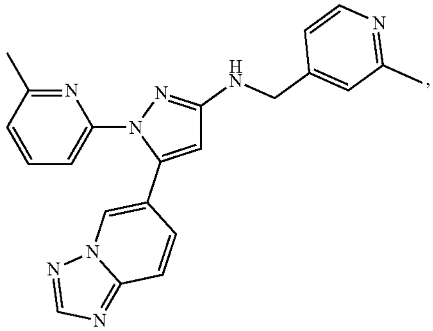

-continued
200
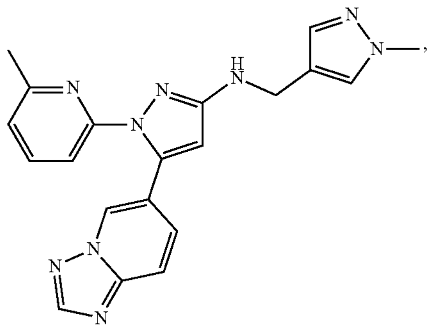
201
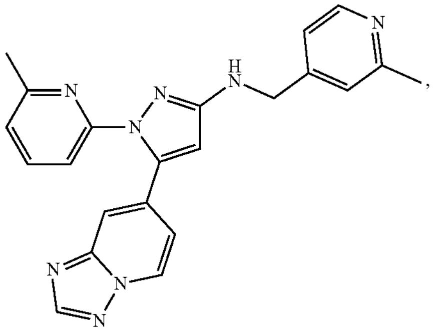
202
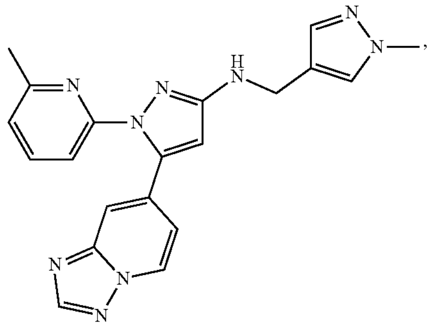
203
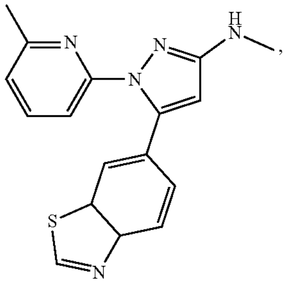
204
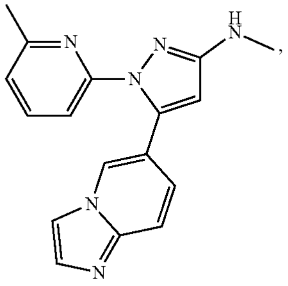
-continued
205
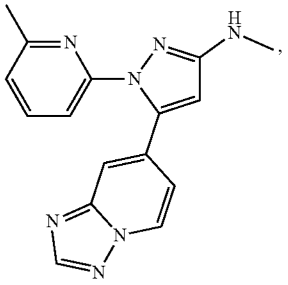
206
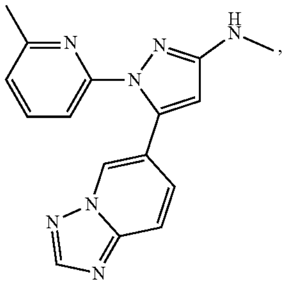
207
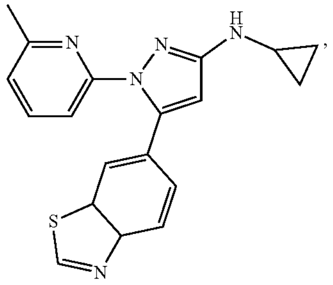
208
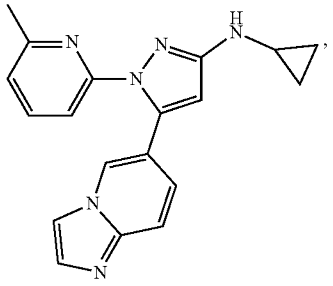
209
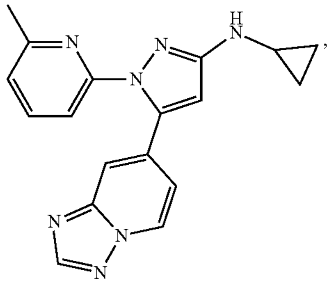

-continued

210

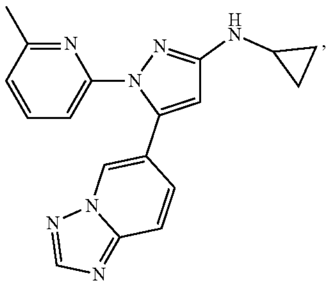

211

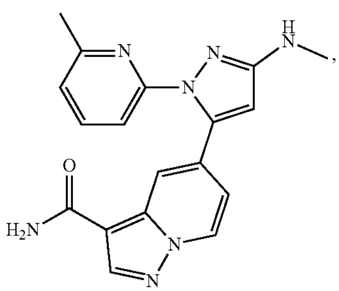

212

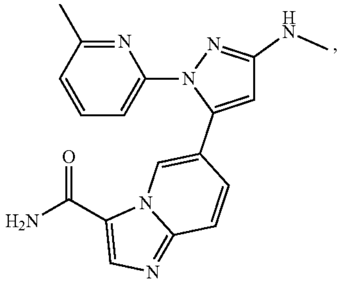

213

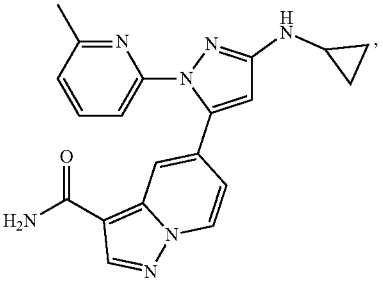

214

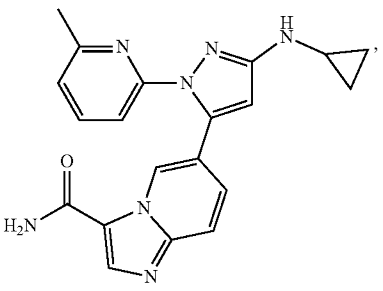

-continued

215

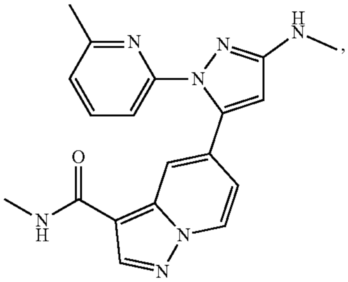

216

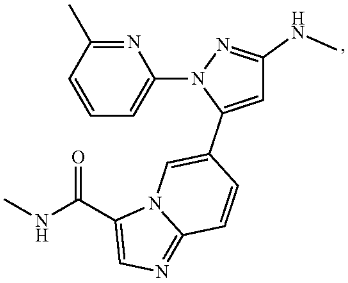

217

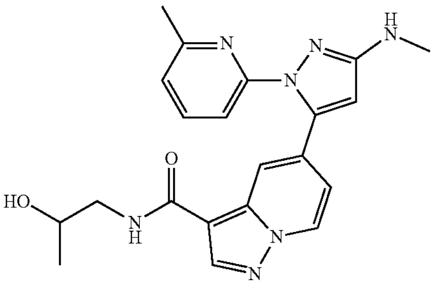

and

218

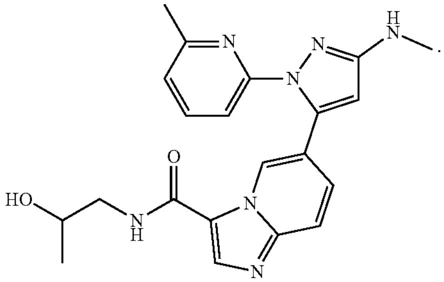

Pharmaceutical Composition

In a second aspect, the present invention provides a pharmaceutical composition comprising a compound according to the first aspect of the present invention or a pharmaceutically acceptable form thereof, and one or more pharmaceutically acceptable carriers.

The term "pharmaceutical composition" refers to a composition that can be used as a medicament, comprising a pharmaceutically active ingredient (API) (or therapeutic agent) and optionally one or more pharmaceutically acceptable carriers. The term "pharmaceutically acceptable carrier" refers to an excipient with which a therapeutic agent is administered and which, within the scope of sound medical judgment, is suitable for contact with human and/or other animal tissue without undue toxicity, irritation, allergic reaction or other problem or complication corresponding to a reasonable benefit/risk ratio.

The present invention provides a pharmaceutical composition, comprising at least one of the above compound of Formula I, Formula I-1, Formula I-2, Formula I-3, and/or Formula I-4, or a pharmaceutically acceptable form thereof.

In some embodiments of the present invention, the above pharmaceutical composition further comprises one or more pharmaceutically acceptable carriers.

The above pharmaceutical composition can act systemically and/or locally achieved by a suitable dosage form.

The above pharmaceutical composition may comprise 0.01 mg to 1000 mg of at least one of the above compound of Formula I, Formula I-1, Formula I-2, Formula I-3 and/or Formula I-4, or a pharmaceutically acceptable form thereof.

The present invention also provides a method for preparing the above pharmaceutical composition or its corresponding preparation form, which comprises combining at least one of the above compound of Formula I, Formula I-1, Formula I-2, Formula I-3 and/or Formula I-4, or a pharmaceutically acceptable form thereof, with one or more pharmaceutically acceptable carriers.

Kit Product

In a third aspect, the present invention provides a kit product, comprising:

a) at least one compound of the first aspect of the present invention or a pharmaceutically acceptable form thereof as a first therapeutic agent, or the pharmaceutical composition of the second aspect as a first pharmaceutical composition;

b) optionally, at least one other therapeutic agent as a second therapeutic agent, or a pharmaceutical composition comprising the other therapeutic agent as a second pharmaceutical composition; and c) optionally, packaging and/or instruction.

The above kit product may comprise 0.01 mg to 1000 mg of at least one of the above compound of Formula I, Formula I-1, Formula I-2, Formula I-3, and/or Formula I-4, or a pharmaceutically acceptable form thereof.

The present invention also provides a method for preparing the above kit, which comprises combing at least one of the above compound of Formula I, Formula I-1, Formula I-2, Formula I-3 and/or Formula I-4, or a pharmaceutically acceptable compound thereof, or the above pharmaceutical composition with at least one of the optional additional therapeutic agent or a pharmaceutical composition comprising the additional therapeutic agent, packaging and/or instruction.

Preparation Method

In a fourth aspect, the present invention provides a method for preparing a compound of Formula I, which is selected from one or more of the following methods.

(1) when the compound is I-1, the method is selected from Method I to Method III:

Method I:

Step 1-1: reacting Compound SM1 with N,O-dimethylhydroxylamine hydrochloride to obtain Weinreb amide IM1;

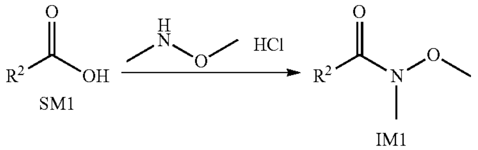

SM1 IM1

Step 1-2: reacting Weinreb amide IM1 with methyl magnesium bromide to obtain Compound IM2;

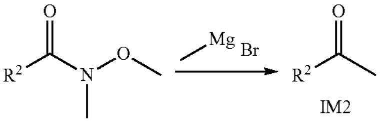

IM1 IM2

Step 1-3: subjecting Compound IM2 and N,N-dimethylformamide dimethyl acetal to a condensation reaction to obtain Compound IM3;

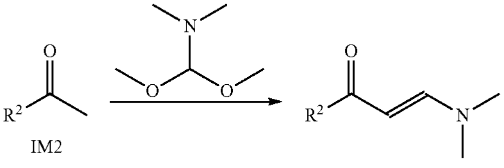

IM2 IM3

Step 1-4: subjecting Compounds IM3 and SM2 to a cyclization reaction to obtain a compound of Formula I-1;

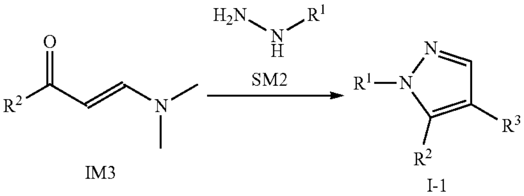

IM3 I-1 wherein, $R^1$ and $R^2$ are as defined in any item of the first aspect of the present invention, and $R^3$ is hydrogen;

In some embodiments, Step 1-1 in the above preparation method is carried out in a suitable organic solvent, which may be selected from halogenated hydrocarbons (e.g., dichloromethane, chloroform, 1,2-dichloroethane, etc.), nitriles (e.g., acetonitrile, etc.), N-methylpyrrolidone, N,N-dimethylformamide, N,N-dimethylacetamide, tetrahydrofuran, 1,4-dioxane, dimethylsulfoxide and any combination thereof, preferably N,N-dimethylformamide.

In some embodiments, Step 1-1 in the above preparation method is carried out in the presence of a suitable condensing agent. The condensing agent may be selected from the group consisting of dicyclohexylcarbodiimide (DCC), 1-ethyl-(3-dimethylaminopropyl)carbodiimide hydrochloride (EDCI), 2-(7-oxybenzotriazole)-N,N,N',N'-tetramethylurea hexafluorophosphate (HATU), O-benzotriazole-tetramethylurea hexafluorophosphate (HBTU), benzotriazol-1-yl-oxytripyrrolidinophosphorus hexafluorophosphate (PyBOP), preferably 2-(7-oxybenzotriazole)-N,N,N',N'-tetramethylurea hexafluorophosphate (HATU).

In some embodiments, Step 1-1 in the above preparation method is carried out in the presence of a suitable organic base, and the organic base may be selected from the group consisting of N,N-diisopropylethylamine, triethylamine, 4-dimethylaminopyridine and pyridine, preferably N,N-diisopropylethylamine.

In some embodiments, Step 1-1 in the above preparation method is carried out at a suitable temperature, and the temperature is 0-200° C., preferably 0-100° C.

In some embodiments, Step 1-2 in the above preparation method is carried out in a suitable organic solvent, and the organic solvent may be selected from the group consisting of hexamethylphosphoric triamide, N-methylpyrrolidone, N,N-dimethylformamide, N,N-dimethylacetamide, tetrahydrofuran, 1,4-dioxane, dimethylsulfoxide and any combination thereof, preferably tetrahydrofuran.

In some embodiments, Step 1-2 in the above preparation method is carried out at a suitable temperature, and the temperature is 0-200° C., preferably 0-100° C.

In some embodiments, Step 1-3 in the above preparation method is carried out at a suitable temperature, and the temperature is 0-200° C., preferably 0-100° C.

In some embodiments, Step 1-4 in the above preparation method is carried out in a suitable organic solvent, and the organic solvent may be selected from the group consisting of toluene, N-methylpyrrolidone, N,N-dimethylformamide, N,N-dimethylacetamide, tetrahydrofuran, 1,4-dioxane, dimethylsulfoxide and any combination thereof, preferably toluene.

In some embodiments, Step 1-4 in the above preparation method is carried out at a suitable temperature, and the temperature is 0-200° C., preferably 100-200° C.

Method II:

Step 2-1: subjecting Compound SM3 and methyl magnesium bromide to an addition reaction to obtain Compound IM4;

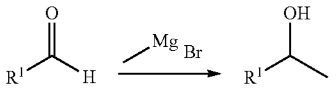

SM3 IM4

Step 2-2: subjecting Compound IM4 to an oxidation reaction to obtain Compound IM2;

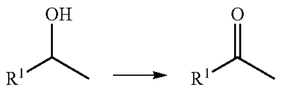

IM4 IM2

Step 2-3: subjecting Compound IM2 and N,N-dimethylformamide dimethyl acetal to a condensation reaction to obtain Compound IM3;

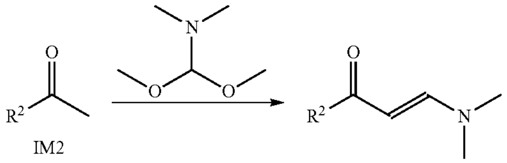

IM2 IM3

Step 2-4: subjecting Compounds IM3 and SM2 to a cyclization reaction to obtain a compound of Formula I-1;

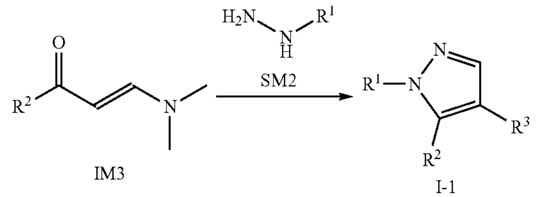

IM3 I-1 wherein, $R^1$ and $R^2$ are as defined in any item of the first aspect of the present invention, and $R^3$ is hydrogen.

In some embodiments, Step 2-1 in the above preparation method is carried out in a suitable organic solvent, and the organic solvent may be selected from the group consisting of hexamethylphosphoric triamide, N-methylpyrrolidone, N,N-dimethylformamide, N,N-dimethylacetamide, tetrahydrofuran, 1,4-dioxane, dimethylsulfoxide and any combination thereof, preferably tetrahydrofuran.

In some embodiments, Step 2-1 in the above preparation method is carried out at a suitable temperature, and the temperature is 0-200° C., preferably 0-100° C.

In some embodiments, Step 2-2 in the above preparation method is carried out in the presence of a suitable oxidizing agent. The oxidizing agent may be selected from the group consisting of Jones Reagent, pyridinium dichlorochromate (PDC), pyridinium chlorochromate (PCC), Dess-Martin reagent (Dess-Martin), Swern oxidization reagent (Swern), preferably Dess-Martin reagent (Dess-Martin).

In some embodiments, Step 2-2 in the above preparation method is carried out in a suitable organic solvent, which may be selected from halogenated hydrocarbons (e.g., dichloromethane, chloroform, 1,2-dichloroethane, etc.), tetrahydrofuran, 1,4-dioxane, dimethylsulfoxide and any combination thereof, preferably dichloromethane.

In some embodiments, Step 2-2 in the above preparation method is carried out at a suitable temperature, and the temperature is 0-200° C., preferably 0-100° C.

In some embodiments, Step 2-3 in the above preparation method is carried out at a suitable temperature, and the temperature is 0-200° C., preferably 0-100° C.

In some embodiments, Step 2-4 in the above preparation method is carried out in a suitable organic solvent, and the organic solvent may be selected from the group consisting of toluene, N-methylpyrrolidone, N,N-dimethylformamide, N,N-dimethylacetamide, tetrahydrofuran, 1,4-dioxane, dimethylsulfoxide and any combination thereof, preferably toluene.

In some embodiments, Step 1-4 in the above preparation method is carried out at a suitable temperature, and the temperature is 0-200° C., preferably 100-200° C.

Method III:

Step 3-1: subjecting Compound SM4 and N,N-dimethylformamide dimethyl acetal to a condensation reaction to obtain Compound IM5;

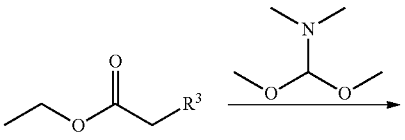

IM4

-continued

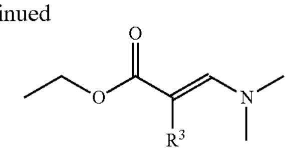

IM5

Step 3-2: subjecting Compounds IM5 and SM2 to a cyclization reaction to obtain Compound IM6;

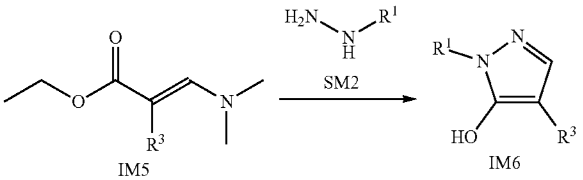

IM5 IM6

Step 3-3: subjecting Compound IM6 to a sulfonylation reaction or halogenation reaction to obtain Compound IM7;

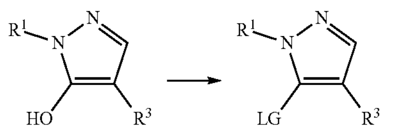

IM6 IM7

Step 3-4: subjecting Compound IM7 and Compound SM5 to a coupling reaction to obtain a compound of Formula I-2;

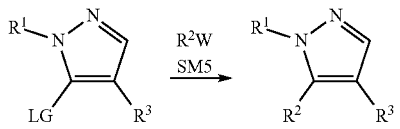

IM7 I-1 wherein, LG is a leaving group, which is selected from the group consisting of methanesulfonyl, trifluoromethanesulfonyloxy and halogen, preferably trifluoromethanesulfonyloxy or chloro; W is selected from the group consisting of boronic acid group, 4,4,5,5-tetramethyl-1,3,2-dioxaborolan-2-yl, tri-$^n$butylstannyl and sodium sulfinate group; wherein, $R^1$, $R^2$ and $R^3$ are as defined in any item of the first aspect of the present invention.

In some embodiments, Step 3-1 in the above preparation method is carried out at a suitable temperature, and the temperature is 0-200° C., preferably 0-100° C.

In some embodiments, Step 3-2 in the above preparation method is carried out in a suitable organic solvent, and the organic solvent may be selected from the group consisting of toluene, N-methylpyrrolidone, N,N-dimethylformamide, N,N-dimethylacetamide, tetrahydrofuran, 1,4-dioxane, dimethylsulfoxide and any combination thereof, preferably toluene.

In some embodiments, Step 3-2 in the above preparation method is carried out at a suitable temperature, and the temperature is 0-200° C., preferably 100-200° C.

In some embodiments, Step 3-3 in the above preparation method is carried out in a suitable organic solvent, which may be selected from the group consisting of halogenated hydrocarbons (e.g., DCM, TCM, 1,2-DCE, etc.), nitriles (e.g., AN etc.), NMP, DMF, DMA, THF, Dioxane, DMSO, aromatic hydrocarbons (e.g., TL, XY) and any combination thereof, preferably THF or DCM.

In some embodiments, Step 3-3 in the above preparation method is carried out in the presence of a suitable acylating reagent or halogenating reagent, and the acylating reagent may be selected from the group consisting of trifluoromethanesulfonic anhydride ($Tf_2O$) and N,N-bis(trifluoromethanesulfonyl)aniline, preferably N,N-bis(trifluoromethanesulfonyl)aniline, and the halogenating reagent may be selected from the group consisting of phosphorus oxytribromide ($POBr_3$) and $POl_3$, preferably $POCl_3$.

In some embodiments, Step 3-3 in the above preparation method is carried out in the presence of a suitable base, the base includes an organic base or an inorganic base, and the organic base may be selected from the group consisting of DIPEA, TEA, t-BuOK and Py, the inorganic base may be selected from the group consisting of $K_3PO_4$, NaH, $K_2CO_3$, $Na_2CO_3$, $Cs_2CO_3$ and NaOH, preferably DIPEA or TEA.

In some embodiments, Step 3-3 in the above preparation method is carried out at a suitable temperature, and the temperature is 0-200° C., preferably 0-50° C.

In some embodiments, Step 3-4 in the above preparation method is carried out in a suitable organic solvent or a mixed solution of organic solvent and water, and the organic solvent may be selected from the group consisting of halogenated hydrocarbons (e.g., DCM, TCM, 1,2-DCE, etc.), MeOH, EtOH, tert-butanol (t-BuOH), DMF, AN, ethers (e.g., ethylene glycol dimethyl ether (DME), THF, Diox), aromatic hydrocarbons (e.g., TL, XY) and any combination thereof, preferably TL or Dioxane.

In some embodiments, Step 3-4 in the above preparation method is carried out in the presence of a suitable catalyst, and the catalyst is preferably a palladium catalyst, which may be selected from the group consisting of tetrakis (triphenylphosphine)palladium(0) ($Pd(PPh_3)_4$), palladium (II) acetate ($Pd(OAc)_2$), $Pd_2(dba)_3$, $Pd(PPh_3)_2Cl_2$, $Pd(PPh_3)_2Cl_2$ dichloromethane complex, $PdCl_2(Amphos)_2$ and $Pd(dppf)Cl_2$, preferably $PdCl_2(Amphos)_2$ or $Pd(PPh_3)_4$.

In some embodiments, Step 3-4 in the above preparation method is carried out in the presence of a suitable ligand, and the ligand may be selected from the group consisting of triphenylphosphine ($PPh_3$), BINAP, tris(o-methylphenyl) phosphine ($P(o\text{-}tol)_3$), tricyclohexylphosphine tetrafluoroborate (TCHP) and X-PHOS, preferably $PPh_3$ or X-PHOS.

In some embodiments, Step 3-4 in the above preparation method is carried out in the presence of a suitable base, the base includes an organic base or an inorganic base, the organic base may be selected from the group consisting of DIPEA, TEA, t-BuOK and Py, and the inorganic base may be selected from the group consisting of $K_3PO_4$, NaH, $K_2CO_3$, $Na_2CO_3$, $Cs_2CO_3$ and NaOH, preferably $K_2CO_3$ or $Cs_2CO_3$.

In some embodiments, Step 3-4 in the above preparation method is performed at a suitable temperature, and the temperature is 0-200° C., preferably 50-150° C.

(2) When the compound is of Formula I-2, the method comprises the following steps:

Step 4-1: subjecting Compounds SM6 and SM2 to a condensation reaction to obtain Compound IM8;

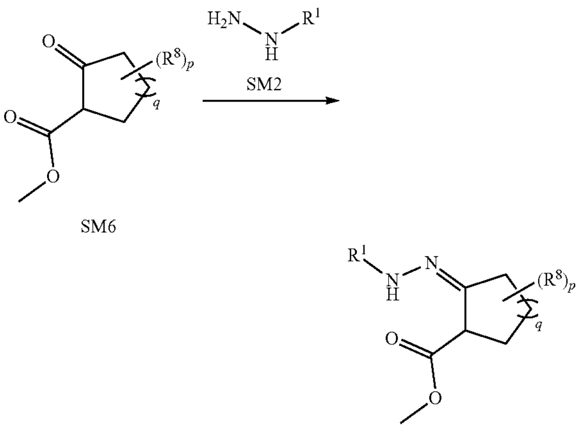

SM6

IM8

Step 4-2: subjecting Compound IM8 to a cyclization reaction with sodium methoxide to obtain Compound IM9;

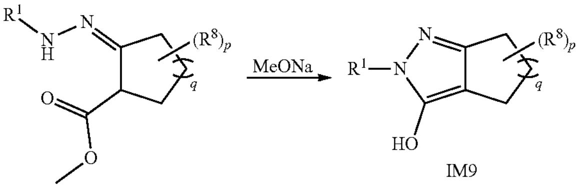

IM8 IM9

Step 4-3: subjecting Compound IM9 to a sulfonylation reaction or halogenation reaction to obtain Compound IM10;

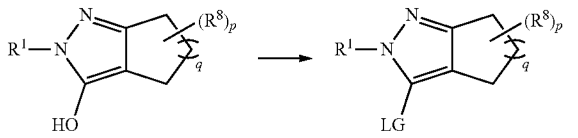

IM9 IM10

Step 4-4: subjecting Compounds IM10 and SM5 to a coupling reaction to obtain a compound of Formula I-2;

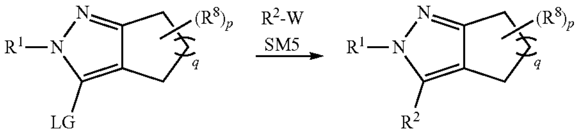

IM10 I-2 wherein, LG is a leaving group, which is selected from the group consisting of methanesulfonyl, trifluoromethanesulfonyloxy and halogen, preferably trifluoromethanesulfonyloxy or chloro; W is selected from the group consisting of boronic acid group, 4,4,5,5-tetramethyl-1,3,2-dioxaborolan-2-yl, tri-$^n$butylstannyl and sodium sulfinate group; wherein $R^1$, $R^2$, p and q are as defined in any item of the first aspect.

In some embodiments, Step 4-1 in the above preparation method is carried out in a suitable organic solvent, and the organic solvent may be selected from the group consisting of methanol, ethanol, isopropanol, tetrahydrofuran, 1,4-dioxane, N-methylpyrrolidone, N,N-dimethylformamide, N,N-dimethylacetamide, dimethylsulfoxide and any combination thereof, preferably ethanol.

In some embodiments, Step 4-1 in the above preparation method is carried out at a suitable temperature, and the temperature is 0-200° C., preferably 0-100° C.

In some embodiments, Step 4-2 in the above preparation method is carried out at a suitable temperature, and the temperature is 0-200° C., preferably 100-200° C.

In some embodiments, Step 4-3 in the above preparation method is carried out in a suitable organic solvent, and the organic solvent may be selected from the group consisting of halogenated hydrocarbons (e.g., dichloromethane, chloroform, etc.), nitriles (e.g., acetonitrile, etc.), N-methylpyrrolidone, N,N-dimethylformamide, N,N-dimethylacetamide, tetrahydrofuran, 1,4-dioxane, dimethylsulfoxide, aromatic hydrocarbons (e.g., toluene) and any combination thereof, preferably tetrahydrofuran or dichloromethane.

In some embodiments, Step 4-3 in the above preparation method is carried out in the presence of a suitable acylating reagent or halogenating reagent, and the acylating reagent may be selected from the group consisting of trifluoromethanesulfonic anhydride and N,N-bis(fluoromethanesulfonyl) aniline, preferably N,N-bis(trifluoromethanesulfonyl)aniline, and the halogenating agent may be selected from the group consisting of phosphorus oxybromide and phosphorus oxychloride, preferably phosphorus oxychloride.

In some embodiments, Step 4-3 in the above preparation method is carried out in the presence of a suitable base, the base includes an organic base or an inorganic base, and the organic base may be selected from the group consisting of N,N-diisopropylethylamine, triethylamine, 4-dimethylaminopyridine and pyridine, the inorganic base can be selected from the group consisting of $K_3PO_4$, NaH, $K_2CO_3$, $Na_2CO_3$, $Cs_2CO_3$ and NaOH, preferably N,N-diisopropylethylamine or triethylamine.

In some embodiments, Step 4-3 in the above preparation method is performed at a suitable temperature, and the temperature is 0-200° C., preferably 0-50° C.

In some embodiments, Step 4-4 in the above preparation method is carried out in a suitable organic solvent or a mixed solution of organic solvent and water, and the organic solvent may be selected from the group consisting of halogenated hydrocarbons (e.g., dichloromethane, chloroform, 1,2-dichloroethane, etc.), methanol, ethanol, tert-butanol, N,N-dimethylformamide, acetonitrile, ethers (e.g., ethylene glycol dimethyl ether, tetrahydrofuran, 1,4-dioxane), aromatic hydrocarbons (e.g., toluene) and any combination thereof, preferably toluene or 1,4-dioxane.

In some embodiments, Step 4-4 in the above preparation method is carried out in the presence of a suitable catalyst, and the catalyst is preferably a palladium catalyst, which may be selected from the group consisting of tetrakis (triphenylphosphine)palladium(0) ($Pd(PPh_3)_4$), palladium(II)acetate ($Pd(OAc)_2$), $Pd_2(dba)_3$, $Pd(PPh_3)_2Cl_2$, $Pd(PPh_3)_2Cl_2$ dichloromethane complex, $PdCl_2(Amphos)_2$ and $Pd(dppf)Cl_2$, preferably $PdCl_2(Amphos)_2$ or $Pd(dppf)Cl_2$.

In some embodiments, Step 4-4 in the above preparation method is carried out in the presence of a suitable ligand, the ligand may be selected from the group consisting of triphenylphosphine ($PPh_3$), BINAP, tris (o-methylphenyl)phosphine (P (o-tol)$_3$), tricyclohexylphosphine tetrafluoroborate (TCHP) and X-PHOS, preferably $PPh_3$ or X-PHOS.

In some embodiments, Step 4-4 in the above preparation method is carried out in the presence of a suitable base, the base includes an organic base or an inorganic base, and the organic base may be selected from the group consisting of N,N-diisopropylethylamine, triethylamine, 4-dimethylaminopyridine and pyridine, and the inorganic base may be selected from the group consisting of $K_3PO_4$, NaH, $K_2CO_3$, $Na_2CO_3$, $Cs_2CO_3$ and NaOH, preferably $K_2CO_3$ or $Cs_2CO_3$.

In some embodiments, Step 4-4 in the above preparation method is carried out at a suitable temperature, and the temperature is 0-200° C., preferably 50-150° C.

(3) When the compound is of Formula I-3, the preparation method comprises the following steps:

Step 5-1: subjecting Compound SM2 to a cyclization reaction with diethyl oxaloacetate sodium salt to obtain Compound IM11;

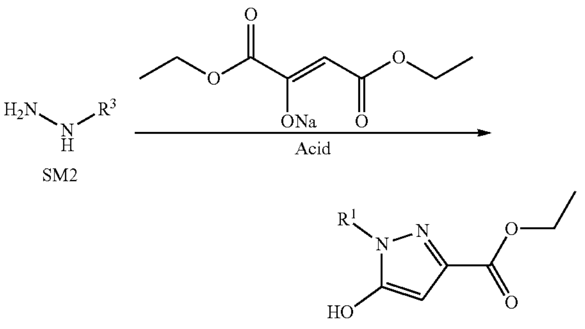

SM2

IM11

Step 5-2: subjecting Compound IM11 to Vilsmeier-Haack reaction to obtain Compound IM12;

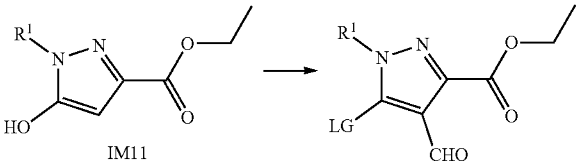

IM11

IM12

Step 5-3: subjecting Compound IM12 to a coupling reaction with Compound SM5 to obtain Compound IM13;

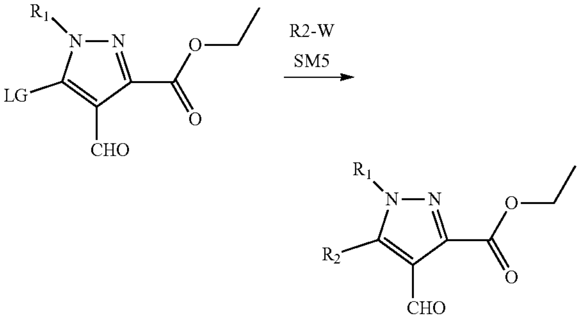

Step 5-4: subjecting Compound IM13 to Wittig reaction with a compound of methoxymethylphosphorus ylide to obtain Compound IM14;

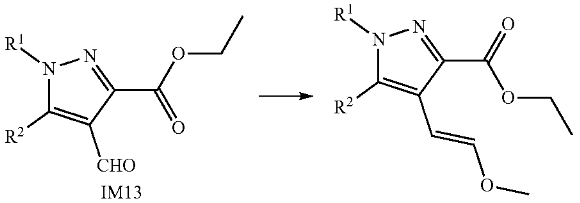

IM13

IM14

Step 5-5: subjecting Compound IM14 to a demethylation reaction to obtain Compound IM15;

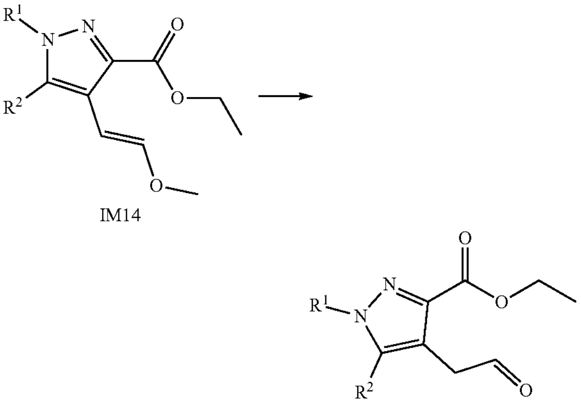

IM14

IM15

Step 5-6: subjecting Compound IM15 to a reduction reaction to obtain Compound IM16;

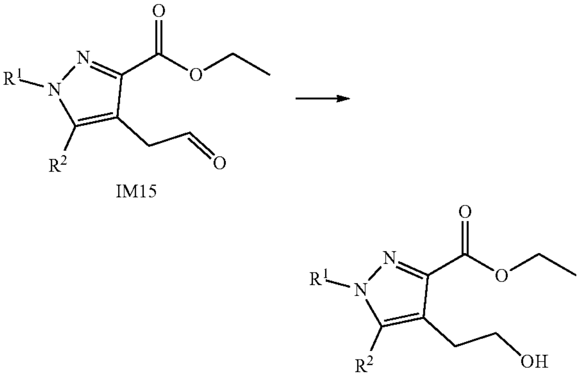

IM15

IM16

Step 5-7: subjecting Compound IM16 to a substitution reaction to obtain Compound IM17;

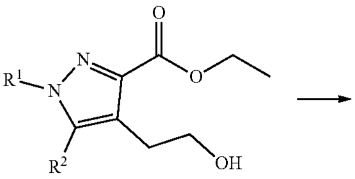

IM16

-continued

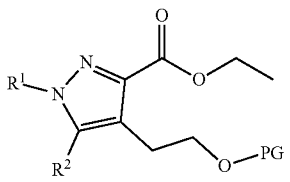

IM17

Step 5-8: subjecting Compound IM17 to a hydrolysis reaction to obtain Compound IM18;

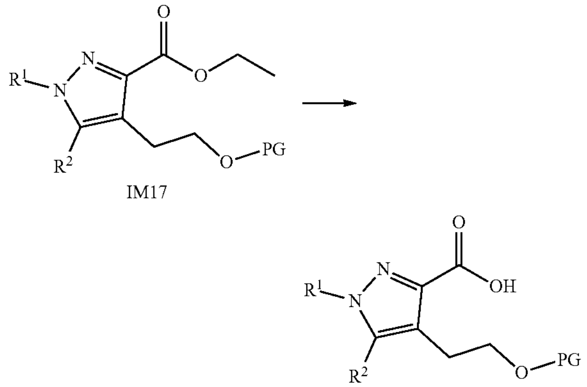

IM17

IM18

Step 5-9: subjecting Compound IM18 to Curtius rearrangement reaction to obtain Compound IM19;

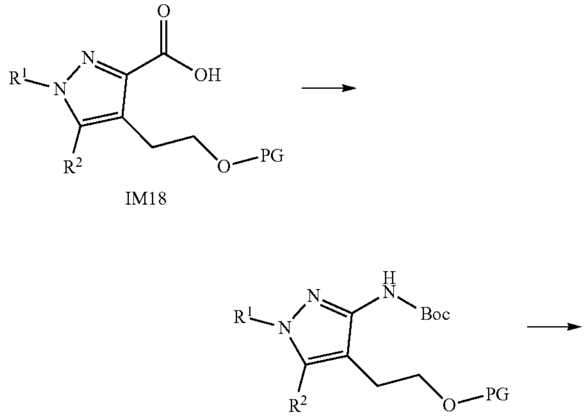

IM18

IM19

Step 5-10: deprotecting Compound IM19 to obtain Compound IM20;

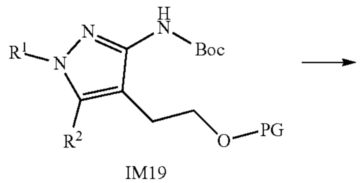

IM19

-continued

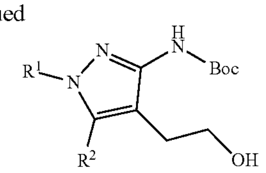

IM20

Step 5-11: subjecting Compound IM20 to a sulfonylation reaction or halogenation reaction to obtain Compound IM21;

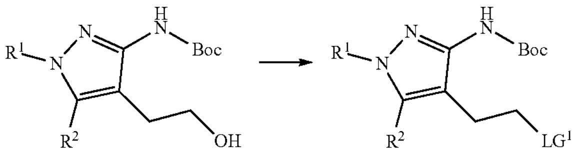

IM20 IM21

Step 5-12: deprotecting Compound IM21 to obtain Compound IM22;

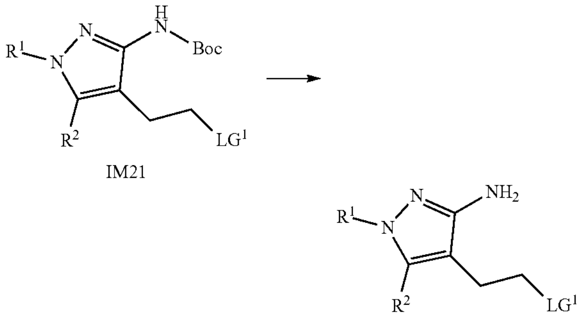

IM21

IM22

Step 5-13: subjecting Compound IM22 to a substitution reaction to obtain a compound of Formula I-3;

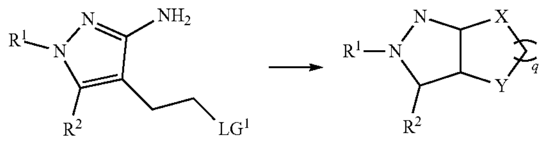

IM22 I-3 wherein, LG is halogen, which is selected from the group consisting of chloro, bromo, preferably chloro; PG is a protecting group, which is selected from the group consisting of trimethylsilyl, triethylsilyl, triisopropylsilyl, tert-butyl-dimethyl-silyl, tert-butyl-diphenyl-silyl, preferably tert-butyl-dimethylsilyl; $LG^1$ is a leaving group, which is selected from the group consisting of methanesulfonyl, trifluoromethanesulfonyloxy and halogen, preferably trifluoromethanesulfonyloxy or chloro; W is selected from the group consisting of boronic acid group, 4,4,5,5-tetramethyl-1,3,2-dioxaborolan-2-yl, tri-butylstannyl and sodium sulfinate group; wherein X is NH, Y is $CH_2$, and $R^1$, $R^2$ and q are as defined in any item of the first aspect of the present invention.

In some embodiments, Step 5-1 in the above preparation method is carried out in a suitable organic solvent, and the organic solvent may be selected from the group consisting of halogenated hydrocarbons (e.g., dichloromethane, chloroform, 1,2-dichloroethane, etc.), nitriles (e.g., acetonitrile, etc.), N-methylpyrrolidone, N,N-dimethylformamide, N,N-dimethylacetamide, tetrahydrofuran, 1,4-dioxane, dimethylsulfoxide, aromatic hydrocarbons (e.g., toluene, xylene, etc.) and any combination thereof, preferably toluene.

In some embodiments, Step 5-1 in the above preparation method is carried out in the presence of a suitable acid, and the acid may be selected from the group consisting of p-toluenesulfonic acid and acetic acid, preferably acetic acid.

In some embodiments, Step 5-1 in the above preparation method is carried out at a suitable temperature, and the temperature is 0-200° C., preferably 25-160° C.

In some embodiments, Step 5-2 in the above preparation method is carried out in the presence of a suitable Vilsmeier-Haack reagent, and the Vilsmeier-Haack reagent may be selected from the group consisting of phosphorous oxychloride-N,N-dimethylformamide, phosphorus oxybromide-N,N-dimethylformamide, preferably phosphorus oxychloride-N,N-dimethylformamide.

In some embodiments, Step 5-2 in the above preparation method is carried out in a suitable organic solvent, and the organic solvent may be selected from the group consisting of halogenated hydrocarbons (e.g., dichloromethane, chloroform, 1,2-dichloroethane, etc.), N,N-dimethylformamide, N,N-dimethylacetamide and any combination thereof, preferably N,N-dimethylformamide.

In some embodiments, Step 5-2 in the above preparation method is carried out at a suitable temperature, and the temperature is 0-200° C., preferably 0-100° C.

In some embodiments, Step 5-3 in the above preparation method is carried out in a suitable organic solvent or a mixed solution of organic solvent and water, and the organic solvent may be selected from the group consisting of halogenated hydrocarbons (e.g., dichloromethane, chloroform, 1,2-dichloroethane, etc.), methanol, ethanol, tert-butanol, N,N-dimethylformamide, acetonitrile, ethers (e.g., ethylene glycol dimethyl ether, tetrahydrofuran, 1,4-dioxane, etc.), aromatic hydrocarbons (e.g., toluene, xylene, etc.), and any combination thereof, preferably toluene or 1,4-dioxane.

In some embodiments, Step 5-3 in the above preparation method is carried out in the presence of a suitable catalyst, and the catalyst is preferably a palladium catalyst, which may be selected from the group consisting of tetrakis (triphenylphosphine)palladium(0) ($Pd(PPh_3)_4$), palladium (II) acetate ($Pd(OAc)_2$), $Pd_2(dba)_3$, $Pd(PPh_3)_2Cl_2$, $Pd(PPh_3)_2Cl_2$ dichloromethane complex, $PdCl_2(Amphos)_2$ and $Pd(dppf)Cl_2$, preferably $Pd(dppf)Cl_2$ or $Pd(PPh_3)_4$.

In some embodiments, Step 5-3 of the above preparation method is carried out in the presence of a suitable ligand, and the ligand may be selected from the group consisting of triphenylphosphine ($PPh_3$), BINAP, tris(o-methylphenyl) phosphine ($P(o\text{-}tol)_3$), tricyclohexylphosphine tetrafluoroborate (TCHP) and X-PHOS, preferably $PPh_3$ or X-PHOS.

In some embodiments, Step 5-3 in the above preparation method is carried out in the presence of a suitable base, the base includes an organic base or an inorganic base, and the organic base may be selected from the group consisting of N,N-diisopropylethylamine, triethylamine, 4-dimethylaminopyridine and pyridine, the inorganic base may be selected from the group consisting of $K_3PO_4$, NaH, $K_2CO_3$, $Na_2CO_3$, $Cs_2CO_3$ and NaOH, preferably $K_2CO_3$ or $Cs_2CO_3$.

In some embodiments, Step 5-3 in the above preparation method is carried out at a suitable temperature, and the temperature is 0-200° C., preferably 50-150° C.

In some embodiments, Step 5-4 in the above preparation method is carried out in a suitable organic solvent, and the organic solvent may be selected from the group consisting of halogenated hydrocarbons (e.g., dichloromethane, chloroform, 1,2-dichloroethane, etc.), N,N-dimethylformamide, ethers (e.g., ethylene glycol dimethyl ether, tetrahydrofuran, 1,4-dioxane), aromatic hydrocarbons (e.g., toluene, xylene, etc.), and any combination thereof, preferably tetrahydrofuran.

In some embodiments, Step 5-4 in the above preparation method is carried out in the presence of a suitable base, the base may be selected from the group consisting of potassium tert-butoxide, sodium tert-butoxide, sodium hydride, n-butyllithium and sodium amide, preferably, potassium tert-butoxide.

In some embodiments, Step 5-4 in the above preparation method is carried out at a suitable temperature, and the temperature is 0-200° C., preferably 0-50° C.

In some embodiments, Step 5-5 in the above preparation method is carried out in the presence of a suitable acid, and the acid may be selected from the group consisting of p-toluenesulfonic acid, formic acid, hydrochloric acid, sulfuric acid, preferably hydrochloric acid.

In some embodiments, Step 5-5 in the above preparation method is carried out in a mixed solution of a suitable organic solvent and water, and the organic solvent may be selected from the group consisting of N,N-dimethylformamide, ethers (e.g., ethylene glycol dimethyl ether, tetrahydrofuran, 1,4-dioxane), aromatic hydrocarbons (e.g., toluene, xylene, etc.) and any combination thereof, preferably tetrahydrofuran.

In some embodiments, Step 5-5 in the above preparation method is carried out at a suitable temperature, and the temperature is 0-200° C., preferably 0-100° C.

In some embodiments, Step 5-6 in the above preparation method is carried out in the presence of a suitable reducing agent, and the reducing agent may be selected from the group consisting of sodium borohydride, lithium tri-tert-butoxyaluminum hydride, and triisopropoxyaluminum, preferably sodium borohydride.

In some embodiments, Step 5-6 in the above preparation method is carried out in a suitable organic solvent, and the organic solvent may be selected from the group consisting of alcohols (e.g., methanol, ethanol), ethers (e.g., ethylene glycol dimethyl ether, tetrahydrofuran, 1,4-dioxane) and any combination thereof, preferably methanol.

In some embodiments, Step 5-6 in the above preparation method is carried out at a suitable temperature, and the temperature is 0-200° C., preferably 0-50° C.

In some embodiments, Step 5-7 in the above preparation method is performed in the presence of a suitable silicon reagent, and the silicon reagent may be selected from the group consisting of trimethylchlorosilane, triethylchlorosilane, triisopropylchlorosilane, tert-butyldimethylchlorosilane and tert-butyldiphenylchlorosilane, preferably tert-butyldimethylchlorosilane.

In some embodiments, Step 5-7 in the above preparation method is carried out in the presence of a suitable base, and the base may be selected from the group consisting of N,N-diisopropylethylamine, triethylamine, 4-dimethylaminopyridine, imidazole and pyridine, preferably imidazole or pyridine.

In some embodiments, Step 5-7 in the above preparation method is carried out in a suitable organic solvent, and the organic solvent may be selected from the group consisting of halogenated hydrocarbons (e.g., dichloromethane, chloroform, 1,2-dichloroethane, etc.), N,N-dimethylformamide, ethers (e.g., ethylene glycol dimethyl ether, tetrahydrofuran, 1,4-dioxane), aromatic hydrocarbons (e.g., toluene, xylene, etc.), and any combination thereof, preferably N,N-dimethylformamide.

In some embodiments, Step 5-7 in the above preparation method is carried out at a suitable temperature, and the temperature is 0-200° C., preferably 0-100° C.

In some embodiments, Step 5-8 in the above preparation method is carried out in the presence of a suitable base, and the base may be selected from the group consisting of sodium hydroxide, lithium hydroxide, potassium hydroxide, sodium methoxide, sodium tert-butoxide, preferably sodium hydroxide.

In some embodiments, Step 5-8 in the above preparation method is carried out in a mixed solution of a suitable organic solvent and water, and the organic solvent may be selected from the group consisting of methanol, ethanol, tetrahydrofuran, 1,4-dioxane, N,N-dimethylformamide and any combination thereof, preferably tetrahydrofuran.

In some embodiments, Step 5-8 in the above preparation method is carried out at a suitable temperature, and the temperature is 0-200° C., preferably 0-100° C.

In some embodiments, Step 5-9 in the above preparation method is carried out in the presence of a suitable azide reagent, and the azide reagent may be selected from the group consisting of sodium azide, azidotrimethylsilane and diphenylphosphoryl azide, preferably diphenylphosphoryl azide.

In some embodiments, Step 5-9 in the above preparation method is carried out in the presence of a suitable base, and the base may be selected from the group consisting of N,N-diisopropylethylamine, triethylamine and pyridine, preferably triethylamine.

In some embodiments, Step 5-9 in the above preparation method is carried out at a suitable temperature, and the temperature is 0-200° C., preferably 0-100° C.

In some embodiments, Step 5-10 of the above preparation method is carried out in a suitable organic solvent, and the organic solvent may be selected from the group consisting of halogenated hydrocarbons (e.g., dichloromethane, chloroform, 1,2-dichloroethane, etc.), N,N-dimethylformamide, ethers (e.g., ethylene glycol dimethyl ether, tetrahydrofuran, 1,4-dioxane), aromatic hydrocarbons (e.g., toluene, xylene, etc.), and any combination thereof, preferably tetrahydrofuran.

In some embodiments, Step 5-10 of the above preparation method is carried out in the presence of a suitable fluorine reagent, and the fluorine reagent may be selected from the group consisting of tetrabutylammonium fluoride (TBAF), tetramethylammonium fluoride, and tetraethylammonium fluoride, preferably tetrabutylammonium fluoride (TBAF).

In some embodiments, Step 5-10 in the above preparation method is carried out at a suitable temperature, and the temperature is 0-200° C., preferably 0-50° C.

In some embodiments, Step 5-11 in the above preparation method is carried out in the presence of a suitable acylating reagent or halogenating reagent, and the acylating reagent may be selected from the group consisting of methanesulfonyl chloride, trifluoromethanesulfonic anhydride and N,N-bis(trifluoromethanesulfonyl)aniline, preferably methanesulfonyl chloride, and the halogenating agent may be selected from the group consisting of thionyl chloride, phosphorus oxybromide and phosphorus oxychloride, preferably thionyl chloride.

In some embodiments, Step 5-11 in the above preparation method is carried out in the presence of a suitable base, the base includes an organic base or an inorganic base, the organic base may be selected from the group consisting of N,N-diisopropylethylamine, triethylamine, 4-dimethylaminopyridine and pyridine, and the inorganic base may be selected from the group consisting of $K_3PO_4$, NaH, $K_2CO_3$, $Na_2CO_3$, $Cs_2CO_3$ and NaOH, preferably N,N-diisopropylethylamine or triethylamine.

In some embodiments, Step 5-11 in the above preparation method is carried out at a suitable temperature, and the temperature is 0-200° C., preferably 0-50° C.

In some embodiments, Step 5-12 in the above preparation method is carried out in a suitable organic solvent, and the organic solvent may be selected from halogenated hydrocarbons (e.g., dichloromethane, chloroform, 1,2-dichloroethane, etc.), N,N-dimethylformamide, ethers (e.g., ethylene glycol dimethyl ether, tetrahydrofuran, 1,4-dioxane), aromatic hydrocarbons (e.g., toluene, xylene, etc.), and any combination thereof, preferably dichloromethane and 1,4-dioxane.

In some embodiments, Step 5-12 of the above preparation method is carried out in a suitable acid, and the acid may be selected from the group consisting of hydrochloric acid, sulfuric acid, acetic acid and trifluoroacetic acid, preferably hydrochloric acid and trifluoroacetic acid.

In some embodiments, Step 5-12 in the above preparation method is carried out at a suitable temperature, and the temperature is 0-200° C., preferably 0-50° C.

In some embodiments, Step 5-13 of the above preparation method is carried out in a suitable organic solvent, and the organic solvent may be selected from the group consisting of halogenated hydrocarbons (e.g., dichloromethane, chloroform, 1,2-dichloroethane, etc.), nitriles (e.g., acetonitrile, etc.), N-methylpyrrolidone, N,N-dimethylformamide, N,N-dimethylacetamide, tetrahydrofuran, 1,4-dioxane, dimethylsulfoxide and any combination thereof, preferably acetonitrile.

In some embodiments, Step 5-13 in the above preparation method is carried out in the presence of a suitable base, the base includes an organic base or an inorganic base, and the organic base may be selected from the group consisting of N,N-diisopropylethylamine (DIPEA), triethylamine, potassium tert-butoxide and pyridine, and the inorganic base may be selected from the group consisting of $K_3PO_4$, NaH, $K_2CO_3$, $Na_2CO_3$, $NaHCO_3$, $Cs_2CO_3$ and NaOH, preferably N,N-diisopropylethylamine (DIPEA) or potassium tert-butoxide.

In some embodiments, Step 5-13 in the above preparation method is carried out at a suitable temperature, and the temperature is 0-200° C., preferably 0-100° C.

(4) When the compound is of Formula I-4, the preparation method optionally comprises the following Method I to Method III:

Method I:

Step 6-1: subjecting Compounds SM2 and SM7 to a cyclization reaction to obtain Compound IM23;

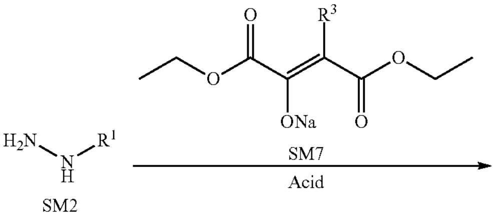

SM2

-continued

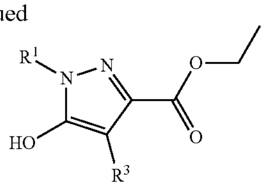

IM23

Step 6-2: subjecting Compound IM23 to a sulfonylation reaction or halogenation reaction to obtain Compound IM24;

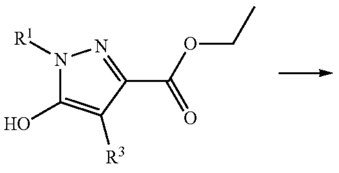

IM23

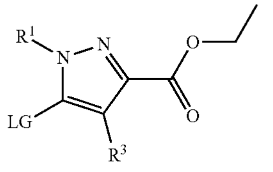

IM24

Step 6-3: subjecting Compound IM24 and Compound SM5 to a coupling reaction to obtain Compound IM25;

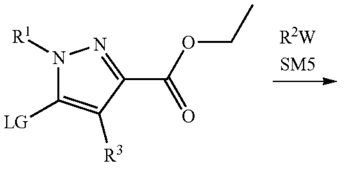

IM24

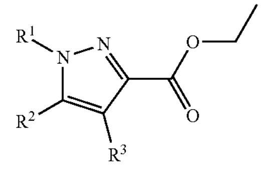

IM25

Step 6-4: subjecting Compound IM25 to a hydrolysis reaction to obtain Compound IM26;

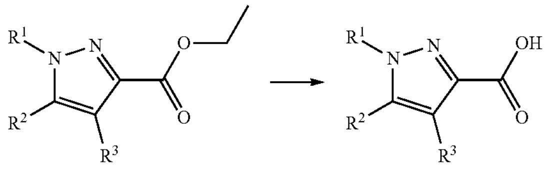

IM25 IM26

Step 6-5: subjecting Compound IM26 to Curtius rearrangement reaction to obtain Compound IM27;

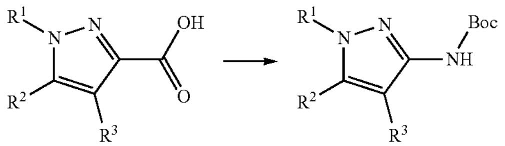

IM26 IM27

Step 6-6: subjecting Compound IM27 and Compound SM8 to a substitution reaction to obtain Compound IM28;

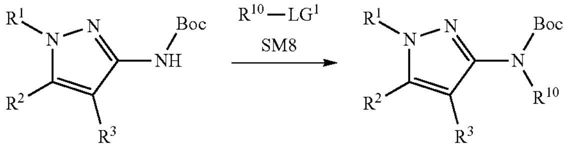

IM27 IM28

Step 6-7: deprotecting Compound IM28 to obtain a compound of Formula I-4;

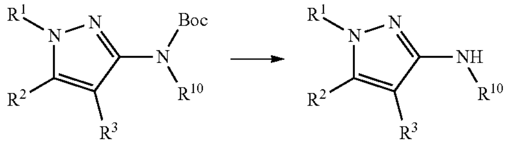

IM28 I-4 wherein, LG is a leaving group, which is selected from the group consisting of methanesulfonyloxy, trifluoromethanesulfonyloxy and halogen, preferably trifluoromethanesulfonyloxy or chloro; $LG^1$ is a leaving group, which is selected from the group consisting of methanesulfonyloxy, trifluoromethanesulfonyloxy and halogen, preferably trifluoromethanesulfonyloxy or iodo; W is selected from the group consisting of boronic acid group, 4,4,5,5-tetramethyl-1,3,2-dioxaborolan-2-yl, tri-$^n$butylstannyl and sodium sulfinate group; $R^1$, $R^2$, $R^3$ and $R^{10}$ are as defined in any item of the first aspect of the present invention.

In some embodiments, Step 6-1 in the above preparation method is carried out in a suitable organic solvent, and the organic solvent may be selected from the group consisting of halogenated hydrocarbons (e.g., dichloromethane (DCM), chloroform (TCM), 1,2-dichloroethane (1,2-DCE), etc.), nitriles (e.g., acetonitrile (AN), etc.), N-methylpyrrolidone (NMP), N,N-dimethylformamide (DMF), N,N-dimethylacetamide (DMA), tetrahydrofuran (THF), 1,4-dioxane (Diox), dimethylsulfoxide (DMSO), aromatic hydrocarbons (e.g., toluene (TL), xylene (XY), etc.) and any combination thereof, preferably TL.

In some embodiments, Step 6-1 in the above preparation method is carried out in the presence of a suitable acid, and the acid may be selected from the group consisting of p-toluenesulfonic acid (TsOH) and acetic acid (AcOH), preferably AcOH.

In some embodiments, Step 6-1 in the above preparation method is carried out at a suitable temperature, and the temperature is 0-200° C., preferably 25-160° C.

In some embodiments, Step 6-2 in the above preparation method is carried out in a suitable organic solvent, and the organic solvent may be selected from the group consisting of halogenated hydrocarbons (e.g., DCM, TCM, 1,2-DCE, etc.), nitriles (e.g., AN, etc.), NMP, DMF, DMA, THF, Dioxane, DMSO, aromatic hydrocarbons (e.g., TL, XY) and any combination thereof, preferably THF or DCM.

In some embodiments, Step 6-2 in the above preparation method is carried out in the presence of a suitable acylating reagent or halogenating reagent, and the acylating reagent may be selected from the group consisting of trifluoromethanesulfonic anhydride ($Tf_2O$) and N,N-bis(trifluoromethanesulfonyl)aniline, preferably N,N-bis(trifluoromethanesulfonyl)aniline, and the halogenating reagent may be selected from the group consisting of phosphorus oxybromide ($POBr_3$) and $POCl_3$, preferably $POCl_3$.

In some embodiments, Step 6-2 in the above preparation method is carried out in the presence of a suitable base, the base includes an organic base or an inorganic base, and the organic base may be selected from the group consisting of DIPEA, TEA, t-BuOK and Py, and the inorganic base may be selected from the group consisting of $K_3PO_4$, NaH, $K_2CO_3$, $Na_2CO_3$, $Cs_2CO_3$ and NaOH, preferably DIPEA or TEA.

In some embodiments, Step 6-2 in the above preparation method is carried out at a suitable temperature, and the temperature is 0-200° C., preferably 0-50° C.

In some embodiments, Step 6-3 in the above preparation method is carried out in a suitable organic solvent or a mixed solution of an organic solvent and water, and the organic solvent may be selected from the group consisting of halogenated hydrocarbons (e.g., DCM, TCM, 1,2-DCE, etc.), MeOH, EtOH, tert-butanol (t-BuOH), DMF, AN, ethers (e.g., ethylene glycol dimethyl ether (DME), THF, Diox), aromatic hydrocarbons (e.g., TL, XY) and any combination thereof, preferably TL or Dioxane.

In some embodiments, Step 6-3 in the above preparation method is carried out in the presence of a suitable catalyst, and the catalyst is preferably a palladium catalyst, which may be selected from the group consisting of tetrakis (triphenylphosphine)palladium(0) ($Pd(PPh_3)_4$), palladium (II) acetate ($Pd(OAc)_2$), $Pd_2(dba)_3$, $Pd(PPh_3)_2Cl_2$, $Pd(PPh_3)_2Cl_2$ dichloromethane complex, $PdCl_2(Amphos)_2$ and $Pd(dppf)Cl_2$, preferably $PdCl_2(Amphos)_2$ or $Pd(PPh_3)_4$.

In some embodiments, Step 6-3 of the above preparation method is carried out in the presence of a suitable ligand, and the ligand may be selected from the group consisting of triphenylphosphine ($PPh_3$), BINAP, tris(o-methylphenyl) phosphine ($P(o\text{-}tol)_3$), tricyclohexylphosphine tetrafluoroborate (TCHP) and X-PHOS, preferably $PPh_3$ or X-PHOS.

In some embodiments, Step 6-3 in the above preparation method is carried out in the presence of a suitable base, the base includes an organic base or an inorganic base, the organic base may be selected from the group consisting of DIPEA, TEA, t-BuOK and Py, and the inorganic base may be selected from the group consisting of $K_3PO_4$, NaH, $K_2CO_3$, $Na_2CO_3$, $Cs_2CO_3$ and NaOH, preferably $K_2CO_3$ or $Cs_2CO_3$.

In some embodiments, Step 6-3 in the above preparation method is carried out at a suitable temperature, and the temperature is 0-200° C., preferably 50-150° C.

In some embodiments, Step 6-4 in the above preparation method is carried out in a suitable organic solvent or a mixed solvent of organic solvent and water, and the organic solvent may be selected from the group consisting of alcohols (e.g., methanol (MeOH), ethanol (EtOH)), n-butanol (n-BuOH, etc.), THF, AcOH, Diox and any combination thereof, preferably THF, EtOH, or a mixed solvent thereof with water.

In some embodiments, Step 6-4 in the above preparation method is carried out in the presence of a suitable base, the base may be selected from the group consisting of sodium hydroxide (NaOH), potassium hydroxide (KOH) and lithium hydroxide (LiOH), preferably LiOH.

In some embodiments, Step 6-4 in the above preparation method is carried out at a suitable temperature, the temperature being 0-100° C., preferably 25-80° C.

In some embodiments, Step 6-5 in the above preparation method is carried out in a suitable organic solvent or a mixed solvent of an organic solvent and water, and the organic solvent may be selected from the group consisting of alcohols (e.g., methanol (MeOH), ethanol (EtOH), tert-butanol (t-BuOH), etc.), NMP, DMF, aromatic hydrocarbons (e.g., TL, XY) and any combination thereof, preferably tert-butanol, DMF and TL.

In some embodiments, Step 6-5 in the above preparation method is carried out in the presence of a suitable azidation reagent, and the azidation reagent may be selected from DPPA and sodium azide, preferably DPPA.

In some embodiments, Step 6-5 in the above preparation method is carried out in the presence of a suitable base, the base includes an organic base or an inorganic base, the organic base may be selected from the group consisting of DIPEA, TEA, t-BuOK and Py, and the inorganic base may be selected from the group consisting of $K_3PO_4$, NaH, $K_2CO_3$, $Na_2CO_3$, $Cs_2CO_3$ and NaOH, preferably DIPEA or TEA.

In some embodiments, Step 6-5 in the above preparation method is carried out at a suitable temperature, and the temperature is 0-200° C., preferably 20-150° C.

In some embodiments, Step 6-6 in the above preparation method is carried out in a suitable organic solvent, and the organic solvent may be selected from the group consisting of halogenated hydrocarbons (e.g., dichloromethane (DCM), chloroform (TCM), 1,2-dichloroethane (1,2-DCE), etc.), nitriles (e.g., acetonitrile (AN), etc.), N-methylpyrrolidone (NMP), N,N-dimethylformamide (DMF), N,N-dimethylacetamide (DMA), tetrahydrofuran (THF), 1,4-dioxane (Diox), dimethylsulfoxide (DMSO) and any combination thereof, preferably acetonitrile.

In some embodiments, Step 6-6 in the above preparation method is carried out in the presence of a suitable base, the base includes an organic base or an inorganic base, and the organic base may be selected from the group consisting of N,N-diisopropylethylamine (DIPEA), triethylamine (TEA), potassium tert-butoxide (t-BuOK) and pyridine (Py), and the inorganic base may be selected from the group consisting of potassium phosphate ($K_3PO_4$), sodium hydride (NaH), potassium carbonate ($K_2CO_3$), sodium carbonate ($Na_2CO_3$), sodium bicarbonate ($NaHCO_3$), cesium carbonate ($Cs_2CO_3$) and NaOH, preferably $Na_2CO_3$ or $NaHCO_3$.

In some embodiments, Step 6-6 in the above preparation method is carried out at a suitable temperature, and the temperature is 0-200° C., preferably 0-100° C.

In some embodiments, Step 6-7 in the above preparation method is carried out in a suitable organic solvent, and the organic solvent may be selected from the group consisting of halogenated hydrocarbons (e.g., dichloromethane (DCM), chloroform (TCM), 1,2-dichloroethane (1,2-DCE), etc.), tetrahydrofuran (THF), 1,4-dioxane (Diox), water and any combination thereof, preferably dichloromethane and 1,4-dioxane.

In some embodiments, Step 6-7 of the above preparation method is carried out in the presence of a suitable acid, and the acid may be selected from the group consisting of trifluoroacetic acid (TFA) and hydrochloric acid, preferably trifluoroacetic acid (TFA).

In some embodiments, Step 6-7 in the above preparation method is carried out at a suitable temperature, and the temperature is 0-200° C., preferably 0-100° C.

Method II:

Step 7-1: deprotecting Compound IM27 to obtain Compound IM28;

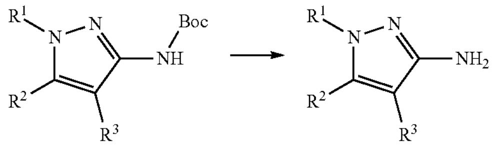

IM27 IM28

Step 7-2: subjecting Compound IM28 and Compound SM9 to a reductive amination reaction to obtain a compound of Formula I-4;

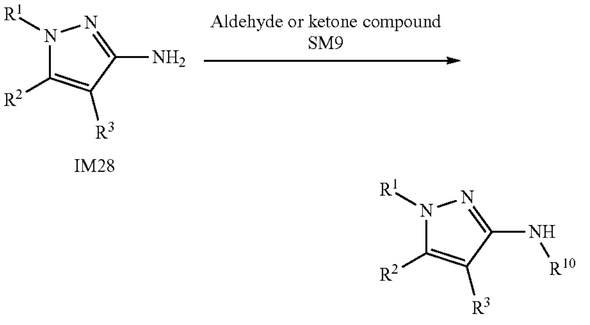

IM28

I-4 wherein $R^1$, $R^2$, $R^3$ and $R^{10}$ are as defined in any item of the first aspect of the present invention.

In some embodiments, Step 7-1 in the above preparation method is carried out in a suitable organic solvent, and the organic solvent may be selected from the group consisting of halogenated hydrocarbons (e.g., dichloromethane (DCM), chloroform (TCM), 1,2-dichloroethane (1,2-DCE), etc.), tetrahydrofuran (THF), 1,4-dioxane (Diox), water and any combination thereof, preferably dichloromethane and 1,4-dioxane.

In some embodiments, Step 7-1 in the above preparation method is carried out in the presence of a suitable acid, the acid may be selected from trifluoroacetic acid (TFA) and hydrochloric acid, preferably trifluoroacetic acid (TFA).

In some embodiments, Step 7-1 in the above preparation method is carried out at a suitable temperature, and the temperature is 0-200° C., preferably 0-100° C.

In some embodiments, Step 7-2 in the above preparation method is carried out in a suitable organic solvent, and the organic solvent may be selected from the group consisting of halogenated hydrocarbons (e.g., DCM, TCM, 1,2-DCE, etc.), THF, MeOH and any combination thereof, preferably DCM or MeOH.

In some embodiments, Step 7-2 of the above preparation method is carried out in the presence of a suitable acid, and the acid is AcOH.

In some embodiments, Step 7-2 in the above preparation method is carried out in the presence of a suitable reducing agent, and the reducing agent may be selected from the group consisting of sodium borohydride ($NaBH_4$), sodium cyanoborohydride ($NaBH_3CN$) and sodium triacetoxyborohydride ($NaBH(OAc)_3$), preferably $NaBH(OAc)_3$.

In some embodiments, Step 7-2 in the above preparation method is carried out at a suitable temperature, and the temperature is 0-100° C., preferably 25-70° C.

Method III: Synthesis of IM27

Step 8-1: hydrolyzing Compound IM23 to obtain Compound IM29;

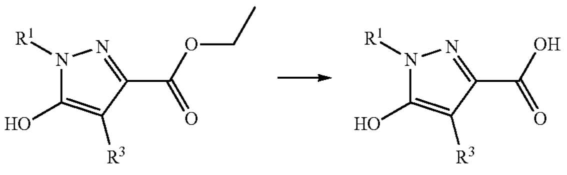

IM23 IM29

Step 8-2: subjecting Compound IM29 to Curtius rearrangement reaction to obtain Compound IM30;

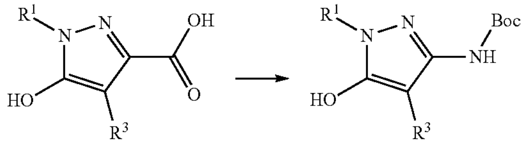

IM29 IM30

Step 8-3: subjecting Compound IM30 to a sulfonylation reaction or halogenation reaction to obtain Compound IM31;

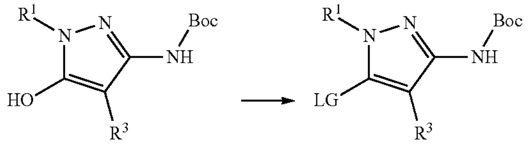

IM30 IM31

Step 8-4: subjecting Compound IM31 and Compound SM5 to a coupling reaction to obtain Compound IM27;

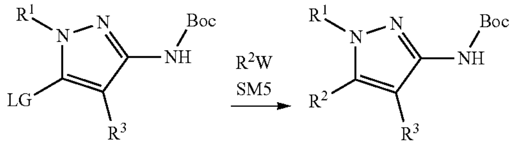

IM31 IM27 wherein, LG is a leaving group, which is selected from the group consisting of methanesulfonyloxy, trifluoromethanesulfonyloxy and halogen, preferably trifluoromethanesulfonyloxy or chloro; W is selected from the group consisting of boronic acid group, 4,4,5,5-tetramethyl-1,3,2-dioxaborolan-2-yl, tri-$^n$butylstannyl and sodium sulfinate group; $R^1$, $R^2$ and $R^3$ are as defined in any item of the first aspect of the present invention definition.

In some embodiments, Step 8-1 in the above preparation method is carried out in a suitable organic solvent or a mixed solvent of an organic solvent and water, and the organic solvent may be selected from the group consisting of alcohols (e.g., methanol (MeOH), ethanol (EtOH), n-butanol (n-BuOH), etc.), THF, AcOH, Diox and any combination thereof, preferably THF, EtOH, or a mixed solvent thereof with water.

In some embodiments, Step 8-1 of the above preparation method is carried out in the presence of a suitable base, and the base may be selected from the group consisting of sodium hydroxide (NaOH), potassium hydroxide (KOH) and lithium hydroxide (LiOH), preferably LiOH.

In some embodiments, Step 8-1 in the above preparation method is carried out at a suitable temperature, and the temperature is 0-100° C., preferably 25-80° C.

In some embodiments, Step 8-2 in the above preparation method is carried out in a suitable organic solvent or a mixed solvent of organic solvent and water, and the organic solvent may be selected from the group consisting of alcohols (e.g., methanol (MeOH), ethanol (EtOH), tert-butanol (t-BuOH), etc.), NMP, DMF, aromatic hydrocarbons (e.g., TL, XY) and any combination thereof, preferably tert-butanol, DMF and TL.

In some embodiments, Step 8-2 of the above preparation method is carried out in the presence of a suitable azidation reagent, and the azidation reagent may be selected from DPPA and sodium azide, preferably DPPA.

In some embodiments, Step 8-2 in the above preparation method is carried out in the presence of a suitable base, the base includes an organic base or an inorganic base, and the organic base may be selected from the group consisting of DIPEA, TEA, t-BuOK and Py, and the inorganic base may be selected from the group consisting of $K_3PO_4$, NaH, $K_2CO_3$, $Na_2CO_3$, $Cs_2CO_3$ and NaOH, preferably DIPEA or TEA.

In some embodiments, Step 8-2 in the above preparation method is carried out at a suitable temperature, and the temperature is 0-200° C., preferably 20-150° C.

In some embodiments, Step 8-3 in the above preparation method is carried out in a suitable organic solvent, and the organic solvent may be selected from the group consisting of halogenated hydrocarbon (e.g., DCM, TCM, 1,2-DCE, etc.), nitrile (e.g., AN, etc.), NMP, DMF, DMA, THF, Dioxane, DMSO, aromatic hydrocarbons (e.g., TL, XY) and any combination thereof, preferably THF or DCM.

In some embodiments, Step 8-3 in the above preparation method is carried out in the presence of a suitable acylating reagent or halogenating reagent, and the acylating reagent may be selected from the group consisting of trifluoromethanesulfonic anhydride ($Tf_2O$) and N,N-bis(trifluoromethanesulfonyl)aniline, preferably N,N-bis(trifluoromethanesulfonyl)aniline, and the halogenating reagent may be selected from the group consisting of phosphorus oxybromide ($POBr_3$) and $POCl_3$, preferably $POCl_3$.

In some embodiments, Step 8-3 in the above preparation method is carried out in the presence of a suitable base, the base includes an organic base or an inorganic base, and the organic base may be selected from the group consisting of DIPEA, TEA, t-BuOK and Py, and the inorganic base may be selected from the group consisting of $K_3PO_4$, NaH, $K_2CO_3$, $Na_2CO_3$, $Cs_2CO_3$ and NaOH, preferably DIPEA or TEA.

In some embodiments, Step 8-3 in the above preparation method is carried out at a suitable temperature, and the temperature is 0-200° C., preferably 0-50° C.

In some embodiments, Step 8-4 in the above preparation method is carried out in a suitable organic solvent or a mixed solution of organic solvent and water, and the organic solvent may be selected from the group consisting of halogenated hydrocarbons (e.g., DCM, TCM, 1,2-DCE, etc.), MeOH, EtOH, tert-butanol (t-BuOH), DMF, AN, ethers (e.g., ethylene glycol dimethyl ether (DME), THF, Diox), aromatic hydrocarbons (e.g., TL, XY) and any combination thereof, preferably TL or Dioxane.

In some embodiments, Step 8-4 in the above preparation method is carried out in the presence of a suitable catalyst, the catalyst is preferably a palladium catalyst, which may be selected from the group consisting of tetrakis(triphenylphosphine)palladium(0) ($Pd(PPh_3)_4$), palladium(II) acetate ($Pd(OAc)_2$), $Pd_2(dba)_3$, $Pd(PPh_3)_2Cl_2$, $Pd(PPh_3)_2Cl_2$ dichloromethane complex, $PdCl_2(Amphos)_2$ and $Pd(dppf)Cl_2$, preferably $PdCl_2(Amphos)_2$ or $Pd(PPh_3)_4$.

In some embodiments, Step 8-4 in the above preparation method is carried out in the presence of a suitable ligand, and the ligand may be selected from the group consisting of triphenylphosphine ($PPh_3$), BINAP, tris(o-methylphenyl) phosphine ($P(o\text{-}tol)_3$), tricyclohexylphosphine tetrafluoroborate (TCHP) and X-PHOS, preferably $PPh_3$ or X-PHOS.

In some embodiments, Step 8-4 in the above preparation method is carried out in the presence of a suitable base, the base includes an organic base or an inorganic base, and the organic base may be selected from the group consisting of DIPEA, TEA, t-BuOK and Py, and the inorganic base may be selected from the group consisting of $K_3PO_4$, NaH, $K_2CO_3$, $Na_2CO_3$, $Cs_2CO_3$ and NaOH, preferably $K_2CO_3$ or $Cs_2CO_3$.

Medicinal Use

The compounds of the present invention show a strong inhibitory effect on TGFβR1, and $IC_{50}$ values mostly reach below 100 nM, and some even reach below 10 nM; at the same time, the compounds show weak inhibitory effect on TGFβR2, and may be used as TGFβR1 inhibitors (especially TGFβR1 selective inhibitors).

Accordingly, the present invention provides use of a compound of Formula I, Formula I-1, Formula I-2, Formula I-3 and/or Formula I-4, or a pharmaceutically acceptable form thereof, or a pharmaceutical composition as described above, as a TGFβR1 inhibitor (especially TGFβR1 selective inhibitor).

In addition, the present application also provides use of the above compound of Formula I, Formula I-1, Formula I-2, Formula I-3 and/or Formula I-4, or a pharmaceutically acceptable form thereof, or the pharmaceutical composition in the manufacture of a medicament for the prevention and/or treatment of a disease or disorder mediated at least in part by TGFβR1.

In some embodiments, the disease or disorder mediated at least in part by TGFβR1 refers to a disease, at least a portion of the pathogenesis of which involves TGFβR1, and the disease includes but is not limited to a cancer or fibrotic disease.

Therapeutic Method

In another aspect, the present invention provides a method for preventing and/or treating a disease mediated at least in part by TGFβR1, comprising the following steps: administering a prophylactically and/or therapeutically effective amount of a compound of Formula I, Formula I-1, Formula I-2, Formula I-3 and/or Formula I-4, or a pharmaceutically acceptable form thereof, or a pharmaceutical composition as described above, to an individual in need thereof.

The present invention provides a compound of Formula I, Formula I-1, Formula I-2, Formula I-3 and/or Formula I-4, or a pharmaceutically acceptable form thereof, or a pharmaceutical composition as described above, for use in the prophylaxis and/or treatment of a disease mediated at least in part by TGFβR1.

The term "effective amount" refers to an amount capable of inducing a biological or medical response in a cell, tissue, organ or organism (e.g., an individual) and sufficient to achieve the desired prophylactic and/or therapeutic effect.

The optimal desired response may be achieved by adjusting dosage regimen. For example, it may be administered in a single dose, administered in divided doses over time, or administered in proportionately reduced or increased doses as appropriate. It would be appreciated that, for any particular individual, the specific dosage regimen should be adjusted as needed and according to the professional judgment of the person administering the composition or supervising the administration of the composition.

The dosage of the compound of the present invention will depend on the individual circumstances, the severity of disease or disorder, the rate of administration, the disposition of the compound, and the judgment of the prescribing physician. in general, an effective amount is about 0.001-10000 mg/kg subject body weight/day. Where appropriate, an effective amount is about 0.01-1000 mg/kg subject body weight/day. It may be administered daily, every two days, or every three days at about 0.01-1000 mg/kg subject body weight, usually about 0.1-500 mg/kg subject body weight. Typical dosage regime is once or more times per day, once or more times per week, or once or more times per month. When multiple doses are given, the interval between single doses can generally be daily, weekly, monthly or yearly. Alternatively, it may be administered in the form of sustained-release formulation, in which case less frequent dosing is required. The dose and frequency of administration can vary depending on the half-life of the drug in the subject, as well as whether it is for prophylactic or therapeutic use. in the prophylactic use, a relatively low dose is administered chronically at relatively infrequent intervals; in the therapeutic use, it is sometimes necessary to administer relatively high doses at shorter intervals until the progression of disease is delayed or stopped, preferably until the individual shows partial or complete improvement in disease symptoms, after which the prophylactic use can be adopted.

The term "treating" refers to alleviating or eliminating a targeted disease or disorder. If a subject receives a therapeutic amount of the compound of the present invention, or a pharmaceutically acceptable form thereof, or the pharmaceutical composition of the present invention, the subject exhibits as observable and/or detectable remission and/or improvement of at least one indicator and symptom, which indicates that the subject has been successfully "treated". It is understood that the treatment includes not only complete treatment, but also incomplete treatment that achieves some biologically or medically relevant results. Specifically, "treating" means that the compound of the present invention, or a pharmaceutically acceptable form thereof, or the pharmaceutical composition of the present invention can achieve at least one of the following effects, for example: (1) inhibiting a disease (i.e., preventing further progression of pathology and/or symptomatology) in an animal that is experiencing or exhibiting a disease pathologically or symptomatologically; (2) ameliorating a disease (i.e., reversing pathology and/or symptomatology) in an animal that is experiencing or exhibiting a disease pathologically or symptomatologically).

The term "administrate/administrating/administration" (or "administration") refers to a procedure in which a pharmaceutically active ingredient (e.g., the compound of the present invention) or a pharmaceutical composition comprising a pharmaceutically active ingredient (e.g., the pharmaceutical composition of the present invention) is applied to an individual or its cells, tissues, organs, biological fluids, etc., so that the pharmaceutical active ingredient or pharmaceutical composition is brought into contact with the individual or its cells, tissues, organs, biological fluids, etc. Common modes of administration include, but are not limited to, oral administration, subcutaneous administration, intramuscular administration, subperitoneal administration, intraocular administration, nasal administration, sublingual administration, rectal administration, vaginal administration, and the like.

The term "in need thereof" refers to a judgment of a physician or other caregiver that an individual needs or will benefit from a prophylactic and/or therapeutic procedure, and the judgment is based on various factors in the specific areas of the physician or other caregiver.

The term "individual" (or subject) refers to a human or non-human animal. The individual of the present invention include an individual (patient) with a disease and/or disorder and normal individual. The non-human animal of the present invention includes all vertebrates, such as non-mammals, such as birds, amphibians, reptiles, etc., and mammals, such as non-human primates, livestock and/or domesticated animals (e.g., sheep, dogs, cats, cows, pigs, etc.).

Combination Medication

The compounds of the present invention have no obvious inhibitory effect on the three main CYP subtypes (CYP1A2, CYP2D6 and CYP3A4), indicating potential relatively low drug interactions, so that the compound of Formula I, Formula I-1, Formula I-2, Formula I-3 and/or Formula I-4 as described above or a pharmaceutically acceptable form thereof, or the pharmaceutical composition as described above, may optionally be administered in combination with an additional therapeutic agent having at least some effect in the treatment of various diseases.

The present invention provides a pharmaceutical combination or combination preparation of the compound of Formula I, Formula I-1, Formula I-2, Formula I-3, and/or Formula I-4 above, or a pharmaceutically acceptable compound thereof, or the pharmaceutical composition above and at least one additional therapeutic agent, especially a TGFβR1 inhibitor, and they are simultaneously, separately or sequentially administered, for the prevention and/treatment of a disease or disorder.

Beneficial Effects of the Invention

The present invention provides pyrazole compounds represented by Formula I and pharmaceutically acceptable forms thereof, as well as pharmaceutical compositions, preparation methods and uses thereof. The compounds can significantly inhibit the activity of TGFβR1 and show high selectivity for TGFβR1, and may be used as TGFβR1 inhibitors for the treatment of proliferative disorders and apoptotic disorders mediated at least in part by TGF-β signaling pathway, especially diseases mediated at least in part by TGFβR1, such as cancers or fibrotic diseases.

Specific Models for Carrying Out the Present Invention

The technical solutions of the present invention will be clearly and completely described below with reference to the examples. Obviously, the described examples are only a part of the examples of the present invention, rather than all the examples. The following description of at least one exemplary example is merely illustrative in nature and is in no way intended to limit the present invention, its applications, or uses in any way. Based on the examples of the present invention, all other examples obtained by those of ordinary skill in the art without creative efforts shall fall within the scope of the present invention.

The reagents or instruments used in the examples were conventional products that could be obtained commercially. If a specific condition was not specified, it was carried out in accordance with the conventional conditions or the conditions suggested by the manufacturers. The term "room temperature" used in the present invention refers to 20° C.±5° C. When used to modify a value or value range, the term "about" as used in the present invention is meant to include the value or value range as well as an error range acceptable to those skilled in the art, for example, the error range is ±10%, ±5%, ±4% %, ±3%, ±2%, ±1%, ±0.5%, etc.

In the conventional synthesis methods, examples and intermediate synthesis examples, the meanings of abbreviations are shown in the following table.

| Abbreviation | Meaning | Abbreviation | Meaning |
|---|---|---|---|
| Tf | Trifluoromethanesulfonyl | Cbz | Benzyloxycarbonyl |
| Boc | tert-Butoxycarbonyl | DIPEA | N,N-Diisopropylethylamine |
| NMM | N-methylmorpholine | DMAP | p-Dimethylaminopyridine |
| DMSO | Dimethylsulfoxide | THF | Tetrahydrofuran |
| DMF | N,N-Dimethylformamide | DMA | N,N-Dimethylacetamide |
| $Pd_2(dba)_3$ | Tris(dibenzylideneacetone) dipalladium(0) | $Pd(PPh_3)_2Cl_2$ | Bis(triphenylphosphino)palladium(II) dichloride |
| $Pd(dppf)Cl_2$ | [1,1'-bis(diphenylphosphino)ferrocene]palladium(II) dichloride | BINAP | (±)-2,2'-Bis(diphenylphosphino)-1,1'-binaphthyl |
| X-PHOS | 2-Dicyclohexylphosphino-2',4',6'-triisopropylbiphenyl | HATU | O-(7-azabenzotriazol-1-y])-N,N,N',N'-tetramethylurea hexafluorophosphate |
| HBTU | O-(benzotriazol-1-yl)-N,N,N',N'-tetramethylurea hexafluorophosphate | EEDQ | 2-ethoxy-1-ethoxycarbonyl-1,2-dihydroquinoline |
| DEPC | Diethyl cyanophosphate | DCC | N,N'-dicyclohexylcarbodiimide |
| DIC | N,N'-Diisopropylcarbodiimide | EDC | 1-(3-Dimethylaminopropyl)-3- |
| BOP | (Benzotriazol-1-yl)oxytris(dimethylamino)phosphonium hexafluorophosphate | PyAOP | 7-Azabenzotriazol-1-yloxytris(pyrrolidin-1-yl)phosphonium hexafluorophosphate |
| PyBOP | Benzotriazol-1-yloxytris(pyrrolidin-1-yl)phosphonium hexafluorophosphate | h | Hour |
| $POCl_3$ | Phosphorus oxychloride | TFA | Trifluoroacetic acid |
| $K_2CO_3$ | Potassium carbonate | $NaHSO_3$ | Sodium bisulfite |
| XantPHOS | 4,5-Bis(diphenylphosphino)-9,9-dimethylxanthene | $PdCl_2(Amphos)_2$ | Bis[(4-dimethylamino)phenyl-di-tert-butylphosphine]palladium(II) dichloride |
| DMF-DMA | N,N-Dimethylformamide dimethyl acetal | Py | Pyridine |
| DPPA | Diphenylphosphoryl azide | | |

The structures of the compounds described in the following examples were determined by nuclear magnetic resonance ($^1H$-NMR) and/or mass spectrometry (MS).

The used instrument for measuring nuclear magnetic resonance ($^1H$-NMR) was a Bruker 400 MHz nuclear magnetic resonance instrument, and the measurement solvents were deuterated methanol ($CD_3OD$), deuterated chloroform (CDCl3), and hexadeuterated dimethylsulfoxide (DMSO-$d_6$). The standard substance was tetramethylsilane (TMS).

The abbreviations in the nuclear magnetic resonance (NMR) data in the following examples have the following meanings:

s: singlet; d: doublet; t: triplet; q: quartet; dd: double doublet; qd: quartet doublet; ddd: double double doublet; ddt: double double triplet; dddd: double double double doublet; m: multiplet; br: broad; J: coupling constant; Hz: hertz; δ: chemical shift.

All chemical shift (δ) values were given in part per million (ppm).

Agilent 6120B mass spectrometer was used as the measuring instrument for mass spectrometry (MS), and an electrospray ion source (ESI) was used ion source.

In the examples of the present invention, purification was performed by preparative high performance liquid chromatography (Prep-HPLC) according to the methods shown below.

Method A:

Column: Waters XBridge Prep $C_{18}$ OBD (5 μm*19 mm*150 mm)

Mobile phase A: acetonitrile; mobile phase B: water (containing 0.05% formic acid)

| Time [min] | Mobile phase A [%] | Mobile phase B [%] | Flow rate [mL/min] |
|---|---|---|---|
| 0.00 | 40 | 60 | 28 |
| 3.00 | 40 | 60 | 28 |
| 18.00 | 90 | 10 | 28 |

Method B:

Column: Waters XBridge Prep $C_{18}$ OBD (5 μm*19 mm*150 mm)

Mobile phase A: acetonitrile; mobile phase B: water (containing 0.05% ammonium bicarbonate)

| Time [min] | Mobile phase A [%] | Mobile phase B [%] | Flow rate [mL/min] |
|---|---|---|---|
| 0.00 | 15 | 85 | 28 |
| 18.00 | 90 | 10 | 28 |

Method C:

Column: Waters SunFire Prep $C_{18}$ OBD 5 μm 19×150 mm

Mobile phase A: acetonitrile; mobile phase B: water (containing 0.05% formic acid)

| Time [min] | Mobile phase A [%] | Mobile phase B [%] | Flow rate [mL/min] |
|---|---|---|---|
| 0.00 | 10.0 | 90.0 | 28 |
| 3.00 | 10.0 | 90.0 | 28 |
| 18.00 | 90.0 | 10.0 | 28 |

Method D:

Column: Waters SunFire Prep $C_{18}$ OBD (5 μm*19 mm*150 mm)

Mobile phase A: acetonitrile; mobile phase B: water (containing 0.05% sodium bicarbonate)

| Time [min] | Mobile phase A [%] | Mobile phase B [%] | Flow rate [mL/min] |
|---|---|---|---|
| 0.00 | 30 | 70 | 28 |
| 2.00 | 30 | 70 | 28 |
| 18.00 | 80 | 20 | 28 |

Method E:

Column: Daisogel $C_{18}$ ODS (8 μm*45 mm*450 mm)

Mobile phase A: acetonitrile; mobile phase B: water (containing 0.05% ammonium bicarbonate, w/v)

| Time [min] | Mobile phase A [%] | Mobile phase B [%] | Flow rate [mL/min] |
|---|---|---|---|
| 0.00 | 0.0 | 100.0 | 70 |
| 50.00 | 50.0 | 50.0 | 70 |

Method F:

Column: Waters SunFire Prep C18 OBD 5 μm 19×150 mm

Mobile phase A: acetonitrile; mobile phase B: water (containing 0.05% formic acid)

| Time [min] | Mobile phase A [%] | Mobile phase B [%] | Flow rate [mL/min] |
|---|---|---|---|
| 0.00 | 30.0 | 70.0 | 28 |
| 16.00 | 90.0 | 10.0 | 28 |

Method G:

Column: Waters SunFire Prep C18 OBD 5 μm 19×150 mm

Mobile phase A: acetonitrile; mobile phase B: water (containing 0.05% formic acid)

| Time [min] | Mobile phase A [%] | Mobile phase B [%] | Flow rate [mL/min] |
|---|---|---|---|
| 0.00 | 30.0 | 70.0 | 28 |
| 18.00 | 90.0 | 10.0 | 28 |

Method H:

Column: YMC (5 μm*19 mm*150 mm)

Mobile phase A: acetonitrile; mobile phase B: water (containing 0.05% formic acid)

| Time [min] | Mobile phase A [%] | Mobile phase B [%] | Flow rate [mL/min] |
|---|---|---|---|
| 0.00 | 5 | 95 | 28 |
| 18.00 | 90 | 10 | 28 |

Preparation of Compounds

Example 1: Synthesis of 6-(1-(6-methylpyridin-2-yl)-1H-pyrazol-5-yl)benzo[d]thiazole (Compound 1)

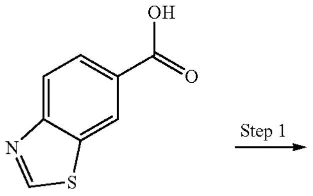

1-1

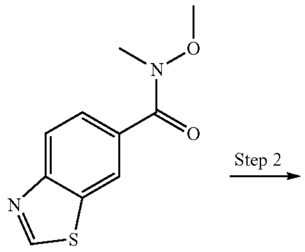

1-2

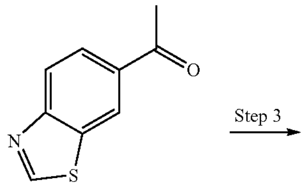

1-3

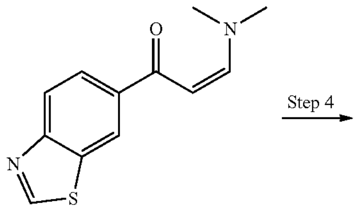

1-4

-continued

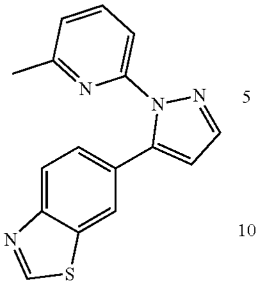

1

Step 1: Synthesis of N-methoxy-N-methylbenzo[d]thiazole-6-carboxamide (Compound 1-2)

Benzo[d]thiazole-6-carboxylic acid (Compound 1-1, 2 g, 11.16 mmol) and N,O-dimethylhydroxylamine hydrochloride (1.2 g, 12.28 mmol) were dissolved in DMF (10 mL), then HATU (4.45 g, 11.72 mmol) and DIPEA (5.96 mL, 33.48 mmol) were added in sequence, after the addition, the reaction was carried out at 90° C. for 1 hour. The reaction solution was slowly poured into water (100 mL), extracted with ethyl acetate (60 mL*5), the organic phases were combined, and the combined organic phase was washed with saturated brine (80 mL), dried over anhydrous sodium sulfate, filtered, and the filtrate was concentrated under reduced pressure to obtain a crude product. The crude product was separated and purified by silica gel column chromatography (eluent: petroleum ether/ethyl acetate=1/1 (v/v)) to obtain the title compound (1.81 g). ESI-MS (m/z): 223.1 $[M+H]^+$.

Step 2: Synthesis of 1-(benzo[d]thiazol-6-yl)ethanone (Compound 1-3)

N-methoxy-N-methylbenzo[d]thiazole-6-carboxamide (Compound 1-2, 1.81 g, 8.14 mmol) was dissolved in THF (15 mL), nitrogen replacement was conducted three times, and cooled to 0° C., then methylmagnesium bromide (3 M, 4.07 mL) was slowly added in a dropwise manner, and after the addition, the reaction was performed at 0° C. for 1 h, the reaction system was transferred to room temperature and continuously stirred for 2 h. 200 mL of saturated ammonium chloride solution was added to quench the reaction, extraction was performed with ethyl acetate (200 mL*3), the organic phases were combined, and the combined organic phase was washed with saturated brine (80 mL), dried over anhydrous sodium sulfate, filtered, and the filtrate was concentrated under reduced pressure to obtain a crude product. The crude product was separated and purified by silica gel column chromatography (eluent: petroleum ether/ethyl acetate=2/1 (v/v)) to obtain the title compound (990 mg). ESI-MS (m/z): 178.0 $[M+H]^+$.

Step 3: Synthesis of (Z)-1-(benzo[d]thiazol-6-yl)-3-(dimethylamino)prop-2-en-1-one (Compound 1-4)

1-(Benzo[d]thiazol-6-yl)ethanone (Compound 1-3, 300 mg, 1.69 mmol) was dissolved in N,N-dimethylformamide dimethyl acetal (2 mL), heated to 120° C., and stirred for 3 h. The reaction solution was concentrated under reduced pressure to obtain a crude product. The crude product was separated and purified by silica gel column chromatography (eluent: petroleum ether/ethyl acetate=2/1 (v/v)) to obtain the title compound (390 mg). ESI-MS (m/z): 233.0 $[M+H]^+$.

Step 4: Synthesis of 6-(1-(6-methylpyridin-2-yl)-1H-pyrazol-5-yl)benzo[d]thiazole (Compound 1)

(Z)-1-(benzo[d]thiazol-6-yl)-3-(dimethylamino)prop-2-en-1-one (50 mg, 215.24 μmol) was dissolved in toluene (1.93 mL), added with 2-hydrazino-6-methylpyridine hydrochloride (26.51 mg, 215.24 μmol) and acetic acid (387.76 mg, 6.46 mmol, 369.30 μL), and reacted at 120° C. for 2 h. The reaction solution was concentrated under reduced pressure, the residue was added with water (100 mL), extracted with ethyl acetate (200 mL*3), washed with saturated brine (200 mL), and the organic phases were combined, dried with anhydrous sodium sulfate and concentrated under reduced pressure to obtain a crude product, which was purified by preparative high performance liquid chromatography (Method A) and lyophilized to obtain the title compound (24 mg).

The structure was characterized as follows:

$^1$H NMR (400 MHz, DMSO-$d_6$) δ 9.42 (s, 1H), 8.19 (d, J=1.7 Hz, 1H), 8.01 (d, J=8.5 Hz, 1H), 7.86 (t, J=7.8 Hz, 1H), 7.83 (d, J=1.8 Hz, 1H), 7.49 (d, J=8.0 Hz, 1H), 7.31 (dd, J=8.5, 1.8 Hz, 1H), 7.24 (d, J=7.6 Hz, 1H), 6.75 (d, J=1.8 Hz, 1H), 2.14 (s, 3H).

ESI-MS (m/z): 293.1$[M+H]^+$.

Example 2: Synthesis of 7-(1-(6-methylpyridin-2-yl)-1H-pyrazol-5-yl)-[1,2,4]triazolo[1,5-a]pyridine (Compound 3)

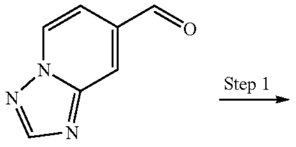

3-1

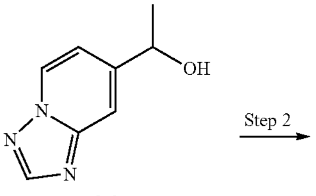

3-2

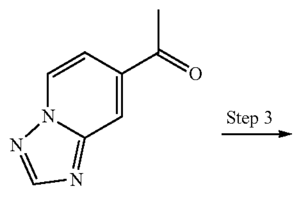

3-3

-continued

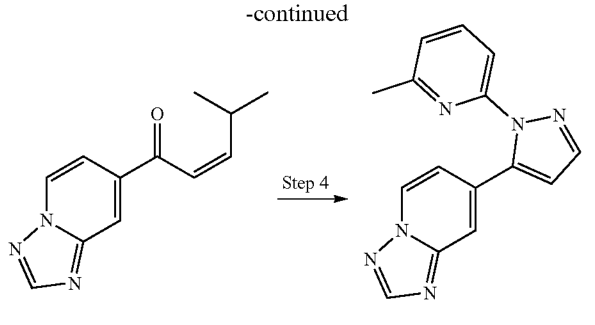

3-4 3

Step 1: Synthesis of 1-([1,2,4]triazolo[1,5-a]pyridin-7-yl) ethan-1-ol (Compound 3-2)

[1,2,4]Triazolo[1,5-a]pyridine-7-formaldehyde (Compound 3-1, 1.0 g, 6.80 mmol) was dissolved in THF (15 mL), after nitrogen replacement was performed three times, it was cooled to 0° C., slowly added with methylmagnesium bromide (3 M, 2.72 mL) dropwise, and after the addition, the reaction was performed at 0° C. for 1 h, then transferred to room temperature and continuously stirred for 2 h. 200 mL of saturated ammonium chloride solution was added to quench the reaction, extracted with ethyl acetate (200 mL*3), washed with saturated brine (200 mL), the organic phases were combined, dried over anhydrous sodium sulfate, and then concentrated under reduced pressure to obtain a crude product. The crude product was separated and purified by silica gel column chromatography (eluent: ethyl acetate) to obtain the title compound (640 mg). ESI-MS (m/z): 164.1 $[M+H]^+$.

Step 2: Synthesis of 1-([1,2,4]triazolo[1,5-a]pyridin-7-yl) ethanone (Compound 3-3)

1-([1,2,4]Triazolo[1,5-a]pyridin-7-yl) ethan-1-ol (Compound 3-2, 320 mg, 1.96 mmol) was dissolved in dichloromethane (2 mL), added with Dess-Martin reagent (915 mg, 2.16 mmol), the reaction solution was placed at 25° C. and subjected to reaction for 2 h, the reaction solution was filtered, concentrated under reduced pressure to obtain a crude product. The crude product was separated and purified by silica gel column chromatography (eluent: petroleum ether/ethyl acetate=1/8 (v/v)) to obtain the title compound (200 mg). ESI-MS (m/z): 162.1 $[M+H]^+$.

Step 3: Synthesis of (Z)-1-([1,2,4]Triazolo[1,5-a]pyridin-7-yl)-3-(dimethylamino) prop-2-en-1-one (Compound 3-4)

1-([1,2,4]Triazolo[1,5-a]pyridin-7-yl) ethanone (Compound 3-3, 100 mg, 620 mmol) was dissolved in N,N-dimethylformamide dimethyl acetal (2 mL), transferred to 120° C. and stirred for 3 h. The reaction solution was cooled to room temperature and concentrated under reduced pressure to obtain a crude product. The crude product was separated and purified by silica gel column chromatography (eluent: dichloromethane/methanol=15/1 (v/v)) to obtain the title compound (130 mg). ESI-MS (m/z): 217.1 $[M+H]^+$.

Step 4: Synthesis of 7-(1-(6-methylpyridin-2-yl)-1H-pyrazol-5-yl)-[1,2,4]triazolo[1,5-a]pyridine (Compound 3)

(Z)-1-([1,2,4]Triazolo[1,5-a]pyridin-7-yl)-3-(dimethylamino) prop-2-en-1-one (Compound 2-4, 50 mg, 215.24 μmol) was dissolved in toluene (1.93 mL), added with 2-hydrazino-6-methylpyridine hydrochloride (34 mg, 277 μmol) and acetic acid (387.76 mg, 6.46 mmol, 369.30 μL), transferred to 120° C. for 2 h. The reaction solution was concentrated under reduced pressure, extracted with ethyl acetate (200 mL*3), washed with saturated brine (200 mL), and the organic phases were combined, dried over anhydrous sodium sulfate, then evaporated to dryness under reduced pressure to obtain a crude product, which was purified by preparative high performance liquid chromatography (Method A) and lyophilized to obtain the title compound (13.49 mg).

The structure was characterized as follows:

$^1H$ NMR (400 MHz, DMSO-$d_6$) δ 9.59 (s, 1H), 8.71 (d, J=2.6 Hz, 1H), 8.57 (s, 1H), 8.31 (dd, J=9.2, 1.6 Hz, 1H), 7.99-7.87 (m, 3H), 7.30 (d, J=2.6 Hz, 1H), 7.26 (d, J=7.2 Hz, 1H), 2.54 (s, 3H).

ESI-MS (m/z): 277.1 $[M+H]^+$.

Example 3: Synthesis of 5-(1-(6-methylpyridin-2-yl)-1H-pyrazol-5-yl) pyrazolo[1,5-a]pyridine (Compound 4)

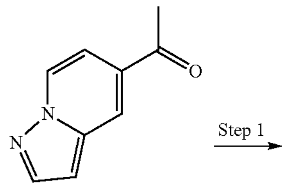

4-1

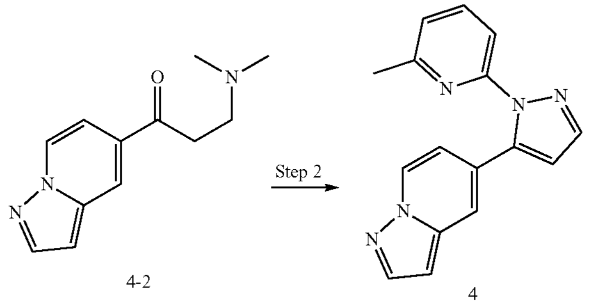

4-2 4

Step 1: Synthesis of (Z)-3-(dimethylamino)-1-(pyrazolo[1,5-a]pyridin-5-yl) prop-2-en-1-one (Compound 4-2)

1-(Pyrazolo[1,5-a]pyridin-5-yl) ethanone (Compound 4-1, 100 mg, 0.624 mmol) was dissolved in N,N-dimethylformamide dimethyl acetal (2 mL), transferred to 120° C. and stirred for 3 h. The reaction solution was concentrated under reduced pressure to obtain a crude product. The crude product was separated and purified by silica gel column chromatography (eluent: petroleum ether/ethyl acetate=2/1 (v/v)) to obtain the title compound (120 mg). ESI-MS (m/z): 216.1 $[M+H]^+$.

Step 2: Synthesis of 5-(1-(6-methylpyridin-2-yl)-1H-pyrazol-5-yl) pyrazolo[1,5-a]pyridine (Compound 4)

(Z)-3-(Dimethylamino)-1-(pyrazolo[1,5-a]pyridin-5-yl) prop-2-en-1-one (Compound 3-2, 50 mg, 215.24 μmol) was dissolved in toluene (2 mL), added with 2-hydrazino-6-methylpyridine hydrochloride (34.33 mg, 278 μmol) and acetic acid (387.76 mg, 6.46 mmol, 369.30 μL), transferred to 120° C. and reacted for 2 h. The reaction solution was concentrated, extracted with ethyl acetate (200 mL*3), washed with saturated brine (200 mL), and the organic phases were combined, dried over anhydrous sodium sulfate, then evaporated to dryness under reduced pressure to obtain a crude product, which was purified by preparative high performance liquid chromatography (Method A) and lyophilized to obtain the title compound (13 mg).

The structure was characterized as follows:

$^{1}$H NMR (400 MHz, DMSO-$d_6$) δ 8.59 (dd, J=7.3, 1.0 Hz, 1H), 8.01 (d, J=2.2 Hz, 1H), 7.89 (t, J=7.8 Hz, 1H), 7.84 (d, J=1.7 Hz, 1H), 7.72-7.67 (m, 1H), 7.56 (d, J=8.0 Hz, 1H), 7.26 (d, J=7.6 Hz, 1H), 6.81 (d, J=1.8 Hz, 1H), 6.66-6.62 (m, 1H), 6.59 (dd, J=7.3, 2.0 Hz, 1H), 2.20 (s, 3H).

$^{13}$C NMR (101 MHz, DMSO-$d_6$) δ 157.29, 142.68, 141.76, 139.44, 128.14, 126.90, 122.78, 117.32, 115.42, 113.41, 109.97, 98.32, 40.54, 39.67, 23.83.

ESI-MS (m/z): 276.1 $[M+H]^+$.

Example 4: Synthesis of 5-[2-(6-methylpyridin-2-yl)-2,4,5,6-tetrahydrocyclopenteno[c]pyrazol-3-yl]pyrazolo[1,5-a]pyridine (Compound 42)

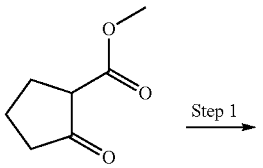

42-1

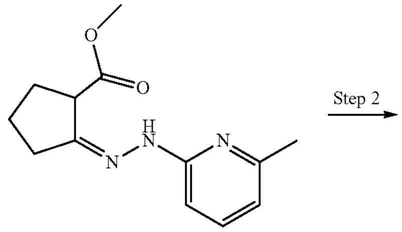

42-2

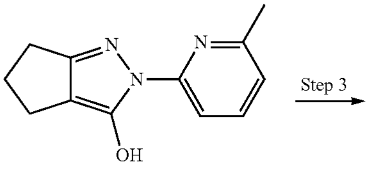

42-3

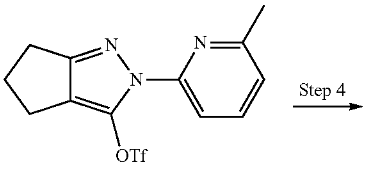

42-4

-continued

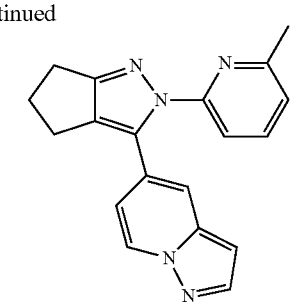

42

Step 1: Synthesis of methyl 2-[2-(6-methylpyridin-2-yl)hydrazinoidene]cyclopentylcarboxylate (Compound 42-2)

Methyl 2-oxo-cyclopentylcarboxylate (Compound 42-1, 500 mg, 3.52 mmol), (6-methylpyridin-2-yl)hydrazine (433.18 mg, 3.52 mmol) were dissolved in ethanol (10 mL), heated to 80° C. under nitrogen protection and reacted for 12 hours. After being cooled to room temperature, the reaction solution was concentrated under reduced pressure, and the crude product was directly subjected to the next step without purification. ESI-MS (m/z): 248.1 $[M+H]^+$.

Step 2: Synthesis of 2-(6-methylpyridin-2-yl)-2,4,5,6-tetrahydrocyclopenteno[c]pyrazol-3-ol (Compound 42-3)

Methyl 2-[2-(6-methylpyridin-2-yl)hydrazinoidene]cyclopentylcarboxylate (Compound 42-2, 800 mg, 3.24 mmol) was dissolved in sodium methoxide-methanol solution (2 mol/L, 3.24 mL), concentrated under reduced pressure, the residue was heated to 160° C. and reacted for 2 hours. The reaction solution was cooled to room temperature, added with water (100 mL) for dissolution, added with hydrochloric acid (1 mol/L, 2 mL) dropwise to adjust the pH to neutrality, extracted with ethyl acetate (50 mL*3), and the organic phases were combined, dried, filtered, the filtrate was concentrated under reduced pressure, and the crude product was directly subjected to the next step without purification. ESI-MS (m/z): 216.1 $[M+H]^+$.

Step 3: Synthesis of 2-(6-methylpyridin-2-yl)-2,4,5,6-tetrahydrocyclopenteno[c]pyrazol-3-yl trifluoromethanesulfonate (Compound 42-4)

2-(6-Methylpyridin-2-yl)-2,4,5,6-tetrahydrocyclopenteno[c]pyrazol-3-ol (Compound 42-3, 300 mg, 1.39 mmol), N,N-bis(trifluoromethanesulfonyl)aniline (746.86 mg, 2.09 mmol) and triethylamine (846.19 mg, 8.36 mmol) were dissolved in 1,2-dichloroethane (5 mL), reacted under nitrogen protection at 25° C. for 0.5 h. The reaction solution was poured into water (50 mL), extracted with dichloromethane (50 mL*3), the organic phases were combined, dried, filtered, the filtrate was concentrated under reduced pressure, and the crude product was directly subjected to the next reaction without purification. ESI-MS (m/z): 348.1 $[M+H]^+$.

Step 4: Synthesis of 5-[2-(6-methylpyridin-2-yl)-2,4,5,6-tetrahydrocyclopenteno[c]pyrazol-3-yl]pyrazolo[1,5-a]pyridine (Compound 42)

2-(6-Methylpyridin-2-yl)-2,4,5,6-tetrahydrocyclopenteno[c]pyrazol-3-yl trifluoromethanesulfonate (Compound 42-4, 20 mg, 0.06 mmol), pyrazolo[1,5-a]pyridine-5-boronic acid pinacol ester (16.87 mg, 0.07 mmol), Pd(dppf)$Cl_2$ (4.21 mg, 0.01 mmol), potassium carbonate (15.92 mg, 0.12 mmol) were dissolved in 1,4-dioxane/water (5 mL/1 mL), heated to 100° C. under nitrogen protection and reacted for 2 h. The reaction solution was cooled to room temperature, filtered, and the filtrate was concentrated under reduced pressure to obtain a crude product, which was purified by preparative high performance liquid chromatography (Method A) and lyophilized to obtain the title compound (2.0 mg).

The structure was characterized as follows:

$^1$H NMR (400 MHz, DMSO-$d_6$) δ 8.57 (d, J=7.3 Hz, 1H), 8.00 (d, J=2.2 Hz, 1H), 7.83 (t, J=7.8 Hz, 1H), 7.64 (d, J=1.0 Hz, 1H), 7.50 (d, J=8.0 Hz, 1H), 7.17 (d, J=7.5 Hz, 1H), 6.64-6.61 (m, 1H), 6.52 (dd, J=7.3, 1.9 Hz, 1H), 2.77 (dt, J=10.9, 7.3 Hz, 4H), 2.43 (dd, J=14.2, 7.2 Hz, 2H), 2.16 (s, 3H).

ESI-MS (m/z): 316.1 [M+H]$^+$.

Example 5: Synthesis of 5-[2-(6-methylpyridin-2-yl)-2,4,5,6-tetrahydrocyclopenteno[c]pyrazol-3-yl]benzo[d]thiazole (Compound 39)

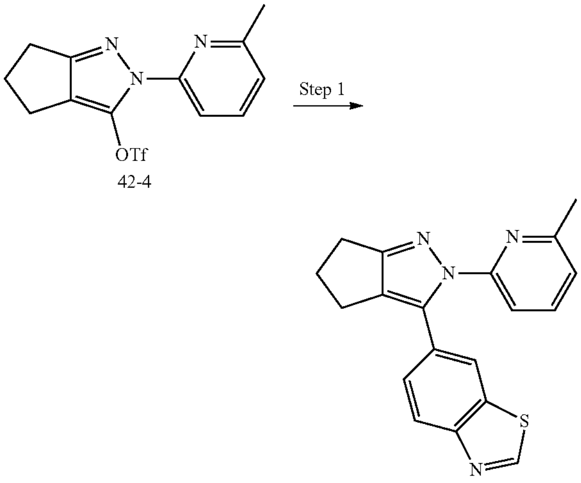

42-4

39

2-(6-Methylpyridin-2-yl)-2,4,5,6-tetrahydrocyclopenteno[c]pyrazol-3-yl trifluoromethanesulfonate (Compound 42-4, 20 mg, 0.06 mmol), benzo[d]thiazole-6-boronic acid pinacol ester (16.54 mg, 0.06 mmol), Pd(dppf)$Cl_2$ (4.21 mg, 0.01 mmol), potassium carbonate (15.92 mg, 0.12 mmol) were dissolved in 1,4-dioxane/water (5 mL/1 mL), heated to 100° C. under nitrogen protection and reacted for 2 hours. The reaction solution was cooled to room temperature, filtered, and the filtrate was concentrated under reduced pressure to obtain a crude product, which was purified by preparative high performance liquid chromatography (Method A) and lyophilized to obtain the title compound (0.48 mg).

The structure was characterized as follows:

$^1$H NMR (400 MHz, DMSO-$d_6$) δ 9.40 (s, 1H), 8.12 (d, J=1.5 Hz, 1H), 7.99 (d, J=8.5 Hz, 1H), 7.80 (t, J=7.8 Hz, 1H), 7.44 (d, J=8.0 Hz, 1H), 7.27 (dd, J=8.5, 1.7 Hz, 1H), 7.15 (d, J=7.5 Hz, 1H), 2.76 (td, J=7.3, 3.7 Hz, 4H), 2.46-2.41 (m, 2H), 2.09 (s, 3H).

ESI-MS (m/z): 333.1 [M+H]$^+$.

Example 6: Synthesis of 5-[2-(6-methylpyridin-2-yl)-2,4,5,6-tetrahydrocyclopenteno[c]pyrazol-3-yl]pyrazolo[1,5-a]pyridine-3-carboxamide (Compound 47)

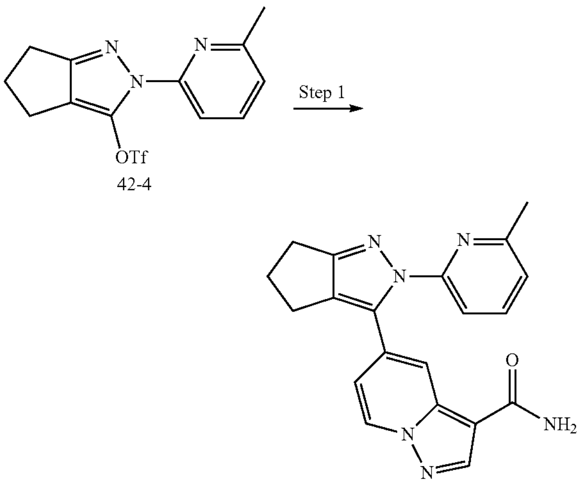

42-4

47

2-(6-Methylpyridin-2-yl)-2,4,5,6-tetrahydrocyclopenteno[c]pyrazol-3-yl trifluoromethanesulfonate (Compound 42-4, 20 mg, 0.06 mmol), (3-carbamoylpyrazolo[1,5-a]pyridine-5-) boronic acid pinacol ester (24.80 mg, 0.08 mmol), Pd (dppf) $Cl_2$ (4.21 mg, 0.01 mmol), potassium carbonate (15.92 mg, 0.12 mmol) were dissolved in 1,4-dioxane/water (5 mL/1 mL), heated to 100° C. under nitrogen protection and reacted for 2 h. The reaction solution was cooled to room temperature, filtered, and the filtrate was concentrated under reduced pressure to obtain a crude product, which was purified by preparative high performance liquid chromatography (Method A) and lyophilized to obtain the title compound (5.6 mg).

The structure was characterized as follows:

$^1$H NMR (400 MHz, DMSO-$d_6$) δ 8.66 (d, J=7.3 Hz, 1H), 8.52 (s, 1H), 8.13 (s, 1H), 7.84 (t, J=7.8 Hz, 1H), 7.52 (d, J=8.0 Hz, 1H), 7.17 (d, J=7.5 Hz, 1H), 6.74 (dd, J=7.3, 1.9 Hz, 1H), 2.76 (dd, J=10.1, 4.8 Hz, 4H), 2.45 (d, J=7.2 Hz, 2H), 2.15 (s, 3H).

ESI-MS (m/z): 359.1 [M+H]$^+$.

Example 7: Synthesis of 5-(benzo[d]thiazol-5-yl)-N-methyl-1-(6-methylpyridin-2-yl)-1H-pyrazol-3-amine (Compound 203)

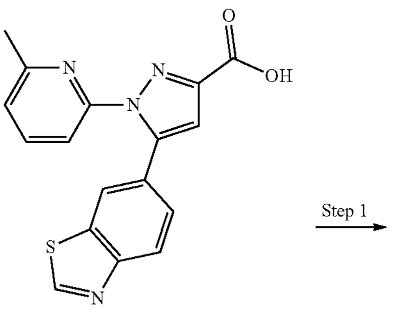

203-1

-continued

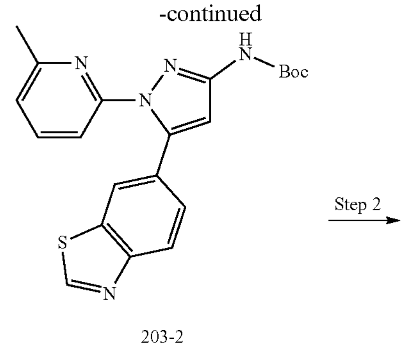

203-2

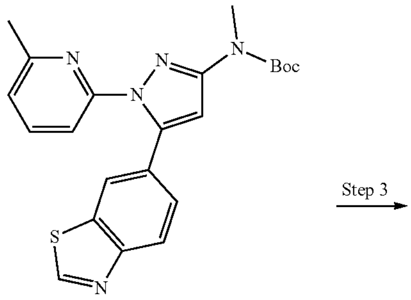

203-3

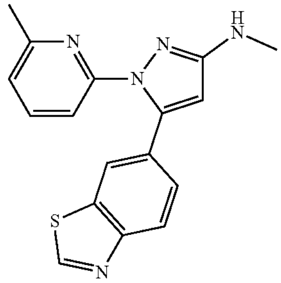

203

Step 1: Synthesis of tert-butyl (5-(benzo[d]thiazol-6-yl)-1-(6-methylpyridin-2-yl)-1H-pyrazol-3-yl) carbamate (Compound 203-2)

5-(Benzo[d]thiazol-6-yl)-1-(6-methylpyridin-2-yl)-1H-pyrazole-3-carboxylic acid (Compound 203-1, 0.38 g, 1.13 mmol) (referring to patent US20190194198(A1) for the synthesis method) was dissolved in tert-butanol (25 mL), added with triethylamine (0.34 g, 3.39 mmol) and diphenylphosphoryl azide (0.47 mg, 1.69 mmol), under nitrogen atmosphere, the reaction system was heated to 80° C. and reacted for 17 h, then cooled to room temperature. The reaction solution was concentrated under reduced pressure and separated by silica gel column chromatography (eluent: petroleum ether/ethyl acetate=5/1 (v/v)) to obtain 0.24 g of the title compound. ESI-MS (m/z): 408.1 $[M+H]^+$.

Step 2: Synthesis of tert-butyl (5-(benzo[d]thiazol-6-yl)-1-(6-methylpyridin-2-yl)-1H-pyrazol-3-yl) (methyl)carbamate (Compound 203-3)

Tert-butyl (5-(Benzo[d]thiazol-6-yl)-1-(6-methylpyridin-2-yl)-1H-pyrazol-3-yl)carbamate (Compound 203-2, 10 mg, 0.025 mmol) was dissolved in tetrahydrofuran (0.5 mL), added with sodium hydride (1.5 mg, 0.037 mmol, 60%) at 0° C. and reacted for 20 min, then added with iodomethane (5.2 mg, 0.037 mmol), and continuously reacted for 2 h. Ice water was added to quench the reaction, the reaction solution was diluted with ethyl acetate (2 mL), the organic phase was dried over anhydrous sodium sulfate and concentrated under reduced pressure to obtain about 10 mg of the crude product of the title compound. ESI-MS (m/z): 422.1 $[M+H]^+$.

Step 3: Synthesis of N-methyl-5-(benzo[d]thiazol-5-yl)-N-methyl-1-(6-methylpyridin-2-yl)-1H-pyrazol-3-amine (Compound 203)

Tert-butyl (5-(benzo[d]thiazol-6-yl)-1-(6-methylpyridin-2-yl)-1H-pyrazol-3-yl)(methyl)carbamate (Compound 203-3, 10 mg, 0.024 mmol) was added with a solution of hydrogen chloride in ethyl acetate (0.5 mL, 4 mol/L), and reacted at room temperature for 1.5 h. The crude product obtained by concentrating the reaction solution under reduced pressure was neutralized with saturated aqueous sodium bicarbonate solution and adjusted to pH 9. The above suspension system was extracted with dichloromethane (3×5 mL), the organic phases were combined, dried over anhydrous sodium sulfate, concentrated under reduced pressure, separated and purified by preparative high performance liquid chromatography (Method B), and the obtained fraction was lyophilized to obtain 6.21 mg of the title compound.

The structure was characterized as follows:

$^1H$ NMR (400 MHz, Methanol-d4) δ9.24 (s, 1H), 8.00 (d, J=1.6 Hz, 1H), 7.95 (d, J=8.5 Hz, 1H), 7.68 (t, J=7.8 Hz, 1H), 7.35 (dd, J=8.5, 1.7 Hz, 1H), 7.20 (d, J=8.0 Hz, 1H), 7.09 (d, J=7.6 Hz, 1H), 6.04 (s, 1H), 2.88 (s, 3H), 2.21 (s, 3H).

ESI-MS (m/z): 322.1 $[M+H]^+$.

Example 8: Synthesis of 5-(3-(methylamino)-1-(6-methylpyridin-2-yl)-1H-pyrazol-5-yl) pyrazolo[1,5-a]pyridine-3-carboxamide (Compound 211)

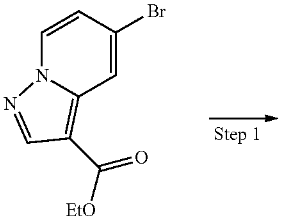

211-1

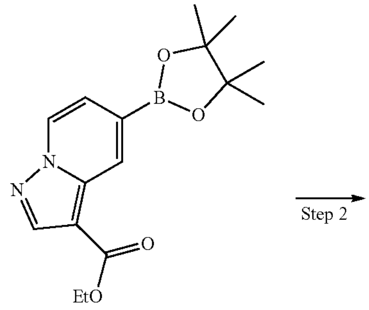

211-2

-continued

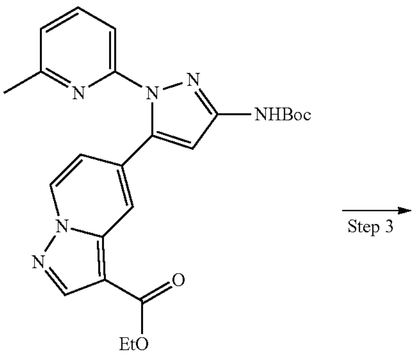

211-3

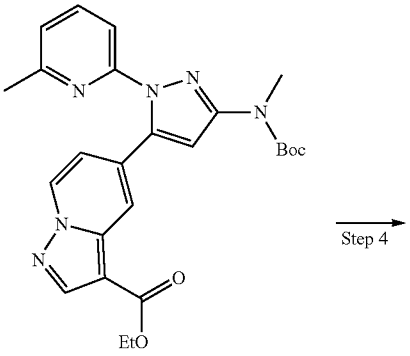

211-4

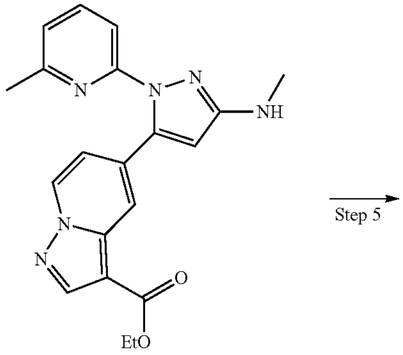

211-5

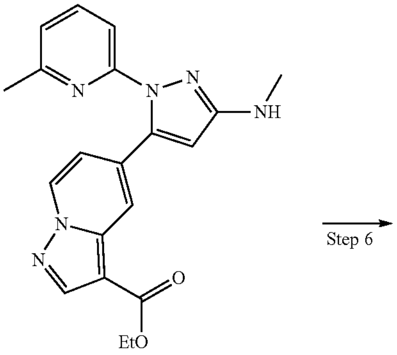

211-6

-continued

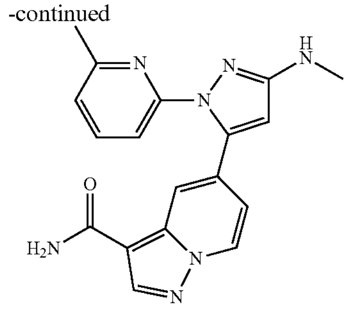

211

Step 1: Synthesis of 5-(4,4,5,5-tetramethyl-1,3,2-dioxaborolan-2-yl) pyrazolo[1,5-a]pyridine-3-carboxylic acid ethyl ester (Compound 211-2)

5-Bromopyrazolo[1,5-a]pyridine-3-carboxylic acid ethyl ester (Compound 211-1, 950 mg, 3.53 mmol), bis (pinacolato)diboron (1.08 g, 4.24 mmol) were dissolved in 1,4-dioxane (40 mL), added with Pd (dppf) $Cl_2$ (129 mg, 0.18 mmol) and potassium acetate (693 mg, 7.06 mmol), heated to 95° C. and reacted for 15 hours under nitrogen atmosphere after the addition. The reaction solution was cooled to room temperature, filtered, and the filtrate was concentrated under reduced pressure to obtain a crude product. The crude product was separated by silica gel column chromatography (eluent: petroleum ether/ethyl acetate-4/1 (v/v)) to obtain the title compound, 945 mg. ESI-MS (m/z): 317.1 $[M+H]^+$.

Step 2: Synthesis of 5-(3-((tert-butoxycarbonyl) amino)-1-(6-methylpyridin-2-yl)-1H-pyrazol-5-yl) pyrazolo[1,5-a]pyridine-3-carboxylic acid ethyl ester (Compound 211-3)

3-((Tert-butoxycarbonyl)amino)-1-(6-methylpyridin-2-yl)-1H-pyrazol-5-yl trifluoromethanesulfonate (Compound 169-9, 50 mg, 0.12 mmol), 5-(4,4,5,5-tetramethyl-1,3,2-dioxaborolan-2-yl) pyrazolo[1,5-a]pyridine-3-carboxylic acid ethyl ester (Compound 211-2, 56 mg, 0.18 mmol), Pd(dppf)$Cl_2$ (9 mg, 11.84 μmol), an aqueous solution of potassium carbonate (0.08 mL, 3 N) were dissolved in 1,4-dioxane (1 mL), heated to 100° C. and reacted for 1.5 h under nitrogen atmosphere, and then cooled to room temperature. The reaction solution was filtered through a pad of celite, and the filtrate was collected and concentrated. The residue was separated by silica gel column chromatography (eluent: petroleum ether/ethyl acetate=2/1 (v/v)) to obtain the title compound, 38 mg. ESI-MS (m/z): 463.2 $[M+H]^+$.

Step 3: Synthesis of 5-(3-((tert-butoxycarbonyl) (methyl)amino)-1-(6-methylpyridin-2-yl)-1H-pyrazol-5-yl)pyrazolo[1,5-a]pyridine-3-carboxylic acid ethyl ester (Compound 211-4)

5-(3-((Tert-butoxycarbonyl)amino)-1-(6-methylpyridin-2-yl)-1H-pyrazol-5-yl)pyrazolo[1,5-a]pyridine-3-carboxylic acid ethyl ester (Compound 211-3, 38 mg, 82.16 μmol) was dissolved in tetrahydrofuran (2 mL), cooled to 0° C., added with sodium hydride (3 mg, 82.16 μmol, 60%), stirred for 20 min, then added with iodomethane (23 mg, 164.32 μmol), and continuously stirred for 1 h. Ice water was added to quench the reaction, ethyl acetate (2 mL) was added for dilution, and anhydrous sodium sulfate was added to dry, and the organic phase was concentrated to obtain the title compound, 39 mg. ESI-MS (m/z): 477.2 $[M+H]^+$.

Step 4: Synthesis of 5-(3-(methylamino)-1-(6-methylpyridin-2-yl)-1H-pyrazol-5-yl) pyrazolo[1,5-a] pyridine-3-carboxylic acid ethyl ester (Compound 211-5)

5-(3-((Tert-butoxycarbonyl)(methyl)amino)-1-(6-methylpyridin-2-yl)-1H-pyrazol-5-yl)pyrazolo[1,5-a]pyridine-3-carboxylic acid ethyl ester (Compound 211-4, 39 mg, 81.84 μmol) was added with hydrochloric acid/1,4-dioxane (1 mL, 4 N), and reacted at room temperature for 1 h. The reaction solution was concentrated under reduced pressure to dryness to obtain the hydrochloride salt of the title compound, 33 mg. ESI-MS (m/z): 377.1 $[M+H]^+$.

Step 5: Synthesis of 5-(3-(methylamino)-1-(6-methylpyridin-2-yl)-1H-pyrazol-5-yl) pyrazolo[1,5-a] pyridine-3-carboxylic acid (Compound 211-6)

To a solution of 5-(3-(methyl amino)-1-(6-methylpyridin-2-yl)-1H-pyrazol-5-yl)pyrazolo[1,5-a]pyridine-3-carboxylic acid ethyl ester (Compound 211-5) hydrochloride (33 mg, 79.93 μmol) in tetrahydrofuran (1 mL), sodium hydroxide aqueous solution (1 mL, 10 N) was added, heated to 80° C. and reacted for 15 h, and then cooled to room temperature. Diluted hydrochloric acid (10 mL, 1 N) was added to the reaction solution to adjust pH≈7. Extraction was carried out with ethyl acetate (4×5 mL), the organic phases were combined, dried over anhydrous sodium sulfate, and the organic phase was concentrated to obtain the title compound, 20 mg. ESI-MS (m/z): 349.1 $[M+H]^+$.

Step 6: Synthesis of 5-(3-(methylamino)-1-(6-methylpyridin-2-yl)-1H-pyrazol-5-yl) pyrazolo[1,5-a] pyridine-3-carboxamide (Compound 211)

5-(3-(Methylamino)-1-(6-methylpyridin-2-yl)-1H-pyrazol-5-yl) pyrazolo[1,5-a]pyridine-3-carboxylic acid (Compound 211-6, 20 mg, 57.41 μmol), ammonium chloride (6 mg, 0.11 mmol) were dissolved in DMF (1 mL), added with DIPEA (15 mg, 0.11 mmol) and HATU (24 mg, 63.15 μmol) in sequence, and reacted at room temperature for 5 h. Water (5 mL) was added to the reaction solution, followed by extraction with ethyl acetate (3×5 mL). The organic phases were combined, dried over anhydrous sodium sulfate, and the organic phase was concentrated, separated by preparative high performance liquid chromatography (Method C), and the obtained fraction was lyophilized to obtain the title compound, 7 mg.

The structure was characterized as follows:

$^1$H NMR (400 MHz, DMSO-$d_6$) δ 8.65 (dd, J=7.2, 0.7 Hz, 1H), 8.53 (s, 1H), 8.15 (dd, J=1.9, 0.7 Hz, 2H), 7.80-7.68 (m, 1H), 7.49 (d, J=8.1 Hz, 1H), 7.10 (s, 1H), 7.02 (d, J=7.5 Hz, 1H), 6.81 (dd, J=7.2, 2.0 Hz, 1H), 6.06 (s, 1H), 5.73 (q, J=5.0 Hz, 1H), 2.78 (d, J=5.1 Hz, 3H), 2.05 (s, 3H).

ESI-MS (m/z): 348.1 $[M+H]^+$.

Example 9: Synthesis of 5-(benzo[d]thiazol-6-yl)-1-(6-methylpyridin-2-yl)-N-((2-methylpyridin-4-yl) methyl)-1H-pyrazol-3-amine (Compound 195)

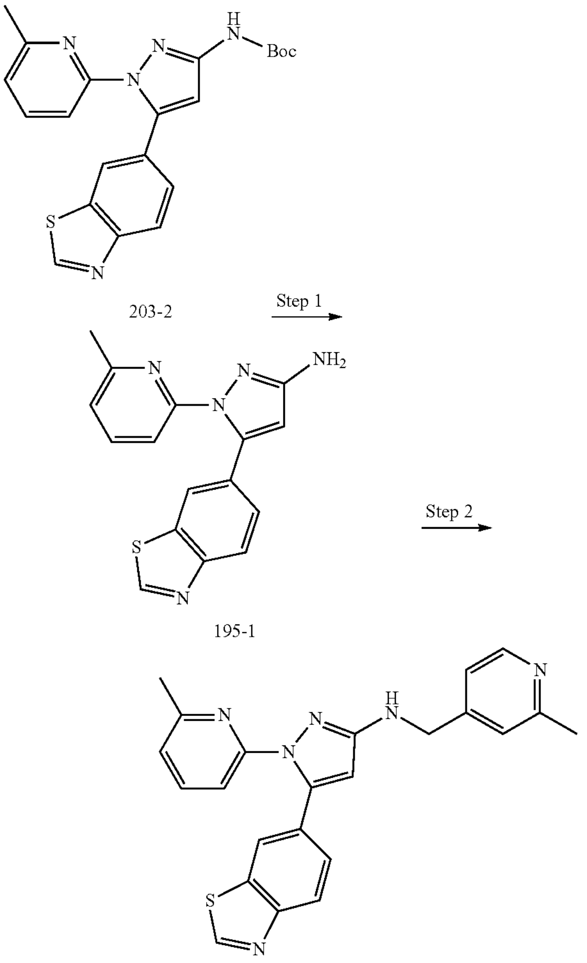

203-2

195-1

195

Step 1: Synthesis of 5-(benzo[d]thiazol-6-yl)-1-(6-methylpyridin-2-yl)-1H-pyrazol-3-amine (Compound 195-1)

To tert-butyl (5-(benzo[d]thiazol-6-yl)-1-(6-methylpyridin-2-yl)-1/-pyrazol-3-yl) carbamate (Compound 203-2, 58 mg, 0.14 mmol), a solution of hydrogen chloride in ethyl acetate (2 mL, 4 mol/L) was added, and reacted at room temperature for 1 h. The reaction solution was concentrated under reduced pressure to obtain 48 mg of the hydrochloride of the title compound.

ESI-MS (m/z): 308.0 $[M+H]^+$.

Step 2: Synthesis of 5-(benzo[d]thiazol-6-yl)-1-(6-methylpyridin-2-yl)-N-((2-methylpyridin-4-yl) methyl)-1H-pyrazol-3-amine (Compound 195)

The 5-(benzo[d]thiazol-6-yl)-1-(6-methylpyridin-2-yl)-1H-pyrazol-3-amine hydrochloride (hydrochloride of Compound 195-1, 10 mg, 0.03 mmol), 2-methylpyridine-4-carbaldehyde (10 mg, 0.09 mmol) were dissolved in methanol (0.5 mL), added with one drop of glacial acetic acid, reacted at room temperature for 2 h, and then heated to 80° C. and reacted for 2 hours. After being cooled to room temperature, sodium borohydride (2 mg, 0.06 mmol) was added, and the reaction was further conducted at room temperature for 0.5 h. The reaction system was quenched with ice water, extracted with ethyl acetate (3×5 mL), and the organic phases were combined. The organic phase was dried over anhydrous sodium sulfate, concentrated under reduced pressure, and separated and purified by preparative high performance liquid chromatography (method D). The obtained fraction was lyophilized to obtain 5.63 mg of the title compound.

The structure was characterized as follows:

$^1H$ NMR (400 MHz, DMSO-d6) δ 9.40 (s, 1H), 8.36 (d, J=5.1 Hz, 1H), 8.15 (d, J=1.4 Hz, 1H), 7.98 (d, J=8.5 Hz, 1H), 7.72 (t, J=7.8 Hz, 1H), 7.43-7.31 (m, 2H), 7.27 (s, 1H), 7.21 (d, J=5.0 Hz, 1H), 7.00 (d, J=7.5 Hz, 1H), 6.44 (t, J=6.3 Hz, 1H), 6.02 (s, 1H), 4.36 (d, J=6.2 Hz, 2H), 2.45 (s, 3H), 1.98 (s, 3H). ESI-MS (m/z): 413.1[M+H]$^+$.

Example 10: Synthesis of 5-(3-(1-(4-fluorophenyl)ethylamino)-1-(6-methylpyridin-2-yl)-1H-pyrazol-5-yl)pyridino[1,5-a]pyridine-3-carboxamide (Compound 169)

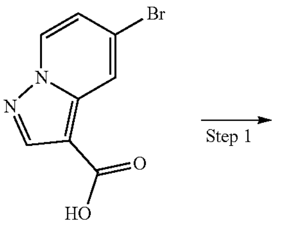

169-1

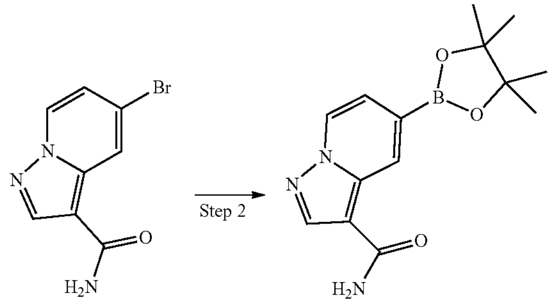

169-2 169-3

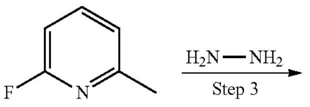

169-4

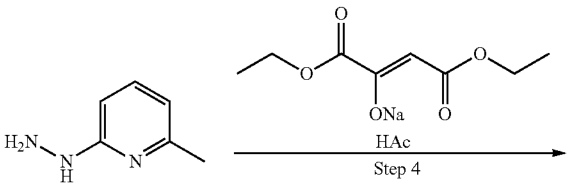

169-5

-continued

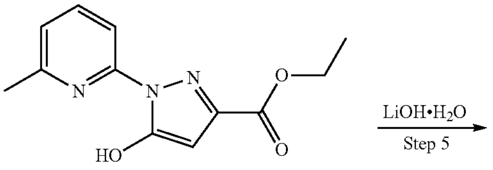

169-6

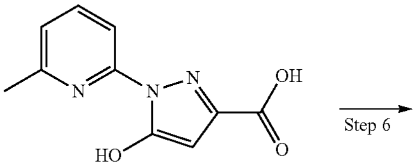

169-7

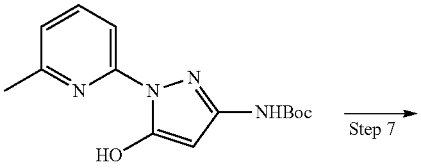

169-8

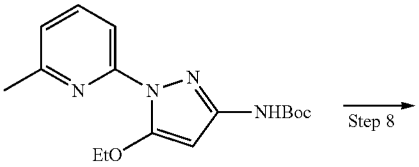

169-9

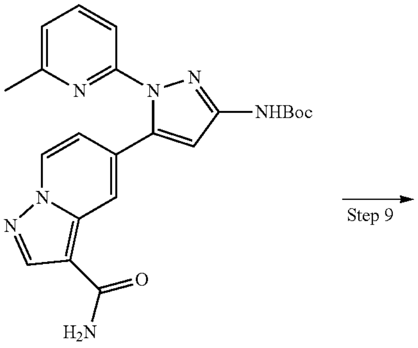

169-10

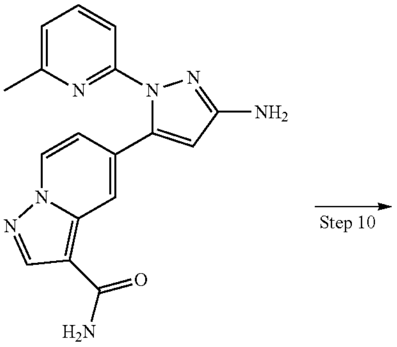

169-11

-continued

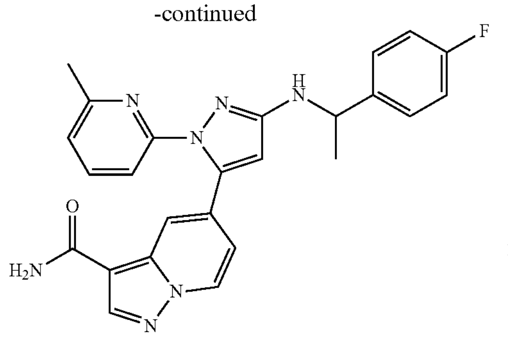

169

Step 1: Synthesis of 5-bromopyrazolo[1,5-a]pyridine-3-carboxamide (Compound 169-2)

5-Bromopyrazolo[1,5-a]pyridine-3-carboxylic acid (1 g, 4.15 mmol), ammonium chloride (444 mg, 8.30 mmol), HATU (1.66 g, 4.36 mmol), DIPEA (1.61 g, 12.45 mmol) were dissolved in DMF (10 mL), and reacted at room temperature for 2 h. The reaction solution was added dropwise to water (100 mL), a solid was precipitated, filtered, and the filter cake was collected to obtain the title compound, 0.885 g. ESI-MS (m/z): 240.0 242.0 $[M+H]^+$.

Step 2: Synthesis of 5-(4,4,5,5-tetramethyl-1,3,2-dioxaborolan-2-yl) pyrazolo[1,5-a]pyridine-3-carboxamide (Compound 169-3)

5-Bromopyrazolo[1,5-a]pyridine-3-carboxamide (Compound 169-2, 0.5 g, 2.08 mmol), bis (pinacolato)diboron (0.79 g, 3.12 mmol), potassium acetate (511.03 mg, 5.21 mmol) were dissolved in 1,4-dioxane (20 mL), then added with Pd (dppf) $Cl_2$ (152 mg, 0.21 mmol), heated to 100° C. under nitrogen atmosphere and reacted for 5 h, and then cooled to room temperature, filtered, and the filtrate was concentrated to obtain the title compound, 0.59 g. ESI-MS (m/z): 288.1 $[M+H]^+$.

Step 3: Synthesis of 2-hydrazino-6-methylpyridine (Compound 169-5)

2-Fluoro-6-methylpyridine (Compound 169-4, 50 g, 449.98 mmol) and hydrazine hydrate (36.60 g, 584.97 mmol) were weighed and dissolved in isopropanol (200 mL), and the reaction system was reacted at 90° C. for 168 h, diluted with water (2000 mL), filtered, and the filtrate was purified by preparative high performance liquid chromatography (Method E) and lyophilized to obtain 16.6 g of the title compound.

$^1$H-NMR (400 MHz, DMSO-$d_6$): δ 7.33 (dd, J=8.3, 7.2 Hz, 1H), 7.24 (s, 1H), 6.50 (d, J=8.3 Hz, 1H), 6.39 (d, J=7.2 Hz, 1H), 2.26 (s, 3H).

MS (ESI): m/z 124.1 $[M+H]^+$.

Step 4: Synthesis of 5-hydroxy-1-(6-methylpyridin-2-yl)-1H-pyrazole-3-carboxylic Acid Ethyl Ester (Compound 169-6)

2-Hydrazino-6-methylpyridine (Compound 169-5, 15 g, 121.80 mmol) and diethyl oxaloacetate sodium salt (51.19 g, 243.59 mmol) were dissolved in toluene (200 mL), then added with acetic acid (208.98 mL, 3.65 mol), after the addition, the reaction system was heated to 100° C. and reacted for 2 hours. After being cooled to room temperature, the reaction solution was slowly poured into water (400 mL), extracted with ethyl acetate (300 mL×3), the organic phases were combined, washed with saturated brine (200 mL×1), and the organic phase was dried over anhydrous sodium sulfate, filtered to remove the desiccant, and the filtrate was concentrated under reduced pressure to give a colorless oil, which was purified by flash silica gel column chromatography (petroleum ether:ethyl acetate=1:1) to obtain 28.0 g of the title compound. MS (ESI): m/z 247.9 $[M+H]^+$.

Step 5: Synthesis of 5-hydroxy-1-(6-methylpyridin-2-yl)-1H-pyrazole-3-carboxylic Acid (Compound 169-7)

5-Hydroxy-1-(6-methylpyridin-2-yl)-1H-pyrazole-3-carboxylic acid ethyl ester (Compound 169-6, 28 g, 113.25 mmol) was dissolved in a mixed solvent of tetrahydrofuran (300 mL) and water (100 mL), then added with lithium hydroxide monohydrate (23.78 g, 566.23 mmol), after the addition, the reaction was carried out at room temperature for 2 hours. The reaction solution was diluted with water (300 mL), extracted with ethyl acetate (200 mL×2), the organic phase was discarded, and the aqueous phase was adjusted with 2N aqueous hydrochloric acid solution to pH=3 with the precipitation of a large amount of solid. The solid was filtered out, washed with clean water (200 mL), and finally the solid obtained by filtration was dried in a constant temperature oven at 50° C. overnight to obtain 16.1 g of the title compound. MS (ESI): m/z 220.1 $[M+H]^+$.

Step 6: Synthesis of tert-butyl (5-hydroxy-1-(6-methylpyridin-2-yl)-1H-pyrazol-3-yl)carbamate (Compound 169-8)

Under nitrogen atmosphere, 5-hydroxy-1-(6-methylpyridin-2-yl)-1H-pyrazole-3-carboxylic acid (Compound 169-7, 2 g, 9.12 mmol) was dissolved in tert-butanol (120 mL), then added with triethylamine (2.77 g, 27.37 mmol, 3.81 mL) and diphenylphosphoryl azide (3.77 g, 13.69 mmol, 2.95 mL). After the addition, the resulting mixture was heated to 80° C. and reacted for 7.5 h, and then cooled to room temperature. The reaction solution was filtered, the filtrate was collected and concentrated, diluted with water (150 mL), then extracted with EA (3×80 mL), the organic phases were combined, dried over anhydrous sodium sulfate, filtered, and concentrated. The residue was separated by silica gel column chromatography (eluent: dichloromethane/methanol=10/1 (v/v)) to obtain the title compound, 1.17 g. ESI-MS (m/z): 291.1 $[M+H]^+$.

Step 7: Synthesis of 3-(tert-butoxycarbonylamino)-1-(6-methylpyridin-2-yl)-1H-pyrazol-5-yl Trifluoromethanesulfonate (Compound 169-9)

Tert-butyl (5-hydroxy-1-(6-methylpyridin-2-yl)-1H-pyrazol-3-yl)carbamate (Compound 169-8, 0.9 g, 3.10 mmol), N-phenyl-bis(trifluoromethanesulfonyl)imide (1.11 g, 3.10 mmol) were dissolved in dichloromethane (30 mL). At room temperature, triethylamine (941 mg, 9.30 mmol, 1.3 mL) was added dropwise and reacted for 48 h. The reaction solution was washed with water and saturated brine in sequence. The organic phase was dried over anhydrous sodium sulfate, concentrated, and separated by silica gel column chromatography (eluent: petroleum ether/ethyl acetate=5/1 (v/v)) to obtain the title compound, 1.06 g. ESI-MS (m/z): 423.1 $[M+H]^+$.

Step 8: Synthesis of tert-butyl (5-(3-formylpyrazolo[1,5-a]pyridin-5-yl)-1-(6-methylpyridin-2-yl)-1H-pyrazol-3-yl)carbamate (Compound 169-10)

3-(Tert-butoxycarbonylamino)-1-(6-methylpyridin-2-yl)-1H-pyrazol-5-yl trifluoromethanesulfonate (Compound 169-9, 0.45 g, 1.07 mmol), and 5-(4,4,5,5-tetramethyl-1,3,2-dioxaborolan-2-yl)pyrazolo[1,5-a]pyridine-3-carboxamide (532 mg, 1.85 mmol) were dissolved in 1,4-dioxane (10 mL), then added with an aqueous solution of potassium carbonate (1.07 mL, 3 N). Under nitrogen atmosphere, $Pd(dppf)Cl_2$ (78 mg, 0.11 mmol) was added, heated to 100° C. and reacted for 1 h, and then cooled to room temperature. The reaction solution was filtered through a pad of celite, the filtrate was collected and concentrated, and separated by silica gel column chromatography (eluent: dichloromethane/methanol=10/1 (v/v)) to obtain the title compound, 0.33 g. ESI-MS (m/z): 434.1 $[M+H]^+$.

Step 9: Synthesis of 5-(3-amino-1-(6-methylpyridin-2-yl)-1H-pyrazol-5-yl)pyrazolo[1,5-a]pyridine-3-carboxamide (Compound 169-11)

To tert-butyl (5-(3-formylpyrazolo[1,5-a]pyridin-5-yl)-1-(6-methylpyridin-2-yl)-1H-pyrazol-3-yl)carbamate (Compound 169-10, 0.25 g, 0.58 mmol), hydrochloric acid/dioxane solution (7 mL, 4N) was added, and reacted at room temperature for 1 h. A solid was precipitated, filtered, and the filter cake was collected to obtain the hydrochloride of the title compound, 0.21 g. ESI-MS (m/z): 334.1 $[M+H]^+$.

Step 10: Synthesis of 5-(3-(1-(4-fluorophenyl)ethylamino)-1-(6-methylpyridin-2-yl)-1H-pyrazol-5-yl)pyrazolo[1,5-a]pyridine-3-carboxamide (Compound 169)

5-(3-Amino-1-(6-methylpyridin-2-yl)-1H-pyrazol-5-yl)pyrazolo[1,5-a]pyridine-3-carboxamide (Compound 169-11) hydrochloride (15 mg, 40.56 μmol) and 4-fluoroacetophenone (16.81 mg, 121.68 μmol) were dissolved in 1,2-dichloroethane (0.5 mL), and 1 drop of glacial acetic acid was added dropwise. After being heated to 80° C. and stirred for 5 h, sodium cyanoborohydride (5 mg, 81.12 μmol) was added, and the reaction was further conducted for 15 h. The reaction was quenched by adding ice water, extracted with ethyl acetate (3×5 mL), the organic phases were combined, dried over anhydrous sodium sulfate, and the organic phase was concentrated, and separated by preparative high performance liquid chromatography (Method F), and the obtained fraction was lyophilized to give the title compound, 5 mg.

The structure was characterized as follows:

$^1$H NMR (400 MHz, DMSO-$d_6$) δ 8.62 (dd, J=7.3, 0.7 Hz, 1H), 8.52 (s, 1H), 8.10 (d, J=1.2 Hz, 1H), 7.79-7.64 (m, 2H), 7.52-7.43 (m, 2H), 7.39 (d, J=8.1 Hz, 1H), 7.21-7.03 (m, 3H), 7.00 (d, J=7.5 Hz, 1H), 6.76 (dd, J=7.2, 2.0 Hz, 1H), 6.43 (d, J=8.0 Hz, 1H), 6.01 (s, 1H), 4.69 (p, J=6.8 Hz, 1H), 2.02 (s, 3H), 1.43 (d, J=6.8 Hz, 3H).

ESI-MS (m/z): 456.1 $[M+H]^+$.

Example 11: Synthesis of 5-(3-(4-fluorobenzylamino)-1-(6-methylpyridin-2-yl)-1H-pyrazol-5-yl)pyrazolo[1,5-a]pyridine-3-carboxamide (Compound 117)

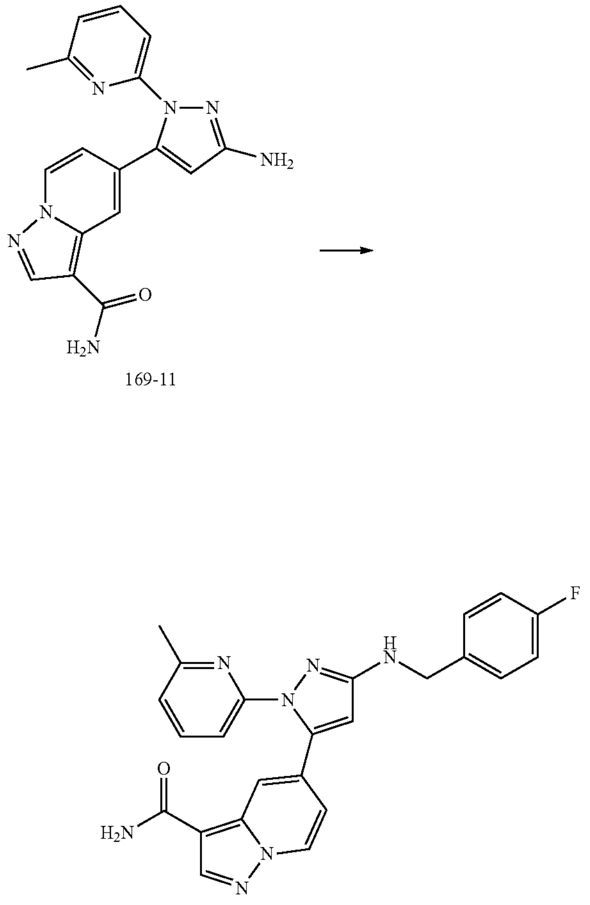

169-11

117

5-(3-Amino-1 (6-methylpyridin-2-yl)-1H-pyrazol-5-yl)pyrazolo[1,5-a]pyridine-3-carboxamide (Compound 169-11) hydrochloride (15 mg, 40.56 μmol) and 4-fluorobenzaldehyde (15 mg, 0.12 mmol) were dissolved in 1,2-dichloroethane (0.5 mL), 1 drop of glacial acetic acid was added dropwise, heated to 80° C. and stirred for 1 h. Then sodium cyanoborohydride (5 mg, 81.12 μmol) was added, and the reaction was further conducted for 2 h. The reaction was quenched by adding ice water, extracted with ethyl acetate (3×5 mL), the organic phases were combined, dried over anhydrous sodium sulfate, the organic phases were concentrated and separated by preparative high performance liquid chromatography (Method G), and the obtained fraction was lyophilized to give the title compound, 1 mg.

The structure was characterized as follows:

$^1$H NMR (400 MHz, DMSO-$d_6$) δ 8.64 (dd, J=7.2, 0.8 Hz, 1H), 8.52 (s, 1H), 8.14 (dd, J=1.9, 0.8 Hz, 1H), 7.79-7.68 (m, 2H), 7.51-7.40 (m, 5H), 7.20-7.06 (m, 3H), 7.02 (d, J=7.5 Hz, 1H), 6.80 (dd, J=7.2, 2.0 Hz, 1H), 6.41 (t, J=6.3 Hz, 1H), 6.09 (s, 1H), 4.35 (d, J=6.2 Hz, 2H), 2.04 (s, 3H).

ESI-MS (m/z): 442.1$[M+H]^+$.

Example 12: Synthesis of 5-(1-(6-methylpyridin-2-yl)-1H-pyrazol-5-yl)pyrazolo[1,5-a]pyridine-3-carboxamide (Compound 9)

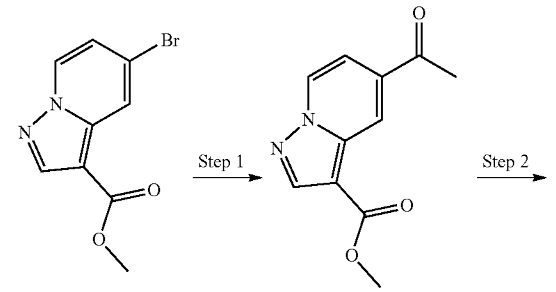

9-1

9-2

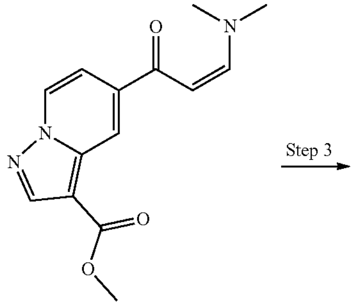

9-3

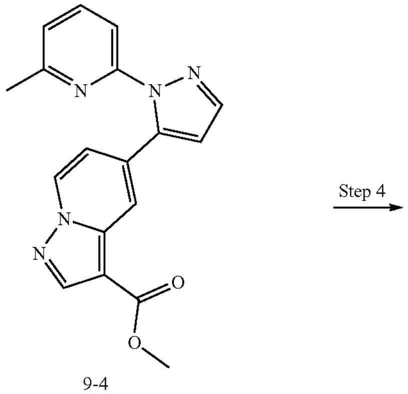

9-4

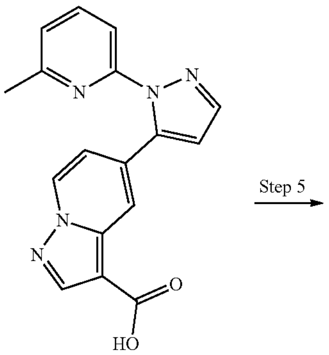

9-5

-continued

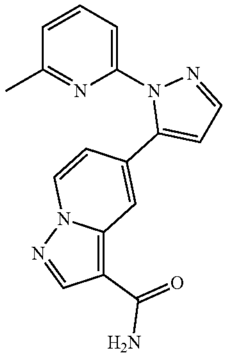

9

Step 1: Synthesis of methyl 5-acetylpyrazolo[1,5-a]pyridine-3-carboxylate (Compound 9-2)

Methyl 5-bromopyrazolo[1,5-a]pyridine-3-carboxylate (Compound 9-1, 380 mg, 1.41 mmol) was dissolved in acetonitrile (1 mL), added with vinyl ethyl ether (1.02 g, 14.12 mmol), [1,1'-bis(diphenylphosphino) ferrocene]palladium dichloride (103.23 mg, 141.21 μmol), and triethylamine (285.79 mg, 2.82 mmol), and reacted under microwave at 110° C. for 1 hour. The reaction solution was extracted with dichloromethane (10 ml*3), washed with water (10 ml), the organic phase was concentrated to dryness, which was then dissolved in acetonitrile (2 ml), added with 2N hydrochloric acid (2 ml), and stirred at 50° C. for 2 hours, extracted with dichloromethane (10 ml*3), washed with water (10 ml), and the organic phase was concentrated to dryness to obtain a crude product. The crude product was separated and purified by silica gel column chromatography (eluent: petroleum ether/ethyl acetate=1/2 (v/v)) and concentrated to give the title compound (150 mg).

ESI-MS (m/z): 233.1 $[M+H]^+$.

Step 2: Synthesis of methyl 5-(3-(dimethylamino) acryloyl) pyrazolo[1,5-a]pyridine-3-carboxylate (Compound 9-3)

Methyl 5-acetylpyrazolo[1,5-a]pyridine-3-carboxylate (Compound 9-2, 140 mg, 602.84 μmol) was dissolved in N,N-dimethylformamide dimethyl acetal (2 mL) at 25° C., heated to 120° C., and stirred for 3 hours. The reaction solution was subjected to rotary evaporation to dryness to obtain a crude product. The crude product was separated and purified by silica gel column chromatography (eluent: ethyl acetate) and concentrated to give the title compound (138 mg).

ESI-MS (m/z): 288.2 $[M+H]^+$.

Step 3: Synthesis of methyl 5-(1-(6-methylpyridin-2-yl)-1H-pyrazol-5-yl)pyrazolo[1,5-a]pyridine-3-carboxylate (Compound 9-4)

At 25° C., methyl 5-(3-(dimethylamino)acryloyl)pyrazolo[1,5-a]pyridine-3-carboxylate (Compound 9-3, 138 mg, 480.31 μmol) was dissolved in toluene (3 mL), added with 2-hydrazino-6-methylpyridine hydrochloride (70.98 mg, 576.37 μmol)) and acetic acid (865.28 mg, 14.41 mmol, 824.86 μL), and reacted at 120° C. for 2 hours. The reaction solution was subjected to rotary evaporation to dryness, extracted with ethyl acetate (50 mL*3), washed with saturated brine (50 mL), and the organic phases were combined, dried with anhydrous sodium sulfate, then evaporated to dryness under reduced pressure to obtain a crude product. The crude product was separated and purified by silica gel column chromatography (eluent: petroleum ether/ethyl acetate=3/2 (v/v)) to obtain the title compound (100 mg).

ESI-MS (m/z): 348.1 $[M+H]^+$.

Step 4: Synthesis of 5-(1-(6-methylpyridin-2-yl)-1H-pyrazol-5-yl)pyrazolo[1,5-a]pyridine-3-carboxylic Acid (Compound 9-5)

At 25° C., methyl 5-(1-(6-methylpyridin-2-yl)-1H-pyrazol-5-yl)pyrazolo[1,5-a]pyridine-3-carboxylate (Compound 9-4, 160 mg, 460.60 μmol) was dissolved in ethanol (1 mL), added with water (1 mL), tetrahydrofuran (1 mL) and lithium hydroxide (33.09 mg, 1.38 mmol), and reacted at 50° C. for 6 hours. The reaction solution was evaporated to remove organic reagent, the remaining aqueous solution was adjusted to pH=3-4 with 1N hydrochloric acid, extracted with ethyl acetate/tetrahydrofuran (1:1, 50 mL*3), washed with saturated brine (50 mL), and the organic phases were combined, dried over anhydrous sodium sulfate, and then evaporated to dryness under reduced pressure to give the title compound (140 mg).

ESI-MS (m/z): 320.1 $[M+H]^+$.

Step 5: Synthesis of 5-(1-(6-methylpyridin-2-yl)-1H-pyrazol-5-yl)pyrazolo[1,5-a]pyridine-3-carboxamide (Compound 9)

At 25° C., 5-(1-(6-methylpyridin-2-yl)-1H-pyrazol-5-yl)pyrazolo[1,5-a]pyridine-3-carboxylic acid (Compound 1-5, 200 mg, 438.44 μmol) was dissolved in N,N-dimethylformamide (3 mL), then added with ammonium chloride (70.36 mg, 1.32 mmol), HATU (261.81 mg, 482.28 μmol), N,N-diisopropylethylamine (169.99 mg, 1.32 mmol) in sequence, reacted at 25° C. for 1 hour, extracted with dichloromethane (50 mL*3), washed with saturated brine (50 mL), and the organic phases were combined, dried over anhydrous sodium sulfate, then evaporated to dryness under reduced pressure to obtain a crude product, which was purified by preparative high performance liquid chromatography (Method H) and lyophilized to obtain the title compound (95 mg).

The structure was characterized as follows:

$^1$H NMR (400 MHz, DMSO-$d_6$) δ 8.69 (dd, J=7.2, 0.9 Hz, 1H), 8.54 (s, 1H), 8.16 (dd, J=2.1, 0.9 Hz, 1H), 7.92-7.85 (m, 2H), 7.71 (s, 1H), 7.57 (dt, J=8.0, 0.8 Hz, 1H), 7.26 (d, J=7.5 Hz, 1H), 7.11 (s, 1H), 6.87 (d, J=1.8 Hz, 1H), 6.83 (dd, J=7.3, 2.0 Hz, 1H), 2.19 (s, 3H).

ESI-MS (m/z): 319.0$[M+H]^+$.

Test of Pharmacological Activity

Test Example 1: In Vitro Enzymatic Activity Inhibition Test (TGFβR1)

Experimental method: According to the instructions of ADP-Glo™ Kinase Detection Kit (Promega), the inhibitory effect of the compounds of the present invention on the enzymatic activity of TGFβR1 was determined, and the steps were as follows:

TGFβR1 enzyme were pre-incubated with different concentrations of test compounds (1000 nM, 100 nM, 10 nM) at 30° C. for 30 min, TGFβR1 peptide and adenosine triphosphate (ATP) were added to initiate the reaction. The incubation was performed at 30° C. for 3 h, followed by an addition of ADP-Glo™ reagent and incubated at room temperature for 90 min, kinase detection reagent was then added. Chemiluminescence signal values were detected after incubation at room temperature for another 30 min. Taking the solvent group (DMSO) as the negative control and the buffer group (without TGFβR1 enzyme) as the blank control, the percent inhibition rates of different concentrations of compounds were calculated according to the following formula:

Percent inhibition rate=(1−(chemiluminescence signal value of different concentration of the test compound−chemiluminescence signal value of the blank control)/(chemiluminescence signal value of the negative control−chemiluminescence signal value of the blank control))×100%;

When the percent inhibition rate was between 30% and 80%, the median inhibitory concentration ($IC_{50}$) or range of the compound was calculated according to the following formula:

$IC_{50}=X\times(1-\text{percent inhibition rate (\%)})/\text{percent inhibition rate (\%)}$, wherein $X$ is the concentration of the compound at which the inhibition rate is between 30% and 80%.

The experimental results are shown in Table 1 below:

TABLE 1

Inhibitory activity of compounds of the present invention on TGFβR1

| Example No. | $IC_{50}$ (nM) for TGFβR1 |
|---|---|
| Example 1 | 48.59 ± 18.64 |
| Example 2 | 9.83 ± 4.79 |
| Example 3 | 43.76 ± 6.08 |
| Example 4 | 11.99 ± 5.40 |
| Example 5 | 6.70 ± 0.55 |
| Example 6 | 2.36 ± 0.68 |
| Example 7 | 27.24 ± 4.08 |
| Example 8 | 8.27 ± 0.11 |
| Example 9 | 27.36 ± 4.89 |
| Example 10 | 4.82 ± 0.51 |
| Example 11 | 0.50 ± 0.21 |
| Example 12 | 9.39 ± 2.15 |

It could be seen from Table 1 that the compounds of the present invention have obvious inhibitory effect on TGFβR1.

Test Example 2: In Vitro Enzymatic Activity Inhibition Test (TGFβR2)

Experimental method: According to the instructions of ADP-Glo™ Kinase Detection Kit (Promega), the inhibitory effect of the compounds of the present invention on the enzymatic activity of TGFβR2 was determined, and the steps were as follows:

TGFβR2 enzyme were pre-incubated with different concentrations of test compounds (1000 nM, 100 nM, 10 nM) at 30° C. for 30 min, myelin basic protein (MBP) and adenosine triphosphate (ATP) were added to initiate the reaction. The incubation was performed at 30° C. for 3 h, followed by an addition of ADP-Glo™ reagent and incubated at room temperature for 90 min, kinase detection reagent was then added. The chemiluminescence signal values were detected after incubation at room temperature for another 30 min. Taking the solvent group (DMSO) as the negative control and the buffer group (without TGFβR2 enzyme) as the blank control, the percent inhibition rates of different concentrations of compounds were calculated according to the following formula:

Percent inhibition rate=(1−(chemiluminescence signal value of different concentration of the test compound−chemiluminescence signal value of the blank control)/(chemiluminescence signal value of the negative control−chemiluminescence signal value of the blank control))×100%;

When the percent inhibition was between 30% and 80%, the median inhibitory concentration ($IC_{50}$) or range of the compound was calculated according to the following formula:

$IC_{50}=X\times(1-\text{percent inhibition rate }(\%))/\text{percent inhibition rate }(\%)$, wherein $X$ is the concentration of the compound at which the inhibition rate is between 30% and 80%.

The experimental results are shown in Table 2 below:

TABLE 2

Inhibitory rates of TGFβR2 enzymatic activity by compounds of the present invention

| Example No. | $IC_{50}$ (nM) for TGFβR2 |
|---|---|
| Example 1 | >1000 |
| Example 2 | >1000 |
| Example 3 | >1000 |
| Example 6 | 690.18 ± 109.95 |
| Example 8 | >1000 |
| Example 10 | >1000 |
| Example 11 | 593.38 ± 129.38 |
| Example 12 | >1000 |

It could be seen from Table 2 that the compounds of the present invention have weak inhibitory activity on TGFβR2.

As could be seen from Table 1 and Table 2, the compounds of the present invention have a selective inhibitory effect on TGFβR1.

Test Example 3: In Vitro Cell Activity Inhibition Test

Experimental method: According to the instructions of Bright-Glo™ luciferase detection kit (Promega), the inhibitory effect of the compounds of the present invention on TGFβ/Smads signaling pathway in HEK293-SBE cells was determined. The steps were as follows:

HEK293-SBE cells (Bps bioscience) were added to a 96-well plate (10% PBS medium), 30,000/well, and cultured overnight at 37° C. and 5% $CO_2$. The medium was changed to 0.5% FBS medium, and the test compound diluted in 0.5% FBS medium was added. The highest final concentration of the test compound was 10 μM with 4-fold dilution, and a total of 8 concentration gradients. After 4-5 hours of incubation, 10 μl of TGFβ was added. The final concentration of TGFβ was 0.5 ng/ml. 10 μl of medium added in replace of TGFβ was the negative control. In the blank control, no test compound was added, and TGFβ was added. Bright Glo reagent was added to each well, and the chemiluminescence signal value was read on a microplate reader.

The percent inhibition rates of different concentrations of the compound were calculated according to the following formula:

Percent inhibition rate=(1−(chemiluminescence signal value of the test compound−chemiluminescence signal value of the blank control)/(chemiluminescence signal value of the negative control−chemiluminescence signal value of the blank control))×100%;

The percent inhibition rates of the test compound at different concentrations were plotted against the compound concentrations, the curve was fitted according to the four-parameter model, and the $IC_{50}$ value was calculated by the following formula:

$y=\text{Min}+(\text{Max}-\text{Min})/(1+(x/IC_{50})\hat{}(-\text{Hillslope}))$, wherein: $y$ is percentage inhibition rate; Max and Min are the maximum and minimum values of the fitted curve, respectively; $x$ is the logarithmic concentration of compound; and Hillslope is the slope of the curve.

The experimental results are shown in Table 3 below:

TABLE 3

Inhibitory effect of the compounds of the present invention on TGFβ/Smads signaling pathway in HEK293-SBE cells

| Example No. | $IC_{50}$ (nM) |
|---|---|
| Example 1 | 12.96 ± 0.92 |
| Example 3 | 29.06 ± 2.50 |
| Example 4 | 34.95 ± 2.69 |
| Example 5 | 42.69 ± 1.49 |
| Example 6 | 20.14 ± 1.00 |
| Example 7 | 33.64 ± 5.81 |
| Example 8 | 29.92 ± 1.27 |
| Example 9 | 43.23 ± 2.54 |
| Example 10 | 43.07 ± 4.19 |
| Example 11 | 19.41 ± 1.52 |
| Example 12 | 26.55 ± 5.43 |

It could be seen from Table 3 that the compounds of the present invention have significant inhibitory effect on the TGFβ/Smads signaling pathway (luciferase reporter gene method) induced by TGFβ in HEK293-SBE cells.

Test Example 4: Biochemical hERG Inhibition Test

1. Test System:

Kit: Predictor™ hERG fluorescence polarization detection kit (ThermoFisher), the kit contained the following components: positive control compound hERG potassium channel blocker E4031; hERG cell membrane; affinity tracer Tracer; and hERG buffer.

2. Test Parameters:

hERG concentration: 1×; Tracer concentration: 1 nM; incubation time: 2 h; BMG PHERAstar FS FP.

3. Test Method:

The test was carried out according to the kit instructions, and the steps were as follows:

Test group: 10 μM and 1 μM of the test compound were added to the microplate containing hERG cell membrane, the Tracer (a tracer with high hERG affinity) was added to each well, the microplate was incubated at room temperature for 2 hours, and a multi-plate reader was used to detect changes of fluorescence polarization values (excitation wavelength: 540 nm; emission wavelength: 590 nm).

Positive control group: 30 μM positive control compound E4031 was used to replace the test compound, and the experimental method was the same as that of the test group.

Blank control group: hERG buffer was used to replace the test compound without the addition of hERG cell membrane, and the experimental method was the same as that of the test group.

4. Data Processing:

According to the data ratio, the percent inhibition rates (%) of the compounds of the present invention to hERG at different concentrations were calculated, and the ranges of the half inhibitory concentration ($IC_{50}$) of the compounds were determined.

Percent inhibition rate (%)=(1−(fluorescence polarization value of the test compound−fluorescence polarization value of the positive control)/(fluorescence polarization value of the blank control−fluorescence polarization value of the positive control))×100%;

5. Experimental Results:

The inhibition effect of the compounds on hERG was determined using the method described above and the results are shown in Table 4 below.

TABLE 4

Results of hERG inhibition test

| Example No. | $IC_{50}$ (μM) |
|---|---|
| Example 1 | >10 |
| Example 4 | >10 |
| Example 6 | >10 |
| Example 7 | >10 |
| Example 8 | >10 |
| Example 10 | >10 |
| Example 11 | >10 |
| Example 12 | >10 |

The test results showed that the compounds of the present invention have low affinity to hERG, and their $IC_{50}$ values as competing with the affinity tracer (Tracer) were all above 10 μM, which confirmed that the compounds of the present invention have a lower risk of cardiotoxicity related to hERG ion channels.

Test Example 5: CYP Enzyme (Cytocrome P450) Inhibition Test

1. Test System:

P450-Glo™ CYP1A2 Screening System (Promega);
P450-Glo™ CYP2D6 Screening System (Promega);
P450-Glo™ CYP3A4 Screening System (Promega).

2. Test Instrument:

BMG PHERAstar FS Luminescent.

3. Test Method:

The test was carried out according to the kit instructions, and the steps were as follows:

3.1. Inhibition of CYP1A2:

Test group: The test compound of different concentration was added to the microplate, Luciferin-ME (100 μM), $K_3PO_4$ (100 mM) and CYP1A2 (0.01 μmol/μL) were added to each well, and pre-incubated at room temperature for 10 mM, followed by an addition of NADPH regeneration system, and reacted at room temperature for 30 min, an equal volume of detection buffer was added at last, and incubated at room temperature for 20 mM, and then chemiluminescence detection was performed.

Negative control group: The experimental method was the same as that of the test group, but the test compound was not added.

Blank control group: The experimental method was the same as that of the test group, but the test compound was not added, and CYP1A2 Membrance (0.01 μmol/μL) was used instead of CYP1A2.

3.2. Inhibition of CYP2D6:

Test group: The test compound of different concentration was added to the microplate, and Luciferin-ME EGE (3 μM), $K_3PO_4$ (100 mM) and CYP2D6 (5 nM) were added to each well, and pre-incubated at room temperature for 10 mM, followed by an addition of the NADPH regeneration system, and reacted at 37° C. for 30 min, an equal volume of detection buffer was added at last, and incubated at room temperature for 20 mM, and then chemiluminescence detection was performed.

Negative control group: The experimental method was the same as that of the test group, but the test compound was not added.

Blank control group: The experimental method was the same as that of the test group, but the test compound was not added, and CYP2D6 Membrance (5 nM) was used instead of CYP2D6.

3.3. Inhibition of CYP3A4:

Test group: The test compound of different concentration was added to the microplate, Luciferin-IPA (3 μM), $K_3PO_4$ (100 mM) and CYP3A4 (2 nM) were added to each well, and pre-incubated at room temperature for 10 mM, followed by an addition of the NADPH regeneration system, and reacted at room temperature for 30 min, an equal volume of detection buffer was added at last, and incubated at room temperature for 20 mM, and then chemiluminescence detection was performed.

Negative control group: The experimental method was the same as that of the test group, but the test compound was not added.

Blank control group: The experimental method was the same as that of the test group, but the test compound was not added, and CYP3A4 Membrance (2 nM) was used instead of CYP3A4.

4. Data Processing:

Percent inhibition rate (%)=(1−(chemiluminescence signal value of the test compound−chemiluminescence signal value of the blank control)/(chemiluminescence signal value of the negative control−chemiluminescence signal value of the blank control))×100%;

The median inhibitory concentration ($IC_{50}$) or range of the compound was estimated according to the inhibition rate of CYP enzymes at different concentrations:

$IC_{50}=X\times(1-\text{percent inhibition rate (\%)})/\text{percent inhibition rate (\%)}$, wherein $X$ is the test concentration of the compound.

5. Experimental Results:

The inhibition effect of the compounds of the present invention on the three CYPs was determined as described above and the results were shown in Table 5 below.

TABLE 5

Results of CYPs inhibition test

| | $IC_{50}$ (μM) | | |
|---|---|---|---|
| Example No. | CYP1A2 | CYP2D6 | CYP3A4 |
| Example 4 | >10 | >10 | >10 |
| Example 6 | >10 | >10 | >10 |
| Example 8 | >10 | >10 | >10 |
| Example 10 | >10 | >10 | >10 |
| Example 11 | >10 | >10 | >10 |
| Example 12 | >10 | >10 | >10 |

The test results showed that the compounds of the present invention have weak inhibitory effect on the three subtypes of CYPs, and had good drug safety.

Test Example 6: Pharmacokinetics (PK) Study in Balb/c Mice

The example compounds were administered to female Balb/c mice via intravenous injection (IV) and gastric perfusion (PO), respectively, and their pharmacokinetic properties were investigated. The administered doses for IV and PO were 1 mg/kg and 10 mg/kg, respectively. The solvent for IV was 5% DMSO+5% Solutol (15-hydroxystearic acid polyethylene glycol ester)+90% normal saline, the solvent for PO was 0.5% MC (sodium methylcellulose). Whole blood samples were collected at various time points after IV and PO administration, and subjected to EDTA-K2 anticoagulation before test.

Whole blood samples were processed by precipitating proteins and then subjected to LC-MS/MS analysis. The pharmacokinetic parameters were calculated by the non-compartmental model using WinNonlin 6.3 software, and the results were shown in Table 6 below.

TABLE 6

Pharmacokinetic parameters of compounds in whole blood in mice

| Example No. | Route of administration | Dose mg/kg | $AUC_{last}$ h*ng/mL | $C_{max}$ ng/mL | Cl ml/min/kg | $T_{1/2}$ h | F % |
|---|---|---|---|---|---|---|---|
| Example | IV | 1 | 578 ± 4 | 1163 ± 58 | 28.4 ± 0.3 | / | / |
| 6 | PO | 10 | 3586 ± 563 | 7440 ± 226 | / | 0.46 ± 0.19 | 61.4 ± 9.5 |
| Example | IV | 1 | 458 ± 27 | 917 ± 29 | 35.0 ± 3.3 | / | / |
| 8 | PO | 10 | 4362 ± 502 | 6273 ± 1571 | / | 1.80 ± 0.35 | 98.1 ± 15.0 |
| Example | IV | 1 | 572 ± 144 | 862 ± 53 | 29.3 ± 6.3 | / | / |
| 12 | PO | 10 | 3040 ± 166 | 5920 ± 516 | / | 0.52 ± 0.18 | 52.1 ± 2.6 |

As shown in Table 6, for the compounds of Example 6, Example 8 and Example 12 in mice via IV administration at a dose of 1 mg/kg, their exposure doses ($AUC_{last}$) were 578 h*ng/mL, 458 h*ng/mL and 572 h*ng/mL, the corresponding maximum plasma concentrations ($C_{max}$) were 1163 ng/mL, 917 ng/mL and 862 ng/mL, respectively, and the clearance rates (Cl) were 28.4 ml/min/kg, 35.0 ml/min/kg and 29.3 ml/min/kg, respectively, indicating that the compounds of the present invention have excellent drug exposure in mice by IV administration.

For the compounds of Example VI, Example VIII and Example XII in mice via PO administration at a dose of 10 mg/kg, their The $AUC_{last}$ values were 3586 h*ng/mL, 4362 h*ng/mL and 3040 h*ng/mL, respectively, and the maximum blood concentrations ($C_{max}$) were 7440 ng/mL, 6273 ng/mL and 5920 ng/mL, respectively, indicating that the compounds of the present invention have excellent drug exposure in the blood system of mice by PO administration.

After calculation, compared with intravenous administration, the half-lives of the compounds of Example VI, Example 8 and Example 12 after oral administration to mice were 0.46 h, 1.80 h and 0.52 h, respectively, and their bioavailability values were 61.4%, 98.1% and 52.1%, respectively.

In sum, the compounds of Example 6, Example 8 and Example 12 have excellent pharmacokinetic properties in mice.

Various modifications of the present invention, in addition to those described herein, shall be apparent to those skilled in the art in view of the foregoing description. Such modifications are also intended to fall within the scope of the appended claims. Each of the references cited in the present application, including all patents, patent applications, journal articles, books, and any other publications, is incorporated by reference in its entirety.

What is claimed is:

1. A compound having the structure of Formula I or a pharmaceutically acceptable form thereof, wherein the pharmaceutically acceptable form is selected from the group consisting of a pharmaceutically acceptable salt, ester, stereoisomer, tautomer, polymorph, solvate, isotopically labeled compound, and prodrug;

I

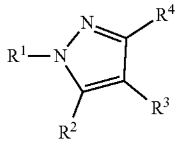

wherein, $R^1$ is selected from the group consisting of

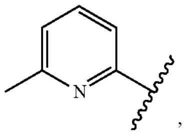
,
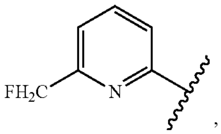
,
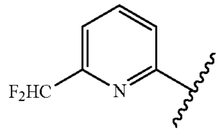
,
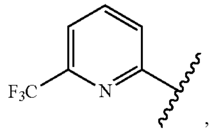
,
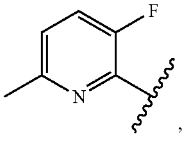
, and
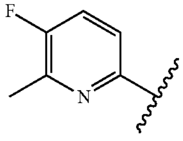

$R^2$ is

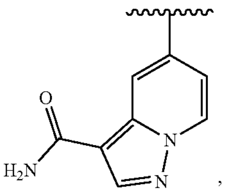
, $R^3$ is selected from the group consisting of hydrogen, halogen, $C_{1-6}$ alkyl, $C_{1-6}$ haloalkyl, $C_{3-8}$ cycloalkyl, $C_{1-6}$ alkoxyl and $C_{1-6}$ alkylamino; and $R^4$ is selected from the group consisting of hydrogen, $C_{3-8}$ cycloalkyl-$C_{1-6}$ alkylamino, 3- to 8-membered heterocyclylamino, $C_{1-6}$ alkylamino, $C_{1-6}$ haloalkylamino, $C_{3-8}$ cycloalkylamino, phenylamino, benzylamino, 5- to 10-membered heteroarylamino and 5- to 10-membered heteroarylalkylamino; wherein the $C_{3-8}$ cycloalkyl-$C_{1-6}$ alkylamino, 3- to 8-membered heterocyclylamino, $C_{1-6}$ alkylamino, $C_{1-6}$ haloalkylamino, $C_{3-8}$ cycloalkylamino, phenylamino, benzylamino, 5- to 10-membered heteroarylamino and 5- to 10-membered heteroarylalkylamino are each optionally substituted with one or more groups independently selected from the group consisting of: $C_{1-6}$ alkyl, halogen, cyano, amido, carbamoyl, mono- or di-$C_{1-6}$ alkyl-substituted carbamoyl, sulfonyl, phenyl, halophenyl and 4- to 6-membered heterocyclyl.

2. The compound according to claim 1, or a pharmaceutically acceptable form thereof, wherein, $R^3$ is selected from the group consisting of hydrogen, $C_{1-6}$ alkyl, $C_{1-6}$ haloalkyl, $C_{3-6}$ cycloalkyl, $C_{1-6}$ alkoxy and $C_{1-6}$ alkylamino; and $R^4$ is selected from the group consisting of hydrogen, $C_{3-8}$ cycloalkyl-$C_{1-6}$ alkylamino, 3- to 8-membered heterocyclylamino, $C_{1-6}$ alkylamino, $C_{1-6}$ haloalkylamino, $C_{3-8}$ cycloalkylamino, phenylamino, benzylamino, 5- to 6-membered heteroarylamino and 5- to 6-membered heteroarylalkylamino; wherein the $C_{3-8}$ cycloalkyl-$C_{1-6}$ alkylamino, 3- to 8-membered heterocyclylamino, $C_{1-6}$ alkylamino, $C_{1-6}$ haloalkylamino, $C_{3-8}$ cycloalkylamino, phenylamino, benzylamino, 5- to 6-membered heteroarylamino, and 5- to 6-membered heteroarylalkylamino are each optionally substituted with one or more groups independently selected from the group consisting of: $C_{1-6}$ alkyl, halogen, cyano, amido, carbamoyl, mono- or di-$C_{1-6}$ alkyl-substituted carbamoyl, sulfonyl, phenyl, halophenyl, $C_{3-6}$ cycloalkyl and 4- to 6-membered heterocyclyl.

3. The compound according to claim 1, or a pharmaceutically acceptable form thereof, wherein the compound has the structure of Formula I-1,

I-1

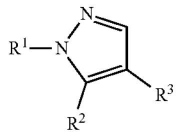

wherein:

$R^1$, $R^2$ and $R^3$ are as defined in claim 1.

4. The compound according to claim 1, or a pharmaceutically acceptable form thereof, wherein the compound has the structure of Formula I-4,

I-4

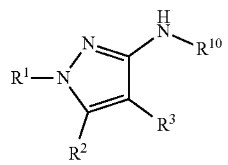

wherein $R^1$, $R^2$ and $R^3$ are as defined in claim 1; and $R^{10}$ is selected from the group consisting of $C_{1-6}$ alkyl, $C_{1-6}$ haloalkyl, $C_{3-8}$ cycloalkyl, $C_{3-8}$ cycloalkyl-$C_{1-6}$ alkyl, 3- to 8-membered heterocyclyl, benzyl, 5- to 6-membered heteroarylalkyl, phenyl and 5- to 6-membered heteroaryl; wherein the $C_{1-6}$ alkyl, $C_{1-6}$ haloalkyl, $C_3$-cycloalkyl, $C_{3-8}$ cycloalkyl-$C_{1-6}$ alkyl, 3- to 8-membered heterocyclyl, benzyl, 5- to 6-membered heteroarylalkyl, phenyl and 5- to 6-membered heteroaryl are each optionally substituted with one or more groups independently selected from the group consisting of $C_{1-6}$ alkyl, halogen, cyano amido, carbamoyl, mono- or di-$C_{1-6}$ alkyl-substituted carbamoyl, sulfonyl, phenyl, halophenyl and 4- to 6-membered heterocyclyl.

5. The compound according to claim 1, or a pharmaceutically acceptable form thereof, wherein, $R^3$ is selected from the group consisting of hydrogen and $C_{1-6}$ alkyl.

6. The compound according to claim 1, or a pharmaceutically acceptable form thereof, wherein, $R^3$ is selected from the group consisting of hydrogen, methyl, ethyl, isopropyl, cyclopropyl, difluoroethyl, $C_{1-6}$ alkoxy and $C_{1-6}$ alkylamino;

$R^4$ is selected from the group consisting of hydrogen and —$NHR^{10}$;

$R^{10}$ is selected from:

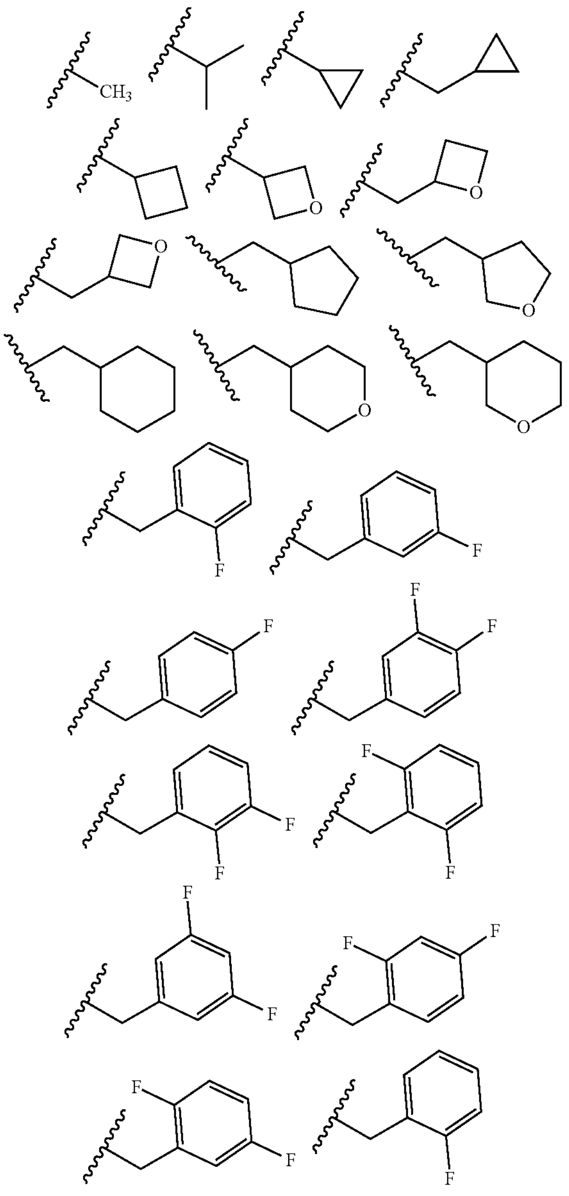

-continued
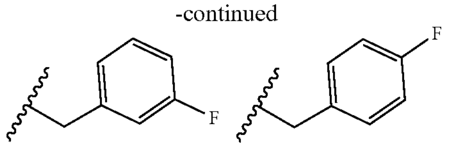
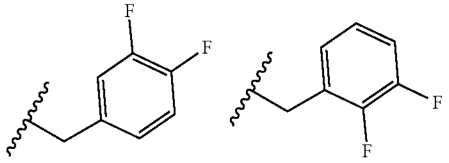
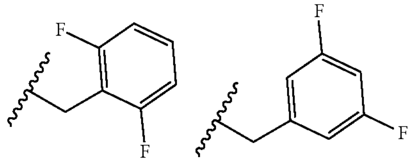
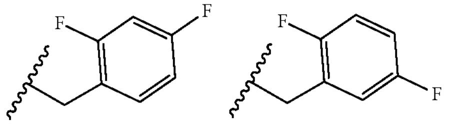
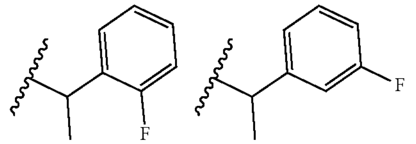
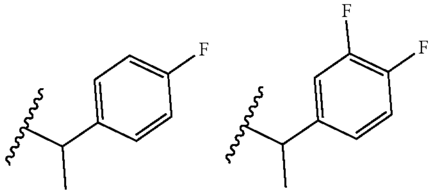
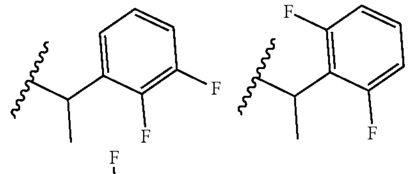
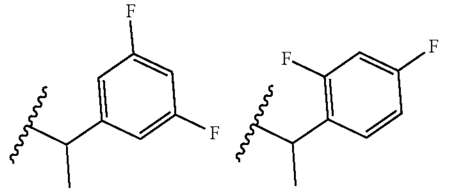
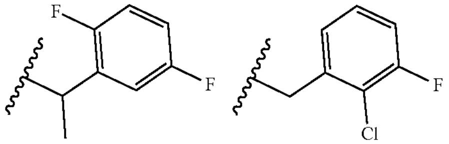
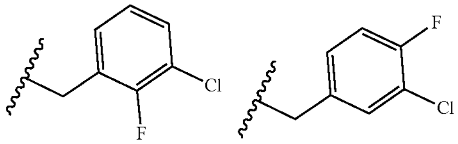
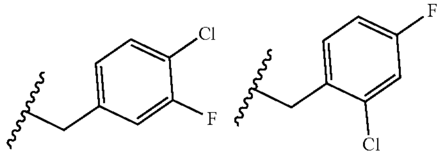
-continued
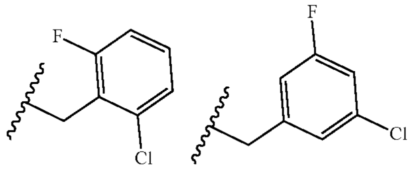
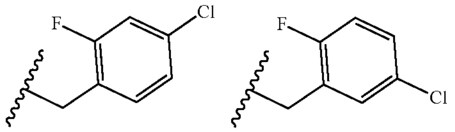
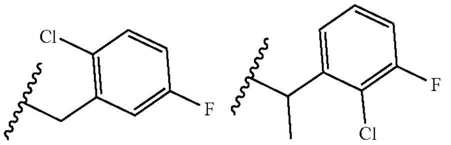
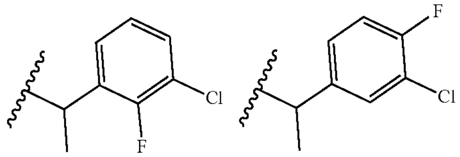
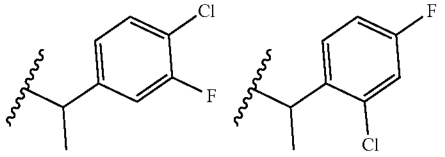
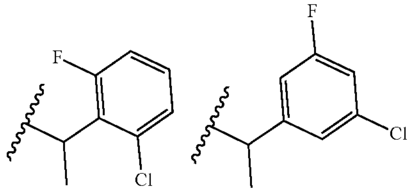
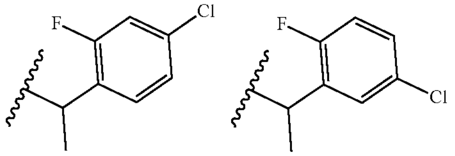
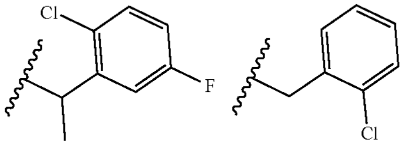
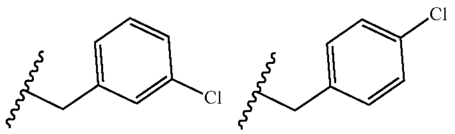
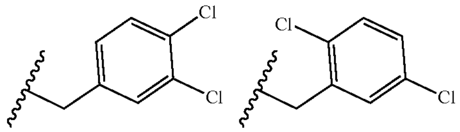
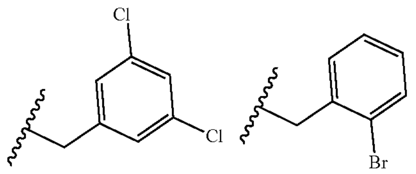

-continued
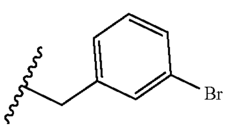 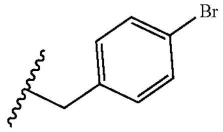
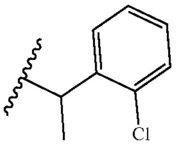 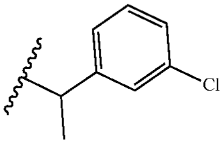
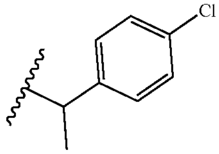 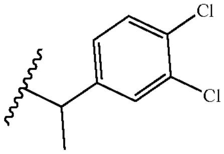
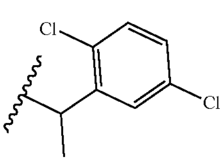 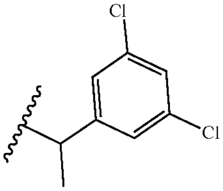
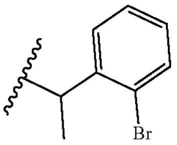 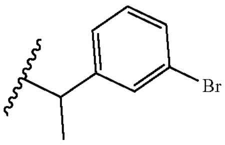
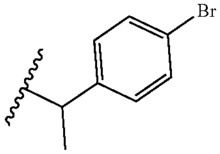 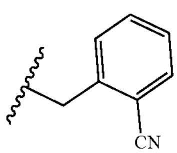
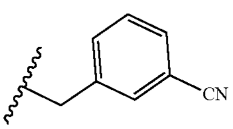 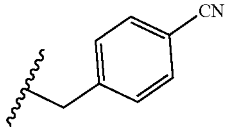
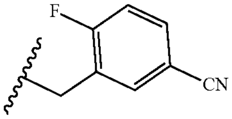 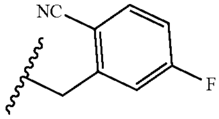
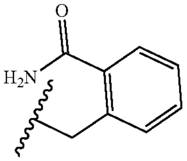 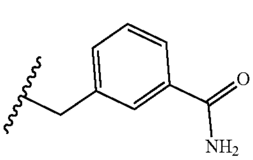
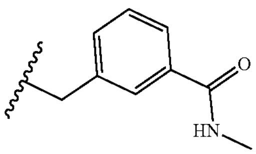 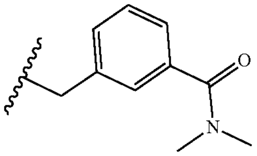
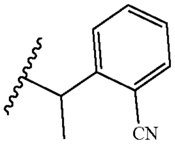 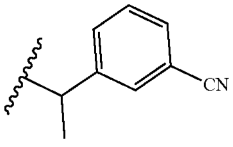
-continued
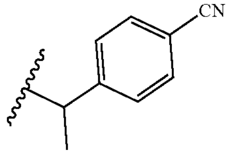 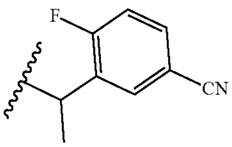
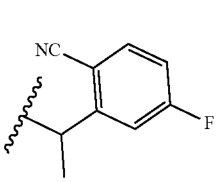 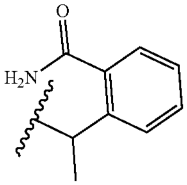
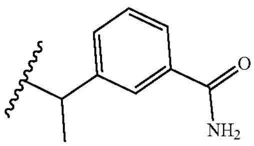 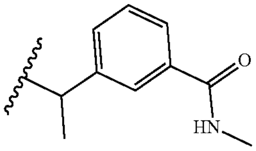
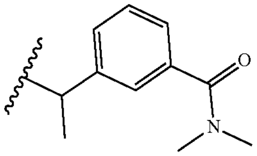 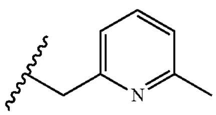
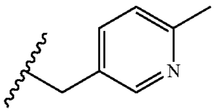 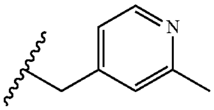
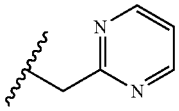 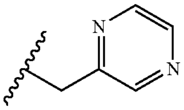
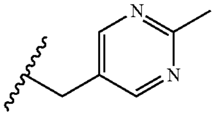 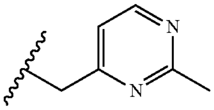
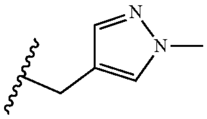 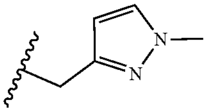
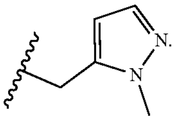
7. The compound according to claim 1, or a pharmaceutically acceptable salt, ester, stereoisomer, tautomer, polymorph, solvate, isotopically labeled compound, or prodrug thereof, wherein the compound is selected from:
9
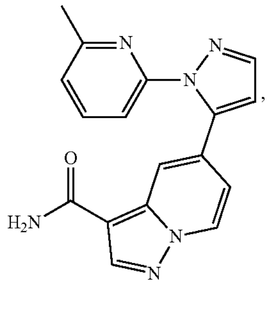

-continued
28
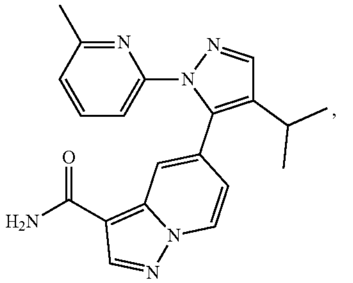
88
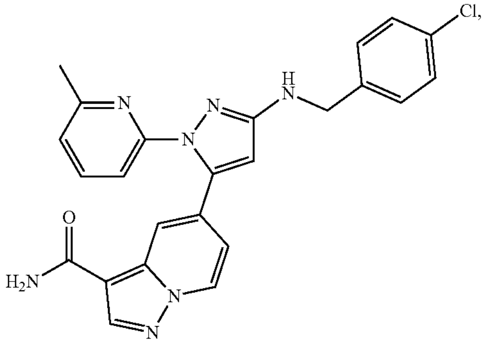
93
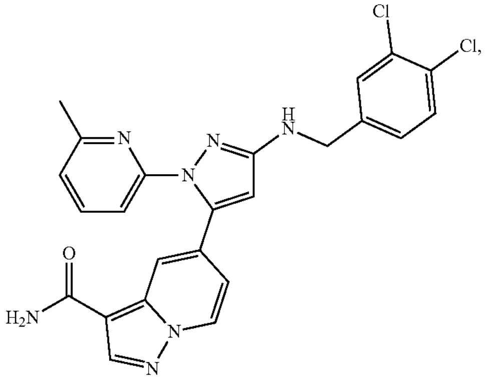
97
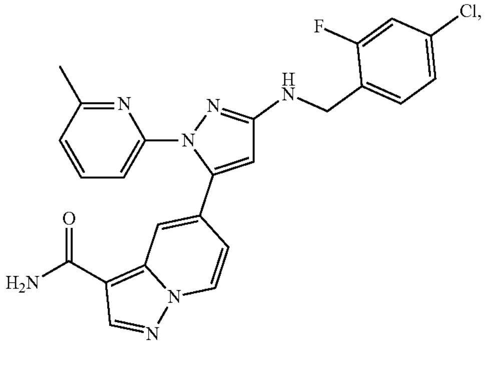
-continued
101
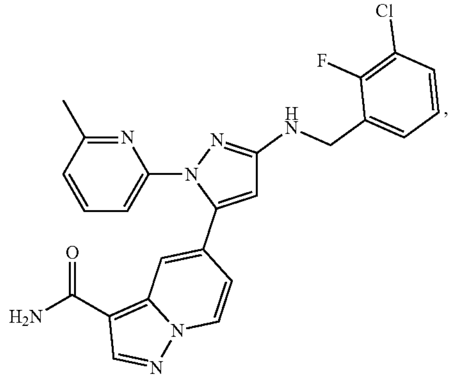
105
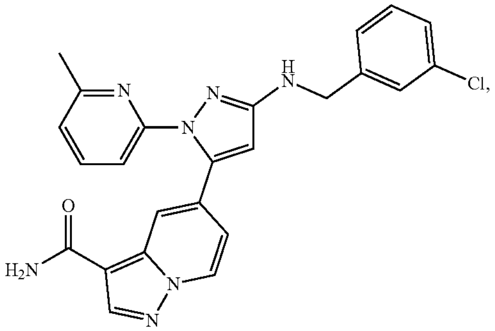
109
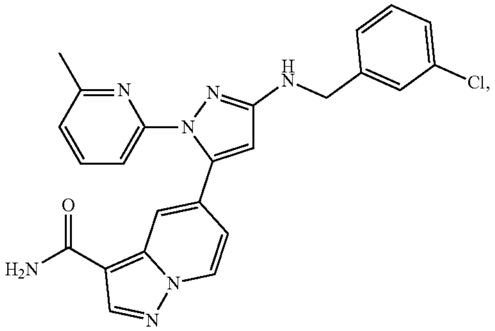
113
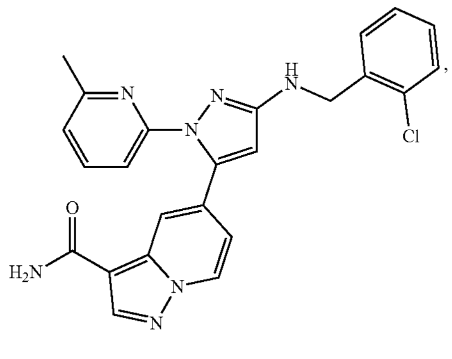

-continued
117
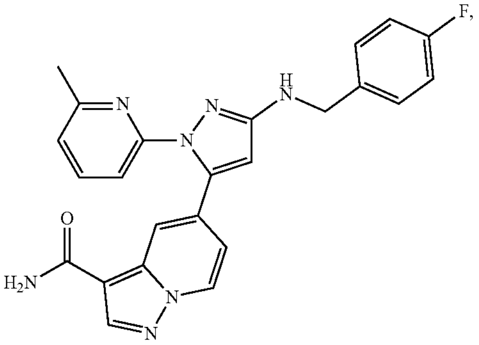
121
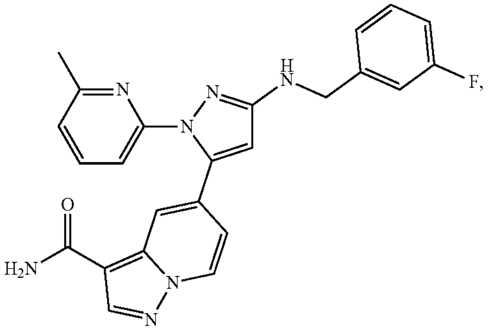
125
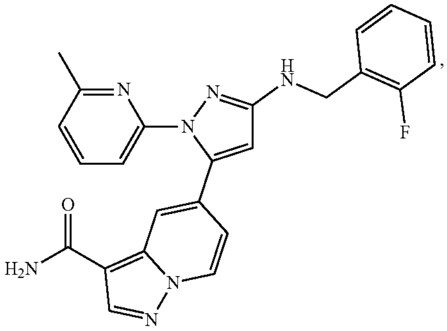
129
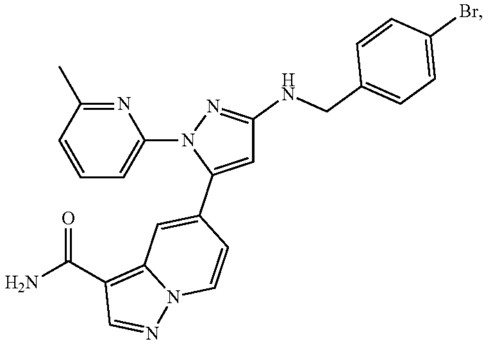
-continued
133
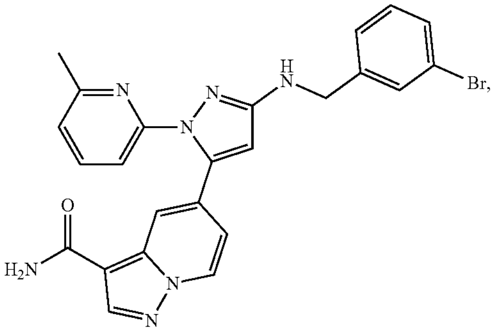
137
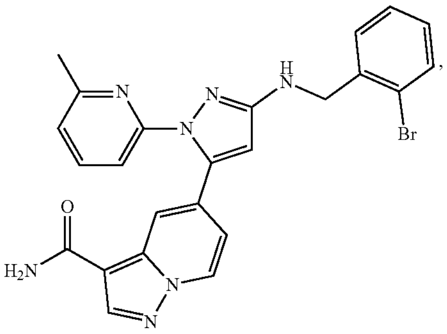
141
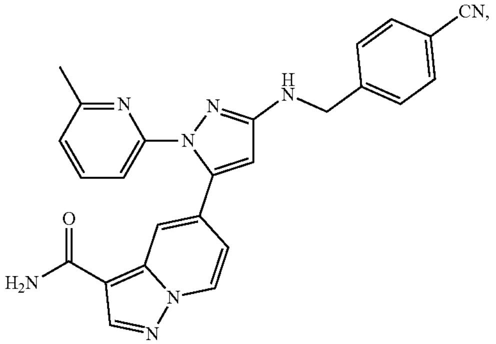
145
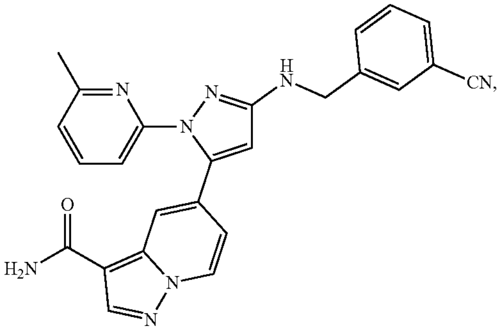

-continued
153
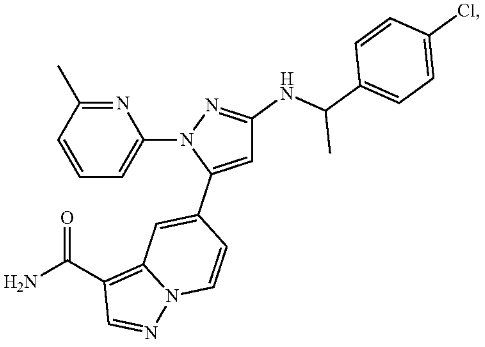
157
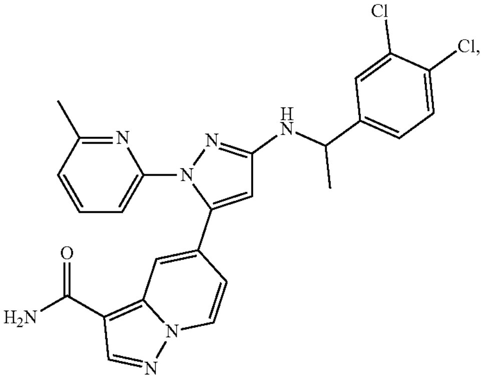
161
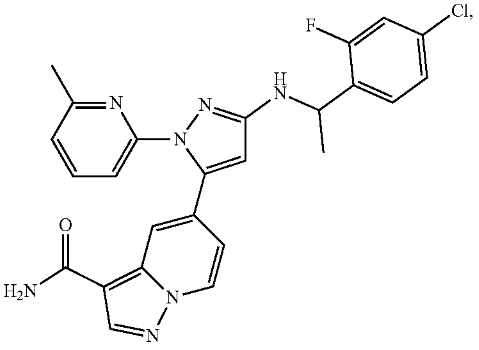
165
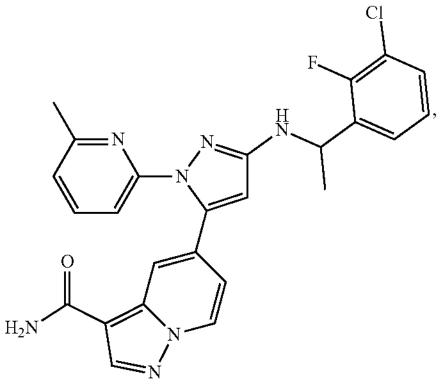
-continued
169
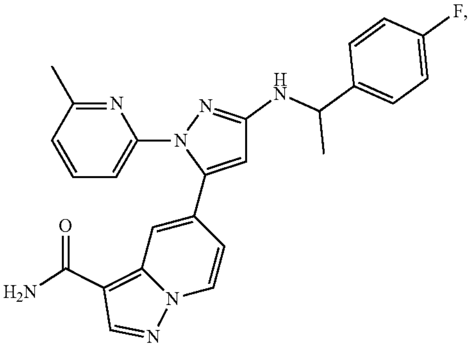
173
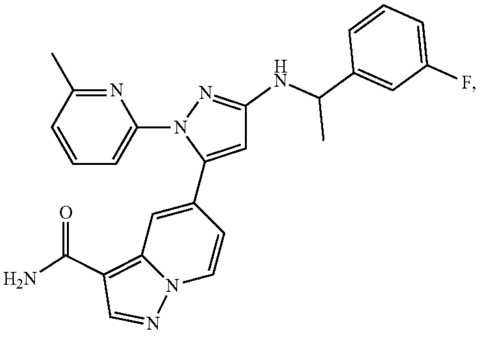
177
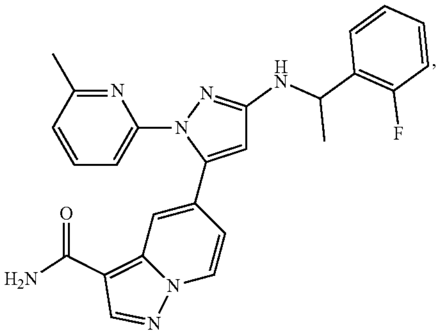
191
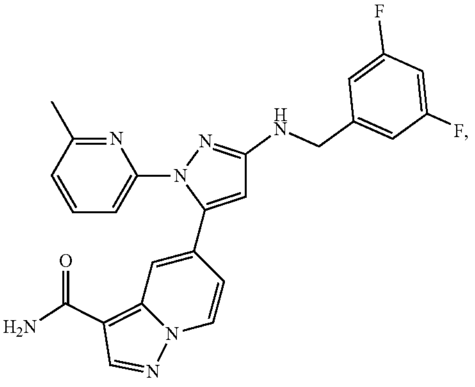

-continued

192

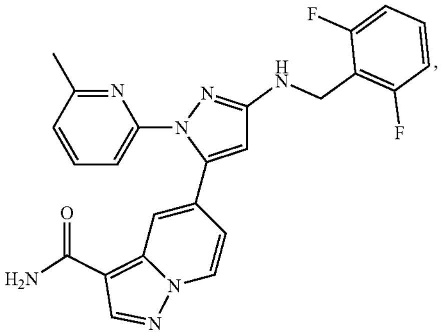

,

193

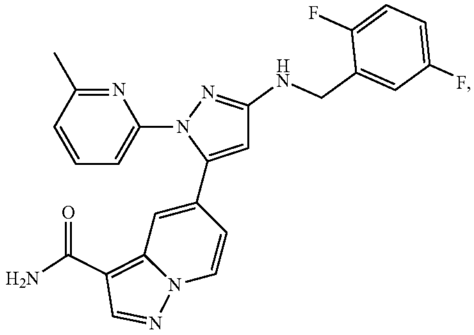

,

194

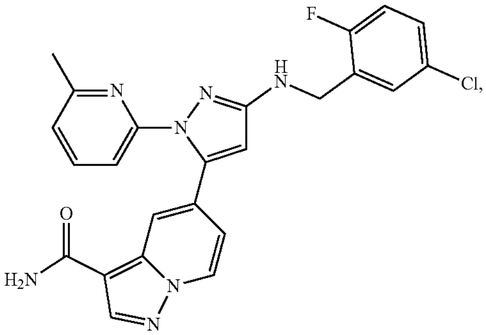

,

211

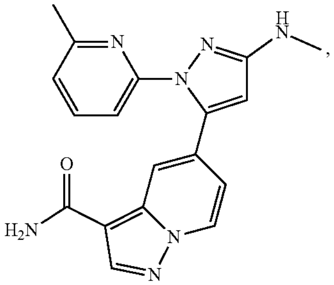

, and

213

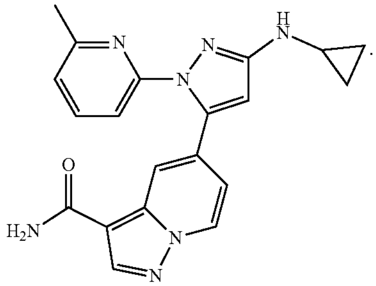

.

8. A pharmaceutical composition, which comprises at least one compound according to claim 1, or a pharmaceutically acceptable form thereof, and one or more pharmaceutically acceptable carriers.

9. A kit product, which comprises:

a) at least one compound according to claim 1 or a pharmaceutically acceptable form thereof as a first therapeutic agent, or pharmaceutical composition as a first pharmaceutical composition.

10. A pharmaceutical composition, which comprises at least one compound according to claim 7, or a pharmaceutically acceptable form thereof, and one or more pharmaceutically acceptable carriers.

11. A kit product, which comprises:

a) at least one compound according to claim 7 or a pharmaceutically acceptable form thereof as a first therapeutic agent, or a pharmaceutical composition comprising the same as a first pharmaceutical composition.

12. The compound of claim 3, wherein $R^3$ is hydrogen or $C_{1-6}$ alkyl.

13. The compound of claim 4, where $R^{10}$ is selected from the group consisting of $C_{1-6}$ alkyl, $C_{3-6}$ cycloalkyl, $C_{3-6}$ cycloalkyl-$C_{1-4}$ alkyl, 3- to 6-membered heterocyclyl, benzyl, 5- to 6-membered heteroarylalkyl, phenyl and 5- to 6-membered heteroaryl; wherein the $C_{1-6}$ alkyl, $C_{3-6}$ cycloalkyl, $C_{3-6}$ cycloalkyl-$C_{1-4}$ alkyl, 3- to 6-membered heterocyclyl, benzyl, 5- to 6-membered heteroarylalkyl, phenyl and 5- to 6-membered heteroaryl are each optionally substituted with one or more groups independently selected from the group consisting of $C_{1-6}$ alkyl, halogen, cyano, amido, carbamoyl, mono- or di-$C_{1-4}$ alkyl-substituted carbamoyl and sulfonyl.

14. The compound of claim 4, wherein $R^{10}$ is selected from the group consisting of $C_{1-6}$ alkyl, $C_{3-6}$ cycloalkyl, benzyl, pyridyl and pyrazolyl; wherein the $C_{1-6}$ alkyl, $C_{3-6}$ cycloalkyl, benzyl, pyridyl and pyrazolyl are each optionally substituted with one or more groups independently selected from the group consisting of methyl, fluoro, chloro, bromo, and cyano.

15. The compound of claim 5, wherein $R^1$ is

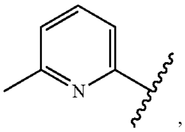 [SMILES: *c1cccc(C)n1]

,

16. The compound of claim 5, wherein $R^3$ is selected from the group consisting of hydrogen, methyl, ethyl, propyl and isopropyl.

17. The compound of claim 5, wherein $R^3$ is selected from the group consisting of hydrogen and isopropyl.

18. The compound of claim 5, wherein $R^3$ is hydrogen.

19. The compound of claim 5, wherein $R^3$ is isopropyl.

20. The compound according to claim 1, or a pharmaceutically acceptable form thereof, wherein, $R^4$ is selected from the group consisting of hydrogen, $C_{1-6}$ alkylamino, $C_{3-8}$ cycloalkylamino, benzylamino and 5- to 10-membered heteroarylalkylamino, wherein the $C_{1-6}$ alkylamino, $C_{3-8}$ cycloalkylamino, benzylamino and 5- to 10-membered heteroarylalkylamino are each optionally substituted with one or more groups independently selected from the group consisting of the followings: $C_{1-6}$ alkyl, halogen and cyano.

21. The compound of claim 20, wherein $R^4$ is selected from the group consisting of hydrogen, $C_{1-6}$ alkylamino, $C_{3-6}$ cycloalkylamino, benzylamino and 5- to 6-membered heteroaryl-$C_{1-4}$ alkylamino, and the $C_{1-6}$ alkylamino, $C_{3-6}$ cycloalkylamino, benzylamino and 5- to 6-membered heteroaryl-$C_{1-4}$ alkylamino are each optionally substituted with one or more groups selected from the group consisting of the followings: $C_{1-6}$ alkyl, halogen and cyano.

22. The compound of claim 20, wherein $R^4$ is selected from the group consisting of hydrogen and —$NHR^{10}$; wherein $R^{10}$ is selected from the group consisting of $C_{1-6}$ alkyl, $C_{3-6}$ cycloalkyl, benzyl and 5- to 6-membered heteroaryl-$C_{1-4}$ alkyl, and the $C_{1-6}$ alkyl, $C_{3-6}$ cycloalkyl, benzyl and 5- to 6-membered heteroaryl-$C_{1-4}$ alkyl are each optionally substituted with one or more groups independently selected from the group consisting of the followings: $C_{1-6}$ alkyl, fluoro, chloro, bromo, and cyano.

23. The compound of claim 20, wherein $R^4$ is selected from the group consisting of hydrogen and —$NHR^{10}$; wherein $R^{10}$ is selected from the group consisting of $C_{1-6}$ alkyl, benzyl and pyridylmethyl, and the benzyl and pyridylmethyl are each optionally substituted with one or more groups independently selected from the group consisting of the followings: $C_{1-6}$ alkyl, fluoro, chloro, bromo, and cyano.

24. The compound of claim 23, wherein $R^{10}$ is selected from the group consisting of $C_{1-6}$ alkyl, benzyl and pyridylmethyl, and the benzyl and pyridylmethyl are each optionally substituted with one or more groups independently selected from the group consisting of the followings: methyl and fluoro.

25. The compound of claim 20, wherein $R^4$ is selected from the group consisting of hydrogen and —$NHR^{10}$; $R^{10}$ is selected from:

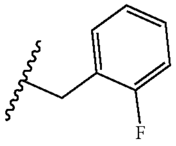 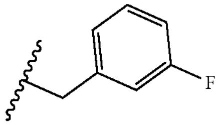

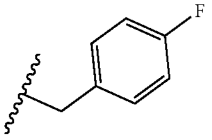 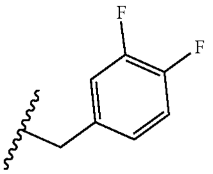

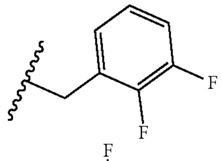 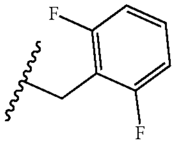

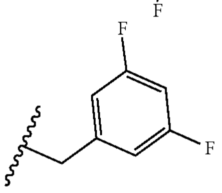 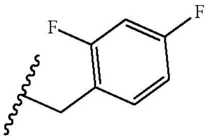

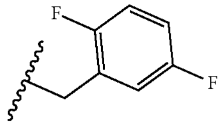 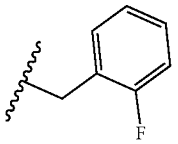

-continued

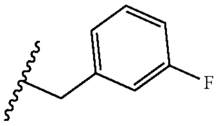 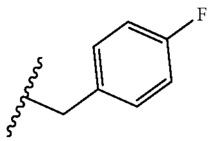

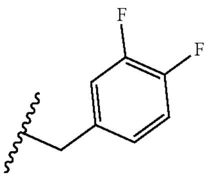 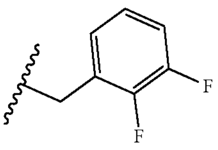

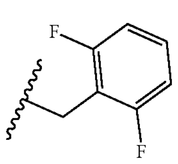 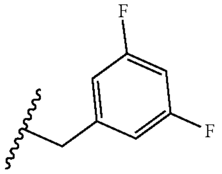

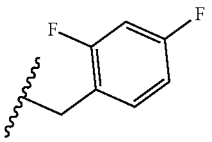 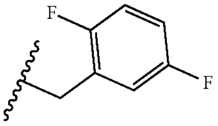

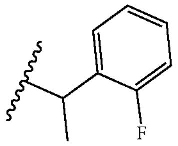 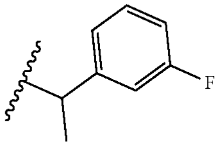

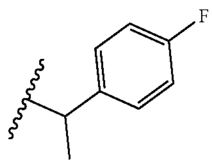 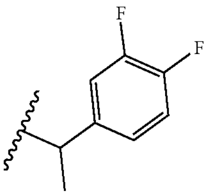

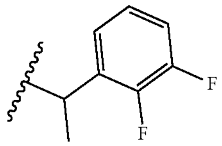 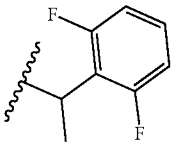

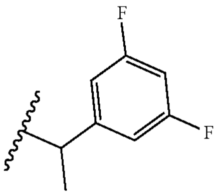 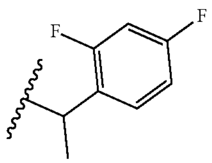

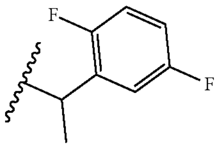 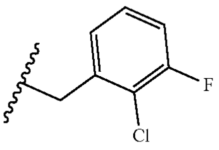

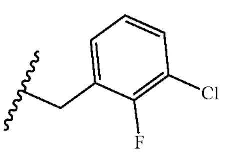 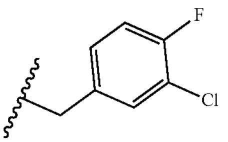

-continued
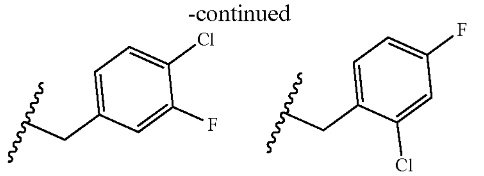
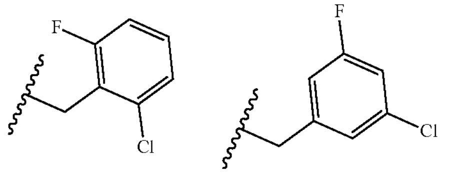
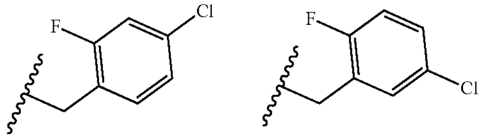
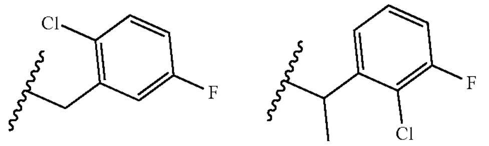
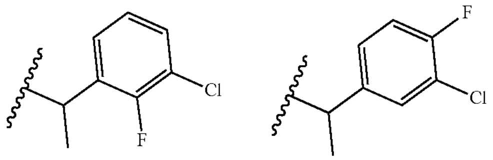
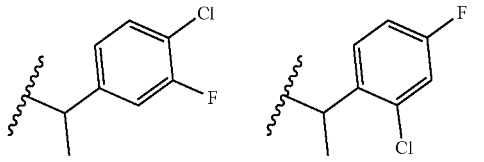
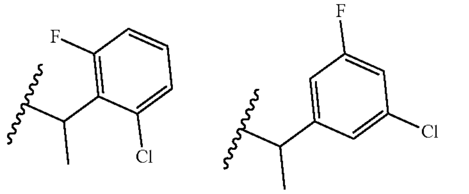
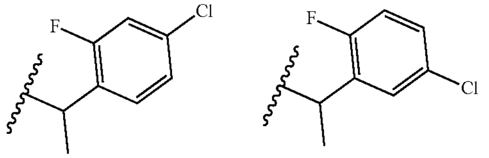
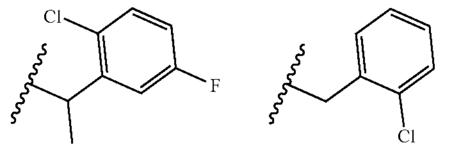
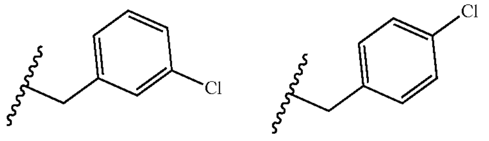
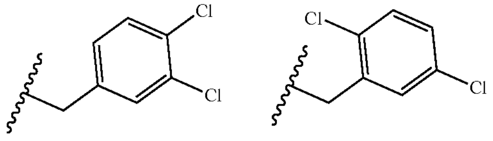
-continued
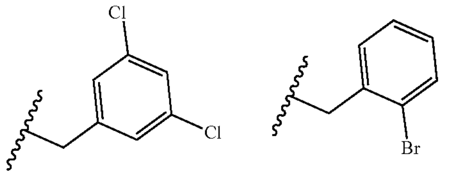
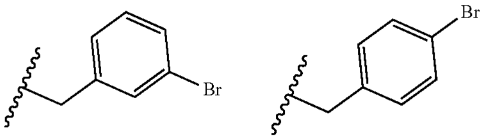
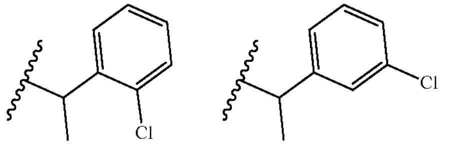
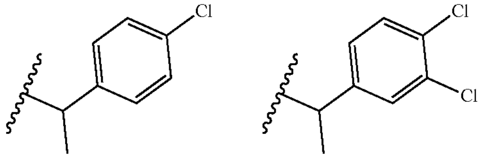
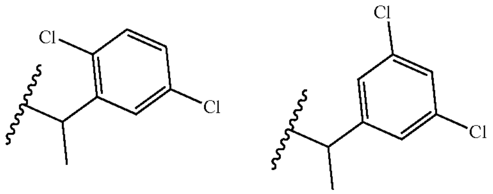
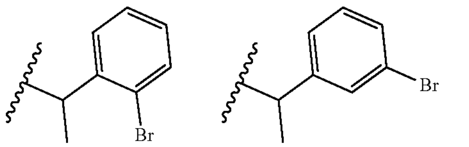
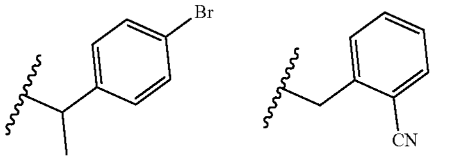
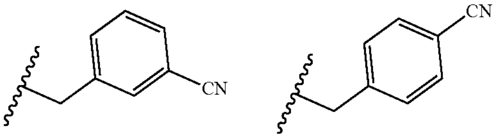
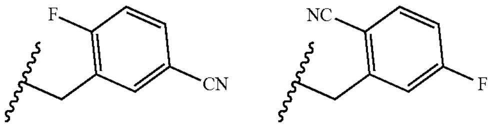
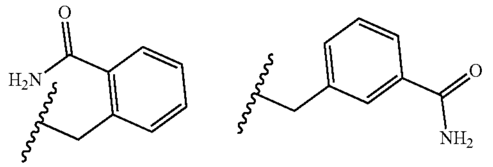
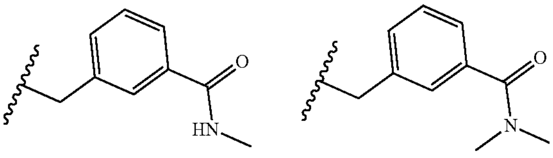

-continued

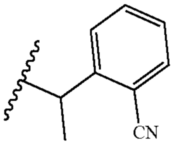 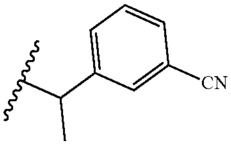

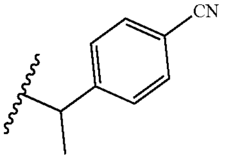 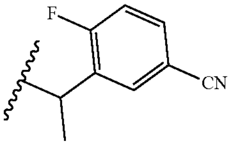

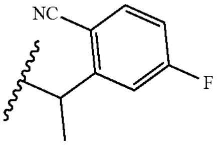 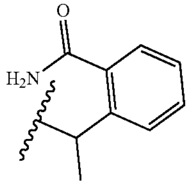

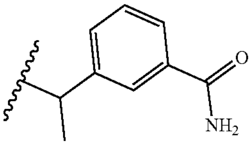 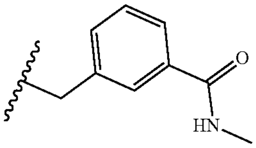

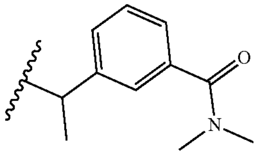 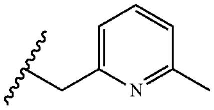

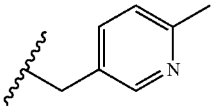 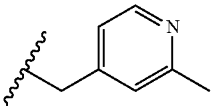

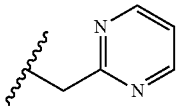 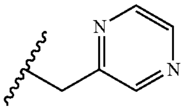

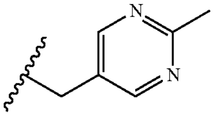 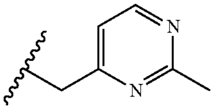

-continued

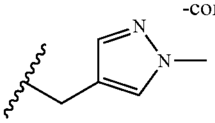 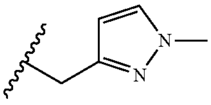

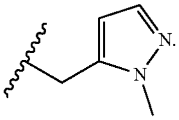

26. The compound of claim 20, wherein $R^4$ is selected from the group consisting of hydrogen and —$NHR^{10}$; $R^{10}$ is selected from:

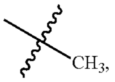

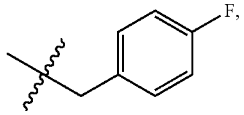

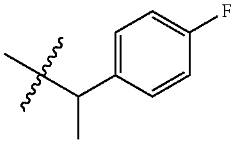

and

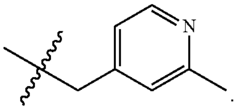

27. The kit of claim 9, wherein the kit further comprises b) at least one additional therapeutic agent as a second therapeutic agent, or a pharmaceutical composition comprising the additional therapeutic agent as a second pharmaceutical composition.

28. The kit of claim 11, wherein the kit further comprises b) at least one additional therapeutic agent as a second therapeutic agent, or a pharmaceutical composition comprising the additional therapeutic agent as a second pharmaceutical composition.

29. The compound of claim 1, wherein $R^3$ is selected from the group consisting of $C_{1-6}$ alkoxyl and $C_{1-6}$ alkylamino.

30. The compound of claim 1, wherein $R^4$ is selected from the group consisting of $C_{1-6}$ alkylamino and $C_{1-6}$ haloalkylamino.

* * * * *